US011230535B2

(12) United States Patent
Verkman et al.

(10) Patent No.: US 11,230,535 B2
(45) Date of Patent: Jan. 25, 2022

(54) CFTR REGULATORS AND METHODS OF USE THEREOF

(71) Applicant: THE REGENTS OF THE UNIVERSITY OF CALIFORNIA, Oakland, CA (US)

(72) Inventors: Alan S. Verkman, San Francisco, CA (US); Marc H. Levin, San Francisco, CA (US); Onur Cil, San Francisco, CA (US); Sujin Lee, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/785,417

(22) Filed: Feb. 7, 2020

(65) Prior Publication Data

US 2020/0181097 A1    Jun. 11, 2020

Related U.S. Application Data

(62) Division of application No. 16/016,290, filed as application No. PCT/US2016/068569 on Dec. 23, 2016, now Pat. No. 10,604,492.

(60) Provisional application No. 62/387,590, filed on Dec. 24, 2015.

(51) Int. Cl.

| | |
|---|---|
| *C07D 251/52* | (2006.01) |
| *C07D 251/46* | (2006.01) |
| *A61P 1/10* | (2006.01) |
| *A61P 27/04* | (2006.01) |
| *A61K 31/496* | (2006.01) |
| *A61K 31/53* | (2006.01) |
| *A61K 31/5377* | (2006.01) |
| *A61K 31/55* | (2006.01) |
| *A61K 45/06* | (2006.01) |
| *C07D 403/04* | (2006.01) |
| *C07D 413/12* | (2006.01) |

(52) U.S. Cl.
CPC .......... *C07D 251/52* (2013.01); *A61K 31/496* (2013.01); *A61K 31/53* (2013.01); *A61K 31/5377* (2013.01); *A61K 31/55* (2013.01); *A61K 45/06* (2013.01); *A61P 1/10* (2018.01); *A61P 27/04* (2018.01); *C07D 251/46* (2013.01); *C07D 403/04* (2013.01); *C07D 413/12* (2013.01)

(58) Field of Classification Search
CPC .......... C07D 251/52; A61P 1/10; A61P 27/04; A61K 31/496
See application file for complete search history.

(56) References Cited

U.S. PATENT DOCUMENTS

| | | | |
|---|---|---|---|
| 4,816,064 | A | 3/1989 | Konno et al. |
| 6,774,235 | B2 | 8/2004 | Daeyaert et al. |
| 2004/0209880 | A1 | 10/2004 | Timmer et al. |
| 2009/0291950 | A1 | 11/2009 | Govek et al. |
| 2010/0168154 | A1 | 7/2010 | Shishikura et al. |
| 2013/0040986 | A1 | 2/2013 | Binch et al. |
| 2016/0317493 | A1 | 11/2016 | Van Der Plas et al. |
| 2019/0031622 | A1 | 1/2019 | Verkman et al. |
| 2019/0337929 | A1 | 11/2019 | Walters et al. |
| 2021/0154201 | A1 | 5/2021 | Verkman et al. |

FOREIGN PATENT DOCUMENTS

| | | |
|---|---|---|
| CN | 102361855 A | 2/2012 |
| CN | 105130948 A | 12/2015 |
| EA | 004540 B1 | 6/2004 |
| EA | 009728 B1 | 2/2008 |
| WO | 99/50254 A1 | 10/1999 |
| WO | 01/47897 A1 | 7/2001 |
| WO | 03/024926 A2 | 3/2003 |
| WO | 2004/031184 A1 | 4/2004 |
| WO | 2005/009980 A1 | 2/2005 |
| WO | 2005/103015 A1 | 11/2005 |
| WO | 2007/095812 A1 | 8/2007 |
| WO | 2009/091388 A2 | 7/2009 |
| WO | 2009/091388 A3 | 7/2009 |
| WO | 2009/091388 A4 | 7/2009 |
| WO | 2009/109258 A1 | 9/2009 |
| WO | 2011/124869 A1 | 10/2011 |
| WO | 2015/168079 A1 | 11/2015 |
| WO | 2017/112950 A1 | 6/2017 |
| WO | 2017/112951 A1 | 6/2017 |

OTHER PUBLICATIONS

Al-Muhammed et al., "In-vivo studies on dexamethasone sodium phosphate liposomes," *J. Microencapsul*. 13(3):293-306, 1996,.
Al-Nakkash et al., "Activation of a CFTR-Mediated Chloride Current in a Rabbit Corneal Epithelial Cell Line," *Invest. Ophthalmol. Vis. Sci.* 42(10):2364-2370, 2001.
Allen, *The Art, Science and Technology of Pharmaceutical Compounding*, Fifth Edition, American Pharmacists Association, 1999. (8 pages).
Alves et al., "Dry Eye Disease Treatment: A Systematic Review of Published Trials and Critical Appraisal of Therapeutic Strategies," *Ocul. Surf.* 11(3): 181-192, 2013.
Anitha et al., "Gut Microbial Products Regulate Murine Gastrointestinal Motility via Toll-Like Receptor 4 Signaling," *Gastroenterology* 143(4): 1006-1016.e4, 2012.
Ansari et al., "Ocular signs and symptoms and vitamin A status in patients with cystic fibrosis treated with daily vitamin A supplements," *Br. J. Ophthalmol.* 83:688-691, 1999.
Asbell et al., "Ophthalmologist Perceptions Regarding Treatment of Moderate-to-Severe Dry Eye: Results of a Physician Survey," *Eye Contact Lens* 36(l):33-38, 2010.
Bijvelds et al., "Activation of Intestinal Cl-Secretion by Lubiprostone Requires the Cystic Fibrosis Transmembrane Conductance Regulator," *Gastroenterology* 137(3):976-985, 2009.

(Continued)

Primary Examiner — Kamal A Saeed
(74) Attorney, Agent, or Firm — Seed IP Law Group LLP

(57) ABSTRACT

Provided herein are compounds that activate CFTR and methods for treating constipation, dry eye disorders, and other diseases and disorders.

12 Claims, 30 Drawing Sheets

(56) References Cited

OTHER PUBLICATIONS

Botelho et al., "Tear sodium, potassium, chloride, and calcium at various flow rates: Children with cystic fibrosis and unaffected siblings with and without corneal staining," *The Journal of Pediatrics* 83(4):601-606, 1973.
Busby et al., "Linaclotide, through activation of guanylate cyclase C, acts locally in the gastrointestinal tract to elicit enhanced intestinal secretion and transit," *European Journal of Pharmacology* 649:328-335, 2010.
Castro et al., "Linaclotide Inhibits Colonic Nociceptors and Relieves Abdominal Pain via Guanylate Cyclase-C and Extracellular Cyclic Guanosine 3',5'-Monophosphate," *Gastroenterology* 145(6):1334-1346, 2013.
Chao et al., "Activation of intestinal CFTR Cl⁻ channel by heat-stable enterotoxin and guanylin via cAMP-dependent protein kinase," *EMBO J.* 13(5):1065-1072, 1994.
Chey et al., "Naloxegol for Opioid-Induced Constipation in Patients with Noncancer Pain," *New England Journal of Medicine* 370(25):2387-2396, 2014.
Cholon et al., "Potentiator Ivacaftor Abrogates Pharmacological Correction of ΔF508 CFTR in Cystic Fibrosis," *Sci. Transl. Med.* 6(246): 1-31, 2014.
Chonn et al., "Recent advances in liposomal drug-delivery systems," *Curr. Opin. Biotechnol.* 6:698-708, 1995.
Cil et al., "Benzopyrimido-pyrrolo-oxazine-dione CFTR inhibitor (R)-BPO-27 for antisecretory therapy of diarrheas caused by bacterial enterotoxins," *FASEB J.* 31:751-760, 2017.
Cil et al., "CFTR Activator Increases Intestinal Fluid Secretion and Normalizes Stool Output in a Mouse Model of Constipation," *Cell Mol. Gastroenterol Hepatol.* 2(3):317-327, 2016.
Cil et al., "Phenylquinoxalinone CFTR activator as potential prosecretory therapy for constipation," *Transl. Res.* 182:14-26, 2017, (23 pages).
Coffman et al., "Constrained Bithiazoles: Small Molecule Correctors of Defective AF508-CFTR Protein Trafficking," *J. Med. Chem.* 57:6729-6738, 2014.
De La Fuente et al., "Small-molecule screen identifies inhibitors of a human intestinal calcium-activated chloride channel," *Mol. Pharmacol.* 73:758-768, 2007, (39 pages).
Dekkers et al., "A Functional CFTR assay using primary cystic fibrosis intestinal organoids," *Nature Medicine* 19(7):939-945, 2013, (9 pages).
Dovlatian et al., "Synthesis and Thermic Decomposition of Halogenalkoxy(thio)-symm-Triazines," *Armyanskii Khimicheskii Zhurnal* 41(6):346-351, 1988.
Dudley et al., "Cyanuric Chloride Derivatives. III. Alkoxy-s-triazines," *Journal of the American Chemical Society* 73:2986-2990, 1951.
Eckford et al., "Cystic Fibrosis Transmembrane Conductance Regulator (CFTR) Potentiator VX-770 (Ivacaftor) Opens the Defective Channel Gate of Mutant CFTR in a Phosphorylation-Dependent but ATP-independent Manner," *Journal of Biological Chemistry* 287(44):36639-36649, 2012.
Esteva-Font et al., "Diuresis and reduced urinary osmolality in rats produced by small-molecule UT-A-selective urea transport inhibitors," *FASEB J.* 28(9):3878-3890, 2014.
Extended European Search Report dated Jul. 10, 2019 in corresponding EP Application No. 16880160.3, 9 pages.
Eyles, "Oral Delivery and Fate of Poly(lactic acid) Microsphere-encapsulated Interferon in Rats," *J. Pharm. Pharmacol.* 49:669-674, 1997.
Fei et al., "Lubiprostone Reverses the Inhibitory Action of Morphine on Intestinal Secretion in Guinea Pig and Mouse," *Journal of Pharmacology and Experimental Therapeutics* 334(1):333-340, 2010. (37 pages).
Field et al., "Effect of Cholera Enterotoxin on Ion Transport across Isolated Ileal Mucosa," *The Journal of Clinical Investigation* 51:796-804, 1972.
Field, "Mechanisms of action of cholera and *Escherichia coli* enterotoxins," *Am. J. Clin. Nutr.* 32(1):189-196, 1979. (10 pages).

Flores et al., "Small-molecule CFTR activators increase tear secretion and prevent experimental dry eye disease," *FASEB J.* 30:1789-1797, 2016.
Foulke-Abel et al., "Human Enteroids as a Model of Upper Small Intestinal Ion Transport Physiology and Pathophysiology," *Gastroenterology* 150:638-649.e8, 2016.
Fox et al., "Discovery of 6-Phenylpyrimido[4,5-b][1,4]oxazines as Potent and Selective Acyl CoA:Diacylglycerol Acyltransferase 1 (DGAT1) Inhibitors with in vivo Efficacy in Rodents," *J. Med. Chem.* 57:3464-3483, 2014.
Galietta et al., "Cell-based assay for high-throughput quantitative screening of CFTR chloride transport agonists." *Am. J. Physiol. Cell Physiol.* 281:C1734-1742, 2001.
Galietta et al., "Green fluorescent protein-based halide indicators with improved chloride and iodide affinities," *FEBS Lett.* 499:220-224, 2001.
Galietta et al., "Novel CFTR Chloride Channel Activators Identified by Screening of Combinatorial Libraries Based on Flavone and Benzoquinolizinium Lead Compounds," *J. Biol. Chem.* 276(23):19723-19728, 2001. (7 pages).
Gao et al., "Controlled Release of a Contraceptive Steroid from Biodegradable and Injectable Gel Formulations: In Vitro Evaluation," *Pharm. Res.* 72(6):857-863, 1995.
Gilbard et al., "Morphologic Effect of Hyperosmolarity on Rabbit Corneal Epithelium," *Ophthalmology* 91(10):1205-1212, 1984.
Gras et al., "Bronchial epithelium as a target for innovative treatments in asthma," *Pharmacology & Therapeutics* 140(3):290-305, 2013.
Haggie et al., "Inhibitors of pendrin anion exchange identified in a small molecule screen increase airway surface liquid volume in cystic fibrosis," *FASEB J.* 30:2187-2197, 2016.
Hecht et al., "Differential regulation of Na⁺/H⁺ exchange isoform activities by enteropathogenic *E. coli* in human intestinal epithelial cells," *American Journal of Physiology—Gastrointestinal and Liver Physiology* 287:G370-G378, 2004.
Hosoda et al., "Targeted and Natural (Piebald-lethal) Mutations of Endothelin-B Receptor Gene Produce Megacolon Associated with Spotted Coat Color in Mice," *Cell* 79:1267-1276, 1994.
Hwang et al., "Identification of a series of 1,3,4-trisubstituted pyrazoles as novel hepatitis C virus entry inhibitors," *Bioorganic & Medicinal Chemistry Letters* 23:6467-6473, 2013.
International Search Report, dated Mar. 30, 2017, for International Application No. PCT/US2016/068569, 4 pages.
International Search Report and Written Opinion, dated Oct. 30, 2018, for International Application No. PCT/US2018/048025, 7 pages.
Jean-Claude et al., "Synthesis of Bi- and Tri-cyclic Tetrazepinones," *J. Chem. Soc., Perkin Trans.* 10:2525-2529, 1991. (7 pages).
Jowa et al., "Should Atrazine and Related Chlorotriazines Be Considered Carcinogenic for Human Health Risk Assessment?," *Journal of Environmental Science and Health, Part C*, 29:91-144, 2011. (55 pages).
Kim et al., "Construction of 1,2,5-Tricarbonyl Compounds using Methyl Cyanoacetate as a Glyoxylate Anion Synthon Combined with Copper(I) Iodide-Catalyzed Aerobic Oxidation," *Adv. Synth. Catal.* 353:3335-3339, 2011.
Koh et al., "Long-term results of treatment with diquafosol ophthalmic solution for aqueous-deficient dry eye," *J. Ophthalmol.* 57:440-446, 2013.
Kompella et al., "Active chloride transport in the pigmented rabbit conjunctiva," *Curr. Eye Res.* 12:1041-1048, 1993.
Lawrence et al., "Structure-Activity Studies of Substituted Quinoxalinones as Multiple-Drug-Resistance Antagonists," *Journal of Medicinal Chemistry* 44:594-601, 2001.
Lembo et al., "Two Randomized Trials of Linaclotide for Chronic Constipation," *New England Journal of Medicine* 365(6):527-536, 2011.
Lemp et al., "Tear Osmolarity in the Diagnosis and Management of Dry Eye Disease," *Am. J. Ophthalmol.* 151(5):792-798, 2011.
Lemp et al., "The definition and classification of dry eye disease: Report of the Definition and Classification Subcommittee of the International Dry Eye WorkShop," DEWS, *Ocul. Surf.* 5:75-204, 2007. (128 pages).

(56) References Cited

OTHER PUBLICATIONS

Lencer et al., "Opening CFTR in the Intestine: Flushing on Demand," *Cellular and Molecular Gastroenterology and Hepatology* 2:256, 2016.
Levin et al., "CFTR-Regulated Chloride Transport at the Ocular Surface in Living Mice Measured by Potential Differences," *Invest. Ophthalmol. Vis. Sci.* 46(4):1428-1434, 2005.
Levin et al., "Potential Difference Measurements of Ocular Surface Na+ Absorption Analyzed Using an Electrokinetic Model," *Invest. Ophthalmol. Vis. Sci.* 47(1):306-316, 2006.
Lipinski et al., "Experimental and computational approaches to estimate solubility and permeability in drug discovery and development settings," *Advanced Drug Delivery Reviews* 23(1997):3-25, 1997.
Liu et al., "A Link between Tear Instability and Hyperosmolarity in Dry Eye," *Invest. Ophthalmol. Vis. Sci.* 50(8):3671-3679, 2009.
Lu et al., "CFTR-mediated Cl(−) Transport in the Acinar and Duct Cells of Rabbit Lacrimal Gland," *Curr. Eye Res.* 37(8):671-677, 2012. (13 pages).
Luo et al., "Hyperosmolar Saline is a Proinflammatory Stress on the Mouse Ocular Surface," *Eye & Contact Lens* 31(5): 186-193, 2005.
Ma et al., "High-affinity Activators of Cystic Fribrosis Transmembrane Conductance Regulator (CFTR) Chloride Conductance Identified by High-throughput Screening," *J. Biol. Chem.* 277(40):37235-37241, 2002.
Menees et al., "Agents that act luminally to treat diarrhoea and constipation," *Nature Reviews Gastroenterology and Hepatology* 9(11):661-674, 2012.
Moon et al., "A Novel Microtubule Destabilizing Entity from Orthogonal Synthesis of Triazine Library and Zebrafish Emryo Screening," *J. Am. Chem. Soc.* 124:11608-11609, 2002.
Moon et al., "Drug-induced secretory diarrhea: A role for CFTR," *Pharmacol Res.* 102:107-112, 2015. (12 pages).
Morkeberg et al. "Ocular findings in cystic fibrosis patients receiving vitamin A supplementation," *Graefes Arch. Clin. Exp. Ophthalmol.* 233:709-713, 1995. (7 pages).
Mrugacz et al., "IL-8 and IFN-gamma in Tear Fluid of Patients with Cystic Fibrosis," *Journal of Interferon & Cytokine Research* 26:71-75, 2006.
Mugie et al., "Constipation in childhood," *Nature Reviews Gastroenterology and Hepatology* 8(9):502-511, 2011.
Namkung et al., "TMEMI6A Inhibitors Reveal TMEMI6A as a Minor Component of Calcium-Activated Chloride Channel Conductance in Airway and Intestinal Epithelial Cells," *J. Biol. Chem.* 286(3):2365-2374, 2011.
Nandoskar et al., "Changes of Chloride Channels in the Lacrimal Glands of a Rabbit Model of Sjögren syndrome," *Cornea* 31(3):273-279, 2012.
Nichols et al., "Diquafosol tetrasodium: a novel dry eye therapy," *Expert. Opin. Investig.. Drugs* 13(1):41-54, 2004.
Ong et al., "New Therapeutic Approaches to Modulate and Correct CFTR," *Pediatr. Clin. North. Am.* 63(4):751-764, 2016.
Ostro, "Use of liposomes as injectable-drug delivery systems." *Am. J. Hosp. Pharm.* 46(8):1576-1587, 1989. (13 pages).
Phuan et al., "Cyanoquinolines with Independent Corrector and Potentiator Activities Restore ΔPhe508-Cystic Fibrosis Transmembrane Conductance Regulator Chloride Channel Function in Cystic Fibrosis," *Mol. Pharmacol.* 80(4):683-693, 2011.
Pinto Sanchez et al., "Epidemiology and burden of chronic constipation," *Canadian Journal of Gastroenterology* 25(Suppl. B): 11B-15B, 2011.
Plebanek et al., "Straightforward synthesis of 2,4,6-trisubstituted 1,3,5-triazine compounds targeting cysteine cathepsins K and S," Manuscript—*Eur. J. Med. Chem.* 121:12-20, 2016. (20 pages).
Qin et al., "Design and Synthesis of Potent and Multifunctional Aldose Reductase Inhibitors Based on Quinoxalinones," *Journal of Medicinal Chemistry* 58:1254-1267, 2015.
Raghunadh et al., "An Efficient and Practical Synthesis of Aryl and Hetaryl α-Keto Esters," *Synthesis* 44:283-289, 2012.

Ramsey et al., "A CFTR Potentiator in Patients with Cystic Fibrosis and the G551D Mutation," *N. Engl. J. Med.* 365(18):1663-1672, 2011.
Rao et al., "Mode of Action of Heat-Stable *Escherichia coli* Enterotoxin: Tissue and Subcellular Specificities and Role of Cyclic GMP," *Biochimica et Biophysica Acta (BBA)—General Subjects* 632(1):35-46, 1980.
Rao, "Recent developments of collagen-based materials for medical applications and drug delivery systems.," *J. Biomater. Sci. Polym.* 7(7):623-645, 1995.
Ratcliff et al., "Production of a severe cystic fibrosis mutation in mice by gene targeting," *Nature Genetics* 4:35-41, 1993.
Schaumberg et al., "Prevalence of Dry Eye Disease Among US Men: Estimates from the Physicians' Health Studies," *Arch. Ophthalmol.* 127(6):763-768, 2009.
Schaumberg et al., "Prevalence of Dry Eye Syndrome Among US Women," *Am. J. Ophthalmol.* 136(2):318-326, 2003.
Schmidt et al., "Cystic fibrosis transmembrane conductance regulator modulators in cystic fibrosis: current perspectives," *Clin. Pharmacol* 8:121-140, 2016.
Shaw et al., "One-Pot Two-Step Synthesis of Quinoxalinones and Diazepinones via a Tandem Oxidative Amidation-Deprotection-Cyclization Sequence," *Synthesis* 45:459-462, 2013.
Sheppard et al., "Lifitegrast Ophthalmic Solution 5.0% for Treatment of Dry Eye Disease: Results of the OPUS-1 Phase 3 Study," *Ophthalmology* 121(2):475-483, 2014.
Shiue et al., "Characterization of cyclic AMP-regulated chloride conductance in the pigmented rabbit conjunctival epithelial cells," *Can. J. Physiol. Pharmacol.* 80:533-540, 2002.
Snyder et al., "Potent, Metabolically Stable Benzopyrimido-Pyrrolo-Oxazine-Dione (BPO) CFTR Inhibitors for Polycystic Kidney Disease," *J. Med. Chem.* 54(15):5468-5477, 2011. (20 pages).
Solomon et al., "Breakthrough Therapies: Cystic Fibrosis (CF) Potentiators and Correctors," *Pediatr. Pulmonol.* 50:S3-S13, 2015.
Solomon et al., "Therapeutic Approaches to Acquired Cystic Fibrosis Transmembrane Conductance Regulator Dysfunction in Chronic Bronchitis," *Ann. Am. Thorac. Soc. Suppl* 13(2):S169-S176, 2016.
Srivastava et al., "Progressive Familial Intrahepatic Cholestasis," *Journal of Clinical and Experimental Hepatology* 4(1):25-36, 2014.
Stevenson et al., "Extraorbital Lacrimal Gland Excision: A Reproducible Model of Severe Aqueous Tear-Deficient Dry Eye Disease," *Cornea* 33(2): 1336-1341, 2014.
Stewart et al., "Effect of Experimental Dry Eye on Tear Sodium Concentration in the Mouse," *Eye & Contact Lens* 31(4):175-178, 2005.
Subramanya et al., "Differential regulation of cholera toxin-inhibited Na-H exchange isoforms by butyrate in rat ileum," *American Journal of Physiology—Gastrointestinal and Liver Physiology* 293:G857-G863, 2007.
Sullivan et al., "Does Androgen Insufficiency Cause Lacrimal Gland Inflammation and Aqueous Tear Deficiency?," *Invest. Ophthalmol. Vis. Sci.* 40(6): 1261-1265, 1999.
Takamura et al., "A randomised, double-masked comparison study of diquafosol versus sodium hyaluronate ophthalmic solutions in dry eye patients," *Br. J. Ophthalmol.* 96:1310-1315, 2012.
Tauber et al., "Double-Masked, Placebo-Controlled Safety and Efficacy Trial of Diquafosol Tetrasodium (INS365) Ophthalmic Solution for the Treatment of Dry Eye," *Cornea* 23(8):784-792, 2004.
Thelin et al., "Effect of Topically Applied Epithelial Sodium Channel Inhibitors on Tear Production in Normal Mice and in Mice with Induced Aqueous Tear Deficiency," *J. Ocul. Pharmacol. Ther.* 28(4):433-438, 2012.
Thiagarajah et al., "Secretory diarrhoea: mechanisms and emerging therapies," *Nature Reviews Gastroenterology and Hepatology* 12(8):446-457, 2015. (24 pages).
Turner et al., "Cyclic AMP-dependent Stimulation of Basolateral K+ Conductance in the Rabbit Conjunctival Epithelium," *Exp. Eye Res.* 70:295-305, 2000.
Turner et al., "Presence of CFTR in the conjunctival epithelium," *Curr. Eye Res.* 24(3):182-187, 2002.

(56) References Cited

OTHER PUBLICATIONS

Van Goor et al., "Pharmacological Rescue of Mutant CFTR Function for the Treatment of Cystic Fibrosis," *Top. Med. Chem.* 3:91-120, 2008.
Veber et al., "Molecular Properties That Influence the Oral Bioavailability of Drug Candidates," *Journal of Medicinal Chemistry* 45:2615-2623, 2002.
Verkman et al., "Chloride channels as drug targets," *Nat. Rev. Drug Discov.* 8(2):153-171, 2009. (39 pages).
Villareal et al., "Effect of Topical Ophthalmic Epinastine and Olopatadine on Tear Volume in Mice," *Eye & Contact Lens* 32(6):272-276, 2006.
Watsky et al., "Comparison of conjunctival and corneal surface area in rabbit and human," *Curr. Eye Res.* 7(5):483-486, 1988.
Webster et al., "Embryogenesis of the enteric ganglia in normal mice and in mice that develop congenital aganglionic megacolon," *J. Embryol. exp. Morph.* 30(3):573-585, 1973.
Wolosin et al., "Cl⁻ secretagogues increase basolateral K⁺ conductance of frog corneal epithelium," *Am. J. Physiol.* 253(4):C555-C560, 1987. (8 pages).
Yao et al., "Triazolothienopyrimidine Inhibitors of Urea Transporter UT-B Reduce Urine Concentration," *J. Am. Soc. Nephrol.* 23:1210-1220, 2012.
Yu et al., "Regional differences in rat conjunctival ion transport activities," *Am. J. Physiol. Cell Physiol.* 303:C767-C780, 2012.
Yu et al., "The Economic Burden of Dry Eye Disease in the United States: A Decision Tree Analysis," *Cornea* 30(4):379-387, 2011.
Zarate et al., "Chronic constipation: Lessons from animal studies," *Best Practice & Research Clinical Gastroenterology* 25(1):59-71, 2011.
Baindur et al., "2-Hydroxy-4,6-diamino-[1,3,5]triazines: A Novel Class of VEGF-R2 (KDR) Tyrosine Kinase Inhibitors," *J Med. Chem.* 48(6): 1717-1720: 2005.
Li et al., "Revealing Interaction Mode Between HIV-1 Reverse Transcriptase and Diaryltriazine Analog Inhibitor," *Chem. Biol. Drug Des.* 72:350-359, 2008.
Ludovici et al., "Evolution of Anti-HIV Drug Candidates Part 2: Diaryltriazine (DATA) Analogues," *Bioorganic & Medicinal Chemistry Letters* 11:2229-2234, 2001.
Moran et al., "Binding site of activators of the cystic fibrosis transmembrane conductance regulator in the nucleotide binding domains," *CMLS Cellular and Molecular Life Sciences* 62:446-460, 2005.
Office Action, dated Mar. 10, 2020, for Russian Patent Application No. 2018126958, 21 pages. (w/ English Translation).
Pubchem, "N-Methyl-N'-phenyl-6-(2,2,2-trifluoroethoxy)-1,3,5-triazine-2,4-diamine," PubChem CID 2266465, 2005. (11 pages).
Shah et al., "Synthesis and Diuretic Activity of 2-Amino-4-arylamino-6-mercapto-s-triazines and Related Derivatives," 1167-1171, 1968.
Somogyi et al., "Cyclisierungsreaktionen von mono- und disubstituierten Biguaniden mit Phenylisothiocyanat," *Chem. Ber.* 100:1975-1982, 1967.
Lee et al., "Nanomolar-Potency Aminophenyl-1,3,5-triazine Activators of the Cystic Fibrosis Transmembrane Conductance Regulator (CFTR) Chloride Channel for Prosecretory Therapy of Dry Eye Diseases," *J. Med. Chem.* 60:1210-1218, 2017.
Office Action, dated Nov. 5, 2020, for European Application No. 16880160.3. (5 pages).
Office Action, dated Mar. 29, 2021, for European Application No. 18849250.8. (7 pages).
Office Action (w/ English Translation), dated Jul. 2, 2020, for Indian Application No. 201817026075. (5 pages).
Office Action (w/ English Translation), dated Nov. 4, 2020, for Japanese Application No. 2018-533169. (12 pages).
STN International, Search Report, dated Feb. 25, 2021. (39 pages).
STN International, CAS Registry No. 301211-36-9, File Registry [online], 1,3,5-Triazine-2,4-diamine, N2,N2-dimethyl-N4-(4-nitrophenyl)-6-(2,2,2-trifluoroethoxy), Nov. 3, 2000. (1 page).
STN International, CAS Registry No. 731836-49-0, File Registry [online], 1,3,5-Triazine-2,4-diamine, N2,N2-diethyl-N4-(4-methylphenyl)-6-[2,2,2-trifluoro-1-(trifluoromethyl)ethoxy], Aug. 24, 2004. (1 page).
STN International, CAS Registry No. 732247-01-7, File Registry [online], 1,3,5-Triazine-2,4-diamine, N4-(4-methoxyphenyl)-N2,N2-dipropyl-6-[2,2,2-trifluoro-1-(trifluoromethyl)ethoxy], Aug. 25, 2004, (1 page).
STN International, CAS Registry No. 732250-34-9, File Registry [online], 1,3,5-Triazine-2,4-diamine, N4-(4-methylphenyl)-N2,N2-dipropyl-6-[2,2,2-trifluoro-1-(trifluoromethyl)ethoxy], Aug. 25, 2004. (1 page).
STN International, CAS Registry No. 733797-64-3, File Registry [online], 1,3,5-Triazine-2,4-diamine, N2,N2-diethyl-N4-(4-methoxyphenyl)-6-[2,2,2-trifluoro-1-(trifluoromethyl)ethoxy], Aug. 27, 2004. (1 page).
STN International, CAS Registry No. 736938-07-1, File Registry [online], 1,3,5-Triazine-2,4-diamine, N2,N2-diethyl-N4-(2-methoxyphenyl)-6-[2,2,2-trifluoro-1-(trifluoromethyl)ethoxy], Sep. 1, 2004. (1 page).
STN International, CAS Registry No. 736970-45-9, File Registry [online], 1,3,5-Triazine-2,4-diamine, N2,N2-dimethyl-N4-phenyl-6-[2,2,2-trifluoro-1-(trifluoromethyl)ethoxy], Sep. 1, 2004. (1 page).
STN International, CAS Registry No. 890717-80-3, File Registry [online], 1,3,5-Triazine-2,4-diamine, N2,N2-dimethyl-N4-1-naphthalenyl-6-[2,2,2-trifluoro-1-(trifluoromethyl)ethoxy], Jul. 6, 2006. (1 page).
Office Action, dated Jul. 27, 2020, for Australian Patent Application No. 2016379444, 7 pages.
Office Action, dated May 15, 2020, for European Patent Application No. 16880160.3, 6 pages.
Office Action, dated Aug. 19, 2020, for Russian Patent Application No. 2018126958/04(042913), 10 pages. (w/ English Translation).

| Compound | Structure | EC50 (nM) | Vmax | ΔPD (mV) |
|---|---|---|---|---|
| CFTR$_{act}$-A043 | 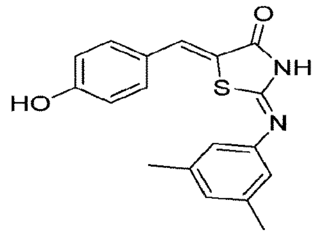 | 332 | 89% | -8.6 ± 0.49 |
| CFTR$_{act}$-B018 | 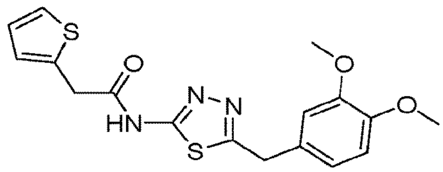 | 685 | 86% | -2.5 ± 0.43 |
| CFTR$_{act}$-B074 | 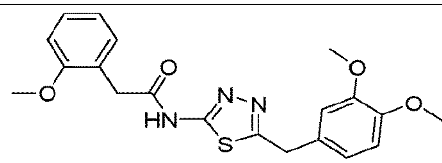 | 340 | 93% | -9.9 ± 0.99 |
| CFTR$_{act}$-B089 | 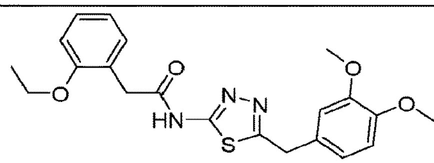 | 377 | 91% | -3.4 ± 0.53 |
| CFTR$_{act}$-B156 | 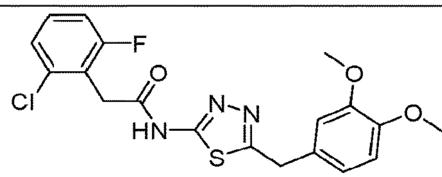 | 571 | 93% | -3.1 ± 1.1 |
| CFTR$_{act}$-E053 | 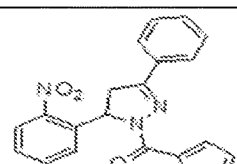 | 385 | 94% | -4.1 ± 1.0 |
| CFTR$_{act}$-J027 | 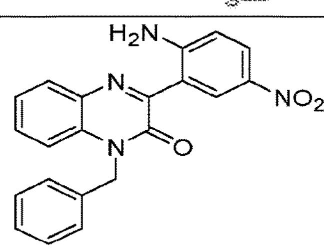 | 138 | 90% | -9.1 ± 0.39 |

FIG. 7 - cont'd.
| Compound | Structure | EC50 (nM) | Vmax | ΔPD (mV) |
|---|---|---|---|---|
| CFTR$_{act}$-K032 | 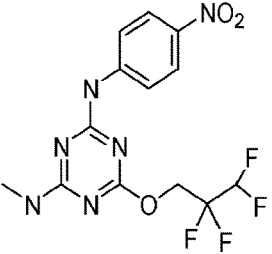 | 70 | 97% | -10 ± 1.1 |
| CFTR$_{act}$-K089 | 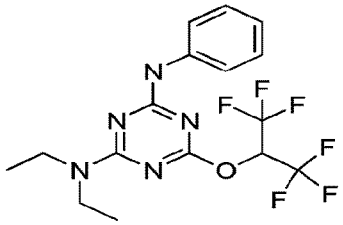 | 251 | 93% | -8.5 ± 0.81 |
| CFTR$_{act}$-O018 | 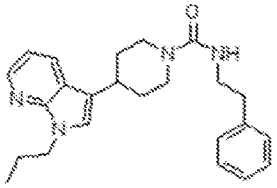 | 752 | 93% | -5.7 ± 1.8 |
| CFTR$_{act}$-O037 | 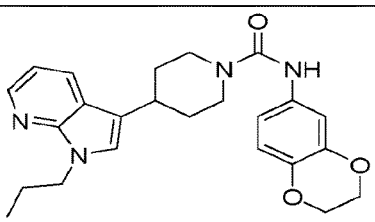 | 513 | 82% | |
| CFTR$_{act}$-Q022 | 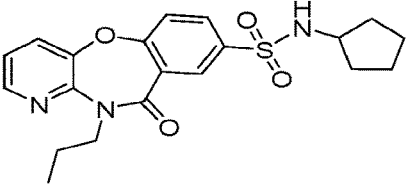 | 802 | 90% | |
| CFTR$_{act}$-Q86 | 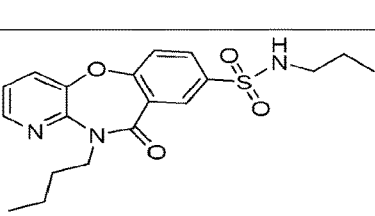 | 640 | 93% | |

FIG. 7 - cont'd.

| Compound | Structure | EC50 (nM) | Vmax | ΔPD (mV) |
|---|---|---|---|---|
| CFTR$_{act}$-R014 | 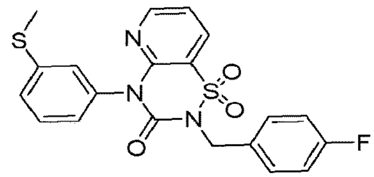 | 21 | 100% | -14 ± 0.42 |
| CFTR$_{act}$-R053 | 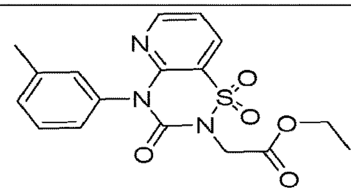 | 399 | 98% | |
| CFTR$_{act}$-R088 | 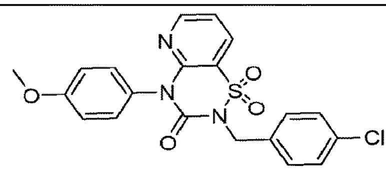 | 379 | 95% | |
| CFTR$_{act}$-R101 | 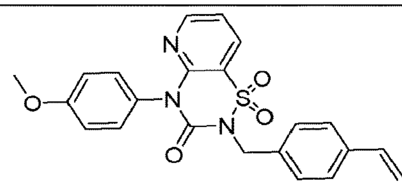 | 174 | 94% | |
| CFTR$_{act}$-R103 | 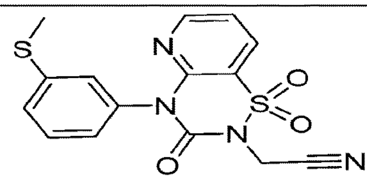 | 126 | 100% | |
| CFTR$_{act}$-R142 | 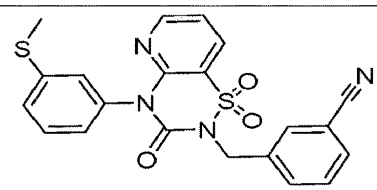 | 31 | 100% | |
| CFTR$_{act}$-R176 | 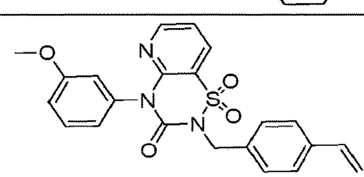 | 36 | 100% | |

FIG. 7 - cont'd.
| Compound | Structure | EC50 (nM) | Vmax | ΔPD (mV) |
|---|---|---|---|---|
| CFTR$_{act}$-R185 | 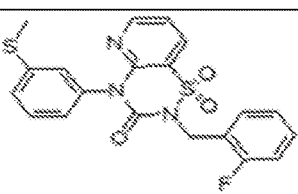 | 35 | 94% | |
| ref. 26 | 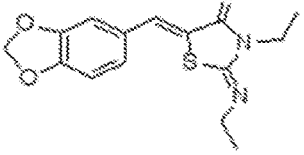 | 2000 | 65% | -2.5 ± 0.38 |
| ref. 26 | 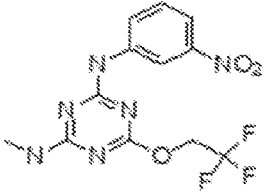 | 400 | 49% | -7.4 ± 0.90 |
| VX-770 | 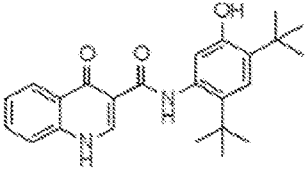 | Variable | 39% | -1.8 ± 0.29 | compound 1

CFTR REGULATORS AND METHODS OF USE THEREOF

CROSS REFERENCE TO RELATED APPLICATIONS

This application is a divisional application of U.S. application Ser. No. 16/016,290, filed on Jun. 22, 2018; which is a national stage application of International Application No. PCT/US2016/068569, filed on Dec. 23, 2016; which claims priority from U.S. Provisional Application No. 62/387,590, filed on Dec. 24, 2015, the entire contents of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with the government support under Grant Nos. TR000004, EY023981, EY013574, EB000415, DK035124, DK072517 and DK101373, awarded by the National Institutes of Health. The government has certain rights in the invention.

BACKGROUND OF THE INVENTION

Constipation is a common clinical complaint in adults and children that negatively impacts quality of life. The prevalence of chronic constipation has been estimated to be 15% in the U.S. population, with health-care costs estimated at approximately 7 billion dollars annually, with in excess of 500 million dollars spent on laxatives. The mainstay of constipation therapy includes laxatives and many of them are available over the counter (soluble fiber, polyethylene glycol, probiotics, etc.). There are two FDA-approved chloride channel activators, lubiprostone and linaclotide, for treatment of constipation, but clinical trials showed variable and unimpressive efficacy of both drugs. Despite the wide range of therapeutic options, there is a continued need for safe and effective drugs to treat constipation.

Dry eye is a heterogeneous tear film disorder that results in eye discomfort, visual disturbance, and ocular surface pathology, and remains an unmet need in ocular disease with limited effective therapeutic options available. Dry eye is a major public health concern in an aging population, affecting up to one-third of the global population, including 5 million Americans aged 50 and over. Over-the-counter artificial tears and implantable punctal plugs are frequently used for symptomatic relief. Therapeutic approaches involve reducing ocular surface inflammation or augmenting tear/mucin secretion. The only medication currently approved for dry eye is topical cyclosporine, an anti-inflammatory that does not eliminate all symptoms in most dry eye patients. Accordingly, additional treatments are needed for moderate-to-severe dry eye. Described herein, inter alia, are solutions to these and other problems in the art.

BRIEF SUMMARY OF THE INVENTION

Provided herein are compounds having the formula:

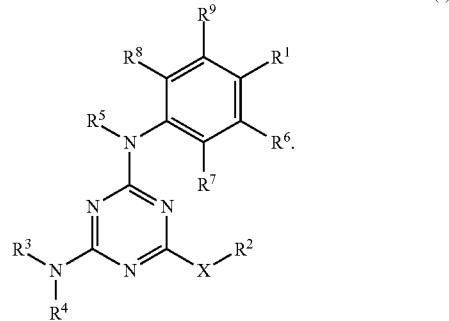

(I)

In the compound of formula I, X is a bond, —O—, —N($R^{10}$)— (e.g. —NH—), or —S—. In embodiments, X is —O—, —N($R^{10}$)— (e.g. NH), — or —S—. In embodiments, X is —O— or —S—. $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}R^{1C}$, —NHC(O)NR$^{1B}R^{1C}$, —N(O)$_{m1}$, —NR$^{1B}R^{1C}$, —C(O)R$^{1D}$, —C(O)OR$^{1D}$, —C(O)NR$^{1B}R^{1C}$, —OR$^{1A}$, —NR$^{1B}SO_2R^{1A}$, —NR$^{1B}C(O)R^{1D}$, —NR$^{1B}C(O)OR^{1D}$, —NR$^{1B}OR^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, —$CX^{2.1}_3$, $CHX^{2.1}_2$, —$(CH_2)_{n2}CX^{2.1}_3$, —$OR^{2A}$, substituted or unsubstituted alkyl (e.g. haloalkyl), substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^2$ is hydrogen, —$CX^{2.1}_3$, —$(CH_2)_{n2}CX^{2.1}_3$, —$OR^{2A}$, substituted or unsubstituted alkyl (e.g. —$CH_3$, $C_2$-$C_8$ alkyl, or $C_2$-$C_4$ alkyl), substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^3$ is hydrogen, —C(O)R$^{3D}$, —C(O)NHNR$^{3B}R^{3C}$, —C(O)OR$^{3D}$, —SO$_2R^{3A}$, —C(O)NR$^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiment, $R^3$ is hydrogen, —C(O)R$^{3D}$, —C(O)NHNR$^{3B}R^{3C}$, —C(O)OR$^{3D}$, —SO$_2R^{3A}$, —C(O)NR$^{3B}R^{3C}$, substituted or unsubstituted alkyl, substituted or unsubstituted heteroalkyl, substituted or unsubstituted heterocycloalkyl, substituted or unsubstituted aryl, substituted or unsubstituted heteroaryl. $R^4$ is hydrogen, —C(O)R$^{4D}$, —C(O)NHNR$^{4B}R^{4C}$, —C(O)OR$^{4D}$, —SO$_2R^{4A}$, —C(O)NR$^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^4$ is hydrogen, —C(O)R$^{4D}$, —C(O)NHNR$^{4B}R^{4C}$, —C(O)OR$^{4D}$, —SO$_2R^{4A}$, —C(O)NR$^{4B}R^{4C}$, substituted or unsubstituted alkyl, substituted or unsubstituted heteroalkyl, substituted or unsubstituted heterocycloalkyl, substituted or unsubstituted aryl, substituted or unsubstituted heteroaryl. $R^3$ and $R^4$ may optionally be joined to form, together with the atoms to which they are attached, a substituted or unsubstituted heterocycloalkyl or substituted or unsubstituted heteroaryl. $R^5$ is hydrogen, —C(O)$R^{5D}$, —C(O)NHNR$^{5B}$R$^{5C}$, —C(O)OR$^{5D}$, —SO$_2$R$^{5A}$, —C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl. $R^6$ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen, halogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$ is hydrogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^8$ is hydrogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl. $R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{6.1}$, $X^{7.1}$, $X^{8.1}$ and $X^{9.1}$ are independently —Cl, —Br, —I or —F. The symbols n1, n2, n6, n7, n8, and n9 are independently an integer from 0 to 4. The symbols m1, m6, m7, m8, m9, v1, v6, v7, v8 and v9 each independently 1 or 2. In embodiments, when X is —O—; $R^2$ is —(CH$_2$)$_{n2}$CX$^{2.1}_3$; n2 is 1; $X^{2.1}$ is fluorine; $R^3$ is hydrogen; and $R^4$ is $R^4$ is —CH$_3$, then $R^6$ is not —NO$_2$. In embodiments, when X is —O—; $R^2$ is —(CH$_2$)$_{n2}$CX$^{2.1}_3$; n2 is 1; $X^{2.1}$ is fluorine; $R^3$ is hydrogen; and $R^4$ is substituted or unsubstituted C$_1$-C$_3$ alkyl, then $R^9$ is not —NO$_2$. In embodiments, when X is —O—; $R^2$ is —CH$_2$(CF$_2$)$_2$H; $R^3$ is hydrogen; and $R^4$ is $R^4$ is —CH$_3$, then $R^1$ is not —NO$_2$. In embodiments, when X is —O—; $R^2$ is —CH(CF$_3$)$_2$; $R^3$ and $R^4$ are independently unsubstituted C$_1$-C$_3$ alkyl, then $R^1$ is not hydrogen. In embodiments, when X is —O— and $R^2$ is methyl substituted with cycloalkyl, then $R^3$ and $R^4$ are hydrogen.

Also provided herein are pharmaceutical compositions. In one aspect is a pharmaceutical composition that includes a compound described herein or pharmaceutically acceptable salt thereof (e.g. a compound of formula I).

Further provided herein are methods of activating a Cystic Fibrosis Transmembrane Conductance Regulator (CFTR). The method includes contacting the CFTR with an effective amount of a compound described herein, thereby activating the CFTR.

Further provided herein are methods of treating a disease or disorder in a subject in need thereof by administering to said subject an effective amount of a compound described herein (e.g. a compound of formula I).

Further provided herein are methods of treating a disease or disorder in a subject in need thereof by administering to said subject an effective amount of a compound as described herein (e.g. a compound of formula I). In one aspect is a method of treating constipation in a subject in need thereof, the method including administering to the subject an effective amount described compound as described herein (e.g. a compound of formula I). In another aspect, is a method of treating a dry eye disorder in a subject in need thereof, the method including administering to the subject an effective amount of a compound as described herein (e.g. a compound of formula I). In yet another aspect, is a method of increasing lacrimation in a subject in need thereof, the method including administering to the subject an effective amount a compound as described herein (e.g. a compound of formula I).

In one aspect, provided is a method of treating a cholestatic liver disease in a subject in need thereof, including administering to the subject an effective amount a compound as described herein (e.g. a compound of formula I). In another aspect, provided is a method of treating a pulmonary disease or disorder in a subject in need thereof, including administering to the subject an effective amount of as described herein (e.g. a compound of formula I). In embodiments, the pulmonary disease or disorder is chronic obstructive pulmonary disease (e.g. bronchitis, asthma, cigarette smoke-induced lung dysfunction).

BRIEF DESCRIPTION OF THE DRAWINGS

FIG. 2A) (Top) Chemical structures. (Bottom) Representative short-circuit current ($I_{sc}$) measured in Fischer rat thyroid (FRT) cells expressing wild-type CFTR. CFTR current was stimulated by test compounds and forskolin, and inhibited by CFTR$_{inh}$-172 (10 μM). FIG. 2B) Concentration-dependence of CFTR activators (each data set derived from a single dose-response experiment as in A and fitted using an exponential curve). One-hundred percent CFTR activation is defined as that produced by 20 μM forskolin. FIG. 2C) $I_{sc}$ measurement for VX-770 done as in A. FIG. 2D) Cellular cAMP concentration in FRT cells in response to incubation for 10 min with 5 μM test compounds without or with forskolin (fsk, 100 nM). Positive controls included forskolin (100 nM and 20 μM), and forskolin plus 3-isobutyl-1-methylxanthine (IBMX, 100 μM) (mean±SEM, n=4-8).

FIG. 3A) (Left) Photograph of an anesthetized mouse demonstrating ocular surface perfusion for PD measurement. The perfusion catheter, attached to the measuring electrode, is oriented perpendicular to the ocular surface. Cross-clamping forceps retract the upper eyelid to expose cornea and bulbar/palbebral conjunctiva for perfusion. The reference electrode is grounded via subcutaneous butterfly needle. (Right) Schematic of PD tracing for a typical experiment testing CFTR activity, as described in Results. FIG. 3B) Representative ocular surface PD measurements in wild-type mice. Solution compositions are detailed in Ref. 22. Concentrations: amiloride, 100 μM; forskolin and CFTR$_{inh}$-172, 10 μM; test compounds, 1-10 μM as indicated. FIG. 3C) Study as in C, but with VX-770, 1-10 μM, as indicated. FIG. 3D) Summary of ΔPD in wild-type mice produced by forskolin (20 μM), or test compounds or VX-770 (each 1 μM). PDs were recorded in the presence of 100 μM amiloride and in the presence of an outward apical Cl$^-$ gradient (mean±SEM, 8-20 eyes per agonist tested). FIG. 3E) Representative ocular surface PD measurements in CF mouse. Study as in B & C, CFTR$_{act}$-K032, 1-10 μM as indicated.

FIG. 4A) Tear fluid was measured just prior to and at indicated times after single-dose topical application of vehicle (PBS, 0.5% polysorbate, 0.5% DMSO), cholera toxin (0.1 μg/mL), forskolin (20 μM), or forskolin+IBMX (250 μM). The effect of cholera toxin was measured after pre-anesthetizing the ocular surface with 4% lidocaine to suppress irritation and reflex tear secretion (mean±SEM, 6-10 eyes per condition). FIG. 4B) Time course of tear secretion following topical delivery of indicated compound. Concentrations: CFTR$_{act}$-B074, 100 μM; CFTR$_{act}$-J027, 50 μM; CFTR$_{act}$-K089, 50 μM; VX-770, 10 μM (mean±SEM, 6-18 eyes). FIG. 4C) Effect of repeated dosing. CFTR$_{act}$-J027 (0.1 nmol) was topically applied three times a day for two days. Tear fluid measurements were done after Dose 1 and Dose 2 on day 1, and Dose 5 on day 2 (mean±SEM, n=6 eyes). FIG. 4D) Lack of effect of CFTR activators on tear fluid secretion in CF mice, with compounds tested at the same concentrations as in B.

FIG. 5A) Liquid chromatography/mass spectroscopy (LC/MS) determination of CFTR$_{act}$-K089 amount in tear fluid at indicated times following single-dose (0.1 nmol) administration. Representative background-subtracted peak areas from tear washes (left) and means of corresponding amount recovered (right) (mean±SEM, 4 eyes per time point). Dashed lines denote the upper and lower calculated quantities of CFTR$_{act}$-K089 required to achieve EC$_{50}$ concentration. FIG. 5B) Lissamine green staining of cornea in BALB/c mice, measured on a 12-point scale (see Methods) after 14-days of three times daily treatment with CFTR activators (0.1 nmol) or vehicle (mean±SEM, 6 eyes per group). Shown as a positive control are scores from vehicle-treated mice following lacrimal gland excision (LGE) on Day 0 (n=1 eyes; *P<0.001 compared with other groups). FIG. 5C) Cytotoxicity measured by Alamar Blue assay in FRT cells incubated with test compounds for 1 or 24 h (10% DMSO as positive control; *P<0.05 compared to untreated cells; P=0.02 and 0.0006 for 1 and 24 h, respectively) (mean±SEM, n=4).

FIG. 6A) Basal tear secretion following extraorbital LGE in BALB/c mice, comparing eyes treated with CFTR$_{act}$-K089 (mean±SEM, 15 eyes) to vehicle (n=1 eyes). Tear volume was measured immediately prior to LGE, and then one hour after the first daily dose on Days 4, 10 and 14 after LGE. *P<0.001. FIG. 6B) Representative photographs of eyes prior to LGE (left) and on Day 14 after LGE (right) in vehicle-treated eyes (top) and CFTR$_{act}$-K089-treated eyes (bottom). FIG. 6C) Corneal epithelial disruption after LGE measured by LG scoring on a 12-point scale in the same eyes as in A (mean±SEM). *P<0.001.

FIG. 8A. Project overview. FIG. 8B. CFTR activator screen using FRT cells coexpressing human wild-type CFTR and YFP iodide-sensing protein. Test compounds at 10 µM were added for 10 min at room temperature in the presence of forskolin (125 nM) before iodide addition. Examples of data from single wells of a 96-well plate showing CFTR activation by $CFTR_{act}$-J027. FIG. 8C. Structures of CFTR activators emerging from the screen. FIG. 8D. Synthesis of $CFTR_{act}$-J027.

FIG. 9B. $CFTR_{act}$-J027 concentration-dependent activation of wild-type CFTR Cl⁻ current (S.E.; n=3 cultures). FIG. 9D. Short-circuit current in mouse colon showing responses to indicated concentrations of forskolin (fsk), $CFTR_{act}$-J027, and $CFTR_{inh}$-172. FIG. 9E. Assay of cAMP concentration in FRT cells measured following 10-min incubation with indicated concentrations of forskolin and 5 µM $CFTR_{act}$-J027. Positive controls included forskolin (100 nM and 20 µM), and forskolin plus 3-isobutyl-1-methylxanthine (IBMX, 100 µM) (mean±SE, n=4-8).

FIG. 10A. Mouse model of constipation with loperamide (left). Three-hour stool weight, number of pellets, and stool water content in mice (mean±S.E., 6 mice per group). FIG. 10B. Same study as in A, but with cystic fibrosis mice lacking function CFTR (3-6 mice per group). FIG. 10C. Same study in A, but with an inactive chemical analog of $CFTR_{act}$-J027 (structure shown). FIG. 10D. Dose-response for intraperitoneal administration of $CFTR_{act}$-J027 in loperamide-treated mice (4-6 mice per group). One-way analysis of variance was used for A and B, Student's t-test was used for C, *p<0.05, ***p<0.001, ns: not significant.

FIG. 11A. Study protocol (left) and stool output, pellet number and water content as done in FIG. 3 (mean±S.E., 6 mice per group). FIG. 11B. Dose-response study of $CFTR_{act}$-J027 administered orally in loperamide-treated mice (4-6 mice per group). FIG. 11C. Same study in FIG. 11A, but with oral lubiprostone (0.5 mg/kg) or linaclotide (0.5 mg/kg) (5-6 mice per group). One-way analysis of variance, *p<0.05, p<0.01, *p<0.001, ns: not significant.

FIG. 12A. Whole-gut transit time in control and loperamide-treated wild-type (left) and cystic fibrosis (right) mice (mean±S.E., 3-5 mice per group). Where indicated loperamide (0.3 mg/kg) and $CFTR_{act}$-J027 (10 mg/kg) was administered intraperitoneally at 0 time (mean±S.E., 6 mice per group). One-way analysis of variance, p<0.01, *p<0.001, ns: not significant. FIG. 12B. Contraction of isolated intestinal strips. Ileum and colon strips (~2 cm) were suspended in Krebs-Henseleit buffer with 0.5 g and 0.2 g tension, respectively. Where indicated $CFTR_{act}$-J027, loperamide and carbachol were added to the organ chamber. FIG. 12C. Intestinal fluid secretion measured in closed mid-jejunal loops in wild-type mice (upper panel). Loops were injected with 100 µL vehicle or 100 µg $CFTR_{act}$-J027. Loop weight/length was measured at 90 min (mean±S.E., 4 loops per group). Similar experiments done in cystic fibrosis mice (lower panel). FIG. 12D. Intestinal fluid absorption measured in mid-jejunal loops in cystic fibrosis mice. Loops were injected with 100 µL vehicle or 0.1 mg $CFTR_{act}$-J027. Loop weight/length was measured at 30 min. Summary of fluid absorption (mean±S.E., 4 loops per group). Student's t-test, p<0.01, *p<0.001, ns: not significant.

FIG. 13A. In vitro metabolic stability of $CFTR_{act}$-J027 assayed in mouse liver microsomes after incubation for specified times. FIG. 13B. Standard plasma concentration curve for LC-MS (left) and kinetics of $CFTR_{act}$-J027 concentration in plasma determined by LC/MS following bolus intraperitoneal or oral administration of 10 mg/kg $CFTR_{act}$-J027 at zero time (right, mean±S.E., 3 mice per group). FIG. 13C. In vitro toxicity measured by Alamar Blue assay in FRT cells. FIG. 13D. Body weight and lung wet/dry weight ratio in mice receiving 10 mg/kg $CFTR_{act}$-J027 orally for 7 days (mean±S.E., 5 mice per group). FIG. 13E. Chronic administration protocol (left) and efficacy of oral $CFTR_{act}$-J027 after 7-day administration (mean±S.E., 5 mice per group). Student's t-test, *p<0.05, p<0.01, *p<0.001, ns: not significant.

FIG. 14A. Chemical structure of $CFTR_{act}$-K089 (1). FIG. 14B. Preliminary SAR analysis based on commercial analogs (see Table 2 for data on all commercial analogs).

FIG. 15A. Measurements done in FRT cells expressing human wildtype CFTR showing responses to indicated concentrations of forskolin, 6k or 12, and 10 µM CFTR inhibitor $CFTR_{inh}$-172. FIG. 15B. Concentration-dependent activation of CFTR (mean±S.E.M., n=3).

FIG. 16A. Cellular cAMP in FRT cells following incubation for 10 min with 10 µM 6k or 12, without or with 90 nM forskolin (fsk), as well as forskolin alone (90 nM and 20 µM) and forskolin (20 µM)+IBMX (100 µM) (mean±S.E.M., n=4). FIG. 16B. Cytoplasmic calcium measured by Fluo-4 fluorescence. FRT cells were pretreated for 5 min with 10 µM 6k or 12 (or control), with 100 µM ATP added as a calcium agonist as indicated. FIG. 16C. TMEM16A activity measured in FRT cells expressing YFP showing no inhibition (left, iodide+ATP addition) or activation (right, iodide addition) by 10 µM 6k or 12. FIG. 16D. CaCC activity measured in HT-29 cells expressing YFP showing no activation (iodide addition) or inhibition (iodide+ATP addition) by 10 µM 6k or 12. FIG. 16E. (left) Short circuit-current in primary cultures of human bronchial epithelial cells in response to agonists and inhibitors that target key ion transport processes: 20 µM amiloride (ami); 20 µM forskolin (fsk); 10 µM $CFTR_{inh}$-172; 100 µM ATP. Experiments were done without activator or following 10-min preincubation with 10 µM 6k or 12 (right). CFTR activation by 12 after 100 nM forskolin (20 µM amil, 10 µM CFTR$_{inh}$-172, 100 µM ATP). Studies in B-E are representative of 2-4 separate sets of experiments.

FIG. 17A. Cytotoxicity was measured by Alamar Blue assay in FRT cells incubated for 8 h with 10 µM 6k or 12, with 33% DMSO as positive control (mean±S.E.M., n=8). FIG. 17B. In vitro metabolic stability. Compounds at 5 µM were incubated for indicated times with 1 mg/ml hepatic microsomes in the presence of NADPH and parent compound assayed by LC/MS (mean±S.E.M., n=3). LC/MS profile of 12 shown on the right with elution time on the x-axis for incubation times of 0, 15 and 60 min.

FIG. 18A. Tear volume was measured just before and at the indicated times after single ocular delivery of vehicle, 1 (250 pmol) or 12 (250 pmol) in a 2.5 µL volume. FIG. 18B. Study as in A but in CF mice lacking functional CFTR. FIG. 18C. Single dose study as in A with different amounts of 12. Data reported as mean±S.E.M, 5 mice, 10 eyes per condition, *p<0.05, **p<0.01 compared to vehicle control.

DETAILED DESCRIPTION OF THE INVENTION

Figure 1:
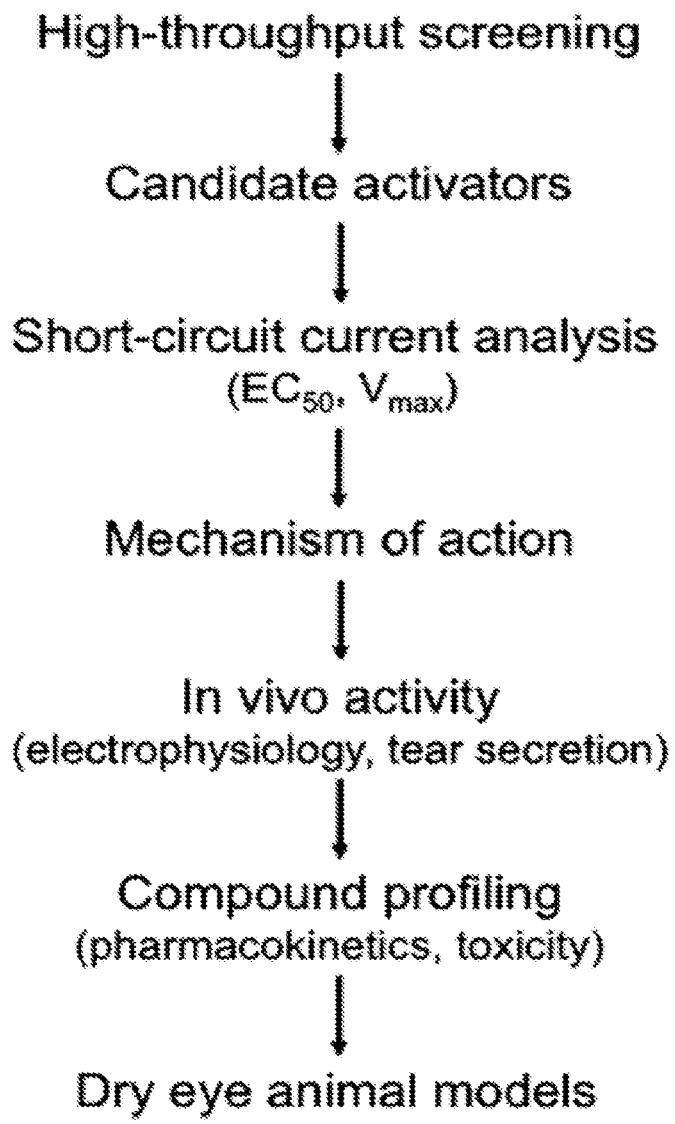
FIG. 1. Strategy for pre-clinical development of CFTR activators for dry eye therapy. Activators of human wild-type CFTR activators identified by high-throughput screening are confirmed and characterized using by electrophysiological and biochemical assays, and then tested in live mice for activity at the ocular surface by measurements of potential difference and tear fluid secretion. The best compounds are then tested for pharmacokinetic properties and efficacy in a dry eye rodent model.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH2O— is equivalent to —OCH2-.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S), and wherein the nitrogen and sulfur atoms may optionally be oxidized, and the nitrogen heteroatom may optionally be quaternized. The heteroatom(s) (e.g., O, N, P, S, B, As, and Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazolyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O) CF₃, —C(O)CH₂OCH₃, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', —CO₂R', —CONR'R'', —OC(O)NR'R'', —NR''C(O)R', —NR'—C(O)NR''R''', —NR''C(O)₂R', —NR—C(NR'R''R''')=NR'''', —NR—C(NR'R'')=NR''', —S(O)R', —S(O)₂R', —S(O)₂NR'R'', —NRSO₂R', —NR'NR''R''', —ONR'R'', —NR'C=(O)NR''NR'''R'''', —CN, —NO₂, —R', —N₃, —CH(Ph)₂, fluoro(C₁-C₄)alkoxy, and fluoro(C₁-C₄)alkyl, —NR'SO₂R'', —NR'C=(O)R'', —NR'C(O)—OR'', —NR'OR'', in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R''R''')$_d$—, where s and d are independently integers of from 0 to 3, and X' is —O—, —NR'—, —S—, —S(O)—, —S(O)₂—, or —S(O)₂NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds described herein possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}$F, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), fluoride ($^{18}$F), iodine-125 ($^{125}$I), or carbon-14 ($^{14}$C). All isotopic variations of the compounds of the present invention, whether radioactive or not, are encompassed within the scope of the present invention.

The symbol "⁓" denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I), or Formula I), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently. The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The terms "cystic fibrosis transmembrane conductance regulator," and "CFTR" are here used interchangeably and according to their common, ordinary meaning and refer to proteins of the same or similar names and functional fragments and homologs thereof. The term includes any recombinant or naturally occurring form of, or variants thereof that maintain CFTR activity (e.g. within at least 30%, 40%, 50%, 60%, 70%, 80%, 90%, 95%, or 100% activity compared to CFTR).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be cystic fibrosis transmembrane conductance regulator. Thus, activation includes, at least in part, partially or totally increasing stimulation, increasing, promoting, or expediting activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. anticonstipation, anti-dry eye, anti-pulmonary disease, anti-liver disease, or anti-lung disease) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anti-constipation or anti-dry eye agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anti-constipation or anti-dry eye agents).

Co-administration includes administering one active agent (e.g. a complex described herein) within 0.5, 1, 2, 4, 6, 8, 10, 12, 16, 20, or 24 hours of a second active agent (e.g. anti-constipation or anti-dry eye agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for constipation and dry eye disorders.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. Disease as used herein may refer to constipation or dry eye disorders.

Examples of anti-constipation agents include, but are not limited to diphenylmethanes, *Lactobacillus paracasei*, linaclotide and lubiprostone. Examples of anti-dry eye agents include, but are not limited to, topical cyclosporine, P321 (an ENaC inhibitor) and Diquafosol.

I. COMPOSITIONS

Provided herein are compounds having the formula:

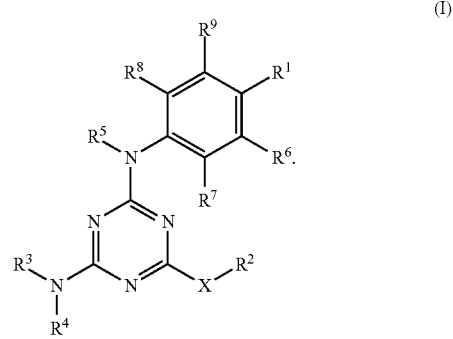

(I)

In the compound of formula I, X is a bond, —O—, —N($R^{10}$)— (e.g. —NH—), or —S—. In embodiments, X is —O—, —N($R^{10}$)— (e.g. NH), — or —S—. In embodiments, X is —O— or —S—. $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl (e.g. haloalkyl), substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^2$ is hydrogen, —CH$_3$, —CX$^{2.1}_3$, —(CH$_2$)$_{n2}$CX$^{2.1}_3$, —OR$^{2A}$, substituted or unsubstituted C$_2$-C$_8$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl. In embodiments, $R^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl (e.g. C$_2$-C$_4$ haloalkyl), substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^2$ is hydrogen, —CH$_3$, —CX$^{2.1}_3$, —(CH$_2$)$_{n2}$CX$^{2.1}_3$, —OR$^{2A}$, substituted or unsubstituted C$_2$-C$_8$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl. $R^3$ is hydrogen, —C(O)$R^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiment, $R^3$ is hydrogen, —C(O)$R^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted heterocycloalkyl, substituted or unsubstituted aryl, substituted or unsubstituted heteroaryl. $R^4$ is hydrogen, —C(O)$R^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^4$ is hydrogen, —C(O)$R^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted heterocycloalkyl, substituted or unsubstituted aryl, substituted or unsubstituted heteroaryl. $R^3$ and $R^4$ may optionally be joined to form, together with the atoms to which they are attached, a substituted or unsubstituted heterocycloalkyl or substituted or unsubstituted heteroaryl. $R^5$ is hydrogen, —C(O)$R^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl. $R^6$ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is hydrogen, halogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^7$ is hydrogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^8$ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^8$ is hydrogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl. $R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl. $X^{1.1}$, $X^{2.1}$, $X^{6.1}$, $X^{7.1}$, $X^{8.1}$ and $X^{9.1}$ are independently —Cl, —Br, —I or —F. n1, n2, n6, n7, n8, and n9 are independently an integer from 0 to 4. m1, m6, m7, m8, m9, v1, v6, v7, v8 and v9 each independently 1 or 2.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n6 is 0. In embodiments, n6 is 1. In embodiments, n6 is 2. In embodiments, n6 is 3. In embodiments, n6 is 4. In embodiments, n7 is 0. In embodiments, n7 is 1. In embodiments, n7 is 2. In embodiments, n7 is 3. In embodiments, n7 is 4. In embodiments, n8 is 0. In embodiments, n8 is 1. In embodiments, n8 is 2. In embodiments, n8 is 3. In embodiments, n8 is 4. In embodiments, n9 is 0. In embodiments, n9 is 1. In embodiments, n9 is 2. In embodiments, n9 is 3. In embodiments, n9 is 4. In embodiments, m1 is 1. In embodiments, m1 is 2. In embodiments, m6 is 1. In embodiments, m6 is 2. In embodiments, m7 is 1. In embodiments, m7 is 2. In embodiments, m8 is 1. In embodiments, m8 is 2. In embodiments, m9 is 1. In embodiments, m9 is 2. In embodiments, v1 is 1. In embodiments, v1 is 2. In embodiments, v6 is 1. In embodiments, v6 is 2. In embodiments, v7 is 1. In embodiments, v7 is 2. In embodiments, v8 is 1. In embodiments, v8 is 2. In embodiments, v9 is 1. In embodiments, v9 is 2.

In embodiments, when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not —$N(O)_{m6}$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not —$N(O)_{m9}$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^6$ is not —$NO_2$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^9$ is not —$NO_2$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not —$NO_2$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not —$NO_2$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^6$ is not —$NO_2$. In embodiments, when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^9$ is not —$NO_2$. In embodiments, when X is —O—; $R^2$ is —$CH_2CF_3$; one of $R^3$ and $R^4$ is hydrogen and one of $R^3$ and $R^4$ is —$CH_3$, then $R^6$ is not —$NO_2$. In embodiments, when X is —O—; $R^2$ is —$CH_2CF_3$; one of $R^3$ and $R^4$ is hydrogen and one of $R^3$ and $R^4$ is ethyl, then $R^6$ is not —$NO_2$. In embodiments, when X is —O—; $R^2$ is —$CH_2CF_3$; one of $R^3$ and $R^4$ is hydrogen and one of $R^3$ and $R^4$ is unsubstituted $C_1$-$C_3$ alkyl, then $R^6$ is not —$NO_2$. In embodiments, when X is —O—; $R^2$ is —$CH_2CF_3$; one of $R^3$ and $R^4$ is unsubstituted $C_1$-$C_3$ alkyl, then $R^6$ is not —$NO_2$. In embodiments, when X is —O—; $R^2$ is —$CH_2CF_3$; $R^3$ and $R^4$ are hydrogen or unsubstituted $C_1$-$C_3$ alkyl, then $R^6$ is not —$NO_2$. In embodiments, when X is —O—; $R^2$ is —$CH_2CF_3$; one of $R^3$ and $R^4$ is hydrogen and one of $R^3$ and $R^4$ is —$CH_3$, then $R^9$ is not —$NO_2$. In embodiments, when X is —O—; $R^2$ is —$CH_2CF_3$; one of $R^3$ and $R^4$ is hydrogen and one of $R^3$ and $R^4$ is ethyl, then $R^9$ is not —$NO_2$. In embodiments, when X is —O—; $R^2$ is —$CH_2CF_3$; one of $R^3$ and $R^4$ is hydrogen and one of $R^3$ and $R^4$ is unsubstituted $C_1$-$C_3$ alkyl, then $R^9$ is not —$NO_2$. In embodiments, when X is —O—; $R^2$ is —$CH_2CF_3$; one of $R^3$ and $R^4$ is unsubstituted $C_1$-$C_3$ alkyl, then $R^9$ is not —$NO_2$. In embodiments, when X is —O—; $R^2$ is —$CH_2CF_3$; $R^3$ and $R^4$ are hydrogen or unsubstituted $C_1$-$C_3$ alkyl, then $R^9$ is not —$NO_2$.

In embodiments, when X is —O—; $R^2$ is —$CH_2(CF_2)_2H$; $R^3$ is hydrogen; and $R^4$ is unsubstituted $C_1$-$C_3$ alkyl, then $R^1$ is not —$N(O)_{m1}$. In embodiments, when X is —O—; $R^2$ is —$CH_2(CF_2)_2H$; $R^3$ is hydrogen; and $R^4$ is unsubstituted $C_1$-$C_3$ alkyl, then $R^1$ is not —$NO_2$. In embodiments, when X is —O—; $R^2$ is —$CH_2(CF_2)_2H$; one of $R^3$ and $R^4$ is hydrogen and one of $R^3$ and $R^4$ is —$CH_3$, then $R^1$ is not —$NO_2$. In embodiments, when X is —O—; $R^2$ is —$CH_2(CF_2)_2H$; one of $R^3$ and $R^4$ is hydrogen and one of $R^3$ and $R^4$ is ethyl, then $R^1$ is not —$NO_2$. In embodiments, when X is —O—; $R^2$ is —$CH_2(CF_2)_2H$; one of $R^3$ and $R^4$ is hydrogen and one of $R^3$ and $R^4$ is unsubstituted $C_1$-$C_3$ alkyl, then $R^1$ is not —$NO_2$. In embodiments, when X is —O—; $R^2$ is —$CH_2(CF_2)_2H$; one of $R^3$ and $R^4$ is unsubstituted $C_1$-$C_3$ alkyl, then $R^1$ is not —$NO_2$. In embodiments, when X is —O—; $R^2$ is —$CH_2(CF_2)_2H$; $R^3$ and $R^4$ are hydrogen or —$CH_3$, then $R^1$ is not —$NO_2$. When X is —O—; $R^2$ is —$CH_2(CF_2)_2H$; $R^3$ is hydrogen; and $R^4$ is substituted or unsubstituted $C_1$-$C_3$ alkyl, then $R^1$ is not —$NO_2$. When X is —O—; $R^2$ is —$CH_2(CF_2)_2H$; $R^3$ is hydrogen; and $R^4$ is substituted or unsubstituted $C_1$-$C_3$ alkyl, then $R^1$ is not —$NO_2$.

In embodiments, when X is —O—; $R^2$ is —$CH(CF_3)_2$; $R^3$ and $R^4$ are independently unsubstituted $C_1$-$C_3$ alkyl, then $R^1$ is not hydrogen. In embodiments, when X is —O—; $R^2$ is —$CH(CF_3)_2$; $R^3$ and $R^4$ are independently methyl or ethyl, then $R^1$ is not hydrogen. In embodiments, when X is —O—; $R^2$ is —$CH(CF_3)_2$; $R^3$ and $R^4$ are independently ethyl, then $R^1$ is not hydrogen. In embodiments, when X is —O—; $R^2$ is —$CH(CF_3)_2$; $R^3$ and $R^4$ are independently methyl, then $R^1$ is not hydrogen. In embodiments, when X is —O—; $R^2$ is —$CH(CF_3)_2$; one of $R^3$ and $R^4$ is methyl, one of $R^3$ and $R^4$ is ethyl, then $R^1$ is not -hydrogen. In embodiments, when X is —O—; $R^2$ is —$CH(CF_3)_2$; $R^3$ and $R^4$ are independently $C_1$-$C_3$ alkyl, then $R^1$ is not hydrogen. When X is —O—; $R^2$ is —$CH(CF_3)_2$; $R^3$ and $R^4$ are independently substituted or unsubstituted $C_1$-$C_3$ alkyl, then $R^1$ is not hydrogen.

In embodiments, when X is —O— and $R^2$ is alkyl substituted with substituted or unsubstituted cycloalkyl, then $R^3$ and $R^4$ are hydrogen. In embodiments, when X is —O— and $R^2$ is methyl substituted with substituted or unsubstituted 5-7 membered cycloalkyl, then $R^3$ and $R^4$ are hydrogen. In embodiments, when X is —O— and $R^2$ is ethyl substituted with 5-7 membered cycloalkyl, then $R^3$ and $R^4$ are hydrogen. In embodiments, when X is —O— and $R^2$ is methyl substituted with substituted or unsubstituted cyclohexyl, then $R^3$ and $R^4$ are hydrogen. In embodiments, when X is —O— and $R^2$ is methyl substituted with cyclohexyl, then $R^3$ and $R^4$ are hydrogen. In embodiments, when X is —O— and $R^2$ is $C_1$-$C_3$ alkyl substituted with cyclohexyl, then $R^3$ and $R^4$ are hydrogen. In embodiments, when X is —O— and $R^2$ is ethyl substituted with cyclohexyl, then $R^3$ and $R^4$ are hydrogen. In embodiments, when X is —O— and $R^2$ is methyl substituted with substituted cyclohexyl, then $R^3$ and $R^4$ are hydrogen. In embodiments, when X is —O— and $R^2$ is ethyl substituted with substituted cyclohexyl, then $R^3$ and $R^4$ are hydrogen.

In embodiments, X is —O—, —NH— or —S—. In embodiments, X is —O— or —S—. In embodiments, X is —NH—. In embodiments, X is —O—.

In embodiments, $R^1$ is hydrogen, halogen, —$CX^{1.1}_3$, —$CHX^{1.1}_2$, —$CH_2X^{1.1}$, —CN, —$N(O)_{m1}$, —$C(O)R^{1D}$, —$C(O)OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl. In embodiments, $R^1$ is hydrogen, halogen, —$CX^{1.1}_3$, —$CHX^{1.1}_2$, —$CH_2X^{1.1}$, —CN, —$N(O)_{m1}$, —C(O)R$^{1D}$, —C(O)OR$^{1D}$, —OCX$^{1.1}_3$, —OCHX$^{1.1}_2$ or substituted or unsubstituted alkyl. In embodiments, R$^1$ is hydrogen, halogen, —CF$_3$, —CCl$_3$, —CBr$_3$, —Cl$_3$, —CHF$_2$, —CH$_2$F, —CN, —N(O)$_{m1}$, —C(O)R$^{1D}$, —C(O)OR$^{1D}$, —OCX$^{1.1}_3$, —OCHX$^{1.1}_2$ or substituted or unsubstituted alkyl. In embodiments, R$^1$ is hydrogen, halogen, —CX$^{1.1}_3$, —CHX$^{1.1}_2$, —CH$_2$X$^{1.1}$, —CN, —NO$_2$, —NO, —C(O)R$^{1A}$, —C(O)OR$^{1D}$, —OCX$^{1.1}_3$, —OCHX$^{1.1}_2$ or substituted or unsubstituted alkyl. In embodiments, R$^{1A}$ and R$^{1D}$ are independently hydrogen or methyl. In embodiments, R$^1$ is a hydrogen, halogen, —CN, —NO$_2$, —COH, —COCH$_3$, —COOCH$_3$, or —COOH. In embodiments, R$^1$ is halogen, —NO$_2$ or —COOH. In embodiments, R$^1$ is halogen or —NO$_2$. In embodiments, R$^1$ is halogen or —COOH. In embodiments, R$^1$ is —NO$_2$. In embodiments, R$^1$ is a halogen.

In embodiments, R$^2$ is hydrogen, —CH$_3$, —CX$^{2.1}_3$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, R$^2$ is hydrogen, —CH$_3$, —CX$^{2.1}_3$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, or substituted or unsubstituted heterocycloalkyl. In embodiments, R$^2$ is hydrogen, —CH$_3$, —CX$^{2.1}_3$, —(CH$_2$)$_{n2}$CX$^{2.1}_3$, —OR$^{2A}$, substituted or unsubstituted alkyl or substituted or unsubstituted heteroalkyl. In embodiments, R$^2$ is hydrogen, —CH$_3$, —CX$^{2.1}_3$, —(CH$_2$)$_{n2}$CX$^{2.1}_3$, substituted or unsubstituted alkyl (e.g. haloalkyl). In embodiments, R$^2$ is hydrogen, —CX$^{2.1}_3$, —(CH$_2$)$_{n2}$CX$^{2.1}_3$, substituted C$_2$-C$_8$ alkyl (e.g. C$_2$-C$_8$ haloalkyl). In embodiments, R$^2$ is -CX$^{2.1}_3$, —(CH$_2$)$_{n2}$CX$^{2.1}_3$, substituted C$_2$-C$_8$ alkyl (e.g. C$_2$-C$_8$ haloalkyl). In embodiments, R$^2$ is CX$^{2.1}_3$, —(CH$_2$)$_{n2}$CX$^{2.1}_3$, substituted C$_2$-C$_8$ alkyl, or C$_2$-C$_8$ haloalkyl. In embodiments, R$^2$ is —(CH$_2$)$_{n2}$CX$^{2.1}_3$, substituted C$_2$-C$_8$ alkyl (e.g C$_2$-C$_8$ haloalkyl). In embodiments, R$^2$ is —(CH$_2$)$_{n2}$CX$^{2.1}_3$ (e.g. C$_2$-C$_8$ haloalkyl). In embodiments, R$^2$ is —CX$^{2.1}_3$. In embodiments, R$^2$ is —(CH$_2$)$_{n2}$CX$^{2.1}_3$. In embodiments, R$^2$ is C$_2$-C$_8$ alkyl substituted with halogen. In embodiments, R$^2$ is C$_2$-C$_8$ alkyl substituted with at least one, two, three, four or five halogen. In embodiments, R$^2$ is C$_2$-C$_8$ haloalkyl substituted with at least one, two, three, four or five halogen. In embodiments, R$^2$ is —C$_2$-C$_8$ haloalkyl. In embodiments, R$^2$ is C$_2$-C$_6$ haloalkyl. In embodiments, R$^2$ is C$_2$-C$_4$ haloalkyl. In embodiments, R$^2$ is C$_2$-C$_4$ alkyl substituted with one or more flourines. In embodiments, R$^2$ is C$_2$-C$_4$ alkyl substituted with one, two, three, four or five flourines. In embodiments, R$^2$ is C$_2$-C$_4$ haloalkyl substituted with one, two, three, four or five halogens. In embodiments, R$^2$ is C$_2$-C$_4$ haloalkyl substituted one fluorine. In embodiments, R$^2$ is C$_2$-C$_4$ haloalkyl substituted two fluorines. In embodiments, R$^2$ is C$_2$-C$_4$ haloalkyl substituted three fluorines. In embodiments, R$^2$ is C$_2$-C$_4$ haloalkyl substituted four fluorines. In embodiments, R$^2$ is C$_2$-C$_4$ haloalkyl substituted five fluorines. In embodiments, R$^2$ is —CH$_2$CF$_2$CHF$_2$. In embodiments, R$^2$ is —CH(CF$_3$)$_2$.

In embodiments, R$^3$ and R$^4$ are independently hydrogen, substituted or unsubstituted alkyl, substituted or unsubstituted heteroalkyl, substituted or unsubstituted heterocycloalkyl, substituted or unsubstituted aryl, substituted or unsubstituted heteroaryl. In embodiments, R$^3$ and R$^4$ are joined to form a substituted or unsubstituted heterocycloalkyl or substituted or unsubstituted heteroaryl. In embodiments, R$^3$ and R$^4$ are joined to form, together with the atoms to which they are attached, a substituted or unsubstituted heterocycloalkyl.

In embodiments, R$^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, R$^5$ is independently hydrogen, substituted or unsubstituted alkyl, or substituted or unsubstituted heteroalkyl. In embodiments, R$^3$, R$^4$ and R$^5$ are independently hydrogen, substituted or unsubstituted alkyl. In embodiments, R$^3$ and R$^4$ are independently hydrogen, substituted or unsubstituted alkyl or substituted or unsubstituted aryl. In embodiments, R$^5$ is hydrogen or substituted or unsubstituted alkyl. In embodiments, R$^3$ is —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted heterocycloalkyl, substituted or unsubstituted aryl, substituted or unsubstituted heteroaryl. In embodiments, R$^4$ is —C(O)R$^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted heterocycloalkyl, substituted or unsubstituted aryl, substituted or unsubstituted heteroaryl. In embodiments, R$^5$ is —C(O)R$^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$ and R$^{5D}$ are independently hydrogen or methyl.

In embodiments, R$^3$, R$^4$ and R$^5$ are independently hydrogen, substituted or unsubstituted alkyl, substituted or unsubstituted heteroalkyl, substituted or unsubstituted heterocycloalkyl, substituted or unsubstituted aryl, substituted or unsubstituted heteroaryl. In embodiments, R$^3$, R$^4$ and R$^5$ are independently hydrogen, substituted or unsubstituted alkyl, substituted or unsubstituted heteroalkyl, substituted or unsubstituted aryl, substituted or unsubstituted heteroaryl. In embodiments, R$^3$, R$^4$ and R$^5$ are independently hydrogen, substituted or unsubstituted alkyl, substituted or unsubstituted heteroalkyl, or substituted or unsubstituted heteroaryl. In embodiments, R$^3$, R$^4$ and R$^5$ are independently hydrogen, substituted or unsubstituted alkyl or substituted or unsubstituted heteroalkyl. In embodiments, R$^3$, R$^4$ and R$^5$ are independently hydrogen or substituted or unsubstituted alkyl. In embodiments, R$^3$, R$^4$ and R$^5$ are independently hydrogen or substituted or unsubstituted C$_1$-C$_4$ alkyl. In embodiments, R$^3$, R$^4$ and R$^5$ are independently hydrogen or unsubstituted C$_1$-C$_4$ alkyl. In embodiments, R$^3$, R$^4$ and R$^5$ are independently hydrogen, methyl or ethyl. In embodiments, R$^3$ and R$^4$ are independently substituted or unsubstituted C$_1$-C$_4$ alkyl and R$^5$ is hydrogen or substituted or unsubstituted C$_1$-C$_4$ alkyl. In embodiments, R$^3$ and R$^4$ are independently hydrogen, methyl or ethyl. In embodiments, R$^3$ and R$^4$ are independently methyl or ethyl. In embodiments, R$^5$ is hydrogen, methyl or ethyl. In embodiments, R$^3$ and R$^4$ are independently methyl or ethyl, and R$^5$ is hydrogen. In embodiments, R$^5$ is hydrogen, and R$^3$ and R$^4$ are independently hydrogen, methyl or ethyl. In embodiments, R$^5$ is hydrogen. In embodiments, R$^3$ and R$^4$ are independently hydrogen. In embodiments, R$^3$, R$^4$ and R$^5$ are independently hydrogen. In embodiments, R$^3$ and R$^4$ are independently methyl. In embodiments, R$^3$ and R$^4$ are independently ethyl.

In embodiments, R$^6$ is hydrogen, halogen, —CX$^{6.1}_3$, —CHX$^{6.1}_2$, —CH$_2$X$^{6.1}$, —CN, —N(O)$_{m6}$, —C(O)R$^{6D}$, —C(O)OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl. In embodiments, $R^6$ is hydrogen, halogen, $-CX^{6.1}_3$, $-CHX^{6.1}_2$, $-CH_2X^{6.1}$, $-CN$, $-N(O)_{m6}$, $-C(O)R^{6D}$, $-C(O)OR^{6D}$, $-OCX^{6.1}_3$, $-OCHX^{6.1}_2$ or substituted or unsubstituted alkyl. In embodiments, $R^6$ is hydrogen, halogen, $-CX^{6.1}_3$, $-CHX^{6.1}_2$, $-CH_2X^{6.1}$, $-CN$, $-NO$, $-C(O)R^{6D}$, $-C(O)OR^{6D}$, $-OCX^{6.1}_3$, $-OCHX^{6.1}_2$ or substituted or unsubstituted alkyl. In embodiments, $R^6$ is hydrogen, halogen, $-CX^{6.1}_3$, $-CHX^{6.1}_2$, $-CH_2X^{6.1}$, $-CN$, $-SO_{n6}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-NO$, $-NR^{6B}R^{6C}$, $-C(O)R^{6A}$, $-C(O)OR^{6A}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^6$ is hydrogen, halogen, $-CX^{6.1}_3$, $-CHX^{6.1}_2$, $-CH_2X^{6.1}$, $-CN$, $-NO$, $-C(O)R^{6D}$, $-C(O)OR^{6D}$, $-OCX^{6.1}_3$, $-OCHX^{6.1}_2$ or substituted or unsubstituted alkyl. In embodiments, $R^{6A}$ and $R^{6D}$ are independently hydrogen or methyl. In embodiments, $R^6$ is a hydrogen, halogen, $-CN$, $-NO_2$, $-COH$, $-COCH_3$, $-COOCH_3$, or $-COOH$. In embodiments, $R^6$ is halogen, $-NO_2$ or $-COOH$. In embodiments, $R^6$ is halogen or $-NO_2$. In embodiments, $R^6$ is halogen or $-COOH$. In embodiments, $R^6$ is $-NO_2$. In embodiments, $R^6$ is a halogen.

In embodiments, $R^7$ is hydrogen, $-CX^{7.1}_3$, $-CHX^{7.1}_2$, $-CH_2X^{7.1}$, $-CN$, $-N(O)_{m7}$, $-C(O)R^{7D}$, $-C(O)OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl. In embodiments, $R^7$ is hydrogen, $-CX^{7.1}_3$, $-CHX^{7.1}_2$, $-CH_2X^{7.1}$, $-CN$, $-N(O)_{m7}$, $-C(O)R^{7D}$, $-C(O)OR^{7D}$, $-OCX^{7.1}_3$, $-OCHX^{7.1}_2$ or substituted or unsubstituted alkyl. In embodiments, $R^7$ is hydrogen, $-CF_3$, $-CCl_3$, $-CBr_3$, $-CI_3$, $-CHF_2$, $-CH_2F$, $-CN$, $-N(O)_{m7}$, $-C(O)R^{7D}$, $-C(O)OR^{7D}$, $-OCX^{7.1}_3$, $-OCHX^{7.1}_2$ or substituted or unsubstituted alkyl. In embodiments, $R^7$ is hydrogen, $-CX^{7.1}_3$, $-CHX^{7.1}_2$, $-CH_2X^{7.1}$, $-CN$, $-NO$, $-C(O)R^{7D}$, $-C(O)OR^{7D}$, $-OCX^{7.1}_3$, $-OCHX^{7.1}_2$ or substituted or unsubstituted alkyl. In embodiments, $R^{7A}$ and $R^{7D}$ are independently hydrogen or methyl. In embodiments, $R^7$ is a hydrogen, $-CN$, $-NO_2$, $-COH$, $-COCH_3$, $-COOCH_3$, or $-COOH$. In embodiments, $R^7$ is a hydrogen, $-NO_2$ or $-COOH$. In embodiments, $R^7$ is a hydrogen, or $-NO_2$. In embodiments, $R^7$ is a hydrogen or $-COOH$. In embodiments, $R^7$ is $-NO_2$. In embodiments, $R^7$ is a hydrogen.

In embodiments, $R^8$ is hydrogen, $-CX^{8.1}_3$, $-CHX^{8.1}_2$, $-CH_2X^{8.1}$, $-CN$, $-N(O)_{m8}$, $-C(O)R^{8D}$, $-C(O)OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl. In embodiments, $R^8$ is hydrogen, $-CX^{8.1}_3$, $-CHX^{8.1}_2$, $-CH_2X^{8.1}$, $-CN$, $-N(O)_{m8}$, $-C(O)R^{8D}$, $-C(O)OR^{8D}$, $-OCX^{8.1}_3$, $-OCHX^{8.1}_2$ or substituted or unsubstituted alkyl. In embodiments, $R^8$ is hydrogen, $-CF_3$, $-CCl_3$, $-CBr_3$, $-CI_3$, $-CHF_2$, $-CH_2F$, $-CN$, $-N(O)_{m8}$, $-C(O)R^{8D}$, $-C(O)OR^{8D}$, $-OCX^{8.1}_3$, $-OCHX^{8.1}_2$ or substituted or unsubstituted alkyl. In embodiments, $R^8$ is hydrogen, $-CX^{8.1}_3$, $-CHX^{8.1}_2$, $-CH_2X^{8.1}$, $-CN$, $-NO$, $-C(O)R^{8D}$, $-C(O)OR^{8D}$, $-OCX^{8.1}_3$, $-OCHX^{8.1}_2$ or substituted or unsubstituted alkyl. In embodiments, $R^{8A}$ and $R^{8D}$ are independently hydrogen or methyl. In embodiments, $R^8$ is a hydrogen, $-CN$, $-NO_2$, $-COH$, $-COCH_3$, $-COOCH_3$, or $-COOH$. In embodiments, $R^8$ is a hydrogen, $-NO_2$ or $-COOH$. In embodiments, $R^8$ is a hydrogen, or $-NO_2$. In embodiments, $R^8$ is a hydrogen or $-COOH$. In embodiments, $R^8$ is $-NO_2$. In embodiments, $R^8$ is hydrogen.

In embodiments, $R^9$ is hydrogen, halogen, $-CX^{9.1}_3$, $-CHX^{9.1}_2$, $-CH_2X^{9.1}$, $-CN$, $-N(O)_{m9}$, $-C(O)R^{9D}$, $-C(O)OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl. In embodiments, $R^9$ is hydrogen, halogen, $-CX^{9.1}_3$, $-CHX^{9.1}_2$, $-CH_2X^{9.1}$, $-CN$, $-N(O)_{m9}$, $-C(O)R^{9D}$, $-C(O)OR^{9D}$, $-OCX^{9.1}_3$, $-OCHX^{9.1}_2$ or substituted or unsubstituted alkyl. In embodiments, $R^9$ is hydrogen, halogen, $-CF_3$, $-CCl_3$, $-CBr_3$, $-CI_3$, $-CHF_2$, $-CH_2F$, $-CN$, $-N(O)_{m9}$, $-C(O)R^{9D}$, $-C(O)OR^{9D}$, $-OCX^{9.1}_3$, $-OCHX^{9.1}_2$ or substituted or unsubstituted alkyl. In embodiments, $R^9$ is hydrogen, halogen, $-CX^{9.1}_3$, $-CHX^{9.1}_2$, $-CH_2X^{9.1}$, $-CN$, $-NO$, $-C(O)R^{9D}$, $-C(O)OR^{9D}$, $-OCX^{9.1}_3$, $-OCHX^{9.1}_2$ or substituted or unsubstituted alkyl. In embodiments, $R^9$ is hydrogen, halogen, $-CX^{9.1}_3$, $-CHX^{9.1}_2$, $-CH_2X^{9.1}$, $-CN$, $-NO$, $-C(O)R^{9D}$, $-C(O)OR^{9D}$, $-OCX^{9.1}_3$, $-OCHX^{9.1}_2$ or substituted or unsubstituted alkyl. In embodiments, $R^{9A}$ and $R^{9D}$ are independently hydrogen or methyl. In embodiments, $R^9$ is a hydrogen, halogen, $-CN$, $-NO_2$, $-COH$, $-COCH_3$, $-COOCH_3$, or $-COOH$. In embodiments, $R^9$ is halogen, $-NO_2$ or $-COOH$. In embodiments, $R^9$ is halogen or $-NO_2$. In embodiments, $R^9$ is halogen or $-COOH$. In embodiments, $R^9$ is $-NO_2$. In embodiments, $R^9$ is a halogen.

In embodiments, $R^1$ is hydrogen, halogen, $-CX^{1.1}_3$, $-CHX^{1.1}_2$, $-CH_2X^{1.1}$, $-CN$, $-N(O)_{m1}$, $-C(O)R^{1D}$, $-C(O)OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; $R^2$ is hydrogen, $-CX^{2.1}_3$, $-CH_3$, $-(CH_2)_{n2}CX^{2.1}_3$, substituted or unsubstituted $C_2$-$C_8$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$, $R^4$ and $R^5$ are independently hydrogen, substituted or unsubstituted alkyl, substituted or unsubstituted heteroalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-N(O)_{m6}$, $-C(O)R^{6D}$, $-C(O)OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; $R^7$ is hydrogen, $-CX^{7.1}_3$, $-CHX^{7.1}_2$, $-CH_2X^{7.1}$, $-CN$, $-N(O)_{m7}$, $-C(O)R^{7D}$, $-C(O)OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; R$^8$ is hydrogen, —CX$^{8.1}_3$, —CHX$^{8.1}_2$, —CH$_2$X$^{8.1}$, —CN, —N(O)$_{m8}$, —C(O)R$^{8D}$, —C(O)OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; and R$^9$ is hydrogen, halogen, —CX$^{9.1}_3$, —CHX$^{9.1}_2$, —CH$_2$X$^{9.1}$, —CN, —N(O)$_{m9}$, —C(O)R$^{9D}$, —C(O)OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl.

In embodiments, R$^1$ is hydrogen, halogen, —CX$^{1.1}_3$, —CHX$^{1.1}_2$, —CH$_2$X$^{1.1}$, —CN, —NO$_2$, —C(O)R$^{1D}$, —C(O)OR$^{1D}$, —OCX$^{1.1}_3$, —OCHX$^{1.1}_2$ or substituted or unsubstituted alkyl; R$^2$ is hydrogen, —CX$^{2.1}_3$, —(CH$_2$)$_{n2}$CX$^{2.1}_3$, substituted C$_2$-C$_6$ alkyl or C$_2$-C$_8$ haloalkyl; R$^3$, R$^4$ and R$^5$ are independently hydrogen, substituted or unsubstituted alkyl; R$^6$ is hydrogen, halogen, —CX$^{6.1}_3$, —CHX$^{6.1}_2$, —CH$_2$X$^{6.1}$, —CN, —NO$_2$, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —NO$_2$, —C(O)R$^{9D}$, —C(O)OR$^{9D}$, —OCX$^{9.1}_3$, —OCHX$^{9.1}_2$ or substituted or unsubstituted alkyl, wherein R$^{1D}$, R$^{6D}$, R$^{7D}$, R$^{8D}$ and R$^{9D}$ are independently hydrogen or methyl.

In embodiments, R$^1$ is hydrogen, halogen, —CF$_3$, —CCl$_3$, —CBr$_3$, —CI$_3$, —CHF$_2$, —CH$_2$F, —CN, —NO$_2$, —C(O)R$^{1D}$, —C(O)OR$^{1D}$, —OCX$^{1.1}_3$, —OCHX$^{1.1}_2$ or substituted or unsubstituted alkyl; R$^2$ is hydrogen, —CX$^{2.1}_3$, CHX$^{2.1}_2$, —(CH$_2$)$_{n1}$CX$^{2.1}_3$, C$_2$-C$_4$ haloalkyl; R$^3$ and R$^4$ are independently, unsubstituted alkyl; R$^5$ is hydrogen; R$^6$ is hydrogen, halogen, —CX$^{6.1}_3$, —CHX$^{6.1}_2$, —CH$_2$X$^{6.1}$, —CN, —NO$_2$, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, —CF$_3$, —CCl$_3$, —CBr$_3$, —CI$_3$, —CHF$_2$, —CH$_2$F, —CN, —NO$_2$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, —CF$_3$, —CCl$_3$, —CBr$_3$, —CI$_3$, —CHF$_2$, —CH$_2$F, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CF$_3$, —CCl$_3$, —CBr$_3$, —CI$_3$, —CHF$_2$, —CH$_2$F, —CN, —NO$_2$, —C(O)R$^{9D}$, —C(O)OR$^{9D}$, —OCX$^{9.1}_3$, —OCHX$^{9.1}_2$ or substituted or unsubstituted alkyl, wherein R$^{1D}$, R$^{6D}$, R$^{7D}$, R$^{8D}$ and R$^{9D}$ are independently hydrogen or methyl, and X$^{1.1}$, X$^{2.1}$, X$^{6.1}$, X$^{7.1}$, X$^{8.1}$ and X$^{9.1}$ are independently are —F.

In embodiments, at least one of R$^1$, R$^6$, R$^7$, R$^8$ and R$^9$ are independently hydrogen. In embodiments, at least two of R$^1$, R$^6$, R$^7$, R$^8$ and R$^9$ are independently hydrogen. In embodiments, at least three of R$^1$, R$^6$, R$^7$, R$^8$ and R$^9$ are independently hydrogen. In embodiments, at least four of R$^1$, R$^6$, R$^7$, R$^8$ and R$^9$ are independently hydrogen. In embodiments, R$^1$, R$^6$, R$^7$, R$^8$ and R$^9$ are independently hydrogen. In embodiments, at least one of R$^7$ and R$^8$ are hydrogen. In embodiments, R$^7$ is hydrogen. In embodiments, R$^8$ is hydrogen. In embodiments, R$^7$ and R$^8$ are independently hydrogen.

In embodiments, X is —O—; R$^1$ is hydrogen, halogen, —CX$^{1.1}_3$, —CHX$^{1.1}_2$, —CH$_2$X$^{1.1}$, —CN, —NO$_2$, —C(O)R$^{1D}$, —C(O)OR$^{1D}$, —OCX$^{1.1}_3$, —OCHX$^{1.1}_2$ or substituted or unsubstituted alkyl; R$^2$ is hydrogen, —CX$^{2.1}_3$, —CH$_3$, —(CH$_2$)$_{n2}$CX$^{2.1}_3$, substituted or unsubstituted C$_2$-C$_6$ alkyl, substituted or unsubstituted aryl or C$_2$-C$_6$ haloalkyl; R$^3$ and R$^4$ are independently substituted or unsubstituted alkyl or substituted or unsubstituted aryl; R$^5$ is hydrogen or substituted or unsubstituted alkyl; R$^6$ is hydrogen, halogen, —CX$^{6.1}_3$, —CHX$^{6.1}_2$, —CH$_2$X$^{6.1}$, —CN, —NO$_2$, —C(O) R$^{6D}$, —C(O)OR$^{6D}$, —OCX$^{6.1}_3$, —OCHX$^{6.1}_2$ or substituted or unsubstituted alkyl; R$^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —NO$_2$, —C(O)R$^{9D}$, —C(O)OR$^{9D}$, —OCX$^{9.1}_3$, —OCHX$^{9.1}_2$ or substituted or unsubstituted alkyl. In embodiments, R$^{1D}$, R$^{6D}$, R$^{7D}$, R$^{8D}$ and R$^{9D}$ are independent hydrogen or methyl.

In embodiments, X is —O—; R$^1$ is hydrogen, halogen, —CF$_3$, —CCl$_3$, —CBr$_3$, —CI$_3$, —CHF$_2$, —CH$_2$F, —CN, —NO$_2$, —C(O)R$^{1D}$, —C(O)OR$^{1D}$, —OCF$_3$, —OCHF$_2$, —OCCl$_3$, —OCBr$_3$ or substituted or unsubstituted alkyl; R$^2$ is hydrogen, —CX$^{2.1}_3$, —(CH$_2$)$_{n2}$CX$^{2.1}_3$, substituted C$_2$-C$_6$ alkyl, substituted or unsubstituted aryl or haloalkyl; R$^3$ and R$^4$ are independently hydrogen, substituted or unsubstituted alkyl or substituted or unsubstituted aryl; R$^5$ is hydrogen or substituted or unsubstituted alkyl; R$^6$ is hydrogen, halogen, —CX$^{6.1}_3$, —CHX$^{6.1}_2$, —CH$_2$X$^{6.1}$, —CN, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, —CF$_3$, —CCl$_3$, —CBr$_3$, —CI$_3$, —CHF$_2$, —CH$_2$F, —CN, —NO$_2$, —C(O) R$^{7D}$, —C(O)OR$^{7D}$, —OCX$^{7.1}_3$, —OCHX$^{7.1}_2$ or substituted or unsubstituted alkyl; R$^8$ is hydrogen, —CF$_3$, —CCl$_3$, —CBr$_3$, —CI$_3$, —CHF$_2$, —CH$_2$F, —CN, —NO$_2$, —C(O) R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CF$_3$, —CCl$_3$, —CBr$_3$, —CI$_3$, —CHF$_2$, —CH$_2$F, —CN, —C(O) R$^{9D}$, —C(O)OR$^{9D}$, —OCX$^{9.1}_3$, —OCHX$^{9.1}_2$ or substituted or unsubstituted alkyl. In embodiments, R$^{1D}$, R$^{6D}$, R$^{7D}$, R$^{8D}$ and R$^{9D}$ are independent hydrogen or methyl.

In embodiments, at least two of R$^1$, R$^6$, R$^7$, R$^8$ and R$^9$ are independently hydrogen. In embodiments, two of R$^1$, R$^6$, R$^7$, R$^8$ and R$^9$ are independently hydrogen. In embodiments, R$^6$, R$^7$, R$^8$ and R$^9$ are independently hydrogen and R$^1$ is —NO$_2$. In embodiments, R$^6$, R$^7$, R$^8$ and R$^9$ are independently hydrogen and R$^1$ is —NO$_2$. In embodiments, R$^6$, R$^7$, R$^8$ and R$^9$ are independently hydrogen and R$^1$ is —COOH. In embodiments, R$^6$, R$^7$, R$^8$ and R$^9$ are independently hydrogen and R$^1$ is —F. In embodiments, R$^1$, R$^7$, R$^8$ and R$^9$ are independently hydrogen and R$^6$ is —COOH. In embodiments, R$^1$, R$^7$, R$^8$ and R$^9$ are independently hydrogen and R$^6$ is —F. In embodiments, R$^1$, R$^7$, R$^8$ and R$^9$ are independently hydrogen and R$^6$ is —Cl. In embodiments, R$^1$, R$^7$, R$^8$ and R$^9$ are independently hydrogen and R$^6$ is —NO$_2$, with proviso that when X is —O—; R$^2$ is —CH$_2$CF$_3$; one of R$^3$ and R$^4$ is hydrogen and one of R$^3$ and R$^4$ is unsubstituted C$_1$-C$_3$ alkyl, then R$^6$ is not —NO$_2$. In embodiments, R$^1$, R$^6$, R$^7$ and R$^8$ are independently hydrogen and R$^9$ is —COOH. In embodiments, R$^1$, R$^6$, R$^7$ and R$^8$ are independently hydrogen and R$^9$ is —F. In embodiments, R$^1$, R$^6$, R$^7$ and R$^8$ are independently hydrogen and R$^9$ is —Cl. In embodiments, R$^1$, R$^6$, R$^7$ and R$^8$ are independently hydrogen and R$^9$ is —NO$_2$, with proviso that when X is —O—; R$^2$ is —CH$_2$CF$_3$; one of R$^3$ and R$^4$ is hydrogen and one of R$^3$ and R$^4$ is unsubstituted C$_1$-C$_3$ alkyl, then R$^9$ is not —NO$_2$. In embodiments, R$^1$, R$^6$, R$^7$, R$^8$ and R$^9$ are independently hydrogen. In embodiments, R$^1$ is not hydrogen and R$^6$, R$^7$, R$^8$ and R$^9$ are independently hydrogen.

In embodiments, the compound has Formula IA:

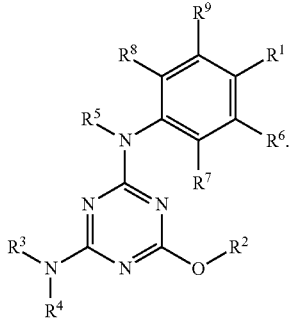

(IA)

R$^1$, R$^2$, R$^3$, R$^4$, R$^5$, R$^6$, R$^7$, R$^8$, and R$^9$ are as described herein.

In embodiments, R$^2$ is —CX$^{2.1}_3$, —(CH$_2$)$_{n2}$CX$^{2.1}_3$, or C$_2$-C$_8$ haloalkyl. In embodiments, R$^3$, R$^4$ and R$^5$ are independently hydrogen, substituted or unsubstituted alkyl. In embodiments, R$^1$ is hydrogen, halogen, —CX$^{1.1}_3$, —CHX$^{1.1}_2$, —CH$_2$X$^{1.1}$, —CN, —NO$_2$, —C(O)R$^{1D}$, —C(O)OR$^{1D}$, —OCX$^{1.1}_3$, —OCHX$^{1.1}_2$ or substituted or unsubstituted alkyl; R$^6$ is hydrogen, halogen, —CX$^{6.1}_3$, —CHX$^{6.1}_2$, —CH$_2$X$^{6.1}$, —CN, —NO$_2$, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, —CX$^{9.1}_3$, —CHX$^{9.1}_2$, —CH$_2$X$^{9.1}$, —CN, —NO$_2$, —C(O)R$^{9D}$, —C(O)OR$^{9D}$, —OCX$^{9.1}_3$, —OCHX$^{9.1}_2$ or substituted or unsubstituted alkyl. In embodiments, R$^7$ and R$^8$ are independently hydrogen. In embodiments, R$^3$ and R$^4$ substituted or unsubstituted alkyl; R$^5$ are independently hydrogen; R$^6$ is hydrogen, halogen, —CX$^{6.1}_3$, —CHX$^{6.1}_2$, —CH$_2$X$^{6.1}$, —CN, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —C(O)R$^{9D}$, —C(O)OR$^{9D}$, —OCX$^{9.1}_3$, —OCHX$^{9.1}_2$ or substituted or unsubstituted alkyl; wherein R$^{1D}$, R$^{6D}$, R$^{7D}$, R$^{8D}$ and R$^{9D}$ are independently hydrogen or methyl, and X$^{1.1}$, X$^{2.1}$, X$^{6.1}$, X$^{7.1}$, X$^{8.1}$ and X$^{9.1}$ are independently are —F. In embodiments, R$^7$ and R$^8$ are independently hydrogen. In embodiments, R$^3$ and R$^4$ are independently methyl or ethyl. In embodiment, R$^5$ is hydrogen. In embodiments, R$^1$ is hydrogen, halogen, —NO$_2$, or —$^-$COOH; R$^5$ is hydrogen; R$^6$ is hydrogen, halogen —NO$_2$, or —COOH; R$^7$ and R$^8$ are independently hydrogen; and R$^9$ is hydrogen, halogen NO$_2$, or —COOH. In embodiments, R$^1$, R$^7$ and R$^8$ are independently hydrogen. In embodiments, R$^6$, R$^7$, R$^8$ and R$^9$ are independently hydrogen. In embodiments, R$^1$, R$^7$, R$^8$ and R$^9$ are independently hydrogen. In embodiments, R$^1$, R$^6$, R$^7$ and R$^8$ are independently hydrogen. In embodiments, R$^1$, R$^6$, R$^7$, R$^8$ and R$^9$ are independently hydrogen.

In embodiments, R$^3$ and R$^4$ are independently hydrogen, methyl or ethyl. In embodiments, R$^2$ is C$_2$-C$_4$ alkyl substituted with fluorines. In embodiments, R$^2$ is C$_2$-C$_4$ alkyl substituted with at least one, two, three, four or five fluorines. In embodiments, R$^2$ is C$_2$-C$_4$ haloalkyl substituted with at least one, two, three, four or five fluorines. In embodiments, R$^1$, R$^6$, R$^7$, R$^8$ and R$^9$ are independently hydrogen. In embodiments, R$^1$ and R$^6$ are joined to form, together with the atoms to which they are attached, a substituted or unsubstituted pyrazolyl, oxazolyl, or thiazolyl; R$^2$ is C$_2$-C$_4$ haloalkyl; R$^3$ and R$^4$ are independently hydrogen, methyl or ethyl. In embodiments, the compound is represented with Formula IB, IC, ID, or IE:

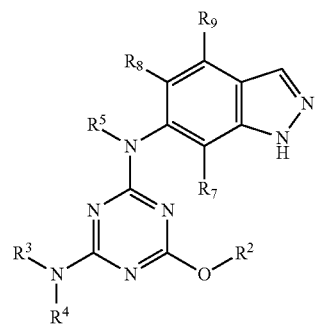

(IB)

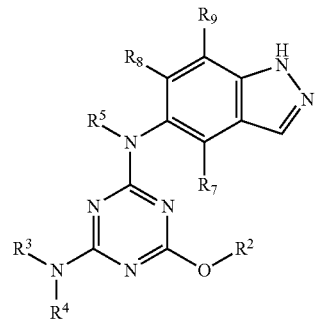

(IC)

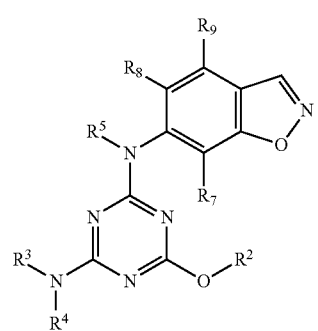

(ID)

-continued

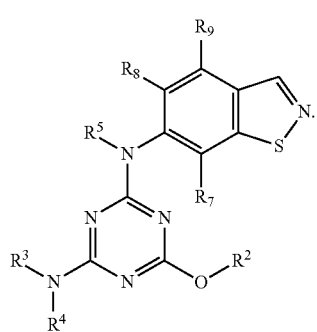

(IE)

In embodiments, $R^5$, $R^7$, $R^8$ and $R^9$ are independently hydrogen. In embodiments, $R^2$ is —CH(CF$_3$)$_2$ or —CH$_2$(CF$_2$)$_2$H.

In embodiments, $R^2$ is —CX$^{2.1}_3$, or C$_2$-C$_4$ haloalkyl. In embodiments, $R^1$ is hydrogen, halogen, —CX$^{1.1}_3$, —CHX$^{1.1}_2$, —CH$_2$X$^{1.1}$, —CN, —NO$_2$, —C(O)R$^{1D}$, —C(O)OR$^{1D}$, —OCX$^{1.1}_3$, —OCHX$^{1.1}_2$ or substituted or unsubstituted alkyl; $R^3$, $R^4$ and $R^5$ are independently hydrogen, substituted or unsubstituted alkyl, or $R^3$ and $R^4$ are optionally be joined to form, together with the atoms to which they are attached, a substituted or unsubstituted heterocycloalkyl; $R^6$ is hydrogen, halogen, —CX$^{6.1}_3$, —CHX$^{6.1}_2$, —CH$_2$X$^{6.1}$, —CN, —NO$_2$, —C(O)R$^{6D}$, —C(O)OR$^{6D}$, —OCX$^{6.1}_3$, —OCHX$^{6.1}_2$ or substituted or unsubstituted alkyl; $R^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; $R^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and $R^9$ is hydrogen, halogen, —CX$^{9.1}_3$, —CHX$^{9.1}_2$, —CH$_2$X$^{9.1}$, —CN, —NO$_2$, —C(O)R$^{9D}$, —C(O)OR$^{9D}$, —OCX$^{9.1}_3$, —OCHX$^{9.1}_2$ or substituted or unsubstituted alkyl. In embodiments, $R^7$ and $R^8$ are independently hydrogen. In embodiments, $R^1$ is hydrogen, halogen, —CX$^{1.1}_3$, —CHX$^{1.1}_2$, —CH$_2$X$^{1.1}$, —CN, —NO$_2$, —C(O)R$^{1D}$, —C(O)OR$^{1D}$, —OCX$^{1.1}_3$, —OCHX$^{1.1}_2$ or substituted or unsubstituted alkyl; $R^3$ and $R^4$ substituted or unsubstituted alkyl; $R^5$ are independently hydrogen; $R^6$ is hydrogen, halogen, —CX$^{6.1}_3$, —CHX$^{6.1}_2$, —CH$_2$X$^{6.1}$, —CN, —NO$_2$, —C(O)R$^{6D}$, —C(O)OR$^{6D}$, —OCX$^{6.1}_3$, —OCHX$^{6.1}_2$ or substituted or unsubstituted alkyl; $R^7$ is hydrogen, —CX$^{7.1}_3$, —CHX$^{7.1}_2$, —CH$_2$X$^{7.1}$, —CN, —NO$_2$, —C(O)R$^{7D}$, —C(O)OR$^{7D}$, —OCX$^{7.1}_3$, —OCHX$^{7.1}_2$ or substituted or unsubstituted alkyl; $R^8$ is hydrogen, —CX$^{8.1}_3$, —CHX$^{8.1}_2$, —CH$_2$X$^{8.1}$, —CN, —NO$_2$, —C(O)R$^{8D}$, —C(O)OR$^{8D}$, —OCX$^{8.1}_3$, —OCHX$^{8.1}_2$ or substituted or unsubstituted alkyl; and $R^9$ is hydrogen, halogen, —CX$^{9.1}_3$, —CHX$^{9.1}_2$, —CH$_2$X$^{9.1}$, —CN, —NO$_2$, —C(O)R$^{9D}$, —C(O)OR$^{9D}$, —OCX$^{9.1}_3$, —OCHX$^{9.1}_2$ or substituted or unsubstituted alkyl; wherein $R^{1D}$, $R^{6D}$, $R^{7D}$, $R^{8D}$ and $R^{9D}$ are independently hydrogen or methyl, and $X^{1.1}$, $X^{2.1}$, $X^{6.1}$, $X^{7.1}$, $X^{8.1}$ and $X^{9.1}$ are independently are —F. In embodiments, $R^3$ and $R^4$ are independently hydrogen, methyl or ethyl. In embodiments, $R^1$ is hydrogen, halogen, —NO$_2$, —COOH; $R^5$ is hydrogen; $R^6$ is hydrogen, halogen —NO$_2$, or —COOH; $R^7$ is hydrogen; $R^8$ is hydrogen; and $R^9$ is hydrogen, halogen NO$_2$, or —COOH. In embodiments, $R^1$ is a hydrogen, halogen, COOH or —NO$_2$; $R^2$ is C$_2$-C$_4$ haloalkyl; $R^5$ is hydrogen; $R^6$ is a hydrogen, halogen, COOH or —NO$_2$; $R^7$ and $R^8$ are independently hydrogen; $R^9$ is a hydrogen, halogen, COOH or —NO$_2$. In embodiments, $R^3$ and $R^4$ are independently hydrogen, methyl or ethyl. In embodiments, $R^2$ is alkyl substituted with at least one fluorine. In embodiments, $R^1$, $R^6$, $R^7$, $R^8$ and $R^9$ are independently hydrogen.

In embodiments, $R^1$ is independently hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), $R^{1E}$-substituted or unsubstituted alkyl, $R^{1E}$-substituted or unsubstituted heteroalkyl, $R^{1E}$-substituted or unsubstituted cycloalkyl, $R^{1E}$-substituted or unsubstituted heterocycloalkyl, $R^{1E}$-substituted or unsubstituted aryl, or $R^{1E}$-substituted or unsubstituted heteroaryl. In embodiments, $R^1$ is independently hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), $R^{1E}$-substituted or unsubstituted C$_1$-C$_6$ alkyl, $R^{1E}$-substituted or unsubstituted 2 to 6 membered heteroalkyl, $R^{1E}$-substituted or unsubstituted C$_3$-C$_6$ cycloalkyl, $R^{1E}$-substituted or unsubstituted 3 to 6 membered heterocycloalkyl, $R^{1E}$-substituted or unsubstituted phenyl, or $R^{1E}$-substituted or unsubstituted 5 to 6 membered heteroaryl.

$R^{1E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{1F}$-substituted or unsubstituted alkyl, $R^{1F}$-substituted or unsubstituted heteroalkyl, $R^{1F}$-substituted or unsubstituted cycloalkyl, $R^{1F}$-substituted or unsubstituted heterocycloalkyl, $R^{1F}$-substituted or unsubstituted aryl, or $R^{1F}$-substituted or unsubstituted heteroaryl. In embodiments, $R^{1E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{1F}$-substituted or unsubstituted C$_1$-C$_6$ alkyl, $R^{1F}$-substituted or unsubstituted 2 to 6 membered heteroalkyl, $R^{1F}$-substituted or unsubstituted C$_3$-C$_6$ cycloalkyl, $R^{1F}$-substituted or unsubstituted 3 to 6 membered heterocycloalkyl, $R^{1F}$-substituted or unsubstituted phenyl, or $R^{1F}$-substituted or unsubstituted 5 to 6 membered heteroaryl.

In embodiments, $R^2$ is independently hydrogen, halogen, —CX$^{2.1}_3$, —CHX$^{2.1}_2$, —CH$_2$X$^{2.1}$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}{}_3$, —OCHX$^{2.1}{}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$), —OCHI$_2$, R$^{2E}$-substituted or unsubstituted alkyl, R$^{2E}$-substituted or unsubstituted heteroalkyl, R$^{2E}$-substituted or unsubstituted cycloalkyl, R$^{2E}$-substituted or unsubstituted heterocycloalkyl, R$^{2E}$-substituted or unsubstituted aryl, or R$^{2E}$-substituted or unsubstituted heteroaryl. In embodiments, R$^2$ is independently hydrogen, halogen, —CX$^{2.1}{}_3$, —CHX$^{2.1}{}_2$, —CH$_2$X$^{2.1}$, —CN, —SO$_{n2}$R$^{2A}$, —SO$_{v2}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}{}_3$, —OCHX$^{2.1}{}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), R$^{2E}$-substituted or unsubstituted C$_1$-C$_6$ alkyl, R$^{2E}$-substituted or unsubstituted 2 to 6 membered heteroalkyl, R$^{2E}$-substituted or unsubstituted C$_3$-C$_6$ cycloalkyl, R$^{2E}$-substituted or unsubstituted 3 to 6 membered heterocycloalkyl, R$^{2E}$-substituted or unsubstituted phenyl, or R$^{2E}$-substituted or unsubstituted 5 to 6 membered heteroaryl. In embodiments, R$^2$ is haloalkyl. In embodiments, R$^2$ is C$_2$-C$_8$ haloalkyl. In embodiments, R$^2$ is C$_2$-C$_6$ haloalkyl. In embodiments, R$^2$ is C$_2$-C$_4$ haloalkyl. In embodiments, R$^2$ is C$_2$-C$_4$ haloalkyl including at least one, two, three, four or five fluorines.

R$^{2E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2F}$-substituted or unsubstituted alkyl, R$^{2F}$-substituted or unsubstituted heteroalkyl, R$^{2F}$-substituted or unsubstituted cycloalkyl, R$^{2F}$-substituted or unsubstituted heterocycloalkyl, R$^{2F}$-substituted or unsubstituted aryl, or R$^{2F}$-substituted or unsubstituted heteroaryl. In embodiments, R$^{2E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2F}$-substituted or unsubstituted C$_1$-C$_6$ alkyl, R$^{2F}$-substituted or unsubstituted 2 to 6 membered heteroalkyl, R$^{2F}$-substituted or unsubstituted C$_3$-C$_6$ cycloalkyl, R$^{2F}$-substituted or unsubstituted 3 to 6 membered heterocycloalkyl, R$^{2F}$-substituted or unsubstituted phenyl, or R$^{2F}$-substituted or unsubstituted 5 to 6 membered heteroaryl.

In embodiments, R$^3$ is independently hydrogen, —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, R$^{3E}$-substituted or unsubstituted alkyl, R$^{3E}$-substituted or unsubstituted heteroalkyl, R$^{3E}$-substituted or unsubstituted cycloalkyl, R$^{3E}$-substituted or unsubstituted heterocycloalkyl, R$^{3E}$-substituted or unsubstituted aryl, or R$^{3E}$-substituted or unsubstituted heteroaryl. In embodiments, R$^3$ is independently hydrogen, R$^{3E}$-substituted or unsubstituted C$_1$-C$_6$ alkyl, R$^{3E}$-substituted or unsubstituted 2 to 6 membered heteroalkyl, R$^{3E}$-substituted or unsubstituted C$_3$-C$_6$ cycloalkyl, R$^{3E}$-substituted or unsubstituted 3 to 6 membered heterocycloalkyl, R$^{3E}$-substituted or unsubstituted phenyl, or R$^{3E}$-substituted or unsubstituted 5 to 6 membered heteroaryl.

R$^{3E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3F}$-substituted or unsubstituted alkyl, R$^{3F}$-substituted or unsubstituted heteroalkyl, R$^{3F}$-substituted or unsubstituted cycloalkyl, R$^{3F}$-substituted or unsubstituted heterocycloalkyl, R$^{3F}$-substituted or unsubstituted aryl, or R$^{3F}$-substituted or unsubstituted heteroaryl. In embodiments, R$^{3E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), R$^{3F}$-substituted or unsubstituted C$_1$-C$_6$ alkyl, R$^{3F}$-substituted or unsubstituted 2 to 6 membered heteroalkyl, R$^{3F}$-substituted or unsubstituted C$_3$-C$_6$ cycloalkyl, R$^{3F}$-substituted or unsubstituted 3 to 6 membered heterocycloalkyl, R$^{3F}$-substituted or unsubstituted phenyl, or R$^{3F}$-substituted or unsubstituted 5 to 6 membered heteroaryl.

In embodiments, R$^4$ is independently hydrogen, —C(O)R$^{4D}$, —C(O)NHNR$^{4B}$R$^{3C}$, —C(O)OR$^{4D}$, —SO$_2$R$^{4A}$, C(O)NR$^{4B}$R$^{4C}$, R$^{4E}$-substituted or unsubstituted alkyl, R$^{4E}$-substituted or unsubstituted heteroalkyl, R$^{4E}$-substituted or unsubstituted cycloalkyl, R$^{4E}$-substituted or unsubstituted heterocycloalkyl, R$^{4E}$-substituted or unsubstituted aryl, or R$^{4E}$-substituted or unsubstituted heteroaryl. In embodiments, R$^4$ is independently hydrogen, R$^{4E}$-substituted or unsubstituted C$_1$-C$_6$ alkyl, R$^{4E}$-substituted or unsubstituted 2 to 6 membered heteroalkyl, R$^{4E}$-substituted or unsubstituted C$_3$-C$_6$ cycloalkyl, R$^{4E}$-substituted or unsubstituted 3 to 6 membered heterocycloalkyl, R$^{4E}$-substituted or unsubstituted phenyl, or R$^{4E}$-substituted or unsubstituted 5 to 6 membered heteroaryl.

R$^{4E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{4F}$-substituted or unsubstituted alkyl, R$^{4F}$-substituted or unsubstituted heteroalkyl, R$^{4F}$-substituted or unsubstituted cycloalkyl, R$^{4F}$-substituted or unsubstituted heterocycloalkyl, R$^{4F}$-substituted or unsubstituted aryl, or R$^{4F}$-substituted or unsubstituted heteroaryl. In embodiments, R$^{4E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{4F}$-substituted or unsubstituted C$_1$-C$_6$ alkyl, $R^{4F}$-substituted or unsubstituted 2 to 6 membered heteroalkyl, $R^{4F}$-substituted or unsubstituted $C_3$-$C_6$ cycloalkyl, $R^{4F}$-substituted or unsubstituted 3 to 6 membered heterocycloalkyl, $R^{4F}$-substituted or unsubstituted phenyl, or $R^{4F}$-substituted or unsubstituted 5 to 6 membered heteroaryl.

In embodiments, $R^3$ and $R^4$ are joined to form, together with the atoms to which they are attached, a substituted or unsubstituted (e.g. $C_3$-$C_6$) cycloalkyl, a substituted or unsubstituted (e.g. 3 to 6 membered) heterocycloalkyl, substituted or unsubstituted (e.g. phenyl) aryl or substituted or unsubstituted (e.g. 5 to 6 membered) heteroaryl. In embodiments, $R^3$ and $R^4$ are joined to form, together with the atoms to which they are attached, a substituted or unsubstituted (e.g. $C_3$-$C_6$) cycloalkyl, a substituted or unsubstituted (e.g. 3 to 6 membered) heterocycloalkyl or substituted or unsubstituted (e.g. 5 to 6 membered) heteroaryl. In embodiments, $R^3$ and $R^4$ are joined to form, together with the atoms to which they are attached, a substituted or unsubstituted (e.g. $C_3$-$C_6$) cycloalkyl or a substituted or unsubstituted (e.g. 3 to 6 membered) heterocycloalkyl. In embodiments, $R^3$ and $R^4$ are joined to form, together with the atoms to which they are attached, a substituted or unsubstituted (e.g. 3 to 6 membered) heterocycloalkyl. In embodiments, $R^3$ and $R^4$ are joined to form, together with the atoms to which they are attached, $R^{3E}$-substituted or unsubstituted (e.g. $C_3$-$C_6$) cycloalkyl, $R^{3E}$-substituted or unsubstituted (e.g. 3 to 6 membered) heterocycloalkyl, $R^{3E}$-substituted or unsubstituted (e.g. phenyl) aryl or $R^{3E}$-substituted or unsubstituted (e.g. 5 to 6 membered) heteroaryl. In embodiments, $R^3$ and $R^4$ are joined to form, together with the atoms to which they are attached, $R^{3E}$-substituted or unsubstituted (e.g. $C_3$-$C_6$) cycloalkyl, $R^{3E}$-substituted or unsubstituted (e.g. 3 to 6 membered) heterocycloalkyl or $R^{3E}$-substituted or unsubstituted (e.g. 5 to 6 membered) heteroaryl. In embodiments, $R^3$ and $R^4$ are joined to form, together with the atoms to which they are attached, $R^{3E}$-substituted or unsubstituted (e.g. $C_3$-$C_6$) cycloalkyl or $R^{3E}$-substituted or unsubstituted (e.g. 3 to 6 membered) heterocycloalkyl. In embodiments, $R^3$ and $R^4$ are joined to form, together with the atoms to which they are attached, $R^{3E}$-substituted or unsubstituted (e.g. 3 to 6 membered) heterocycloalkyl. In embodiments, $R^3$ and $R^4$ are joined to form, together with the atoms to which they are attached, $R^{3E}$-substituted or unsubstituted piperidinyl or morpholinyl. In embodiments, $R^3$ and $R^4$ are joined to form, together with the atoms to which they are attached, unsubstituted piperidinyl or morpholinyl. In embodiments, the compound is

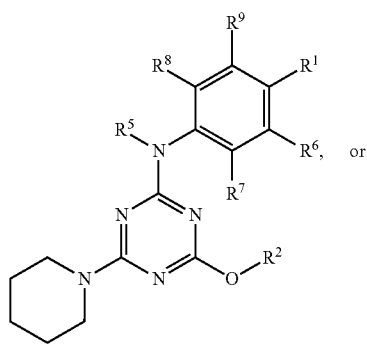

, or

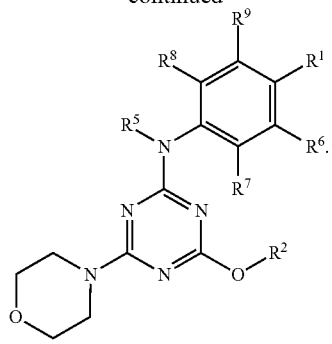

In embodiments, $R^5$ is independently hydrogen, —C(O)$R^{5D}$, —C(O)NHNR$^{5B}$R$^{5C}$, —C(O)OR$^{5D}$, —SO$_2$R$^{5A}$, C(O)NR$^{5B}$R$^{5C}$, $R^{5E}$-substituted or unsubstituted alkyl, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl. In embodiments, $R^5$ is independently hydrogen, $R^{5E}$-substituted or unsubstituted $C_1$-$C_6$ alkyl, $R^{5E}$-substituted or unsubstituted 2 to 6 membered heteroalkyl, $R^{5E}$-substituted or unsubstituted $C_3$-$C_6$ cycloalkyl, $R^{5E}$-substituted or unsubstituted 3 to 6 membered heterocycloalkyl, $R^{5E}$-substituted or unsubstituted phenyl, or $R^{5E}$-substituted or unsubstituted 5 to 6 membered heteroaryl.

$R^{5E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{5F}$-substituted or unsubstituted alkyl, $R^{5F}$-substituted or unsubstituted heteroalkyl, $R^{5F}$-substituted or unsubstituted cycloalkyl, $R^{5F}$-substituted or unsubstituted heterocycloalkyl, $R^{5F}$-substituted or unsubstituted aryl, or $R^{5F}$-substituted or unsubstituted heteroaryl. In embodiments, $R^{5E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{5F}$-substituted or unsubstituted $C_1$-$C_6$ alkyl, $R^{5F}$-substituted or unsubstituted 2 to 6 membered heteroalkyl, $R^{5F}$-substituted or unsubstituted $C_3$-$C_6$ cycloalkyl, $R^{5F}$-substituted or unsubstituted 3 to 6 membered heterocycloalkyl, $R^{5F}$-substituted or unsubstituted phenyl, or $R^{5F}$-substituted or unsubstituted 5 to 6 membered heteroaryl.

In embodiments, $R^6$ is independently hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), $R^{6E}$-substituted or unsubstituted alkyl, $R^{6E}$-substituted or unsubstituted heteroalkyl, $R^{6E}$-substituted or unsubstituted cycloalkyl, $R^{6E}$-substituted or unsubstituted heterocycloalkyl, $R^{6E}$-substituted or unsubstituted aryl, or $R^{6E}$-substituted or unsubstituted heteroaryl. In embodiments, $R^6$ is independently hydrogen, halogen, $-CX^{6.1}_3$, $-CHX^{6.1}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$ (e.g. hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$), $R^{6E}$-substituted or unsubstituted $C_1$-$C_6$ alkyl, $R^{6E}$-substituted or unsubstituted 2 to 6 membered heteroalkyl, $R^{6E}$-substituted or unsubstituted $C_3$-$C_6$ cycloalkyl, $R^{6E}$-substituted or unsubstituted 3 to 6 membered heterocycloalkyl, $R^{6E}$-substituted or unsubstituted phenyl, or $R^{6E}$-substituted or unsubstituted 5 to 6 membered heteroaryl.

$R^{6E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{6F}$-substituted or unsubstituted alkyl, $R^{6F}$-substituted or unsubstituted heteroalkyl, $R^{6F}$-substituted or unsubstituted cycloalkyl, $R^{6F}$-substituted or unsubstituted heterocycloalkyl, $R^{6F}$-substituted or unsubstituted aryl, or $R^{6F}$-substituted or unsubstituted heteroaryl. In embodiments, $R^{6E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{6F}$-substituted or unsubstituted $C_1$-$C_6$ alkyl, $R^{6F}$-substituted or unsubstituted 2 to 6 membered heteroalkyl, $R^{6F}$-substituted or unsubstituted $C_3$-$C_6$ cycloalkyl, $R^{6F}$-substituted or unsubstituted 3 to 6 membered heterocycloalkyl, $R^{6F}$-substituted or unsubstituted phenyl, or $R^{6F}$-substituted or unsubstituted 5 to 6 membered heteroaryl.

In embodiments, $R^7$ is independently hydrogen, halogen, $-CX^{7.1}_3$, $-CHX^{7.1}_2$, $-CH_2X^{7.1}$, $-CN$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^7$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$ (e.g. hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$), $R^{7E}$-substituted or unsubstituted alkyl, $R^{7E}$-substituted or unsubstituted heteroalkyl, $R^{7E}$-substituted or unsubstituted cycloalkyl, $R^{7E}$-substituted or unsubstituted heterocycloalkyl, $R^{7E}$-substituted or unsubstituted aryl, or $R^{7E}$-substituted or unsubstituted heteroaryl. In embodiments, $R^7$ is independently hydrogen, halogen, $-CX^{7.1}_3$, $-CHX^{7.1}_2$, $-CH_2X^{7.1}$, $-CN$, $-SO_{n7}R^{7A}$, $-SO_7NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$ (e.g. hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$), $R^{7E}$-substituted or unsubstituted $C_1$-$C_6$ alkyl, $R^{7E}$-substituted or unsubstituted 2 to 6 membered heteroalkyl, $R^{7E}$-substituted or unsubstituted $C_3$-$C_6$ cycloalkyl, $R^{7E}$-substituted or unsubstituted 3 to 6 membered heterocycloalkyl, $R^{7E}$-substituted or unsubstituted phenyl, or $R^{7E}$-substituted or unsubstituted 5 to 6 membered heteroaryl.

$R^{7E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{7F}$-substituted or unsubstituted alkyl, $R^{7F}$-substituted or unsubstituted heteroalkyl, $R^{7F}$-substituted or unsubstituted cycloalkyl, $R^{7F}$-substituted or unsubstituted heterocycloalkyl, $R^{7F}$-substituted or unsubstituted aryl, or $R^{7F}$-substituted or unsubstituted heteroaryl. In embodiments, $R^{7E}$ is independently oxo, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{7F}$-substituted or unsubstituted $C_1$-$C_6$ alkyl, $R^{7F}$-substituted or unsubstituted 2 to 6 membered heteroalkyl, $R^{7F}$-substituted or unsubstituted $C_3$-$C_6$ cycloalkyl, $R^{7F}$-substituted or unsubstituted 3 to 6 membered heterocycloalkyl, $R^{7F}$-substituted or unsubstituted phenyl, or $R^{7F}$-substituted or unsubstituted 5 to 6 membered heteroaryl.

In embodiments, $R^8$ is independently hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$ (e.g. hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$), $R^{8E}$-substituted or unsubstituted alkyl, $R^{8E}$-substituted or unsubstituted heteroalkyl, $R^{8E}$-substituted or unsubstituted cycloalkyl, $R^{8E}$-substituted or unsubstituted heterocycloalkyl, $R^{8E}$-substituted or unsubstituted aryl, or $R^{8E}$-substituted or unsubstituted heteroaryl. In embodiments, $R^8$ is independently hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$ (e.g. hydrogen, halogen, $-CF_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), R$^{8E}$-substituted or unsubstituted C$_1$-C$_6$ alkyl, R$^{8E}$-substituted or unsubstituted 2 to 6 membered heteroalkyl, R$^{8E}$-substituted or unsubstituted C$_3$-C$_6$ cycloalkyl, R$^{8E}$-substituted or unsubstituted 3 to 6 membered heterocycloalkyl, R$^{8E}$-substituted or unsubstituted phenyl, or R$^{8E}$-substituted or unsubstituted 5 to 6 membered heteroaryl.

R$^{8E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8F}$-substituted or unsubstituted alkyl, R$^{8F}$-substituted or unsubstituted heteroalkyl, R$^{8F}$-substituted or unsubstituted cycloalkyl, R$^{8F}$-substituted or unsubstituted heterocycloalkyl, R$^{8F}$-substituted or unsubstituted aryl, or R$^{8F}$-substituted or unsubstituted heteroaryl. In embodiments, R$^{8E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{8F}$-substituted or unsubstituted C$_1$-C$_6$ alkyl, R$^{8F}$-substituted or unsubstituted 2 to 6 membered heteroalkyl, R$^{8F}$-substituted or unsubstituted C$_3$-C$_6$ cycloalkyl, R$^{8F}$-substituted or unsubstituted 3 to 6 membered heterocycloalkyl, R$^{8F}$-substituted or unsubstituted phenyl, or R$^{8F}$-substituted or unsubstituted 5 to 6 membered heteroaryl.

In embodiments, R$^9$ is independently hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$), R$^{9E}$-substituted or unsubstituted alkyl, R$^{9E}$-substituted or unsubstituted heteroalkyl, R$^{9E}$-substituted or unsubstituted cycloalkyl, R$^{9E}$-substituted or unsubstituted heterocycloalkyl, R$^{9E}$-substituted or unsubstituted aryl, or R$^{9E}$-substituted or unsubstituted heteroaryl. In embodiments, R$^9$ is independently hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$ (e.g. hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHI$_2$), R$^{9E}$-substituted or unsubstituted C$_1$-C$_6$ alkyl, R$^{9E}$-substituted or unsubstituted 2 to 6 membered heteroalkyl, R$^{9E}$-substituted or unsubstituted C$_3$-C$_6$ cycloalkyl, R$^{9E}$-substituted or unsubstituted 3 to 6 membered heterocycloalkyl, R$^{9E}$-substituted or unsubstituted phenyl, or R$^{9E}$-substituted or unsubstituted 5 to 6 membered heteroaryl.

R$^{9E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9F}$-substituted or unsubstituted alkyl, R$^{9F}$-substituted or unsubstituted heteroalkyl, R$^{9F}$-substituted or unsubstituted cycloalkyl, R$^{9F}$-substituted or unsubstituted heterocycloalkyl, R$^{9F}$-substituted or unsubstituted aryl, or R$^{9F}$-substituted or unsubstituted heteroaryl. In embodiments, R$^{9E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9F}$-substituted or unsubstituted C$_1$-C$_6$ alkyl, R$^{9F}$-substituted or unsubstituted 2 to 6 membered heteroalkyl, R$^{9F}$-substituted or unsubstituted C$_3$-C$_6$ cycloalkyl, R$^{9F}$-substituted or unsubstituted 3 to 6 membered heterocycloalkyl, R$^{9F}$-substituted or unsubstituted phenyl, or R$^{9F}$-substituted or unsubstituted 5 to 6 membered heteroaryl.

In embodiments, R$^{1A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1AF}$-substituted or unsubstituted alkyl, R$^{1AF}$-substituted or unsubstituted heteroalkyl, R$^{1AF}$-substituted or unsubstituted cycloalkyl, R$^{1AF}$-substituted or unsubstituted heterocycloalkyl, R$^{1AF}$-substituted or unsubstituted aryl, or R$^{1AF}$-substituted or unsubstituted heteroaryl. In embodiments, R$^{1A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1AF}$-substituted or unsubstituted C$_1$-C$_6$ alkyl, R$^{1AF}$-substituted or unsubstituted 2 to 6 membered heteroalkyl, R$^{1AF}$-substituted or unsubstituted C$_3$-C$_6$ cycloalkyl, R$^{1AF}$-substituted or unsubstituted 3 to 6 membered heterocycloalkyl, R$^{1AF}$-substituted or unsubstituted phenyl, or R$^{1A}$-substituted or unsubstituted 5 to 6 membered heteroaryl.

In embodiments, R$^{1B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1BF}$-substituted or unsubstituted alkyl, R$^{1BF}$-substituted or unsubstituted heteroalkyl, R$^{1BF}$-substituted or unsubstituted cycloalkyl, R$^{1BF}$-substituted or unsubstituted heterocycloalkyl, R$^{1BF}$-substituted or unsubstituted aryl, or R$^{1BF}$-substituted or unsubstituted heteroaryl. In embodiments, R$^{1B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1BF}$-substituted or unsubstituted C$_1$-C$_6$ alkyl, R$^{1BF}$-substituted or unsubstituted 2 to 6 membered heteroalkyl, R$^{1BF}$-substituted or unsubstituted C$_3$-C$_6$ cycloalkyl, R$^{1BF}$-substituted or unsubstituted 3 to 6 membered heterocycloalkyl, R$^{1BF}$-substituted or unsubstituted phenyl, or R$^{1BF}$-substituted or unsubstituted 5 to 6 membered heteroaryl.

In embodiments, R$^{1C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1CF}$-substituted or unsubstituted alkyl, R$^{1CF}$-substituted or unsubstituted heteroalkyl, R$^{1CF}$-substituted or unsubstituted cycloalkyl, R$^{1CF}$-substituted or unsubstituted heterocycloalkyl, R$^{1CF}$-substituted or unsubstituted aryl, or R$^{1CF}$-substituted or unsubstituted heteroaryl. In embodiments, R$^{1C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1CF}$-substituted or unsubstituted C$_1$-C$_6$ alkyl, R$^{1CF}$-substituted or unsubstituted 2 to 6 membered heteroalkyl, R$^{1CF}$-substituted or unsubstituted C$_3$-C$_6$ cycloalkyl, R$^{1CF}$-substituted or unsubstituted 3 to 6 membered heterocycloalkyl, R$^{1CF}$-substituted or unsubstituted phenyl, or R$^{1CF}$-substituted or unsubstituted 5 to 6 membered heteroaryl. R$^{1B}$ and R$^{1C}$ bonded to the same nitrogen atom may optionally be joined to form a R$^{1CF}$-substituted or unsubstituted 3 to 6 membered heterocycloalkyl or R$^{1CF}$-substituted or unsubstituted 5 to 6 membered heteroaryl.

In embodiments, R$^{1D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1DF}$-substituted or unsubstituted alkyl, R$^{1DF}$-substituted or unsubstituted heteroalkyl, R$^{1DF}$-substituted or unsubstituted cycloalkyl, R$^{1DF}$-substituted or unsubstituted heterocycloalkyl, R$^{1DF}$-substituted or unsubstituted aryl, or R$^{1DF}$-substituted or unsubstituted heteroaryl. In embodiments, R$^{1D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{1DF}$-substituted or unsubstituted C$_1$-C$_6$ alkyl, R$^{1DF}$-substituted or unsubstituted 2 to 6 membered heteroalkyl, R$^{1DF}$-substituted or unsubstituted C$_3$-C$_6$ cycloalkyl, R$^{1DF}$-substituted or unsubstituted 3 to 6 membered heterocycloalkyl, R$^{1DF}$-substituted or unsubstituted phenyl, or R$^{1DF}$-substituted or unsubstituted 5 to 6 membered heteroaryl.

In embodiments, R$^{2A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2AF}$-substituted or unsubstituted alkyl, R$^{2AF}$-substituted or unsubstituted heteroalkyl, R$^{2AF}$-substituted or unsubstituted cycloalkyl, R$^{2AF}$-substituted or unsubstituted heterocycloalkyl, R$^{2AF}$-substituted or unsubstituted aryl, or R$^{2AF}$-substituted or unsubstituted heteroaryl. In embodiments, R$^{2A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2AF}$-substituted or unsubstituted C$_1$-C$_6$ alkyl, R$^{2AF}$-substituted or unsubstituted 2 to 6 membered heteroalkyl, R$^{2AF}$-substituted or unsubstituted C$_3$-C$_6$ cycloalkyl, R$^{2AF}$-substituted or unsubstituted 3 to 6 membered heterocycloalkyl, R$^{2AF}$-substituted or unsubstituted phenyl, or R$^{2AF}$-substituted or unsubstituted 5 to 6 membered heteroaryl.

In embodiments, R$^{2B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2BF}$-substituted or unsubstituted alkyl, R$^{2BF}$-substituted or unsubstituted heteroalkyl, R$^{2BF}$-substituted or unsubstituted cycloalkyl, R$^{2BF}$-substituted or unsubstituted heterocycloalkyl, R$^{2BF}$-substituted or unsubstituted aryl, or R$^{2BF}$-substituted or unsubstituted heteroaryl. In embodiments, R$^{2B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2BF}$-substituted or unsubstituted C$_1$-C$_6$ alkyl, R$^{2BF}$-substituted or unsubstituted 2 to 6 membered heteroalkyl, R$^{2BF}$-substituted or unsubstituted C$_3$-C$_6$ cycloalkyl, R$^{2BF}$-substituted or unsubstituted 3 to 6 membered heterocycloalkyl, R$^{2BF}$-substituted or unsubstituted phenyl, or R$^{2BF}$-substituted or unsubstituted 5 to 6 membered heteroaryl.

In embodiments, R$^{2C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2CF}$-substituted or unsubstituted alkyl, R$^{2CF}$-substituted or unsubstituted heteroalkyl, R$^{2CF}$-substituted or unsubstituted cycloalkyl, R$^{2CF}$-substituted or unsubstituted heterocycloalkyl, R$^{2CF}$-substituted or unsubstituted aryl, or R$^{2CF}$-substituted or unsubstituted heteroaryl. In embodiments, R$^{2C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2CF}$-substituted or unsubstituted C$_1$-C$_6$ alkyl, R$^{2CF}$-substituted or unsubstituted 2 to 6 membered heteroalkyl, R$^{2CF}$-substituted or unsubstituted C$_3$-C$_6$ cycloalkyl, R$^{2CF}$-substituted or unsubstituted 3 to 6 membered heterocycloalkyl, R$^{2CF}$-substituted or unsubstituted phenyl, or R$^{2CF}$-substituted or unsubstituted 5 to 6 membered heteroaryl. R$^{2B}$ and R$^{2C}$ bonded to the same nitrogen atom may optionally be joined to form a R$^{2CF}$-substituted or unsubstituted 3 to 6 membered heterocycloalkyl or R$^{2CF}$-substituted or unsubstituted 5 to 6 membered heteroaryl.

In embodiments, R$^{2D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2DF}$-substituted or unsubstituted alkyl, R$^{2DF}$-substituted or unsubstituted heteroalkyl, R$^{2DF}$-substituted or unsubstituted cycloalkyl, R$^{2DF}$-substituted or unsubstituted heterocycloalkyl, R$^{2DF}$-substituted or unsubstituted aryl, or R$^{2DF}$-substituted or unsubstituted heteroaryl. In embodiments, R$^{2D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{2DF}$-substituted or unsubstituted C$_1$-C$_6$ alkyl, R$^{2DF}$-substituted or unsubstituted 2 to 6 membered heteroalkyl, R$^{2DF}$-substituted or unsubstituted C$_3$-C$_6$ cycloalkyl, R$^{2DF}$-substituted or unsubstituted 3 to 6 membered heterocycloalkyl, R$^{2DF}$-substituted or unsubstituted phenyl, or R$^{2DF}$-substituted or unsubstituted 5 to 6 membered heteroaryl.

In embodiments, R$^{3A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3AF}$-substituted or unsubstituted alkyl, R$^{3AF}$-substituted or unsubstituted heteroalkyl, R$^{3AF}$-substituted or unsubstituted cycloalkyl, R$^{3AF}$-substituted or unsubstituted heterocycloalkyl, R$^{3AF}$-substituted or unsubstituted aryl, or R$^{3AF}$-substituted or unsubstituted heteroaryl. In embodiments, R$^{3A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3AF}$-substituted or unsubstituted C$_1$-C$_6$ alkyl, R$^{3AF}$-substituted or unsubstituted 2 to 6 membered heteroalkyl, R$^{3AF}$-substituted or unsubstituted C$_3$-C$_6$ cycloalkyl, R$^{3AF}$-substituted or unsubstituted 3 to 6 membered heterocycloalkyl, R$^{3AF}$-substituted or unsubstituted phenyl, or R$^{3AF}$-substituted or unsubstituted 5 to 6 membered heteroaryl.

In embodiments, R$^{3B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3BF}$-substituted or unsubstituted alkyl, R$^{3BF}$-substituted or unsubstituted heteroalkyl, R$^{3BF}$-substituted or unsubstituted cycloalkyl, R$^{3BF}$-substituted or unsubstituted heterocycloalkyl, R$^{3BF}$-substituted or unsubstituted aryl, or R$^{3BF}$-substituted or unsubstituted heteroaryl. In embodiments, R$^{3B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3BF}$-substituted or unsubstituted C$_1$-C$_6$ alkyl, R$^{3BF}$-substituted or unsubstituted 2 to 6 membered heteroalkyl, R$^{3BF}$-substituted or unsubstituted C$_3$-C$_6$ cycloalkyl, R$^{3BF}$-substituted or unsubstituted 3 to 6 membered heterocycloalkyl, R$^{3BF}$-substituted or unsubstituted phenyl, or R$^{3BF}$-substituted or unsubstituted 5 to 6 membered heteroaryl.

In embodiments, R$^{3C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3CF}$-substituted or unsubstituted alkyl, R$^{3CF}$-substituted or unsubstituted heteroalkyl, R$^{3CF}$-substituted or unsubstituted cycloalkyl, R$^{3CF}$-substituted or unsubstituted heterocycloalkyl, R$^{3CF}$-substituted or unsubstituted aryl, or R$^{3CF}$-substituted or unsubstituted heteroaryl. In embodiments, R$^{3C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3CF}$-substituted or unsubstituted C$_1$-C$_6$ alkyl, R$^{3CF}$-substituted or unsubstituted 2 to 6 membered heteroalkyl, R$^{3CF}$-substituted or unsubstituted C$_3$-C$_6$ cycloalkyl, R$^{3CF}$-substituted or unsubstituted 3 to 6 membered heterocycloalkyl, R$^{3CF}$-substituted or unsubstituted phenyl, or R$^{3CF}$-substituted or unsubstituted 5 to 6 membered heteroaryl. R$^{3B}$ and R$^{3C}$ bonded to the same nitrogen atom may optionally be joined to form a R$^{3CF}$-substituted or unsubstituted 3 to 6 membered heterocycloalkyl or R$^{3CF}$-substituted or unsubstituted 5 to 6 membered heteroaryl.

In embodiments, R$^{3D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3DF}$-substituted or unsubstituted alkyl, R$^{3DF}$-substituted or unsubstituted heteroalkyl, R$^{3DF}$-substituted or unsubstituted cycloalkyl, R$^{3DF}$-substituted or unsubstituted heterocycloalkyl, R$^{3DF}$-substituted or unsubstituted aryl, or R$^{3DF}$-substituted or unsubstituted heteroaryl. In embodiments, R$^{3D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{3DF}$-substituted or unsubstituted C$_1$-C$_6$ alkyl, R$^{3DF}$-substituted or unsubstituted 2 to 6 membered heteroalkyl, $R^{3DF}$-substituted or unsubstituted $C_3$-$C_6$ cycloalkyl, $R^{3DF}$-substituted or unsubstituted 3 to 6 membered heterocycloalkyl, $R^{3DF}$-substituted or unsubstituted phenyl, or $R^{3DF}$-substituted or unsubstituted 5 to 6 membered heteroaryl.

In embodiments, $R^{4A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4AF}$-substituted or unsubstituted alkyl, $R^{4AF}$-substituted or unsubstituted heteroalkyl, $R^{4AF}$-substituted or unsubstituted cycloalkyl, $R^{4AF}$-substituted or unsubstituted heterocycloalkyl, $R^{4AF}$-substituted or unsubstituted aryl, or $R^{4AF}$-substituted or unsubstituted heteroaryl. In embodiments, $R^{4A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4AF}$-substituted or unsubstituted $C_1$-$C_6$ alkyl, $R^{4AF}$-substituted or unsubstituted 2 to 6 membered heteroalkyl, $R^{4AF}$-substituted or unsubstituted $C_3$-$C_6$ cycloalkyl, $R^{4AF}$-substituted or unsubstituted 3 to 6 membered heterocycloalkyl, $R^{4AF}$-substituted or unsubstituted phenyl, or $R^{4AF}$-substituted or unsubstituted 5 to 6 membered heteroaryl.

In embodiments, $R^{4B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4BF}$-substituted or unsubstituted alkyl, $R^{4BF}$-substituted or unsubstituted heteroalkyl, $R^{4BF}$-substituted or unsubstituted cycloalkyl, $R^{4BF}$-substituted or unsubstituted heterocycloalkyl, $R^{4BF}$-substituted or unsubstituted aryl, or $R^{4BF}$-substituted or unsubstituted heteroaryl. In embodiments, $R^{4B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4BF}$-substituted or unsubstituted $C_1$-$C_6$ alkyl, $R^{4BF}$-substituted or unsubstituted 2 to 6 membered heteroalkyl, $R^{4BF}$-substituted or unsubstituted $C_3$-$C_6$ cycloalkyl, $R^{4BF}$-substituted or unsubstituted 3 to 6 membered heterocycloalkyl, $R^{4BF}$-substituted or unsubstituted phenyl, or $R^{4BF}$-substituted or unsubstituted 5 to 6 membered heteroaryl.

In embodiments, $R^{4C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4CF}$-substituted or unsubstituted alkyl, $R^{4CF}$-substituted or unsubstituted heteroalkyl, $R^{4CF}$-substituted or unsubstituted cycloalkyl, $R^{4CF}$-substituted or unsubstituted heterocycloalkyl, $R^{4CF}$-substituted or unsubstituted aryl, or $R^{4CF}$-substituted or unsubstituted heteroaryl. In embodiments, $R^{4C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4CF}$-substituted or unsubstituted $C_1$-$C_6$ alkyl, $R^{4CF}$-substituted or unsubstituted 2 to 6 membered heteroalkyl, $R^{4CF}$-substituted or unsubstituted $C_3$-$C_6$ cycloalkyl, $R^{4CF}$-substituted or unsubstituted 3 to 6 membered heterocycloalkyl, $R^{4CF}$-substituted or unsubstituted phenyl, or $R^{4CF}$-substituted or unsubstituted 5 to 6 membered heteroaryl. $R^{4B}$ and $R^{4C}$ bonded to the same nitrogen atom may optionally be joined to form a $R^{4CF}$-substituted or unsubstituted 3 to 6 membered heterocycloalkyl or $R^{4CF}$-substituted or unsubstituted 5 to 6 membered heteroaryl.

In embodiments, $R^{4D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4DF}$-substituted or unsubstituted alkyl, $R^{4DF}$-substituted or unsubstituted heteroalkyl, $R^{4DF}$-substituted or unsubstituted cycloalkyl, $R^{4DF}$-substituted or unsubstituted heterocycloalkyl, $R^{4DF}$-substituted or unsubstituted aryl, or $R^{4DF}$-substituted or unsubstituted heteroaryl. In embodiments, $R^{4D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{4DF}$-substituted or unsubstituted $C_1$-$C_6$ alkyl, $R^{4DF}$-substituted or unsubstituted 2 to 6 membered heteroalkyl, $R^{4DF}$-substituted or unsubstituted $C_3$-$C_6$ cycloalkyl, $R^{4DF}$-substituted or unsubstituted 3 to 6 membered heterocycloalkyl, $R^{4DF}$-substituted or unsubstituted phenyl, or $R^{4DF}$-substituted or unsubstituted 5 to 6 membered heteroaryl.

In embodiments, $R^{5A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5AF}$-substituted or unsubstituted alkyl, $R^{5AF}$-substituted or unsubstituted heteroalkyl, $R^{5AF}$-substituted or unsubstituted cycloalkyl, $R^{5AF}$-substituted or unsubstituted heterocycloalkyl, $R^{5AF}$-substituted or unsubstituted aryl, or $R^{5AF}$-substituted or unsubstituted heteroaryl. In embodiments, $R^{5A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5AF}$-substituted or unsubstituted $C_1$-$C_6$ alkyl, $R^{5AF}$-substituted or unsubstituted 2 to 6 membered heteroalkyl, $R^{5AF}$-substituted or unsubstituted $C_3$-$C_6$ cycloalkyl, $R^{5AF}$-substituted or unsubstituted 3 to 6 membered heterocycloalkyl, $R^{5AF}$-substituted or unsubstituted phenyl, or $R^{5AF}$-substituted or unsubstituted 5 to 6 membered heteroaryl.

In embodiments, $R^{5B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5BF}$-substituted or unsubstituted alkyl, $R^{5BF}$-substituted or unsubstituted heteroalkyl, $R^{5BF}$-substituted or unsubstituted cycloalkyl, $R^{5BF}$-substituted or unsubstituted heterocycloalkyl, $R^{5BF}$-substituted or unsubstituted aryl, or $R^{5BF}$-substituted or unsubstituted heteroaryl. In embodiments, $R^{5B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5BF}$-substituted or unsubstituted $C_1$-$C_6$ alkyl, $R^{5BF}$-substituted or unsubstituted 2 to 6 membered heteroalkyl, $R^{5BF}$-substituted or unsubstituted $C_3$-$C_6$ cycloalkyl, $R^{5BF}$-substituted or unsubstituted 3 to 6 membered heterocycloalkyl, $R^{5BF}$-substituted or unsubstituted phenyl, or $R^{5BF}$-substituted or unsubstituted 5 to 6 membered heteroaryl.

In embodiments, $R^{5C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5CF}$-substituted or unsubstituted alkyl, $R^{5CF}$-substituted or unsubstituted heteroalkyl, $R^{5CF}$-substituted or unsubstituted cycloalkyl, $R^{5CF}$-substituted or unsubstituted heterocycloalkyl, $R^{5CF}$-substituted or unsubstituted aryl, or $R^{5CF}$-substituted or unsubstituted heteroaryl. In embodiments, $R^{5C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5CF}$-substituted or unsubstituted $C_1$-$C_6$ alkyl, $R^{5CF}$-substituted or unsubstituted 2 to 6 membered heteroalkyl, $R^{5CF}$-substituted or unsubstituted $C_3$-$C_6$ cycloalkyl, $R^{5CF}$-substituted or unsubstituted 3 to 6 membered heterocycloalkyl, $R^{5CF}$-substituted or unsubstituted phenyl, or $R^{5CF}$-substituted or unsubstituted 5 to 6 membered heteroaryl. $R^{5B}$ and $R^{5C}$ bonded to the same nitrogen atom may optionally be joined to form a $R^{5CF}$-substituted or unsubstituted 3 to 6 membered heterocycloalkyl or $R^{5CF}$-substituted or unsubstituted 5 to 6 membered heteroaryl.

In embodiments, $R^{5D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5DF}$-substituted or unsubstituted alkyl, $R^{5DF}$-substituted or unsubstituted heteroalkyl, $R^{5DF}$-substituted or unsubstituted cycloalkyl, $R^{5DF}$-substituted or unsubstituted heterocycloalkyl, $R^{5DF}$-substituted or unsubstituted aryl, or $R^{5DF}$-substituted or unsubstituted heteroaryl. In embodiments, $R^{5D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{5DF}$-substituted or unsubstituted $C_1$-$C_6$ alkyl, $R^{5DF}$-substituted or unsubstituted 2 to 6 membered heteroalkyl, $R^{5DF}$-substituted or unsubstituted $C_3$-$C_6$ cycloalkyl, $R^{5DF}$-substituted or unsubstituted 3 to 6 membered heterocycloalkyl, $R^{5DF}$-substituted or unsubstituted phenyl, or $R^{5DF}$-substituted or unsubstituted 5 to 6 membered heteroaryl.

In embodiments, $R^{6A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{6AF}$-substituted or unsubstituted alkyl, $R^{6AF}$-substituted or unsubstituted heteroalkyl, $R^{6AF}$-substituted or unsubstituted cycloalkyl, $R^{6AF}$-substituted or unsubstituted heterocycloalkyl, $R^{6AF}$-substituted or unsubstituted aryl, or $R^{6AF}$-substituted or unsubstituted heteroaryl. In embodiments, $R^{6A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{6AF}$-substituted or unsubstituted $C_1$-$C_6$ alkyl, $R^{6AF}$-substituted or unsubstituted 2 to 6 membered heteroalkyl, $R^{6AF}$-substituted or unsubstituted $C_3$-$C_6$ cycloalkyl, $R^{6AF}$-substituted or unsubstituted 3 to 6 membered heterocycloalkyl, $R^{6AF}$-substituted or unsubstituted phenyl, or $R^{6AF}$-substituted or unsubstituted 5 to 6 membered heteroaryl.

In embodiments, $R^{6B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{6BF}$-substituted or unsubstituted alkyl, $R^{6BF}$-substituted or unsubstituted heteroalkyl, $R^{6BF}$-substituted or unsubstituted cycloalkyl, $R^{6BF}$-substituted or unsubstituted heterocycloalkyl, $R^{6BF}$-substituted or unsubstituted aryl, or $R^{6BF}$-substituted or unsubstituted heteroaryl. In embodiments, $R^{6B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{6BF}$-substituted or unsubstituted $C_1$-$C_6$ alkyl, $R^{6BF}$-substituted or unsubstituted 2 to 6 membered heteroalkyl, $R^{6BF}$-substituted or unsubstituted $C_3$-$C_6$ cycloalkyl, $R^{6BF}$-substituted or unsubstituted 3 to 6 membered heterocycloalkyl, $R^{6BF}$-substituted or unsubstituted phenyl, or $R^{6BF}$-substituted or unsubstituted 5 to 6 membered heteroaryl.

In embodiments, $R^{6C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —OCHF$_2$, —OCHCl$_2$, —OCHBr$_2$, —OCHI$_2$, R$^{6CF}$-substituted or unsubstituted alkyl, R$^{6CF}$-substituted or unsubstituted heteroalkyl, R$^{6CF}$-substituted or unsubstituted cycloalkyl, R$^{6CF}$-substituted or unsubstituted heterocycloalkyl, R$^{6CF}$-substituted or unsubstituted aryl, or R$^{6CF}$-substituted or unsubstituted heteroaryl. In embodiments, R$^{6C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{6CF}$-substituted or unsubstituted C$_1$-C$_6$ alkyl, R$^{6CF}$-substituted or unsubstituted 2 to 6 membered heteroalkyl, R$^{6CF}$-substituted or unsubstituted C$_3$-C$_6$ cycloalkyl, R$^{6CF}$-substituted or unsubstituted 3 to 6 membered heterocycloalkyl, R$^{6CF}$-substituted or unsubstituted phenyl, or R$^{6CF}$-substituted or unsubstituted 5 to 6 membered heteroaryl. R$^{6B}$ and R$^{6C}$ bonded to the same nitrogen atom may optionally be joined to form a R$^{6CF}$-substituted or unsubstituted 3 to 6 membered heterocycloalkyl or R$^{6CF}$-substituted or unsubstituted 5 to 6 membered heteroaryl.

In embodiments, R$^{6D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{6DF}$-substituted or unsubstituted alkyl, R$^{6DF}$-substituted or unsubstituted heteroalkyl, R$^{6DF}$-substituted or unsubstituted cycloalkyl, R$^{6DF}$-substituted or unsubstituted heterocycloalkyl, R$^{6DF}$-substituted or unsubstituted aryl, or R$^{6DF}$-substituted or unsubstituted heteroaryl. In embodiments, R$^{6D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{6DF}$-substituted or unsubstituted C$_1$-C$_6$ alkyl, R$^{6DF}$-substituted or unsubstituted 2 to 6 membered heteroalkyl, R$^{6DF}$-substituted or unsubstituted C$_3$-C$_6$ cycloalkyl, R$^{6DF}$-substituted or unsubstituted 3 to 6 membered heterocycloalkyl, R$^{6DF}$-substituted or unsubstituted phenyl, or R$^{6DF}$-substituted or unsubstituted 5 to 6 membered heteroaryl.

In embodiments, R$^{7A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7AF}$-substituted or unsubstituted alkyl, R$^{7AF}$-substituted or unsubstituted heteroalkyl, R$^{7AF}$-substituted or unsubstituted cycloalkyl, R$^{7AF}$-substituted or unsubstituted heterocycloalkyl, R$^{7AF}$-substituted or unsubstituted aryl, or R$^{7AF}$-substituted or unsubstituted heteroaryl. In embodiments, R$^{7A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7AF}$-substituted or unsubstituted C$_1$-C$_6$ alkyl, R$^{7AF}$-substituted or unsubstituted 2 to 6 membered heteroalkyl, R$^{7AF}$-substituted or unsubstituted C$_3$-C$_6$ cycloalkyl, R$^{7AF}$-substituted or unsubstituted 3 to 6 membered heterocycloalkyl, R$^{7AF}$-substituted or unsubstituted phenyl, or R$^{7AF}$-substituted or unsubstituted 5 to 6 membered heteroaryl.

In embodiments, R$^{7B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7BF}$-substituted or unsubstituted alkyl, R$^{7BF}$-substituted or unsubstituted heteroalkyl, R$^{7BF}$-substituted or unsubstituted cycloalkyl, R$^{7BF}$-substituted or unsubstituted heterocycloalkyl, R$^{7BF}$-substituted or unsubstituted aryl, or R$^{7BF}$-substituted or unsubstituted heteroaryl. In embodiments, R$^{7B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7BF}$-substituted or unsubstituted C$_1$-C$_6$ alkyl, R$^{7BF}$-substituted or unsubstituted 2 to 6 membered heteroalkyl, R$^{7BF}$-substituted or unsubstituted C$_3$-C$_6$ cycloalkyl, R$^{7BF}$-substituted or unsubstituted 3 to 6 membered heterocycloalkyl, R$^{7BF}$-substituted or unsubstituted phenyl, or R$^{7BF}$-substituted or unsubstituted 5 to 6 membered heteroaryl.

In embodiments, R$^{7C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7CF}$-substituted or unsubstituted alkyl, R$^{7CF}$-substituted or unsubstituted heteroalkyl, R$^{7CF}$-substituted or unsubstituted cycloalkyl, R$^{7CF}$-substituted or unsubstituted heterocycloalkyl, R$^{7CF}$-substituted or unsubstituted aryl, or R$^{7CF}$-substituted or unsubstituted heteroaryl. In embodiments, R$^{7C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7CF}$-substituted or unsubstituted C$_1$-C$_6$ alkyl, R$^{7CF}$-substituted or unsubstituted 2 to 6 membered heteroalkyl, R$^{7CF}$-substituted or unsubstituted C$_3$-C$_6$ cycloalkyl, R$^{7CF}$-substituted or unsubstituted 3 to 6 membered heterocycloalkyl, R$^{7CF}$-substituted or unsubstituted phenyl, or R$^{7CF}$-substituted or unsubstituted 5 to 6 membered heteroaryl. R$^{7B}$ and R$^{7C}$ bonded to the same nitrogen atom may optionally be joined to form a R$^{7CF}$-substituted or unsubstituted 3 to 6 membered heterocycloalkyl or R$^{7CF}$-substituted or unsubstituted 5 to 6 membered heteroaryl.

In embodiments, R$^{7D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{7DF}$-substituted or unsubstituted alkyl, R$^{7DF}$-substituted or unsubstituted heteroalkyl, R$^{7DF}$-substituted or unsubstituted cycloalkyl, $R^{7DF}$-substituted or unsubstituted heterocycloalkyl, $R^{7DF}$-substituted or unsubstituted aryl, or $R^{7DF}$-substituted or unsubstituted heteroaryl. In embodiments, $R^{7D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{7DF}$-substituted or unsubstituted C$_1$-C$_6$ alkyl, $R^{7DF}$-substituted or unsubstituted 2 to 6 membered heteroalkyl, $R^{7DF}$-substituted or unsubstituted C$_3$-C$_6$ cycloalkyl, $R^{7DF}$-substituted or unsubstituted 3 to 6 membered heterocycloalkyl, $R^{7DF}$-substituted or unsubstituted phenyl, or $R^{7DF}$-substituted or unsubstituted 5 to 6 membered heteroaryl.

In embodiments, $R^{8A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8AF}$-substituted or unsubstituted alkyl, $R^{8AF}$-substituted or unsubstituted heteroalkyl, $R^{8AF}$-substituted or unsubstituted cycloalkyl, $R^{8AF}$-substituted or unsubstituted heterocycloalkyl, $R^{8AF}$-substituted or unsubstituted aryl, or $R^{8AF}$-substituted or unsubstituted heteroaryl. In embodiments, $R^{8A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8AF}$-substituted or unsubstituted C$_1$-C$_6$ alkyl, $R^{8AF}$-substituted or unsubstituted 2 to 6 membered heteroalkyl, $R^{8AF}$-substituted or unsubstituted C$_3$-C$_6$ cycloalkyl, $R^{8AF}$-substituted or unsubstituted 3 to 6 membered heterocycloalkyl, $R^{8AF}$-substituted or unsubstituted phenyl, or $R^{8AF}$-substituted or unsubstituted 5 to 6 membered heteroaryl.

In embodiments, $R^{8B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8BF}$-substituted or unsubstituted alkyl, $R^{8BF}$-substituted or unsubstituted heteroalkyl, $R^{8BF}$-substituted or unsubstituted cycloalkyl, $R^{8BF}$-substituted or unsubstituted heterocycloalkyl, $R^{8BF}$-substituted or unsubstituted aryl, or $R^{8BF}$-substituted or unsubstituted heteroaryl. In embodiments, $R^{8B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8BF}$-substituted or unsubstituted C$_1$-C$_6$ alkyl, $R^{8BF}$-substituted or unsubstituted 2 to 6 membered heteroalkyl, $R^{8BF}$-substituted or unsubstituted C$_3$-C$_6$ cycloalkyl, $R^{8BF}$-substituted or unsubstituted 3 to 6 membered heterocycloalkyl, $R^{8BF}$-substituted or unsubstituted phenyl, or $R^{8BF}$-substituted or unsubstituted 5 to 6 membered heteroaryl.

In embodiments, $R^{8C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8CF}$-substituted or unsubstituted alkyl, $R^{8CF}$-substituted or unsubstituted heteroalkyl, $R^{8CF}$-substituted or unsubstituted cycloalkyl, $R^{8CF}$-substituted or unsubstituted heterocycloalkyl, $R^{8CF}$-substituted or unsubstituted aryl, or $R^{8CF}$-substituted or unsubstituted heteroaryl. In embodiments, $R^{8C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8CF}$-substituted or unsubstituted C$_1$-C$_6$ alkyl, $R^{8CF}$-substituted or unsubstituted 2 to 6 membered heteroalkyl, $R^{8CF}$-substituted or unsubstituted C$_3$-C$_6$ cycloalkyl, $R^{8CF}$-substituted or unsubstituted 3 to 6 membered heterocycloalkyl, $R^{8CF}$-substituted or unsubstituted phenyl, or $R^{8CF}$-substituted or unsubstituted 5 to 6 membered heteroaryl. $R^{8B}$ and $R^{8C}$ bonded to the same nitrogen atom may optionally be joined to form a $R^{8CF}$-substituted or unsubstituted 3 to 6 membered heterocycloalkyl or $R^{8CF}$-substituted or unsubstituted 5 to 6 membered heteroaryl.

In embodiments, $R^{8D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8DF}$-substituted or unsubstituted alkyl, $R^{8DF}$-substituted or unsubstituted heteroalkyl, $R^{8DF}$-substituted or unsubstituted cycloalkyl, $R^{8DF}$-substituted or unsubstituted heterocycloalkyl, $R^{8DF}$-substituted or unsubstituted aryl, or $R^{8DF}$-substituted or unsubstituted heteroaryl. In embodiments, $R^{8D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{8DF}$-substituted or unsubstituted C$_1$-C$_6$ alkyl, $R^{8DF}$-substituted or unsubstituted 2 to 6 membered heteroalkyl, $R^{8DF}$-substituted or unsubstituted C$_3$-C$_6$ cycloalkyl, $R^{8DF}$-substituted or unsubstituted 3 to 6 membered heterocycloalkyl, $R^{8DF}$-substituted or unsubstituted phenyl, or $R^{8DF}$-substituted or unsubstituted 5 to 6 membered heteroaryl.

In embodiments, $R^{9A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{9AF}$-substituted or unsubstituted alkyl, $R^{9AF}$-substituted or unsubstituted heteroalkyl, $R^{9AF}$-substituted or unsubstituted cycloalkyl, $R^{9AF}$-substituted or unsubstituted heterocycloalkyl, $R^{9AF}$-substituted or unsubstituted aryl, or $R^{9AF}$-substituted or unsubstituted heteroaryl. In embodiments, $R^{9A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9AF}$-substituted or unsubstituted $C_1$-$C_6$ alkyl, $R^{9AF}$-substituted or unsubstituted 2 to 6 membered heteroalkyl, $R^{9AF}$-substituted or unsubstituted $C_3$-$C_6$ cycloalkyl, $R^{9AF}$-substituted or unsubstituted 3 to 6 membered heterocycloalkyl, $R^{9AF}$-substituted or unsubstituted phenyl, or $R^{9AF}$-substituted or unsubstituted 5 to 6 membered heteroaryl.

In embodiments, $R^{9B}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9BF}$-substituted or unsubstituted alkyl, $R^{9BF}$-substituted or unsubstituted heteroalkyl, $R^{9BF}$-substituted or unsubstituted cycloalkyl, $R^{9BF}$-substituted or unsubstituted heterocycloalkyl, $R^{9BF}$-substituted or unsubstituted aryl, or $R^{9BF}$-substituted or unsubstituted heteroaryl. In embodiments, $R^{9B}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9BF}$-substituted or unsubstituted $C_1$-$C_6$ alkyl, $R^{9BF}$-substituted or unsubstituted 2 to 6 membered heteroalkyl, $R^{9BF}$-substituted or unsubstituted $C_3$-$C_6$ cycloalkyl, $R^{9BF}$-substituted or unsubstituted 3 to 6 membered heterocycloalkyl, $R^{9BF}$-substituted or unsubstituted phenyl, or $R^{9BF}$-substituted or unsubstituted 5 to 6 membered heteroaryl.

In embodiments, $R^{9C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9CF}$-substituted or unsubstituted alkyl, $R^{9CF}$-substituted or unsubstituted heteroalkyl, $R^{9CF}$-substituted or unsubstituted cycloalkyl, $R^{9CF}$-substituted or unsubstituted heterocycloalkyl, $R^{9CF}$-substituted or unsubstituted aryl, or $R^{9CF}$-substituted or unsubstituted heteroaryl. In embodiments, $R^{9C}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9CF}$-substituted or unsubstituted $C_1$-$C_6$ alkyl, $R^{9CF}$-substituted or unsubstituted 2 to 6 membered heteroalkyl, $R^{9CF}$-substituted or unsubstituted $C_3$-$C_6$ cycloalkyl, $R^{9CF}$-substituted or unsubstituted 3 to 6 membered heterocycloalkyl, $R^{9CF}$-substituted or unsubstituted phenyl, or $R^{9CF}$-substituted or unsubstituted 5 to 6 membered heteroaryl. $R^{9B}$ and $R^{9C}$ bonded to the same nitrogen atom may optionally be joined to form a $R^{9CF}$-substituted or unsubstituted 3 to 6 membered heterocycloalkyl or $R^{9CF}$-substituted or unsubstituted 5 to 6 membered heteroaryl.

In embodiments, $R^{9D}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9DF}$-substituted or unsubstituted alkyl, $R^{9DF}$-substituted or unsubstituted heteroalkyl, $R^{9DF}$-substituted or unsubstituted cycloalkyl, $R^{9DF}$-substituted or unsubstituted heterocycloalkyl, $R^{9DF}$-substituted or unsubstituted aryl, or $R^{9DF}$-substituted or unsubstituted heteroaryl. In embodiments, $R^{9D}$ is independently hydrogen, halogen, —CF₃, —CCl₃, —CBr₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, $R^{9DF}$-substituted or unsubstituted $C_1$-$C_6$ alkyl, $R^{9DF}$-substituted or unsubstituted 2 to 6 membered heteroalkyl, $R^{9DF}$-substituted or unsubstituted $C_3$-$C_6$ cycloalkyl, $R^{9DF}$-substituted or unsubstituted 3 to 6 membered heterocycloalkyl, $R^{9DF}$-substituted or unsubstituted phenyl, or $R^{9DF}$-substituted or unsubstituted 5 to 6 membered heteroaryl.

$R^{1F}$, $R^{2F}$, $R^{3F}$, $R^{4F}$, $R^{5F}$, $R^{6F}$, $R^{7F}$, $R^{8F}$, $R^{9F}$, $R^{1AF}$, $R^{1BF}$, $R^{1CF}$, $R^{1DF}$, $R^{2AF}$, $R^{2BF}$, $R^{2CF}$, $R^{2DF}$, $R^{3AF}$, $R^{3BF}$, $R^{3CF}$, $R^{3DF}$, $R^{4AF}$, $R^{4BF}$, $R^{4CF}$, $R^{4DF}$, $R^{5AF}$, $R^{5BF}$, $R^{5CF}$, $R^{5DF}$, $R^{6AF}$, $R^{6BF}$, $R^{6CF}$, $R^{6DF}$, $R^{7AF}$, $R^{7BF}$, $R^{7CF}$, $R^{7DF}$, $R^{8AF}$, $R^{8BF}$, $R^{8CF}$, $R^{8DF}$, $R^{9AF}$, $R^{9BF}$, $R^{9CF}$ and $R^{9DF}$ are independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{1F}$, $R^{2F}$, $R^{3F}$, $R^{4F}$, $R^{5F}$, $R^{6F}$, $R^{7F}$, $R^{8F}$, $R^{9F}$, $R^{1AF}$, $R^{1BF}$, $R^{1CF}$, $R^{1DF}$, $R^{2AF}$, $R^{2BF}$, $R^{2CF}$, $R^{2DF}$, $R^{3AF}$, $R^{3BF}$, $R^{3CF}$, $R^{3DF}$, $R^{4AF}$, $R^{4BF}$, $R^{4CF}$, $R^{4DF}$, $R^{5AF}$, $R^{5BF}$, $R^{5CF}$, $R^{5DF}$, $R^{6AF}$, $R^{6BF}$, $R^{6CF}$, $R^{6DF}$, $R^{7AF}$, $R^{7BF}$, $R^{7CF}$, $R^{7DF}$, $R^{8AF}$, $R^{8BF}$, $R^{8CF}$, $R^{8DF}$, $R^{9AF}$, $R^{9BF}$, $R^{9CF}$ and $R^{9DF}$ are independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OCF₃, —OCHF₂, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In some embodiments, a compound as described herein may include multiple instances of $R^1$, $R^2$, $R^3$, $R^4$, $R^5$, $R^6$, $R^7$, $R^8$, $R^9$, m1, m2, m6, m7, m8, m9, n1, n2, n6, n7, n8, n9, v1, v2, v6, v7, v8, v9, and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^8$, $R^9$, m1, m2, m6, m7, m8, m9, n1, n2, n6, n7, n8, n9, v1, v2, v6, v7, v8 and/or v9 is different, they may be referred to, for example, as $R^{1.1}$, $R^{1.2}$, $R^{1.3}$, $R^{1.4}$, $R^{1.5}$, $R^{1.6}$, $R^{1.7}$, $R^{2.1}$, $R^{2.2}$, $R^{2.3}$, $R^{2.4}$, $R^{2.5}$, $R^{2.6}$, $R^{2.7}$, $R^{3.1}$, $R^{3.2}$, $R^{3.3}$, $R^{3.4}$, $R^{3.5}$, $R^{3.6}$, $R^{3.7}$, $R^{4.1}$, $R^{4.2}$, $R^{4.3}$, $R^{4.4}$, $R^{4.5}$, $R^{4.6}$, $R^{4.7}$, $R^{5.1}$, $R^{5.2}$, $R^{5.3}$, $R^{5.4}$, $R^{5.5}$, $R^{5.6}$, $R^{5.7}$, $R^{6.1}$, $R^{6.2}$, $R^{6.3}$, $R^{6.4}$, $R^{6.5}$, $R^{6.6}$, $R^{6.7}$, $R^{7.1}$, $R^{7.2}$, $R^{7.3}$, $R^{7.4}$, $R^{7.5}$, $R^{7.6}$, $R^{7.7}$, $R^{8.1}$, $R^{8.2}$, $R^{8.3}$, $R^{8.4}$, $R^{8.5}$, $R^{8.6}$, $R^{8.7}$, $R^{9.1}$, $R^{9.2}$, $R^{9.3}$, $R^{9.4}$, $R^{9.5}$, $R^{9.6}$, $R^{9.7}$, m1¹, m1², m1³, m1⁴, m1⁵, m1⁶, m1⁷, m2¹, m2², m2³, m2⁴, m2⁵, m2⁶, m2⁷, m6¹, m6², m6³, m6⁴, m6⁵, m6⁶, m6⁷, m7¹, m7², m7³, m7⁴, m7⁵, m7⁶, m7⁷, m8¹, m8², m8³, m8⁴, m8⁵, m8⁶, m8⁷, m9¹, m9², m9³, m9⁴, m9⁵, m9⁶, m9⁷, n1¹, n1², n1³, n1⁴, n1⁵, n1⁶, n1⁷, n2¹, n2², n2³, n2⁴, n2⁵, n2⁶, n2⁷, n6¹, n6², n6³, n6⁴, n6⁵, n6⁶, n6⁷n7¹, n7², n7³, n7⁴, n7⁵, n7⁶, n7⁷ n8¹, n8², n8³, n8⁴, n8⁵, n8⁶, n8⁷, n9¹, n9², n9³, n9⁴, n9⁵, n9⁶, n9⁷, v1¹, v1², v1³, v1⁴, v1⁵, v1⁶, v1⁷, v2¹, v2², v2³, v2⁴, v2⁵, v2⁶, v2⁷, v6¹, v6², v6³, v6⁴, v6⁵, v6⁶, v6⁷, v7¹, v7², v7³, v7⁴, v7⁵, v7⁶, v7⁷, v8¹, v8², v8³, v8⁴, v8⁵, v8⁶, v8⁷, v9¹, v9², v9³, v9⁴, v9⁵, v9⁶, v9⁷, respectively, wherein the definition of $R^1$ is assumed by $R^{1.1}$, $R^{1.2}$, $R^{1.3}$, $R^{1.4}$, $R^{1.5}$, $R^{1.6}$, $R^{1.7}$, the definition of $R^2$ is assumed by $R^{2.1}$, $R^{2.2}$, $R^{2.3}$, $R^{2.4}$, $R^{2.5}$, $R^{2.6}$, $R^{2.7}$, the definition of $R^3$ is assumed by $R^{3.1}$, $R^{3.2}$, $R^{3.3}$, $R^{3.4}$, $R^{3.5}$, $R^{3.6}$, $R^{3.7}$, the definition of $R^4$ is assumed by $R^{4.1}$, $R^{4.2}$, $R^{4.3}$, $R^{4.4}$, $R^{4.5}$, $R^{4.6}$, $R^{4.7}$, the definition of $R^5$ is assumed by $R^{5.1}$, $R^{5.2}$, $R^{5.3}$, $R^{5.4}$, $R^{5.5}$, $R^{5.6}$, $R^{5.7}$, the definition of $R^6$ is assumed by $R^{6.1}$, $R^{6.2}$, $R^{6.3}$, $R^{6.4}$, $R^{6.5}$, $R^{6.6}$, $R^{6.7}$ the definition of $R^7$ is assumed by $R^{7.1}$, $R^{7.2}$, $R^{7.3}$, $R^{7.4}$, $R^{7.5}$, $R^{7.6}$, $R^{7.7}$ the definition of $R^8$ is assumed by $R^{8.1}$, $R^{8.2}$, $R^{8.3}$, $R^{8.4}$, $R^{8.5}$, $R^{8.6}$, $R^{8.7}$, the definition of $R^9$ is assumed by $R^{9.1}$, $R^{9.2}$, $R^{9.3}$, $R^{9.4}$, $R^{9.5}$, $R^{9.6}$, $R^{9.7}$, the definition of m1 is assumed by m1¹, m1², m1³, m1⁴, m1⁵, m1⁶, m1⁷, the definition of m2 is assumed by m2¹, m2², m2³, m2⁴, m2⁵, m2⁶, m2⁷, the definition of m6 is assumed by m6¹, m6², m6³, m6⁴, m6⁵, m6⁶, m6⁶, the definition of m7 is assumed by m7¹, m7², m7³, m7⁴, m7⁵, m7⁶, m7⁶, the definition of m8 is assumed by m8¹, m8², m8³, m8⁴, m8⁵, m8⁶, m8⁷, the definition of m9 is assumed by m9¹, m9², m9³, m9⁴, m9⁵, m9⁶, m9⁷, the definition of n1 is assumed by n1¹, n1², n1³, n1⁴, n1⁵, n1⁶, n1⁷, the definition of n2 is assumed by n2¹, n2², n2³, n2⁴, n2⁵, n2⁶, n2⁷, is assumed by n3¹, n3², n3³, n3⁴, n3⁵, n3⁶, n3⁷, the definition of n4 is assumed by n4¹, n4², n4³, n4⁴, n4⁵, n4⁶, n4⁷, the definition of n5 is assumed by n5¹, n5², n5³, n5⁴, n5⁵, n5⁶, n5⁷, the definition of n6 is assumed by n6¹, n6², n6³, n6⁴, n6⁵, n6⁶, n6⁷, the definition of n7 is assumed by n7¹, n7², n7³, n7⁴, n7⁵, n7⁶, n7⁷, the definition of n8 is assumed by n8¹, n8², n8³, n8⁴, n8⁵, n8⁶, n8⁷, the definition of n9 is assumed by n9¹, n9², n9³, n9⁴, n9⁵, n9⁶, n9⁷, the definition of v1 is assumed by v1¹, v1², v1³, V1⁴, V1⁵, V1⁶, V1⁷, the definition of v2 is assumed by v2¹, v2², v2³, v2⁴, v2⁵, v2⁶, v2⁷, the definition of v3 is assumed by v3¹, v3², v3³, v3⁴, v3⁵, v3⁶, v3⁷, the definition of v4 is assumed by v4¹, v4², v4³, v4⁴, v4⁵, v4⁶, v4⁷, the definition of v5 is assumed by v5¹, v5², v5³, v5⁴, v5⁵, v5⁶, v5⁷, the definition of v6 is assumed by v6¹, v6², v6³, v6⁴, v6⁵, v6⁶, v6⁷, the definition of v7 is assumed by v7¹, v7², v7³, v7⁴, v7⁵, v7⁶, v7⁷, the definition of v8 is assumed by v8¹, v8², v8³, v8⁴, v8⁵, v8⁶, v8⁷ and the definition of v9 is assumed by v9¹, v9², v9³, v9⁴, v9⁵, v9⁶, v9⁷. The variables used within a definition of $R^1$, $R^2$, $R^3$, $R^4$, $R^5$, $R^6$, $R^7$, $R^8$, $R^9$, m1, m2, m3, m4, m5, m6, m7, m8, m9, n1, n2, n3, n4, n5, n6, n7, n8, n9, v1, v2, v3, v4, v5, v6, v7, v8, v9 and/or other variables that appear at multiple instances and are different may similarly be appropriately labeled to distinguish each group for greater clarity.

In embodiments, $R^1$ and $R^6$, $R^6$ and $R^7$, $R^1$ and $R^9$, or $R^8$, and $R^9$ are joined to form, together with the atoms to which they are attached, substituted or unsubstituted (e.g. $C_3$-$C_6$) cycloalkyl, substituted or unsubstituted (3 to 6 membered) heterocycloalkyl, substituted or unsubstituted (e.g. phenyl) aryl, or substituted or unsubstituted (e.g. 5 to 6 membered) heteroaryl. In embodiments, $R^1$ and $R^6$, $R^6$ and $R^7$, $R^1$ and $R^9$, or $R^8$, and $R^9$ are joined to substituted or unsubstituted (e.g. 3 to 6 membered) heterocycloalkyl, substituted or unsubstituted (e.g. phenyl) aryl, or substituted or unsubstituted (e.g. 5 to 6 membered) heteroaryl. In embodiments, $R^1$ and $R^6$, $R^6$ and $R^7$, $R^1$ and $R^9$, or $R^8$, and $R^9$ are joined to substituted or unsubstituted (e.g. phenyl) aryl, or substituted or unsubstituted (e.g. 5 to 6 membered) heteroaryl. In embodiments, $R^1$ and $R^6$, $R^6$ and $R^7$, $R^1$ and $R^9$, or $R^8$, and $R^9$ are joined to substituted or unsubstituted (e.g. 5 to 6 membered) heteroaryl. In embodiments, $R^1$ and $R^6$, $R^6$ and $R^7$, $R^1$ and $R^9$, or $R^8$ and $R^9$ are joined to form, together with the atoms to which they are attached, a substituted or unsubstituted pyrazolyl, oxazolyl, or thiazolyl. In embodiments, $R^1$ and $R^6$, $R^6$ and $R^7$, $R^1$ and $R^9$, or $R^8$ and $R^9$ are joined to form, together with the atoms to which they are attached, unsubstituted pyrazolyl, oxazolyl, or thiazolyl.

In embodiments, $R^1$ and $R^6$ are joined to form, together with the atoms to which they are attached, $R^{1E}$-substituted or unsubstituted (e.g. $C_3$-$C_6$) cycloalkyl, $R^{1E}$-substituted or unsubstituted (e.g. 3 to 6 membered) heterocycloalkyl, $R^{1E}$-substituted or unsubstituted (e.g. phenyl) aryl, or $R^{1E}$-substituted or unsubstituted (e.g. 5 to 6 membered) heteroaryl. In embodiments, $R^1$ and $R^6$ are joined to form, together with the atoms to which they are attached, $R^{1E}$-substituted or unsubstituted (e.g. 3 to 6 membered) heterocycloalkyl, $R^{1E}$-substituted or unsubstituted (e.g. phenyl) aryl, or $R^{1E}$-substituted or unsubstituted (e.g. 5 to 6 membered) heteroaryl. In embodiments, $R^1$ and $R^6$ are joined to form, together with the atoms to which they are attached, $R^{1E}$-substituted or unsubstituted (e.g. phenyl) aryl, or $R^{1E}$-substituted or unsubstituted (e.g. 5 to 6 membered) heteroaryl. In embodiments, $R^1$ and $R^6$ are joined to form, together with the atoms to which they are attached, $R^{1E}$-substituted or unsubstituted (e.g. 5 to 6 membered) heteroaryl. In embodiments, $R^1$ and $R^6$ are joined to form, together with the atoms to which they are attached, $R^{1E}$-substituted or unsubstituted pyrazolyl, oxazolyl, or thiazolyl. In embodiments, $R^1$ and $R^6$ are joined to form, together with the atoms to which they are attached, unsubstituted pyrazolyl, oxazolyl, or thiazolyl. In embodiments, the compound is represented formula $IB^1$, $IC^1$, $ID^1$, or $IE^1$:

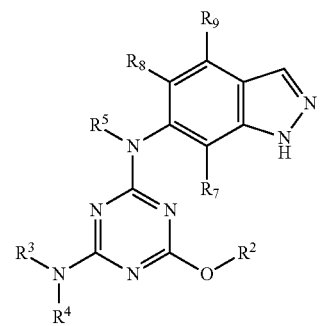

(IB1)

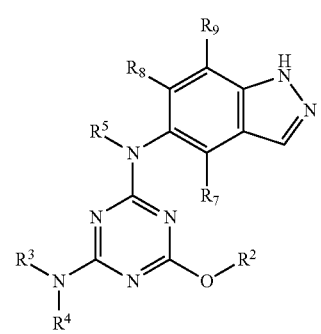

(IC1)

-continued

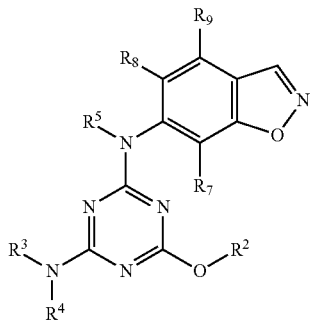
(ID1)

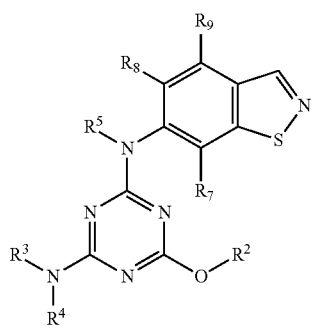
(IE1)

In embodiments, the compound is represented formula IB1A, IC1A, IB1A', IC1A', ID1A, or IE1A:

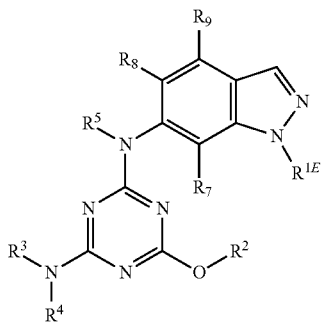
(IB1A)

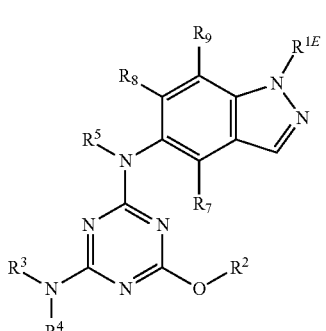
(IC1A)

-continued

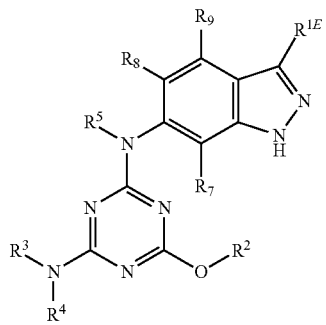
(IB1A')

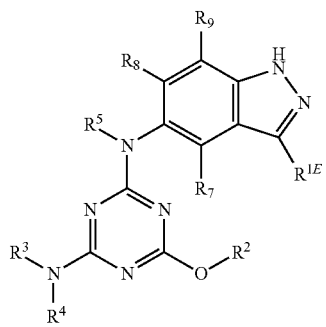
(IC1A')

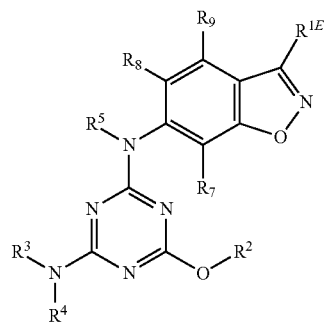
(ID1A)

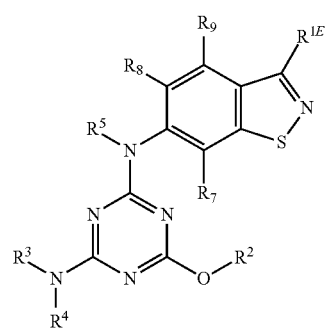
(IE1A)

In embodiments, $R^6$ and $R^7$ are joined to form, together with the atoms to which they are attached, $R^{6E}$-substituted or unsubstituted (e.g. $C_3$-$C_6$) cycloalkyl, $R^{6E}$-substituted or unsubstituted (e.g. 3 to 6 membered) heterocycloalkyl, $R^{6E}$-substituted or unsubstituted (e.g. phenyl) aryl, or $R^{6E}$-substituted or unsubstituted (e.g. 5 to 6 membered) heteroaryl. In embodiments, $R^6$ and $R^7$ are joined to form, together with the atoms to which they are attached, $R^{6E}$-substituted or unsubstituted (e.g. 3 to 6 membered) heterocycloalkyl, $R^{6E}$-substituted or unsubstituted (e.g. phenyl) aryl, or $R^{6E}$-substituted or unsubstituted (e.g. 5 to 6 membered) heteroaryl. In embodiments, $R^6$ and $R^7$ are joined to form, together with the atoms to which they are attached, $R^{6E}$-substituted or unsubstituted (e.g. phenyl) aryl, or $R^{6E}$-substituted or unsubstituted (e.g. 5 to 6 membered) heteroaryl. In embodiments, $R^6$ and $R^7$ are joined to form, together with the atoms to which they are attached, $R^{6E}$-substituted or unsubstituted (e.g. 5 to 6 membered) heteroaryl. In embodiments, $R^6$ and $R^7$ are joined to form, together with the atoms to which they are attached, $R^{6E}$-substituted or unsubstituted pyrazolyl, oxazolyl, or thiazolyl. In embodiments, $R^6$ and $R^7$ are joined to form, together with the atoms to which they are attached, unsubstituted pyrazolyl, oxazolyl, or thiazolyl. In embodiments, the compound is represented formula IB2, IC2, ID2, or IE2:

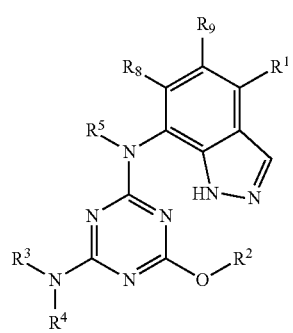
(IB2)

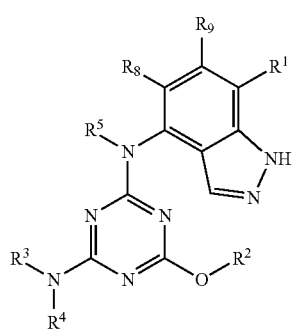
(IC2)

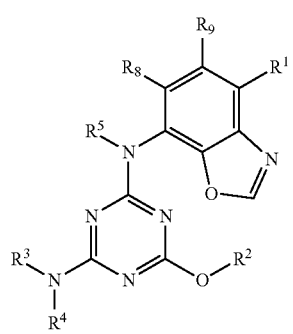
(ID2)

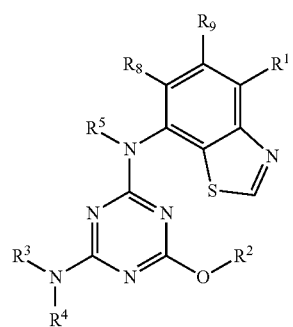
(IE2)

In embodiments, the compound is represented formula IB2A, IC2A, IB2A', IC2A', ID2A, or IE2A.

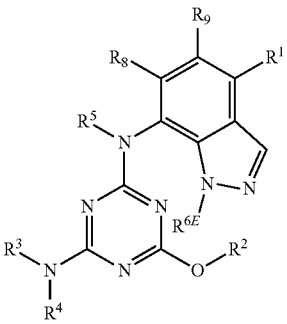
(IB2A)

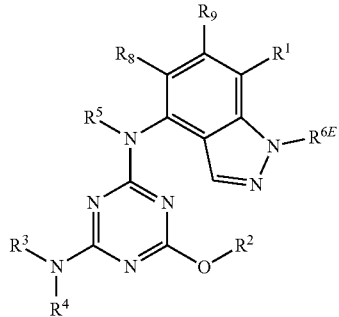
(IC2A)

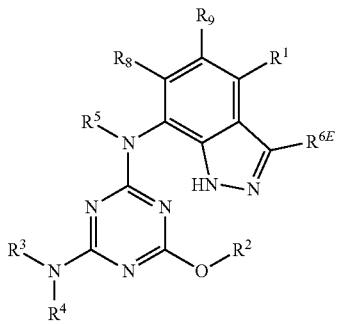
(IB2A')

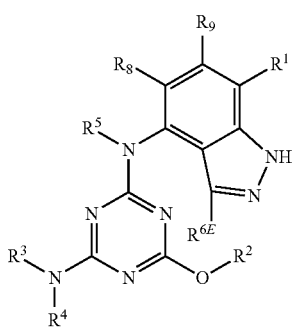
(IC2A')

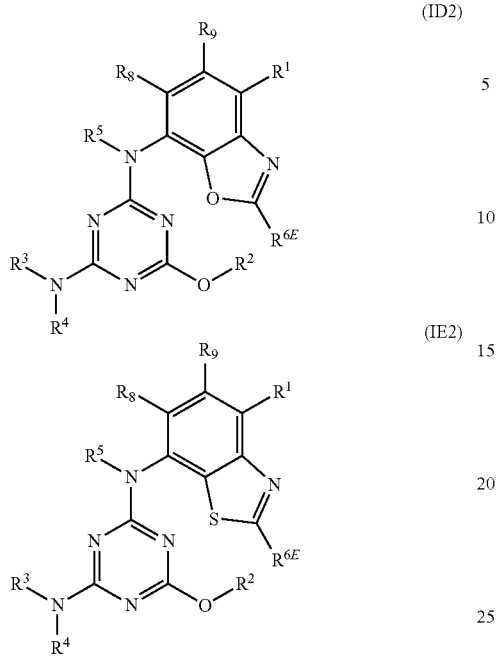

(ID2)

(IE2)

In embodiments, R¹ and R⁹ are joined to form, together with the atoms to which they are attached, $R^{9E}$-substituted or unsubstituted (e.g. $C_3$-$C_6$) cycloalkyl, $R^{9E}$-substituted or unsubstituted (e.g. 3 to 6 membered) heterocycloalkyl, $R^{9E}$-substituted or unsubstituted (e.g. phenyl) aryl, or $R^{9E}$-substituted or unsubstituted (e.g. 5 to 6 membered) heteroaryl. In embodiments, R¹ and R⁹ are joined to form, together with the atoms to which they are attached, $R^{9E}$-substituted or unsubstituted (e.g. 3 to 6 membered) heterocycloalkyl, $R^{9E}$-substituted or unsubstituted (e.g. phenyl) aryl, or $R^{9E}$-substituted or unsubstituted (e.g. 5 to 6 membered) heteroaryl. In embodiments, R¹ and R⁹ are joined to form, together with the atoms to which they are attached, $R^{9E}$-substituted or unsubstituted (e.g. phenyl) aryl, or $R^{9E}$-substituted or unsubstituted (e.g. 5 to 6 membered) heteroaryl. In embodiments, R¹ and R⁹ are joined to form, together with the atoms to which they are attached, $R^{9E}$-substituted or unsubstituted (e.g. 5 to 6 membered) heteroaryl. In embodiments, R¹ and R⁹ are joined to form, together with the atoms to which they are attached, $R^{9E}$-substituted or unsubstituted pyrazolyl, oxazolyl, or thiazolyl. In embodiments, R¹ and R⁹ are joined to form, together with the atoms to which they are attached, unsubstituted pyrazolyl, oxazolyl, or thiazolyl. In embodiments, the compound is represented formula IB3, IC3, ID3, or IE3:

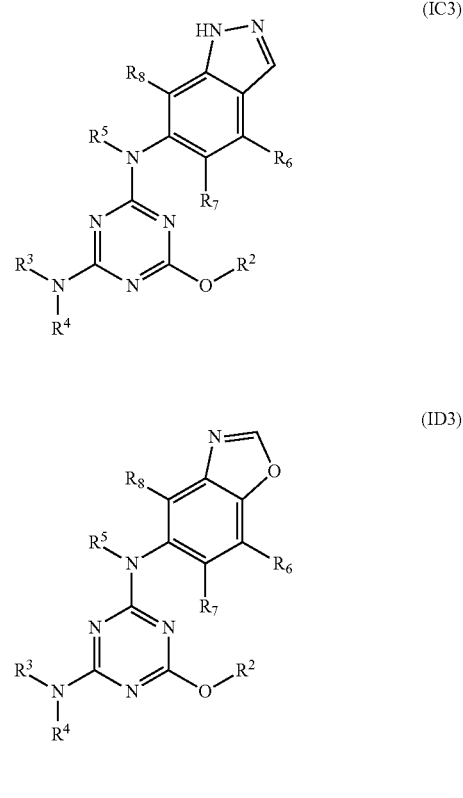

(IC3)

(ID3)

(IE3)

In embodiments, the compound is represented formula IB3A, IC3A, IB3A', IC3A', ID3A, or IE3A:

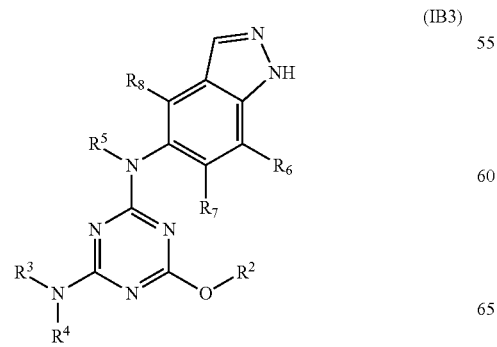

(IB3)

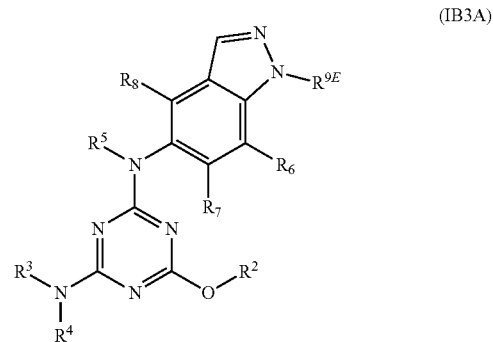

(IB3A)

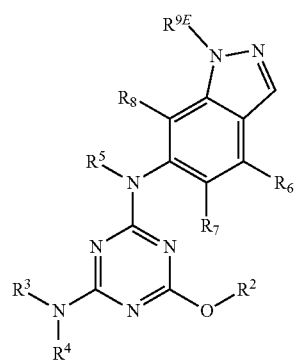
(IC3A)

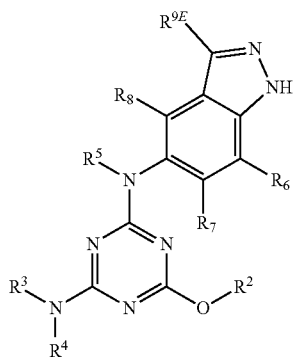
(IB3A′)

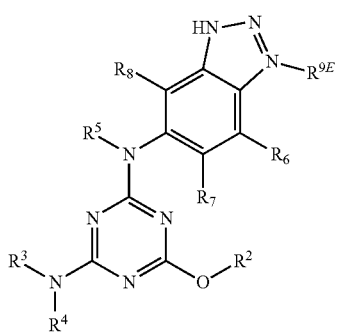
(IC3A′)

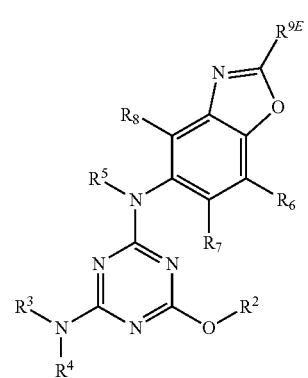
(ID3)

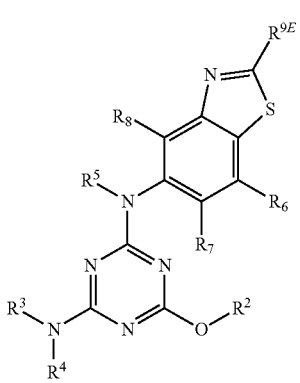
(IE3)

In embodiments, $R^8$ and $R^9$ are joined to form, together with the atoms to which they are attached, $R^{8E}$-substituted or unsubstituted (e.g. $C_3$-$C_6$) cycloalkyl, $R^{8E}$-substituted or unsubstituted (e.g. 3 to 6 membered) heterocycloalkyl, $R^{8E}$-substituted or unsubstituted (e.g. phenyl) aryl, or $R^{8E}$-substituted or unsubstituted (e.g. 5 to 6 membered) heteroaryl. In embodiments, $R^8$ and $R^9$ are joined to form, together with the atoms to which they are attached, $R^{8E}$-substituted or unsubstituted (e.g. 3 to 6 membered) heterocycloalkyl, $R^{8E}$-substituted or unsubstituted (e.g. phenyl) aryl, or $R^{8E}$-substituted or unsubstituted (e.g. 5 to 6 membered) heteroaryl. In embodiments, $R^8$ and $R^9$ are joined to form, together with the atoms to which they are attached, $R^{8E}$-substituted or unsubstituted (e.g. phenyl) aryl, or $R^{8E}$-substituted or unsubstituted (e.g. 5 to 6 membered) heteroaryl. In embodiments, $R^8$ and $R^9$ are joined to form, together with the atoms to which they are attached, $R^{8E}$-substituted or unsubstituted (e.g. 5 to 6 membered) heteroaryl. In embodiments, $R^8$ and $R^9$ are joined to form, together with the atoms to which they are attached, $R^{8E}$-substituted or unsubstituted pyrazolyl, oxazolyl, or thiazolyl. In embodiments, $R^8$ and $R^9$ are joined to form, together with the atoms to which they are attached, unsubstituted pyrazolyl, oxazolyl, or thiazolyl. In embodiments, the compound is represented formula IB4, IC4, ID4, or IE4:

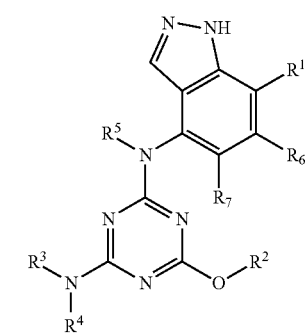
(IB4)

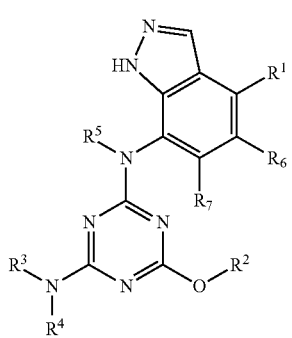
(IC4)
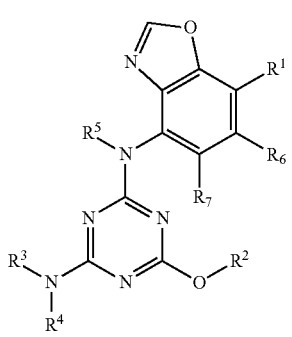
(ID4)
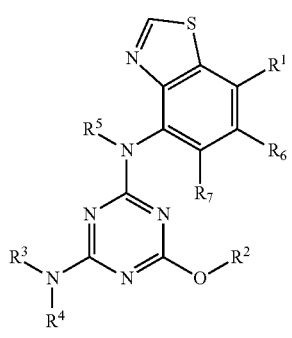
(IE4)
In embodiments, the compound is represented formula IB4A, IC4A, IB4A', IC4A', ID4, or IE4:
(IB4A)
(IC4A)
(IB4A')
(IC4A')
(ID4A)

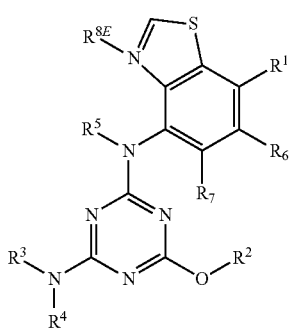

(IE4A)

$R^1$, $R^2$, $R^3$, $R^4$, $R^5$, $R^7$, $R^8$, and/or $R^9$ are as described herein. In embodiments, $R^2$ is $C_2$-$C_4$ haloalkyl, $R^3$ and $R^4$ are independently hydrogen, methyl or ethyl; $R^5$, $R^7$, $R^8$ and $R^9$ are hydrogen. In embodiments, $R^2$ is $C_2$-$C_6$ alkyl substituted with at least one fluorine; $R^3$ are $R^4$ are independently methyl or ethyl; $R^5$, $R^7$, $R^8$ and $R^9$ are hydrogen. In embodiments, $R^2$ is —$CH(CF_3)_2$ or —$CH_2(CF_2)_2H$.

In embodiments, the compound is not

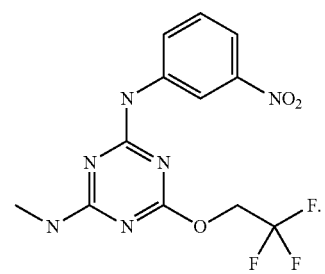 [SMILES: CNc1nc(Nc2cccc([N+](=O)[O-])c2)nc(OCC(F)(F)F)n1]

In embodiments, the compound is:

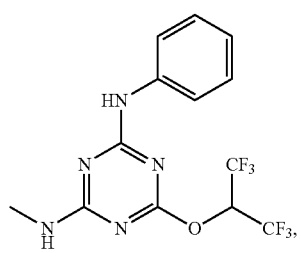

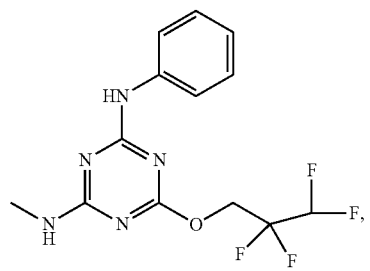

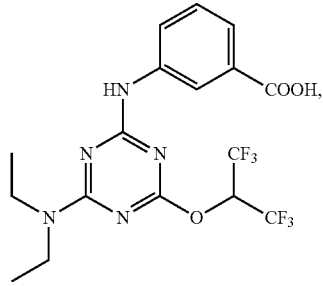

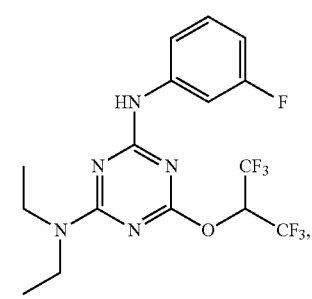

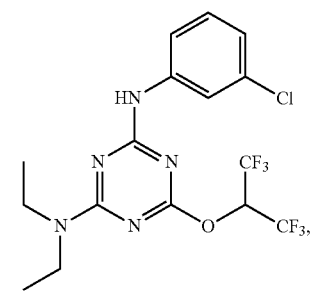

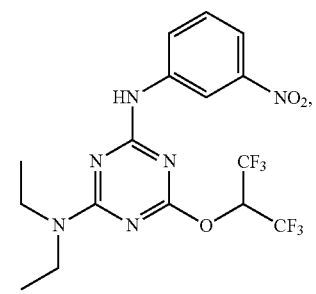

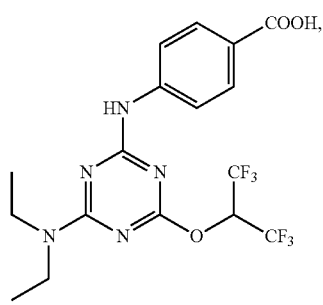

-continued
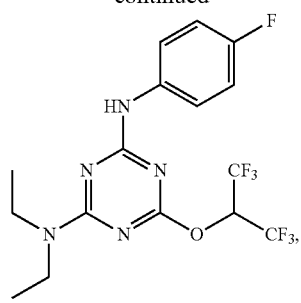
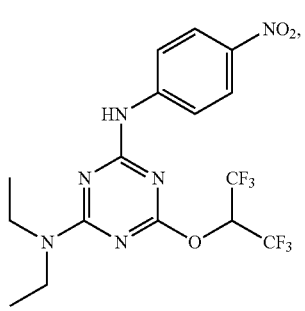
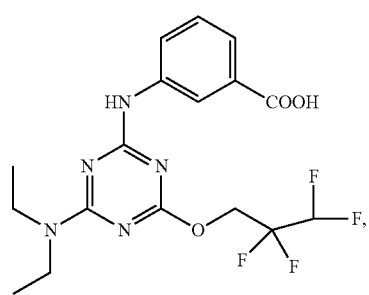
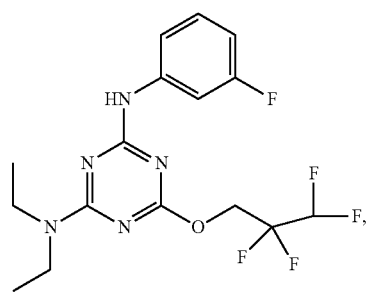
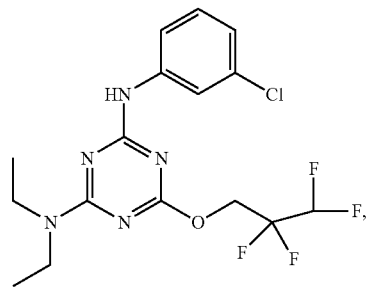
-continued
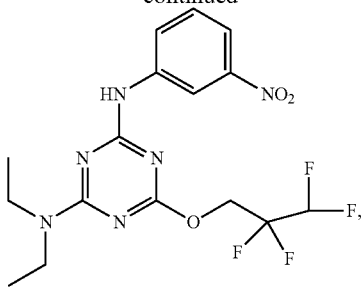
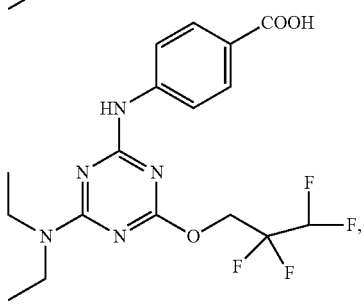
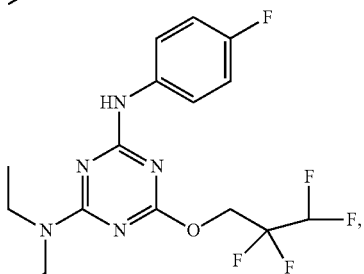
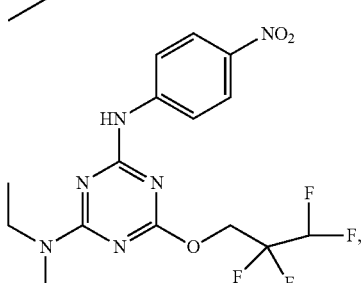
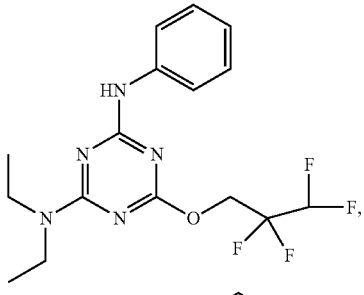
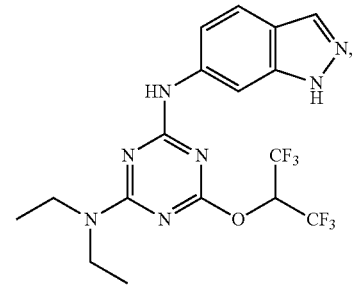

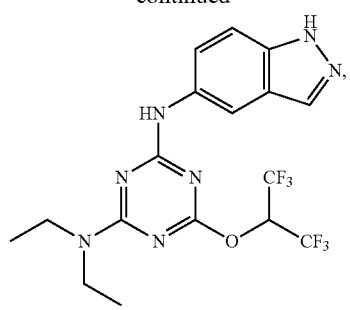

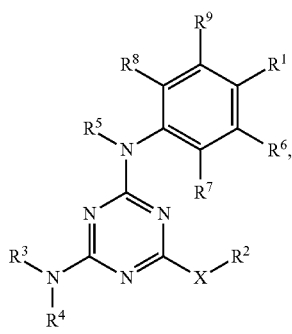

In embodiments, the compound is formula I,

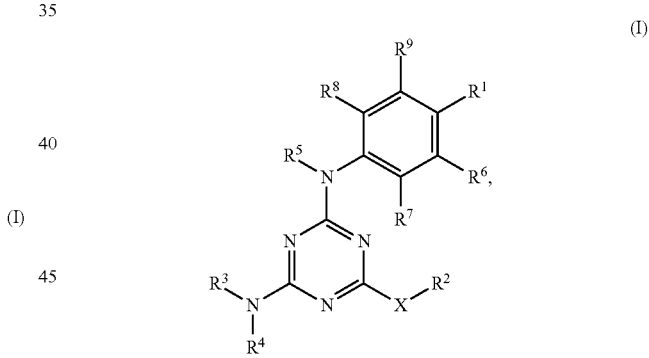

or a pharmaceutically acceptable salt thereof. In embodiments, X is —O—. In embodiments, $R^2$ is $C_2$-$C_4$ haloalkyl. In embodiments, $R^3$ is hydrogen. In embodiments, $R^4$ is —CH$_3$ or —CH$_2$CH$_3$. In embodiments, $R^1$, $R^6$, $R^7$, $R^8$ and $R^9$ are hydrogen. In embodiments, $R^2$ is substituted with at least four fluorines. In embodiments, $R^2$ is substituted with four fluorines. In embodiments, $R^2$ is —CH$_2$(CF$_2$)$_2$H. In embodiments, X is —O—; $R^2$ is —CH$_2$(CF$_2$)$_2$H; $R^3$ is hydrogen; $R^4$ is —CH$_3$ or —CH$_2$CH$_3$; and $R^1$, $R^6$, $R^7$, $R^8$ and $R^9$ are hydrogen. In embodiments, the compound is In embodiments, the compound is a compound described herein (e.g., in an aspect, embodiment, example, table, figure, scheme, appendix, or claim).

II. PHARMACEUTICAL COMPOSITIONS

Also provided herein are pharmaceutical formulations. In embodiments, the pharmaceutical formulations include the compounds described above (including all embodiments thereof) (e.g. formulae I, IA, IB1, IC1, ID1, IE1, IB1A, IC1A, IB1A', IC1A', ID1A, IE1A, IB2, IC2, ID2, IE2, IB2A, IC2A, B2A', IC2A', ID2A, IE2A, IB3A, IC3A, IB3A', IC3A', ID3A, IE3A, IB4A, IC4A, IB4A', IC4A', ID4A and IE4A) and a pharmaceutically acceptable excipient. In one aspect is a pharmaceutical composition that includes a compound described herein and a pharmaceutically acceptable excipient.

In embodiments, the pharmaceutical composition comprises a pharmaceutically acceptable excipient, and a compound of Formula I:

(I)

or a pharmaceutically acceptable salt thereof,
X, $R^1$, $R^2$, $R^3$, $R^4$, $R^5$, $R^7$, $R^8$, and $R^9$ are as described herein.

In embodiments, X is —O— or —S—. In embodiments, X is NH. In embodiments, X is —O—.

In embodiment, $R^2$ is —CX$^{2.1}$$_3$, —(CH$_2$)$_{n2}$CX$^{2.1}$$_3$ or $C_2$-$C_4$ haloalkyl. In embodiments, $R^3$, $R^4$ and $R^5$ are independently hydrogen, or substituted or unsubstituted $C_2$-$C_6$ alkyl. In embodiments, $R^1$ is hydrogen, halogen, —CF$_3$, —CCl$_3$, —CBr$_3$, —Cl$_3$, —CHF$_2$, —CH$_2F$, —CN, —NO$_2$, —C(O)R$^{1D}$, —C(O)OR$^{1D}$, —OCX$^{1.1}$$_3$, —OCHX$^{1.1}$$_2$ or substituted or unsubstituted alkyl; $R^6$ is hydrogen, halogen, —CX$^{6.1}$$_3$, —CHX$^{6.1}$$_2$, —CH$_2$X$^{6.1}$, —CN, —NO$_2$, —C(O)R$^{6D}$, —C(O)OR$^{6D}$, —OCX$^{6.1}$$_3$, —OCHX$^{6.1}$$_2$ or substituted or unsubstituted alkyl; $R^7$ is hydrogen, —CF$_3$, —CCl$_3$, —CBr$_3$, —Cl$_3$, —CHF$_2$, —CH$_2F$, —CN, —NO$_2$, —C(O)R$^{7D}$, —C(O)OR$^{7D}$, —OCX$^{7.1}$$_3$, —OCHX$^{7.1}$$_2$ or substituted or unsubstituted alkyl; $R^8$ is hydrogen, —CF$_3$, —CCl$_3$, —CBr₃, —CI₃, —CHF₂, —CH₂F, —CN, —NO₂, —C(O)R$^{8D}$, —C(O)OR$^{8D}$, —OCX$^{8.1}$₃, —OCHX$^{8.1}$₂ or substituted or unsubstituted alkyl; and R⁹ is hydrogen, halogen, —CF₃, —CCl₃, —CBr₃, —CI₃, —CHF₂, —CH₂F, —CN, —NO₂, —C(O)R$^{9D}$, —C(O)OR$^{9D}$, —OCX$^{9.1}$₃, —OCHX$^{9.1}$₂ or substituted or unsubstituted alkyl. In embodiments, R$^{1D}$, R$^{6D}$, R$^{7D}$, R$^{8D}$ and R$^{9D}$ are independent hydrogen or methyl. In embodiments, R⁷ and R⁸ are independently hydrogen.

In embodiments, the compound is formula IA:

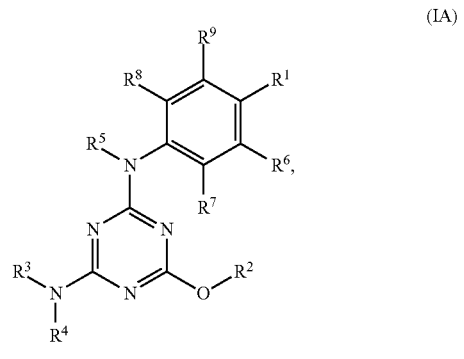

(IA)

wherein R¹, R², R³, R⁴, R⁵, R⁶, R⁷, R⁸, and R⁹ are as described herein.

In embodiments, R² is —CX$^{2.1}$₃, —(CH₂)$_{n2}$CX$^{2.1}$₃, or C₂-C₄ haloalkyl. In embodiments, R³, R⁴ and R⁵ are independently hydrogen, substituted or unsubstituted alkyl. In embodiments, R¹ is hydrogen, halogen, —CX$^{1.1}$₃, —CHX$^{1.1}$₂, —CH₂X$^{1.1}$, —CN, —NO₂, —C(O)R$^{1D}$, —C(O)OR$^{1D}$, —OCX$^{1.1}$₃, —OCHX$^{1.1}$₂ or substituted or unsubstituted alkyl; R⁶ is hydrogen, halogen, —CX$^{6.1}$₃, —CHX$^{6.1}$₂, —CH₂X$^{6.1}$, —CN, —NO₂, —C(O)R$^{6D}$, —C(O)OR$^{6D}$, —OCX$^{6.1}$₃, —OCHX$^{6.1}$₂ or substituted or unsubstituted alkyl; R⁷ is hydrogen, —CX$^{7.1}$₃, —CHX$^{7.1}$₂, —CH₂X$^{7.1}$, —CN, —NO₂, —C(O)R$^{7D}$, —C(O)OR$^{7D}$, —OCX$^{7.1}$₃, —OCHX$^{7.1}$₂ or substituted or unsubstituted alkyl; R⁸ is hydrogen, —CX$^{8.1}$₃, —CHX$^{8.1}$₂, —CH₂X$^{8.1}$, —CN, —NO₂, —C(O)R$^{8D}$, —C(O)OR$^{8D}$, —OCX$^{8.1}$₃, —OCHX$^{8.1}$₂ or substituted or unsubstituted alkyl; and R⁹ is hydrogen, halogen, —CX$^{9.1}$₃, —CHX$^{9.1}$₂, —CH₂X$^{9.1}$, —CN, —NO₂, —C(O)R$^{9D}$, —C(O)OR$^{9D}$, —OCX$^{9.1}$₃, —OCHX$^{9.1}$₂ or substituted or unsubstituted alkyl. In embodiments, R⁷ and R⁸ are independently hydrogen. In embodiments, R³ and R⁴ substituted or unsubstituted alkyl; R⁵ are independently hydrogen; R⁶ is hydrogen, halogen, —CX$^{6.1}$₃, —CHX$^{6.1}$₂, —CH₂X$^{6.1}$, —CN, —C(O)R$^{6D}$, —C(O)OR$^{6D}$, —OCX$^{6.1}$₃, —OCHX$^{6.1}$₂ or substituted or unsubstituted alkyl; R⁷ is hydrogen, —CX$^{7.1}$₃, —CHX$^{7.1}$₂, —CH₂X$^{7.1}$, —CN, —NO₂, —C(O)R$^{7D}$, —C(O)OR$^{7D}$, —OCX$^{7.1}$₃, —OCHX$^{7.1}$₂ or substituted or unsubstituted alkyl; R⁸ is hydrogen, —CX$^{8.1}$₃, —CHX$^{8.1}$₂, —CH₂X$^{8.1}$, —CN, —NO₂, —C(O)R$^{8D}$, —C(O)OR$^{8D}$, —OCX$^{8.1}$₃, —OCHX$^{8.1}$₂ or substituted or unsubstituted alkyl; and R⁹ is hydrogen, halogen, —CX$^{9.1}$₃, —CHX$^{9.1}$₂, —CH₂X$^{9.1}$, —CN, —C(O)R$^{9D}$, —C(O)OR$^{9D}$, —OCX$^{9.1}$₃, —OCHX$^{9.1}$₂ or substituted or unsubstituted alkyl; wherein R$^{1D}$, R$^{6D}$, R$^{7D}$, R$^{8D}$ and R$^{9D}$ are independently hydrogen or methyl, and X$^{1.1}$, X$^{2.1}$, X$^{6.1}$, X$^{7.1}$, X$^{8.1}$ and X$^{9.1}$ are independently are —F. In embodiments, R³ and R⁴ are independently methyl or ethyl. In embodiments, R¹ is hydrogen, halogen, —NO₂, or —COOH; R⁵ is hydrogen; R⁶ is hydrogen, halogen —NO₂, or —COOH; R⁷ and R⁸ are independently hydrogen; and R⁹ is hydrogen, halogen NO₂, or —COOH. In embodiments, wherein R³ and R⁴ are independently hydrogen, methyl or ethyl. In embodiments, wherein R² is C₂-C₄ alkyl substituted with at least one fluorine. In embodiments, R¹, R⁶, R⁷, R⁸ and R⁹ are independently hydrogen.

In embodiments, R¹ and R⁶ are joined to form, together with the atoms to which they are attached, a substituted or unsubstituted pyrazolyl, oxazolyl, or thiazolyl; R² is C₂-C₄ haloalkyl; R³ and R⁴ are independently hydrogen, methyl or ethyl. In embodiments, the compound is represented with Formula IB, IC, ID, or IE:

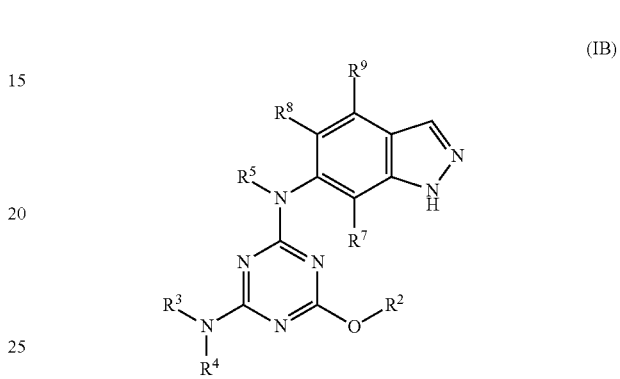

(IB)

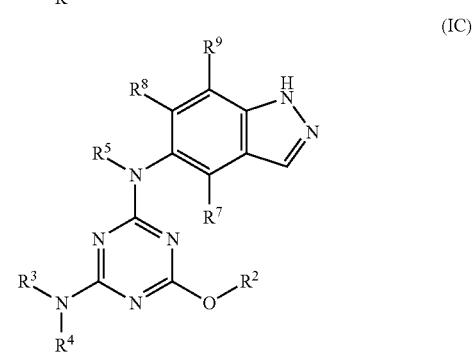

(IC)

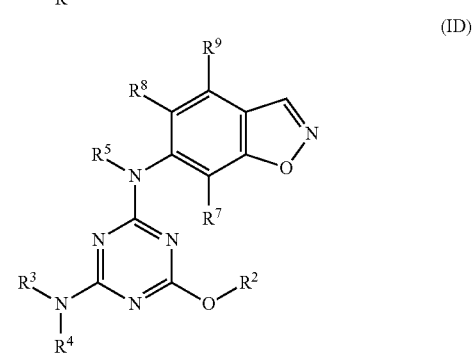

(ID)

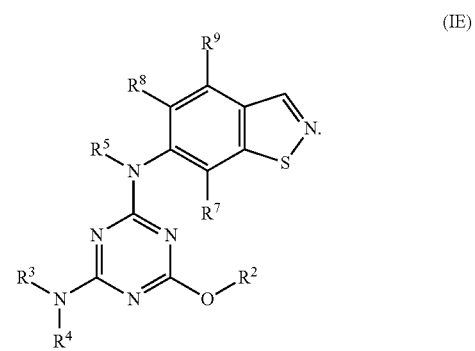

(IE)

In embodiments, $R^5$, $R^7$, $R^8$ and $R^9$ are independently hydrogen. In embodiments, $R^2$ is —CH(CF$_3$)$_2$ or —CH$_2$(CF$_2$)$_2$H.
In embodiments, the pharmaceutical composition comprises a compound selected from:
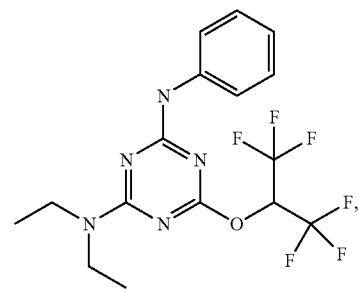
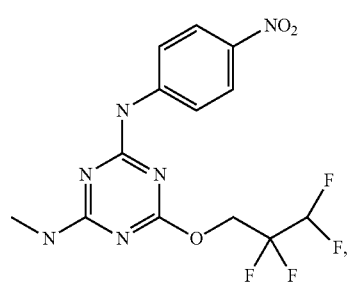
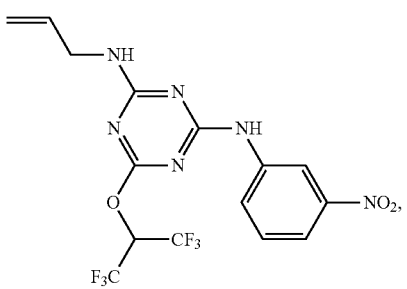
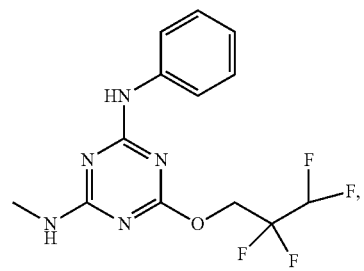 [SMILES: CNc1nc(Nc2ccccc2)nc(OCC(F)(F)C(F)F)n1]
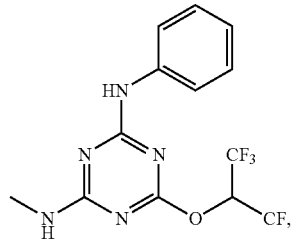
-continued
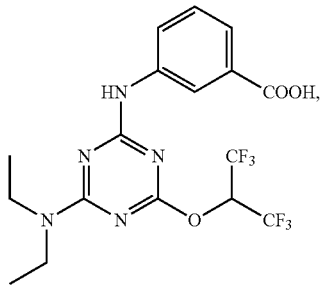
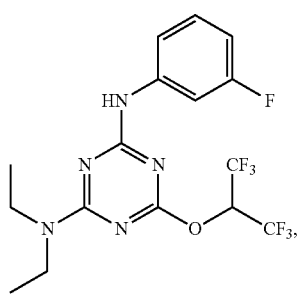
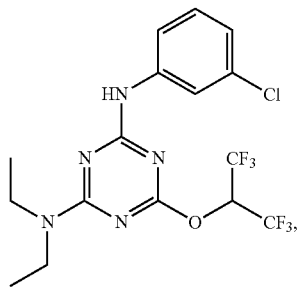
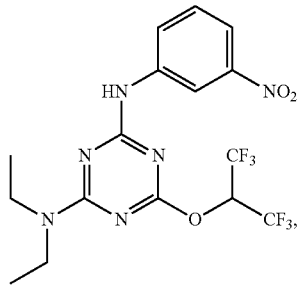
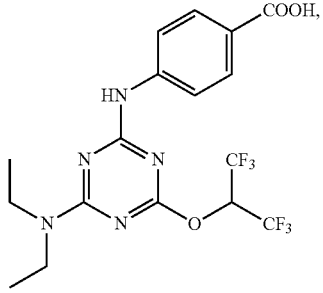

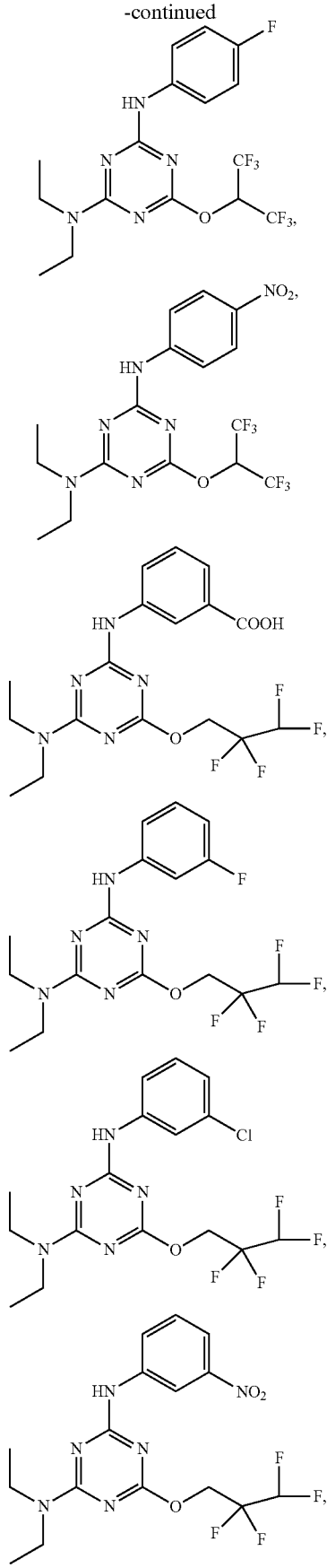
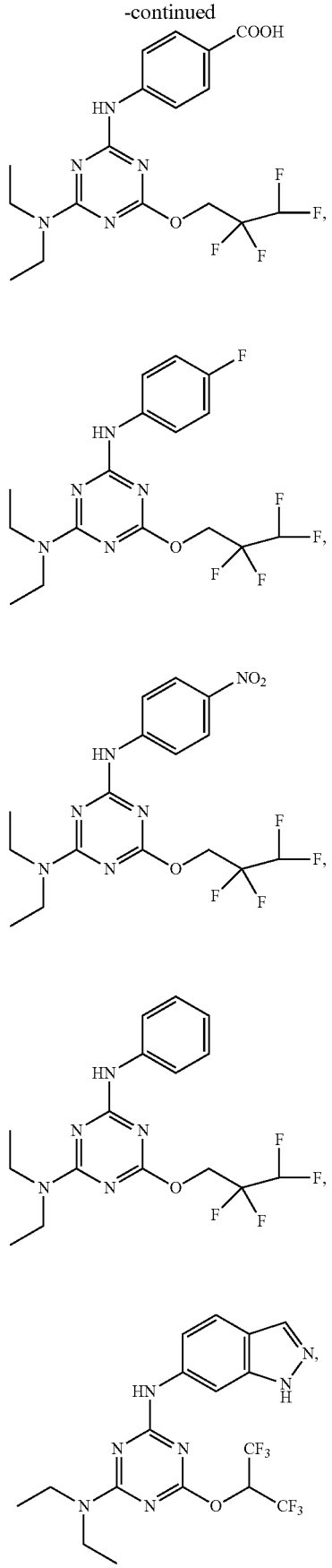

-continued

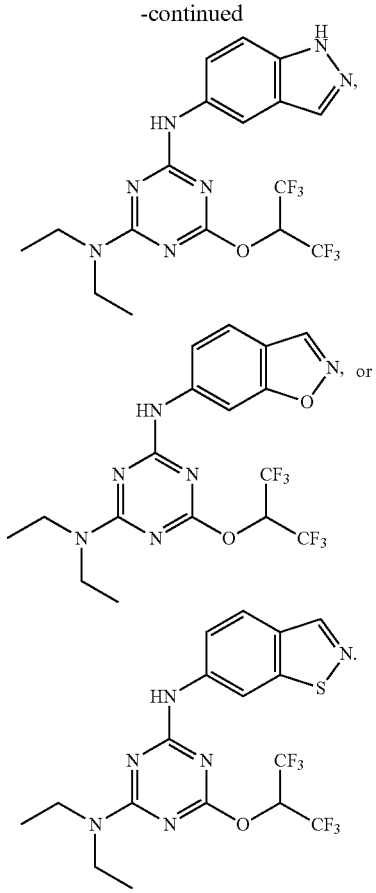

In embodiments of the pharmaceutical compositions, the compound, or pharmaceutically acceptable salt thereof, is included in a therapeutically effective amount.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In embodiments, liquid form preparation or solid form preparation comprising the compounds as described herein may not include DMSO in the formulations. In embodiments, the liquid form preparation may not include solvating agent such as DMSO and the compound included in the preparation may maintain the same or substantially same amounts of dissolved or suspended compounds, for example, greater than about 50 wt %, 55 wt %, 60 wt %, 65 wt %, 70 wt %, 75 wt %, 80 wt %, 85 wt %, 90 wt %, 95 wt %, or 99 wt % of the dissolved or suspended compounds which are being prepared in the liquid form preparation including DMSO. In some embodiments, the liquid form preparation or solid form preparation not including DMSO may exhibit the same or substantially same penetration of the compound across mucus, mucous membrane or skin, for example, greater than about 50%, 55%, 60%, 65%, 70%, 75%, 80%, 85%, 90%, 95%, or 99% of penetration of the compounds which are prepared in the formulation including DMSO, when administered topically, transmucousally or transdermally.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects.

Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. METHODS OF ACTIVATING

Further provided herein are methods of activating a Cystic Fibrosis Transmembrane Conductance Regulator (CFTR). The method includes contacting the CFTR with an effective amount of a compound described herein, thereby activating the CFTR. In one aspect, the method includes contacting CFTR with an effective amount of the compound of Formula I:

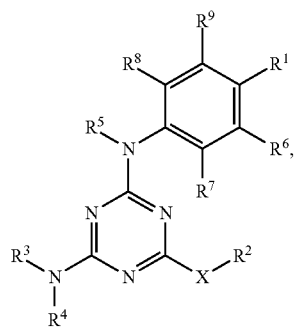

(I)

or a pharmaceutically acceptable salt thereof. X, $R^1$, $R^2$, $R^3$, $R^4$, $R^5$, $R^6$, $R^7$, $R^8$ and $R^9$ are described herein.

In embodiments, the method includes contacting CFTR with an effective amount of the compound as described herein thereby activating CFTR. The contacting may be performed in vitro. The contacting may be performed in vivo.

IV. METHODS OF TREATING

Further provided herein are methods of treating a disease or disorder in a subject in need thereof by administering to said subject an effective amount of a compound as described herein (e.g. a compound of formula I):

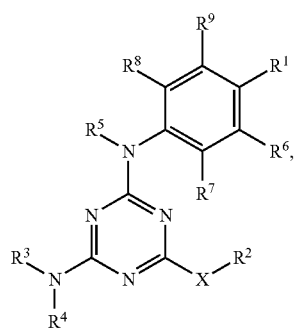

(I)

or a pharmaceutically acceptable salt thereof. X, $R^1$, $R^2$, $R^3$, $R^4$, $R^5$, $R^6$, $R^7$, $R^8$ and $R^9$ are described herein.

In one aspect is a method of treating constipation in a subject in need thereof, the method including administering to the subject an effective amount described compound as described herein (e.g. a compound of formula I). In another aspect, is a method of treating a dry eye disorder in a subject in need thereof, the method including administering to the subject an effective amount of a compound as described herein (e.g. a compound of formula I). In yet another aspect, is a method of increasing lacrimation in a subject in need thereof, the method including administering to the subject an effective amount a compound as described herein (e.g. a compound of formula I).

In one aspect, provided is a method of treating a cholestatic liver disease in a subject in need thereof, including administering to the subject an effective amount a compound as described herein (e.g. a compound of formula I). In another aspect, provided is a method of treating a pulmonary disease or disorder in a subject in need thereof, including administering to the subject an effective amount of as described herein (e.g. a compound of formula I). In embodiments, the pulmonary disease or disorder is chronic obstructive pulmonary disease (e.g. bronchitis, asthma, cigarette smoke-induced lung dysfunction).

Other Aspects

Provided herein, in another aspect, are compositions and methods of treating a disease. The following definitions and embodiments apply to only to the compounds of formula (pI), this section (i.e. section V) and embodiments P1 to P28 listed herein.

For purposes of this section, the term "alkyl" refers to and includes linear or branched univalent hydrocarbon structures and combination thereof, which may be fully saturated, mono- or polyunsaturated, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of saturated $C_1$-$C_4$ alkyl include methyl ($CH_3$), ethyl ($C_2H_5$), propyl ($C_3H_7$) and butyl ($C_4H_9$). Examples of saturated $C_1$-$C_6$ alkyl include methyl ($CH_3$), ethyl ($C_2H_5$), propyl ($C_3H_7$), butyl ($C_4H_9$), pentyl ($C_5H_{11}$) and hexyl ($C_6H_{13}$).

An alkyl group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and heteroaryl, and other functional groups known in the art. A "perfluoroalkyl" refers to an alkyl group where every hydrogen atom is replaced with a fluorine atom. Examples of saturated $C_1$-$C_6$ perfluoroalkyl include trifluoromethyl ($CF_3$), pentafluoroethyl ($C_2F_5$), heptafluoropropyl ($C_3F_7$), nonafluorobutyl ($C_4F_9$), undecafluoropentyl ($C_5F_{11}$) and tridecafluorohexyl ($C_6F_{13}$).

For purposes of this section, the term "cycloalkyl" refers to and includes cyclic univalent hydrocarbon structures, which may be fully saturated, mono- or polyunsaturated, having the number of carbon atoms designated (i.e., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

For purposes of this section, the term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

For purposes of this section, the term "aryl" refers to and includes polyunsaturated aromatic hydrocarbon substituents. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

For purposes of this section, the term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

Cycloalkyl, aryl, heterocyclyl and heteroaryl groups as referred to within this section may also be substituted with one or more substituents, such as radicals detailed herein, for example, fluoro, chloro, bromo, iodo, hydroxyl, alkoxy, thio, amino, acylamino, alkoxycarbonylamido, carboxyl, acyl, alkoxycarbonyl, sulfonyl, alkyl, cycloalkyl, aryl, heterocyclyl and heteroaryl, and other functional groups known in the art.

For purposes of this section, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in *Remington's Pharmaceutical Sciences* 16th edition, Osol, A. Ed. (1980).

As used in this section, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used in this section, the phrase "delaying development of a disease" means to defer, hinder, slow, retard, stabilize, and/or postpone development of the disease (such as constipation, dry eye, pulmonary disease or disorder, lung disease or liver disease). This delay can be of varying lengths of time, depending on the history of the disease and/or individual being treated. As is evident to one skilled in the art, a sufficient or significant delay can, in effect, encompass prevention, in that the individual does not develop the disease.

As used in this section, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this section, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used in this section, "in conjunction with" refers to administration of one treatment modality in addition to another treatment modality. As such, "in conjunction with" refers to administration of one treatment modality before, during or after administration of the other treatment modality to the individual.

Unless clearly indicated otherwise, for purposes of this section, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The aspects described in this section may find use in both human medicine and in the veterinary context.

As used in this section and in the appended embodiments P1-P25, the singular forms "a," "an," and "the" include plural reference unless the context clearly indicates otherwise.

It is understood that aspect and variations of the aspects described in this section include "consisting" and/or "consisting essentially of" aspects and variations.

Constipation therapy includes laxatives that increase stool bulk, such as soluble fiber; create an osmotic load, such as polyethylene glycol; or stimulate intestinal contraction, such as the diphenylmethanes. There are also surface laxatives that soften stool such as docusate sodium and probiotics such as *Lactobacillus paracasei* [3]. The FDA-approved drug linaclotide, a peptide agonist of the guanylate cyclase C receptor, acts by inhibiting visceral pain, stimulating intestinal motility, and increasing intestinal secretion [4, 5]. A second approved drug, lubiprostone, a prostaglandin E analog, is thought to activate a putative enterocyte ClC-2 channel [6], though the mechanistic data are less clear. Despite the wide range of therapeutic options, there is a continued need for safe and effective drugs to treat constipation.

Without wishing to be bound by theory, in embodiments of this section, activation of the cystic fibrosis transmembrane regulator (CFTR) chloride channel drives fluid secretion in the intestine, which maintains lubrication of luminal contents. It is hypothesized that direct activation of CFTR may cause fluid secretion and reverse excessive dehydration of stool found in constipation.

Intestinal fluid secretion involves active $Cl^-$ secretion across the enterocyte epithelium through the basolateral membrane $Na^+/K^+/2Cl^-$ cotransporter (NKCC1) and the luminal membrane cystic fibrosis transmembrane regulator (CFTR) $Cl^-$ channel and $Ca^{2+}$-activated $Cl^-$ channel (CaCC). The electrochemical and osmotic forces created by $Cl^-$ secretion drive $Na^+$ and water secretion [7]. In cholera and Traveler's diarrhea CFTR is strongly activated by bacterial enterotoxins through elevation of intracellular cyclic nucleotides [8, 9]. CFTR is an attractive target to increase intestinal fluid secretion in constipation as it is robustly expressed throughout the intestine and its activation strongly increases intestinal fluid secretion. An activator targeting CFTR directly is unlikely to produce the massive, uncontrolled intestinal fluid secretion seen in cholera because the enterotoxins in cholera act irreversibly to produce sustained elevation of cytoplasmic cAMP, which not only activates CFTR but also basolateral $K^+$ channels, which increase the electrochemical driving force for $Cl^-$ secretion; cholera enterotoxins also inhibit the luminal NHE3 $Na^+/H^+$ exchanger involved in intestinal fluid absorption [10, 11].

Motivated by these considerations and the continuing need for safe and effective drug therapy of constipation, the identification and characterization of a nanomolar-potency, CFTR-targeted small-molecule activators with pro-secretory action in intestine and efficacy in constipation are reported herein.

By high-throughput screening a nanomolar-affinity, small-molecule CFTR activator, $CFTR_{act}$-J027 was identified and demonstrated to have pro-secretory action in mouse intestine and efficacy in normalizing stool output in a loperamide-induced mouse model of constipation. Constipation remains a significant clinical problem in outpatient and hospitalized settings. Opioid-induced constipation is a common adverse effect in patients after surgery, undergoing chemotherapy and with chronic pain.

CFTR-targeted activation adds to the various mechanisms of action of anti-constipation therapeutics. It is notable that pure CFTR activation is able to produce a robust $Cl^-$ current and fluid secretion response in the intestine, without causing global elevation of cyclic nucleotide concentration, direct stimulation of intestinal contractility, or alteration of intestinal fluid absorption. Linaclotide, a peptide agonist of the guanylate cyclase C receptor that increases intestinal cell cGMP concentration. Linaclotide inhibits activation of colonic sensory neurons and activates motor neurons, which reduces pain and increases intestinal smooth muscle contraction; in addition, elevation in cGMP concentration in enterocytes may activate CFTR and have a pro-secretory action [4, 5]. A second approved drug, the prostaglandin E analog lubiprostone, is thought to activate a putative enterocyte ClC-2 channel [6], though the mechanistic data are less clear. Compared with these drugs, a pure CFTR activator has a single, well-validated mechanism of action and does not produce a global cyclic nucleotide response in multiple cell types. Of note, linaclotide and lubiprostone showed limited efficacy in clinical trials. Linaclotide was effective in ~20% of chronic constipation patients of whom ~5% also responded to placebo [15], and lubiprostone was effective in ~13% of IBS-C patients of whom ~7% responded to placebo [16]. Based on our mouse data showing substantially greater efficacy of $CFTR_{act}$-J027 compared to supramaximal doses of linaclotide or lubiprostone, we speculate that CFTR activators may have greater efficacy in clinical trials.

$CFTR_{act}$-J027 is more potent for activation of wildtype CFTR than VX-770 (ivacaftor), the FDA-approved drug for treatment of cystic fibrosis (CF) caused by certain CFTR gating mutations. In FRT cells expressing wild-type CFTR, short-circuit current measurement showed nearly full activation of CFTR by $CFTR_{act}$-J027 at 3 µM whereas VX-770 maximally activated CFTR by only 15%. However, $CFTR_{act}$-J027 was substantially less potent than ivacaftor as a 'potentiator' of defective chloride channel gating of the most common CF-causing mutation, ΔF508, which is not unexpected, as potentiator efficacy in CF is mutation-specific. In addition to its potential therapeutic utility for constipation, a small-molecule activator of wildtype CFTR may be useful for treatment of chronic obstructive pulmonary disease and bronchitis, asthma, cigarette smoke-induced lung dysfunction, dry eye and cholestatic liver disease [17-19].

Substituted quinoxalinones were reported as selective antagonists of the membrane efflux transporter multiple-drug-resistance protein 1 [20]. Quinoxalinones have also been reported to show anti-diabetic activity by stimulating insulin secretion in pancreatic INS-1 cells [21], and inhibitory activity against serine proteases for potential therapy of thrombotic disorders [22]. Recently, quinoxalinones have been reported to inhibit aldose reductase [23]. These reports suggest that the quinoxalinone scaffold has drug-like properties. Synthetically, quinoxalinone can be prepared in one to four steps from commercially available starting materials [24], which allows facile synthesis of targeted analogs.

In addition to compound-specific off-target actions, the potential side-effects profile of a CFTR activator could include pro-secretory activity in the airway/lungs and various glandular and other epithelia. Off-target effects for constipation therapy could be limited by oral administration of a CFTR activator with limited intestinal absorption and/or rapid systemic clearance to minimize systemic exposure. $CFTR_{act}$-J027 when administered orally at a high dose (10 mg/kg) showed very low bioavailability with blood levels well below the $EC_{50}$ for CFTR activation, which may be due to first-pass effect as evidenced its rapid in vitro metabolism in liver microsomes. $CFTR_{act}$-J027 did not show significant in vitro cytotoxicity at a concentration of 25 µM, >100-fold greater than its $EC_{50}$ for CFTR activation, or in vivo toxicity in mice in a 7-day study at a maximal efficacious dose that normalized stool output in the loperamide model of constipation. The potentially most significant off-target action, stimulation of lung/airway fluid secretion, was not seen as evidenced by normal lung water content in the 7-day treated mice. These limited toxicity studies offer proof of concept for application of a CFTR activator in constipation.

In summary, the data presented herein demonstrate the pro-secretory action of a CFTR activator in mouse intestine for use in treatment of various types of constipation, which could include opioid-induced constipation, chronic idiopathic constipation, and irritable bowel syndrome with constipation predominance.

Dry eye disorders, including Sjögren's syndrome, constitute a common problem in the aging population with limited effective therapeutic options available. The cAMP-activated Cl⁻ channel CFTR (cystic fibrosis transmembrane conductance regulator) is a major pro-secretory chloride channel at the ocular surface. It was investigated whether compounds that target CFTR can correct the abnormal tear film in dry eye. Small-molecule activators of human wild-type CFTR identified by high-throughput screening were evaluated in cell culture and in vivo assays to select compounds that stimulate Cl⁻-driven fluid secretion across the ocular surface in mice. An aminophenyl-1,3,5-triazine, $CFTR_{act}$-K089, fully activated CFTR in cell cultures with $EC_{50}$ ~250 nM and produced a ~8.5 mV hyperpolarization in ocular surface potential difference. When delivered topically, $CFTR_{act}$-K089 doubled basal tear secretion for four hours and had no effect in CF mice. $CFTR_{act}$-K089 showed sustained tear film bioavailability without detectable systemic absorption. In a mouse model of aqueous-deficient dry eye produced by lacrimal gland excision, topical administration of 0.1 nmol $CFTR_{act}$-K089 three times daily restored tear secretion to basal levels and fully prevented the corneal epithelial disruption seen in vehicle-treated controls. The data presented herein demonstrate potential utility of CFTR-targeted activators as a novel pro-secretory treatment for dry eye.

Ninety-four percent of surveyed ophthalmologists believe that additional treatments are needed for moderate-to-severe dry eye (7).

The ocular surface is a collection of anatomically continuous epithelial and glandular tissues that are functionally linked to maintain the tear film (8). While lacrimation contributes the bulk of reflex tearing, the cornea and conjunctiva regulate basal tear volume and composition. The principal determinants of water movement across the ocular surface into the tear film include apical chloride (Cl⁻) secretion through cAMP- and calcium ($Ca^{2+}$)-dependent Cl⁻ transporters, and sodium ($Na^+$) absorption largely though the epithelial $Na^+$ channel (ENaC).

With regard to pro-secretory candidates for dry eye therapy, an ENaC inhibitor, P321, has recently entered phase ½ studies (9). Diquafosol, a UTP analog that targets surface epithelial $P2Y_2$ receptors and stimulates Cl⁻ and mucin secretion by $Ca^{2+}$ signaling (10), is approved for dry eye in Japan (11, 12) but failed phase III trials in the United States.

The cystic fibrosis transmembrane conductance regulator (CFTR) is a cAMP-activated Cl⁻ channel expressed in some secretory epithelial cells, including those in cornea and conjunctiva (14-16). We found substantial capacity for active CFTR-facilitated Cl⁻ at the ocular surface in mice (21, 22), as subsequently shown in rat conjunctiva (23), providing a rational basis for investigation of CFTR activators as a pro-secretory strategy for dry eye. The only clinically approved CFTR activator, VX-770 (ivacaftor), is indicated for potentiating the channel gating of certain CFTR mutants causing CF, but only weakly activates wild-type CFTR (24, 25).

Novel small-molecule activators of wild-type CFTR identified by high-throughput screening as potential topical therapy for dry eye were evaluated to demonstrate efficacy of newly identified CFTR activator(s) in a mouse model of dry eye.

The potential utility of small-molecule activators of CFTR for dry eye therapy was investigated. After several prior development failures, dry eye remains an unmet need in ocular disease. It was hypothesized that CFTR-targeted pro-secretory compounds could normalize tear film volume and ocular surface properties in dry eye (21, 22). In dry eye disorders, tear film hyperosmolarity stimulates pro-inflammatory signaling, secretion of cytokines and metalloproteinases, and disruption of corneal epithelial cell integrity (35-38). By minimizing tear film hyperosmolarity, CFTR activation is predicted to prevent these downstream ocular surface changes.

Small-molecule CFTR activators were identified by high-throughput screening that produced sustained Cl⁻-driven aqueous fluid secretion across the ocular surface by a mechanism involving direct CFTR activation rather than upstream cAMP signaling. The rationale to choose compounds that activate CFTR directly was to minimize potential off-target effects of generalized cAMP stimulation and to reduce the likelihood of tachyphylaxis for compounds targeting signaling receptors. These compounds had low-nanomolar $EC_{50}$ for activation of human CFTR in vitro and produced full activation at higher concentrations. Large CFTR-dependent PD hyperpolarizations and tear hypersecretion were demonstrated in mice.

Substantial compound activities in mice and humans will facilitate translation of data here to humans.

It was found that $CFTR_{act}$-K089 restored tear secretion and prevented epithelial disruption in an experimental mouse model of lacrimal insufficiency. CFTR activators may be particularly suited for disorders of the lacrimal gland, such as primary Sjögren's syndrome, by stimulating fluid transport across the intact corneal and conjunctival epithelia. CFTR activators probably exert their major pro-secretory effect at the ocular surface, although there is indirect for CFTR expression and function in lacrimal gland (39-42). Direct stimulation of lacrimal secretion is unlikely in the studies here because of minimal compound penetration to lacrimal tissues following topical delivery, and the demonstrated compound efficacy in a model of lacrimal insufficiency. At the ocular surface, the conjunctiva probably contributes the bulk of fluid secretion given its much larger surface area compared to cornea (43).

Alternative pro-secretory therapies targeting different ocular surface ion channels have been considered. The only FDA-approved CFTR activator, VX-770, was developed as a "potentiator" to treat CF by correcting the channel gating of certain CFTR mutations (44). However, VX-770 showed relatively little activity against wild-type CFTR in cell cultures and in mice in vivo. Chronic application of VX-770 may also diminish CFTR functional expression (24) and cause cataracts (seen in juvenile rats; ref. 42), which is likely an off-target effect because CFTR is not expressed in lens.

An indirect agonist of $Ca^{2+}$-activated Cl⁻ channel(s), diquafosol, augments both aqueous and mucin secretion. However, diquafosol failed phase III trials, likely due to transient induced $Ca^{2+}$ elevation and Cl⁻ channel activation, producing minimal net fluid secretion. CFTR activators, which produce sustained tear fluid secretion, overcome this limitation. $CFTR_{act}$-K089 and $CFTR_{act}$-J027 showed favorable pharmacodynamics and could be conveniently administered topically several times daily in a standard ophthalmic formulation.

The data presented herein show that CFTR activation alone facilitates sustained outward Cl⁻ flux and fluid secretion, suggesting that basal $K^+$ conductance, without augmented cyclic nucleotide or $Ca^{2+}$ signaling, is sufficient to support ocular surface fluid transport. Still, the potential synergy of a CFTR agonist and a $K^+$ channel activator or an ENaC inhibitor could be explored to further increase tear secretion for dry eye therapy.

The efficacy of $CFTR_{act}$-K089 in a clinically relevant mouse model of aqueous-deficient dry eye disease was demonstrated for topical, pro-secretory CFTR activator therapy to restore basal tear secretion and prevent ocular surface pathology. Compared with immunosuppressive approaches, CFTR activation has the advantage of addressing an early event in dry eye pathogenesis. Our data thus support the development potential of CFTR activators as first-in-class dry eye therapy.

Examples herein provide further disclosure on aspects and embodiments of this section.

Although the foregoing section has been described in some detail by way of illustration and example for purposes of clarity of understanding, it is apparent to those skilled in the art that certain minor changes and modifications will be practiced in light of the above teaching. Therefore, the description and examples should not be construed as limiting the scope of any invention described herein.

All references cited herein, including patent applications and publications, are hereby incorporated by reference in their entirety.

Embodiments contemplated herein include embodiments P1 to P28 following.

Embodiment P1

A pharmaceutical composition, comprising a pharmaceutically acceptable excipient, and a compound of Formula I:

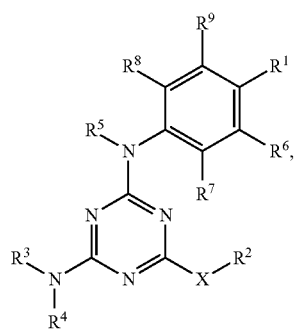

(I)

or a pharmaceutically acceptable salt thereof, wherein: X is O, NH or S; n1 is independently an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$ and $X^{9.1}$ are independently —Cl, —Br, —I or —F; with the proviso that when X is O; $R^2$ is —(CH$_2$)$_{n1}$CX$^{2.1}_3$; n1 is 1; $X^{2.1}$ is fluorine; $R^3$ is hydrogen; and $R^4$ is methyl, then $R^6$ is not —NO$_2$; and when X is O; $R^2$ is —(CH$_2$)$_{n1}$CX$^{2.1}_3$; n1 is 1; $X^{2.1}$ is fluorine; $R^3$ is hydrogen; and $R^4$ is methyl, then $R^9$ is not —NO$_2$.

Embodiment P2

The pharmaceutical composition of embodiment P1, wherein: X is O; $R^1$ is hydrogen, halogen, —CX$^{1.1}_3$, —CHX$^{1.1}_2$, —CH$_2$X$^{1.1}$, —CN, —N(O)$_{m1}$, —C(O)R$^{1D}$, —C(O)OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; $R^3$, $R^4$ and $R^5$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, —CX$^{6.1}_3$, —CHX$^{6.1}_2$, —CH$_2$X$^{6.1}$, —CN, —N(O)$_{m1}$, —C(O)R$^{6D}$, —C(O)OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; $R^7$ is hydrogen, halogen, —CX$^{7.1}_3$, —CHX$^{7.1}_2$, —CH$_2$X$^{7.1}$, —CN, —N(O)$_{m1}$, —C(O)R$^{7D}$, —C(O)OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; $R^8$ is hydrogen, halogen, —CX$^{8.1}_3$, —CHX$^{8.1}_2$, —CH$_2$X$^{8.1}$, —CN, —N(O)$_{m1}$, —C(O)R$^{8D}$, —C(O)OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl; and $R^9$ is hydrogen, halogen, —CX$^{9.1}_3$, —CHX$^{9.1}_2$, —CH$_2$X$^{9.1}$, —CN, —N(O)$_{m1}$, —C(O)R$^{9D}$, —C(O)OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, or substituted or unsubstituted heteroaryl.

Embodiment P3

The pharmaceutical composition of embodiment P1, wherein: X is O; $R^1$ is hydrogen, halogen, —CX$^{1.1}_3$, —CHX$^{1.1}_2$, —CH$_2$X$^{1.1}$, —CN, —N(O)$_{m1}$, —C(O)R$^{1D}$, —C(O)OR$^{1D}$, —OCX$^{1.1}_3$, —OCHX$^{1.1}_2$ or substituted or unsubstituted alkyl; $R^2$ is hydrogen, —CX$^{2.1}_3$, CHX$^{2.1}_2$, —(CH$_2$)$_{n1}$CX$^{2.1}_3$, substituted or unsubstituted alkyl, substituted or unsubstituted aryl or haloalkyl; $R^3$, $R^4$ and $R^5$ are independently hydrogen, substituted or unsubstituted alkyl or substituted or unsubstituted aryl; $R^6$ is hydrogen, halogen, —CX$^{6.1}_3$, —CHX$^{6.1}_2$, —CH$_2$X$^{6.1}$, —CN, —N(O)$_{m1}$, —C(O)R$^{6D}$, —C(O)OR$^{6D}$, —OCX$^{6.1}_3$, —OCHX$^{6.1}_2$ or substituted or unsubstituted alkyl; $R^7$ is hydrogen, halogen, —CX$^{7.1}_3$, —CHX$^{7.1}_2$, —CH$_2$X$^{7.1}$, —CN, —N(O)$_{m1}$, —C(O)R$^{7D}$, —C(O)OR$^{7D}$, —OCX$^{7.1}_3$, —OCHX$^{7.1}_2$ or substituted or unsubstituted alkyl; $R^8$ is hydrogen, halogen, —CX$^{8.1}_3$, —CHX$^{8.1}_2$, —CH$_2$X$^{8.1}$, —CN, —N(O)$_{m1}$, —C(O)R$^{8D}$, —C(O)OR$^{8D}$, —OCX$^{8.1}_3$, —OCHX$^{8.1}_2$ or substituted or unsubstituted alkyl; and $R^9$ is hydrogen, halogen, —CX$^{9.1}_3$, —CHX$^{9.1}_2$, —CH$_2$X$^{9.1}$, —CN, —N(O)$_{m1}$, —C(O)R$^{9D}$, —C(O)OR$^{9D}$, —OCX$^{9.1}_3$, —OCHX$^{9.1}_2$ or substituted or unsubstituted alkyl.

Embodiment P4

The pharmaceutical composition of embodiment P1, wherein: X is O; $R^1$ is hydrogen, halogen, —CF$_3$, —CCl$_3$, —CBr$_3$, —CI$_3$, —CHF$_2$, —CH$_{2F}$, —CN, —N(O)$_{m1}$, —C(O)R$^{1D}$, —C(O)OR$^{1D}$, —OCX$^{1.1}_3$, —OCHX$^{1.1}_2$ or substituted or unsubstituted alkyl; $R^2$ is hydrogen, —CX$^{2.1}_3$, CHX$^{2.1}_2$, —(CH$_2$)$_{n1}$CX$^{2.1}_3$, substituted alkyl, substituted or unsubstituted aryl or haloalkyl; $R^3$ and $R^4$ are independently hydrogen, substituted or unsubstituted alkyl or substituted or unsubstituted aryl; $R^5$ is hydrogen or substituted or unsubstituted alkyl; $R^6$ is hydrogen, halogen, —CX$^{6.1}_3$, —CHX$^{6.1}_2$, —CH$_2$X$^{6.1}$, —CN, —NO, —C(O)R$^{6D}$, —C(O)OR$^{6D}$, —OCX$^{6.1}_3$, —OCHX$^{6.1}_2$ or substituted or unsubstituted alkyl; $R^7$ is hydrogen, halogen, —CF$_3$, —CCl$_3$, —CBr$_3$, —CI$_3$, —CHF$_2$, —CH$_{2F}$, —CN, —N(O)$_{m1}$, —C(O)R$^{7D}$, —C(O)OR$^{7D}$, —OCX$^{7.1}_3$, —OCHX$^{7.1}_2$ or substituted or unsubstituted alkyl; $R^8$ is hydrogen, halogen, —CF$_3$, —CCl$_3$, —CBr$_3$, —CI$_3$, —CHF$_2$, —CH$_{2F}$, —CN, —N(O)$_{m1}$, —C(O)R$^{8D}$, —C(O)OR$^{8D}$, —OCX$^{8.1}_3$, —OCHX$^{8.1}_2$ or substituted or unsubstituted alkyl; and $R^9$ is hydrogen, halogen, —CF$_3$, —CCl$_3$, —CBr$_3$, —CI$_3$, —CHF$_2$, —CH$_{2F}$, —CN, —N(O)$_{m1}$, —C(O)R$^{9D}$, —C(O)OR$^{9D}$, —OCX$^{9.1}_3$, —OCHX$^{9.1}_2$ or substituted or unsubstituted alkyl.

Embodiment P5

The pharmaceutical composition of embodiment P4, wherein at least two of $R^1$, $R^6$, $R^7$, $R^8$ and $R^9$ are independently hydrogen.

Embodiment P6

A pharmaceutical composition, comprising a pharmaceutically acceptable excipient, and a compound of Formula IA:

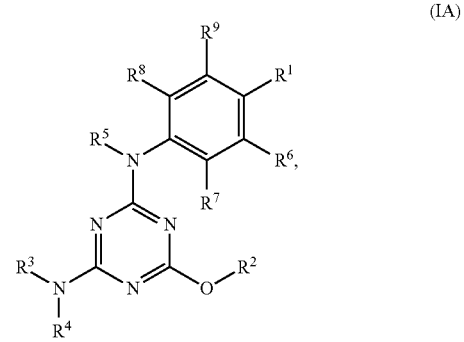

(IA)

or a pharmaceutically acceptable salt thereof, wherein: n1 is an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, X3.1, X4.1, $X^{5.1}$, $X^{6.1}$, $X^{7.1}$, $X^{8.1}$ and $X^{9.1}$ are independently $-Cl$, $-Br$, $-I$ or $-F$; with the proviso that when X is O; $R^2$ is $-(CH_2)_{n1}CX^{1.1}_3$; n1 is 1; $X^{1.1}$ is fluorine; $R^3$ is hydrogen; and $R^4$ is methyl, then $R^6$ is not $-NO_2$.

Embodiment P7

The pharmaceutical composition of embodiment P6, wherein $R^2$ is hydrogen, $-CX^{2.1}_3$, $CHX^{2.1}_2$, $-OR^{2A}$, unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Embodiment P8

The pharmaceutical composition of embodiment P7, wherein: $R^1$ is hydrogen, halogen, $-CX^{1.1}_3$, $-CHX^{1.1}_2$, $-CH_2X^{1.1}$, $-CN$, $-N(O)_{m1}$, $-C(O)R^{1D}$, $-C(O)OR^{1D}$, $-OCX^{1.1}_3$, $-OCHX^{1.1}_2$ or substituted or unsubstituted alkyl; $R^3$, $R^4$ and $R^5$ are independently hydrogen, substituted or unsubstituted alkyl or substituted or unsubstituted aryl; $R^6$ is hydrogen, halogen, $-CX^{6.1}_3$, $-CHX^{6.1}_2$, $-CH_2X^{6.1}$, $-CN$, $-N(O)_{m1}$, $-C(O)R^{6D}$, $-C(O)OR^{6D}$, $-OCX^{6.1}_3$, $-OCHX^{6.1}_2$ or substituted or unsubstituted alkyl; $R^7$ is hydrogen, halogen, $-CX^{7.1}_3$, $-CHX^{7.1}_2$, $-CH_2X^{7.1}$, $-CN$, $-N(O)_{m1}$, $-C(O)R^{7D}$, $-C(O)OR^{7D}$, $-OCX^{7.1}_3$, $-OCHX^{7.1}_2$ or substituted or unsubstituted alkyl; $R^8$ is hydrogen, halogen, $-CX^{8.1}_3$, $-CHX^{8.1}_2$, $-CH_2X^{8.1}$, $-CN$, $-N(O)_{m1}$, $-C(O)R^{8D}$, $-C(O)OR^{8D}$, $-OCX^{8.1}_3$, $-OCHX^{8.1}_2$ or substituted or unsubstituted alkyl; and $R^9$ is hydrogen, halogen, $-CX^{9.1}_3$, $-CHX^{9.1}_2$, $-CH_2X^{9.1}$, —CN, —N(O)$_{m1}$, —C(O)R$^{9D}$, —C(O)OR$^{9D}$, —OCX$^{9.1}_3$, —OCHX$^{9.1}_2$ or substituted or unsubstituted alkyl.

Embodiment P9

The pharmaceutical composition of embodiment P6, wherein R$^6$ is hydrogen, halogen, —CX$^{6.1}_3$, —CHX$^{6.1}_2$, —CH$_2$X$^{6.1}$, —CN, —SO$_{n1}$R$^{6A}$, —SO$_{v1}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —NO, —NR$^{6B}$R$^{6C}$, —C(O)R$^{6A}$, —C(O)OR$^{6A}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P10

The pharmaceutical composition of embodiment P9, wherein: R$^1$ is hydrogen, halogen, —CX$^{1.1}_3$, —CHX$^{1.1}_2$, —CH$_2$X$^{1.1}$, —CN, —N(O)$_{m1}$, —C(O)R$^{1D}$, —C(O)OR$^{1D}$, —OCX$^{1.1}_3$, —OCHX$^{1.1}_2$ or substituted or unsubstituted alkyl; R$^3$, R$^4$ and R$^5$ are independently hydrogen, substituted or unsubstituted alkyl or substituted or unsubstituted aryl; R$^6$ is hydrogen, halogen, —CX$^{6.1}_3$, —CHX$^{6.1}_2$, —CH$_2$X$^{6.1}$, —CN, —N(O)$_{m1}$, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, halogen, —CX$^{7.1}_3$, —CHX$^{7.1}_2$, —CH$_2$X$^{7.1}$, —CN, —N(O)$_{m1}$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, halogen, —CX$^{8.1}_3$, —CHX$^{8.1}_2$, —CH$_2$X$^{8.1}$, —CN, —N(O)$_{m1}$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —N(O)$_{m1}$, —C(O)R$^{9D}$, —C(O)OR$^{9D}$, —OCX$^{9.1}_3$, —OCHX$^{9.1}_2$ or substituted or unsubstituted alkyl.

Embodiment P11

The pharmaceutical composition of embodiment P6, wherein R$^3$ is —COR$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form a substituted or unsubstituted heterocycloalkyl or substituted or unsubstituted heteroaryl.

Embodiment P12

The pharmaceutical composition of embodiment P11, wherein: R$^1$ is hydrogen, halogen, —CX$^{1.1}_3$, —CHX$^{1.1}_2$, —CH$_2$X$^{1.1}$, —CN, —N(O)$_{m1}$, —C(O)R$^{1D}$, —C(O)OR$^{1D}$, —OCX$^{1.1}_3$, —OCHX$^{1.1}_2$ or substituted or unsubstituted alkyl; R$^3$, R$^4$ and R$^5$ are independently hydrogen, substituted or unsubstituted alkyl or substituted or unsubstituted aryl; R$^6$ is hydrogen, halogen, —CX$^{6.1}_3$, —CHX$^{6.1}_2$, —CH$_2$X$^{6.1}$, —CN, —N(O)$_{m1}$, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, halogen, —CX$^{7.1}_3$, —CHX$^{7.1}_2$, —CH$_2$X$^{7.1}$, —CN, —N(O)$_{m1}$, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, halogen, —CX$^{8.1}_3$, —CHX$^{8.1}_2$, —CH$_2$X$^{8s1}$, —CN, —N(O)$_{m1}$, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —N(O)$_{m1}$, —C(O)R$^{9D}$, —C(O)OR$^{9D}$, —OCX$^{9.1}_3$, —OCHX$^{9.1}_2$ or substituted or unsubstituted alkyl.

Embodiment P13

The pharmaceutical composition of embodiment P6, wherein at least two of R$^1$, R$^6$, R$^7$, R$^8$ and R$^9$ are independently hydrogen.

Embodiment P14

The pharmaceutical composition of embodiment P13, wherein: R$^1$ is hydrogen, halogen, —CX$^{1.1}_3$, —CHX$^{1.1}_2$, —CH$_2$X$^{1.1}$, —CN, —NO$_2$, —NO, —C(O)R$^{1A}$, —C(O)OR$^{1D}$, —OCX$^{1.1}_3$, —OCHX$^{1.1}_2$ or substituted or unsubstituted alkyl; R$^2$ is hydrogen, —CX$^{2.1}_3$, CHX$^{2.1}_2$, —(CH$_2$)$_{n1}$CX$^{2.1}_3$, substituted alkyl, substituted or unsubstituted aryl or haloalkyl; R$^3$ and R$^4$ are independently hydrogen, substituted or unsubstituted alkyl or substituted or unsubstituted aryl; R$^5$ is hydrogen or substituted or unsubstituted alkyl; R$^6$ is hydrogen, halogen, —CX$^{6.1}_3$, —CHX$^{6.1}_2$, —CH$_2$X$^{6.1}$, —CN, —NO, —C(O)R$^{6D}$, —C(O)OR$^{6D}$, —OCX$^{6.1}_3$, —OCHX$^{6.1}_2$ or substituted or unsubstituted alkyl; R$^7$ is hydrogen, halogen, —CX$^{7.1}_3$, —CHX$^{7.1}_2$, —CH$_2$X$^{7.1}$, —CN, —NO, —C(O)R$^{7D}$, —C(O)OR$^{7D}$, —OCX$^{7.1}_3$, —OCHX$^{7.1}_2$ or substituted or unsubstituted alkyl; R$^8$ is hydrogen, halogen, —CX$^{8.1}_3$, —CHX$^{8.1}_2$, —CH$_2$X$^{8.1}$, —CN, —NO, —C(O)R$^{8D}$, —C(O)OR$^{8D}$, —OCX$^{8.1}_3$, —OCHX$^{8.1}_2$ or substituted or unsubstituted alkyl; and R$^9$ is hydrogen, halogen, —CX$^{9.1}_3$, —CHX$^{9.1}_2$, —CH$_2$X$^{9.1}$, —CN, —NO, —C(O)R$^{9D}$, —C(O)OR$^{9D}$, —OCX$^{9.1}_3$, —OCHX$^{9.1}_2$ or substituted or unsubstituted alkyl.

Embodiment P15

The pharmaceutical composition of embodiment P14, wherein: R$^1$ is a hydrogen, halogen or —NO$_2$; R$^2$ is —(CH$_2$)$_{n1}$CX$^{2.1}_3$ or substituted alkyl; and R$^5$ is hydrogen.

Embodiment P16

The pharmaceutical composition of embodiment P15, wherein R$^3$ and R$^4$ are independently hydrogen, methyl or ethyl.

Embodiment P17

The pharmaceutical composition of embodiment P16, wherein R$^2$ is alkyl substituted with at least one fluorine.

Embodiment P18

The pharmaceutical composition of embodiment P17, wherein R$^6$, R$^7$, R$^8$ and R$^9$ are independently hydrogen and R$^1$ is —NO$_2$.

Embodiment P19

The pharmaceutical composition of embodiment P17, wherein R$^1$, R$^6$, R$^7$, R$^8$ and R$^9$ are independently hydrogen.

Embodiment P20

A method of treating constipation, comprising administering to a subject in need thereof a therapeutically effective amount of a compound of structural Formula (I):

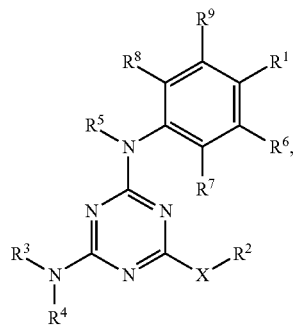

(I)

or a pharmaceutically acceptable salt thereof, wherein: X is O, NH or S; n1 is an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{1D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$ and $X^{9.1}$ are independently $-Cl$, $-Br$, $-I$ or $-F$.

Embodiment P21

The method of embodiment P20, further comprising administering to the subject an anti-constipation agent.

Embodiment P22

The method of embodiment P20, wherein the compound is administered orally.

Embodiment P23

The method of embodiment P20, wherein the constipation is opioid-induced constipation, chronic idiopathic constipation or irritable bowel syndrome with constipation predominance.

Embodiment P24

A method of treating a dry eye disorder, comprising administering to a subject in need thereof a therapeutically effective amount of a compound of structural Formula (I):

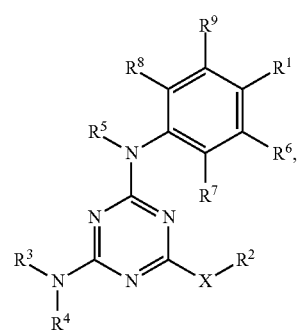

or a pharmaceutically acceptable salt thereof, wherein: X is O, NH or S; n1 is an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-Cl_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCl_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$ and $X^{9.1}$ are independently $-Cl$, $-Br$, $-I$ or $-F$.

Embodiment P25

The method of embodiment P24, wherein the dry eye disorder is a lacrimal gland disorder.

Embodiment P26

The method of embodiment P24, further comprising administering to the subject an anti-dry eye agent.

Embodiment P27

A method of increasing lacrimation, comprising administering to a subject in need thereof a therapeutically effective amount of a compound of structural Formula (I):

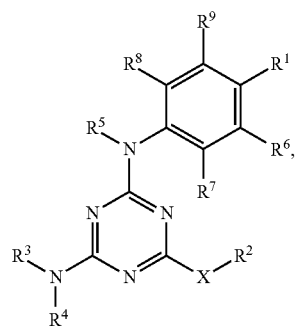

(I)

or a pharmaceutically acceptable salt thereof, wherein: X is O, NH or S; n1 is an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{1D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$ and $X^{9.1}$ are independently $-Cl$, $-Br$, $-I$ or $-F$.

Embodiment P28

A method of activating Cystic Fibrosis Transmembrane Conductance Regulator (CFTR), comprising contacting CFTR with a compound of structural Formula (I):

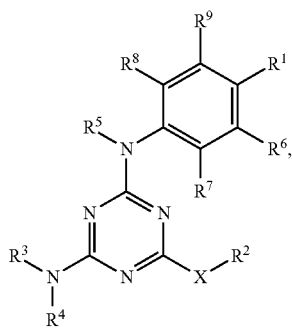

(I)

or a pharmaceutically acceptable salt thereof, wherein: X is O, NH or S; n1 is an integer from 0 to 4; m1 and v1 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n1}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-COR^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-COR^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^5$ is hydrogen, $-COR^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n1}R^{7A}$, $-SO_{v1}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m1}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{1D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$ and $X^{9.1}$ are independently $-Cl$, $-Br$, $-I$ or $-F$.

Further embodiments contemplated herein include embodiment 1 to 69 following.

Embodiment 1

A compound of Formula I:

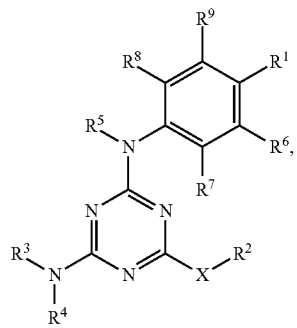

(I)

or a pharmaceutically acceptable salt thereof, wherein: X is —O— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $-CH_3$, $-(CH_2)_{n2}CX^{2.1}_3$, $-OR^{2A}$, substituted or unsubstituted $C_2$-$C_8$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or $C_2$-$C_4$ haloalkyl; $R^3$ is hydrogen, $-C(O)R^{3D}$, $-C(O)NHNR^{3B}R^{3C}$, $-C(O)OR^{3D}$, $-SO_2R^{3A}$, $-C(O)NR^{3B}R^{3C}$, substituted or unsubstituted alkyl, substituted or unsubstituted heteroalkyl, substituted or unsubstituted heterocycloalkyl, substituted or unsubstituted aryl, substituted or unsubstituted heteroaryl; $R^4$ is hydrogen, $-C(O)R^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, $-C(O)R^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, $-CX^{7.1}_3$, $-CHX^{7.1}_2$, $-CH_2X^{7.1}$, $-CN$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently $-Cl$, $-Br$, $-I$ or $-F$; with the proviso that when X is —O—; $R^2$ is —$(CH_2)_{n2}CX^{2.1}{}_3$; n2 is 1; $X^{2.1}$ is fluorine; $R^3$ is hydrogen; and $R^4$ is substituted or unsubstituted $C_1$-$C_3$ alkyl, then $R^6$ is not —$NO_2$; and when X is —O—; $R^2$ is —$(CH_2)_{n2}CX^{2.1}{}_3$; n2 is 1; $X^{2.1}$ is fluorine; $R^3$ is hydrogen; and $R^4$ is substituted or unsubstituted $C_1$-$C_3$ alkyl, then $R^9$ is not —$NO_2$, with the proviso that when X is —O—; $R^2$ is —$CH_2(CF_2)_2H$; $R^3$ is hydrogen; and $R^4$ is unsubstituted $C_1$-$C_3$ alkyl, then $R^1$ is not —$NO_2$; with the proviso that when X is —O—; $R^2$ is —$CH(CF_3)_2$; $R^3$ and $R^4$ are independently unsubstituted $C_1$-$C_3$ alkyl, then $R^1$ is not hydrogen; and with the proviso that when X is —O— and $R^2$ is methyl substituted with cycloalkyl, then $R^3$ and $R^4$ are hydrogen.

Embodiment 2

The compound of embodiment 1, wherein $R^2$ is —$CX^{2.1}{}_3$, —$(CH_2)_{n2}CX^{2.1}{}_3$ or $C_2$-$C_4$ haloalkyl.

Embodiment 3

The compound of embodiment 1 or 2, wherein $R^3$, $R^4$ and $R^5$ are independently hydrogen, or substituted or unsubstituted $C_1$-$C_4$ alkyl.

Embodiment 4

The compound of embodiment 1, 2 or 3, wherein: $R^1$ is hydrogen, halogen, —$CF_3$, —$CCl_3$, —$CBr_3$, —$CI_3$, —$CHF_2$, —$CH_{2F}$, —CN, —$NO_2$, —$C(O)R^{1D}$, —$C(O)OR^{1D}$, —$OCX^{1.1}{}_3$, —$OCHX^{1.1}{}_2$ or substituted or unsubstituted alkyl; $R^6$ is hydrogen, halogen, —$CX^{6.1}{}_3$, —$CHX^{6.1}{}_2$, —$CH_2X^{6.1}$, —CN, —$NO_2$, —$C(O)R^{6D}$, —$C(O)OR^{6D}$, —$OCX^{6.1}{}_3$, —$OCHX^{6.1}{}_2$ or substituted or unsubstituted alkyl; $R^7$ is hydrogen, —$CF_3$, —$CCl_3$, —$CBr_3$, —$CI_3$, —$CHF_2$, —$CH_{2F}$, —CN, —$NO_2$, —$C(O)R^{7D}$, —$C(O)OR^{7D}$, —$OCX^{7.1}{}_3$, —$OCHX^{7.1}{}_2$ or substituted or unsubstituted alkyl; $R^8$ is hydrogen, —$CF_3$, —$CCl_3$, —$CBr_3$, —$CI_3$, —$CHF_2$, —$CH_{2F}$, —CN, —$NO_2$, —$C(O)R^{8D}$, —$C(O)OR^{8D}$, —$OCX^{8.1}{}_3$, —$OCHX^{8.1}{}_2$ or substituted or unsubstituted alkyl; and $R^9$ is hydrogen, halogen, —$CF_3$, —$CCl_3$, —$CBr_3$, —$CI_3$, —$CHF_2$, —$CH_{2F}$, —CN, —$NO_2$, —$C(O)R^{9D}$, —$C(O)OR^{9D}$, —$OCX^{9.1}{}_3$, —$OCHX^{9.1}{}_2$ or substituted or unsubstituted alkyl, wherein $R^{1D}$, $R^{6D}$, $R^{7D}$, $R^{8D}$ and $R^{9D}$ are independent hydrogen or methyl.

Embodiment 5

The compound of embodiment 4, wherein $R^7$ and $R^8$ are independently hydrogen.

Embodiment 6

The compound of embodiment 1, wherein the compound is represented by Formula IA:

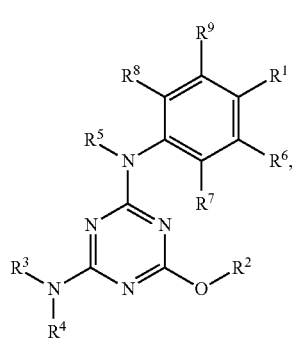

(IA)

or a pharmaceutically acceptable salt thereof.

Embodiment 7

The compound of embodiment 6, wherein $R^2$ is —$CX^{2.1}{}_3$, —$(CH_2)_{n2}CX^{2.1}{}_3$, or $C_2$-$C_4$ haloalkyl.

Embodiment 8

The compound of embodiment 6 or 7, wherein $R^3$, $R^4$ and $R^5$ are independently hydrogen, substituted or unsubstituted alkyl.

Embodiment 9

The compound of embodiment 6, 7 or 8, wherein: $R^1$ is hydrogen, halogen, —$CX^{1.1}{}_3$, —$CHX^{1.1}{}_2$, —$CH_2X^{1.1}$, —CN, —$NO_2$, —$C(O)R^{1D}$, —$C(O)OR^{1D}$, —$OCX^{1.1}{}_3$, —$OCHX^{1.1}{}_2$ or substituted or unsubstituted alkyl; $R^6$ is hydrogen, halogen, —$CX^{6.1}{}_3$, —$CHX^{6.1}{}_2$, —$CH_2X^{6.1}$, —CN, —$NO_2$, —$C(O)R^{6D}$, —$C(O)OR^{6D}$, —$OCX^{6.1}{}_3$, —$OCHX^{6.1}{}_2$ or substituted or unsubstituted alkyl; $R^7$ is hydrogen, —$CX^{7.1}{}_3$, —$CHX^{7.1}{}_2$, —$CH_2X^{7.1}$, —CN, —$NO_2$, —$C(O)R^{7D}$, —$C(O)OR^{7D}$, —$OCX^{7.1}{}_3$, —$OCHX^{7.1}{}_2$ or substituted or unsubstituted alkyl; $R^8$ is hydrogen, —$CX^{8.1}{}_3$, —$CHX^{8.1}{}_2$, —$CH_2X^{8.1}$, —CN, —$NO_2$, —$C(O)R^{8D}$, —$C(O)OR^{8D}$, —$OCX^{8.1}{}_3$, —$OCHX^{8.1}{}_2$ or substituted or unsubstituted alkyl; and $R^9$ is hydrogen, halogen, —$CX^{9.1}{}_3$, —$CHX^{9.1}{}_2$, —$CH_2X^{9.1}$, —CN, —$NO_2$, —$C(O)R^{9D}$, —$C(O)OR^{9D}$, —$OCX^{9.1}{}_3$, —$OCHX^{9.1}{}_2$ or substituted or unsubstituted alkyl.

Embodiment 10

The compound of embodiment 9, wherein $R^7$ and $R^8$ are independently hydrogen.

Embodiment 11

The compound of embodiment 6 or 7, wherein: $R^3$ and $R^4$ are independently methyl or ethyl; $R^5$ are hydrogen; $R^6$ is hydrogen, halogen, —$CX^{6.1}{}_3$, —$CHX^{6.1}{}_2$, —$CH_2X^{6.1}$, —CN, —$C(O)R^{6D}$, —$C(O)OR^{6D}$, —$OCX^{6.1}{}_3$, —$OCHX^{6.1}{}_2$ or substituted or unsubstituted alkyl; $R^7$ is hydrogen, —$CX^{7.1}{}_3$, —$CHX^{7.1}{}_2$, —$CH_2X^{7.1}$, —CN, —$NO_2$, —$C(O)R^{7D}$, —$C(O)OR^{7D}$, —$OCX^{7.1}{}_3$, —$OCHX^{7.1}{}_2$ or substituted or unsubstituted alkyl; $R^8$ is hydrogen, —$CX^{8.1}{}_3$, —$CHX^{8.1}{}_2$, —$CH_2X^{8.1}$, —CN, —$NO_2$, —$C(O)R^{8D}$, —$C(O)OR^{8D}$, —$OCX^{8.1}{}_3$, —$OCHX^{8.1}{}_2$ or substituted or unsubstituted alkyl; and $R^9$ is hydrogen, halogen, —$CX^{9.1}{}_3$, —$CHX^{9.1}{}_2$, —$CH_2X^{9.1}$, —CN, —$C(O)R^{9D}$, —$C(O)OR^{9D}$, —$OCX^{9.1}{}_3$, —$OCHX^{9.1}{}_2$ or substituted or unsubstituted alkyl; wherein $R^{1D}$, $R^{6D}$, $R^{7D}$, $R^{8D}$ and $R^{9D}$ are independently hydrogen or methyl, and $X^{1.1}$, $X^{2.1}$, $X^{6.1}$, $X^{7.1}$, $X^{8.1}$ and $X^{9.1}$ are independently are —F.

Embodiment 12

The compound of embodiment 11, wherein: $R^1$ is hydrogen, halogen, —$NO_2$, or —$COOH$; $R^5$ is hydrogen; $R^6$ is hydrogen, halogen —$NO_2$, or —$COOH$; $R^7$ and $R^8$ are independently hydrogen; and $R^9$ is hydrogen, halogen $NO_2$, or —$COOH$.

Embodiment 13

The compound of embodiment 6 or 7, wherein $R^3$ and $R^4$ are independently hydrogen, methyl or ethyl.

Embodiment 14

The compound of embodiment 4, wherein $R^2$ is $C_2$-$C_4$ alkyl substituted with at least one fluorine.

Embodiment 15

The compound of embodiment 6, 7 or 14, wherein $R^1$, $R^5$, $R^6$, $R^7$, $R^8$ and $R^9$ are hydrogen.

Embodiment 16

The compound of embodiment 6 or 7, wherein $R^1$ and $R^6$ are joined to form, together with the atoms to which they are attached, a substituted or unsubstituted pyrazolyl, oxazolyl, or thiazolyl.

Embodiment 17

The compound of embodiment 16, wherein $R^3$ and $R^4$ are independently hydrogen, methyl or ethyl.

Embodiment 18

The compound of embodiment 16, wherein the compound is represented with Formula IB, IC, ID, or IE:

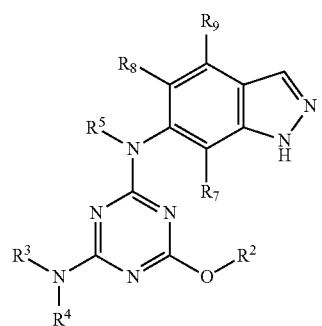

(IB)

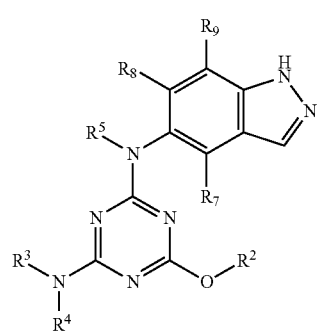

(IC)

(ID)

(IE)

Embodiment 19

The compound of embodiment 18, wherein $R^7$, $R^8$ and $R^9$ are hydrogen.

Embodiment 20

The compound of embodiment 14, 15, 16, 18 or 19, wherein $R^2$ is —CH(CF$_3$)$_2$ or —CH$_2$(CF$_2$)$_2$H.

Embodiment 21

The compound of embodiment 1, wherein the compound is selected from:

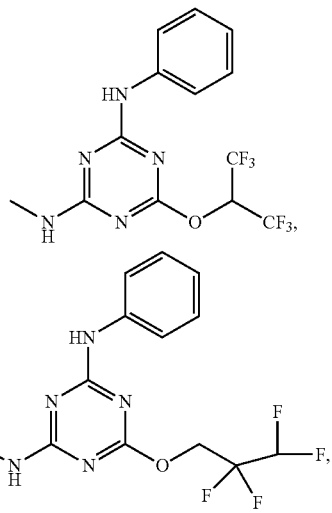

119
-continued
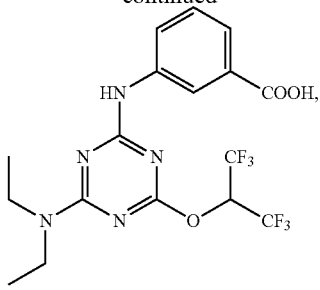
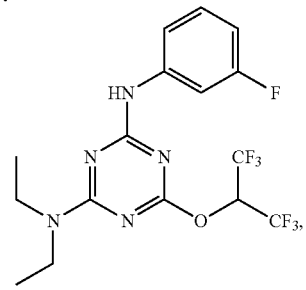
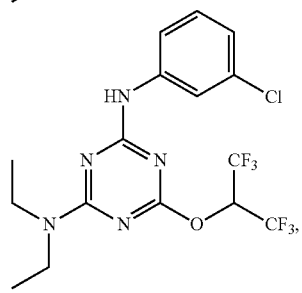
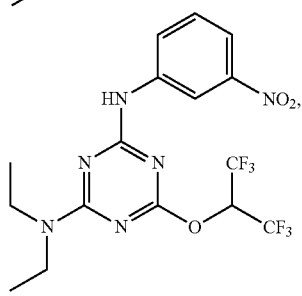
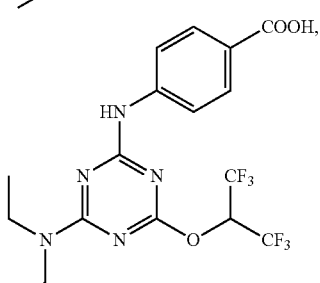
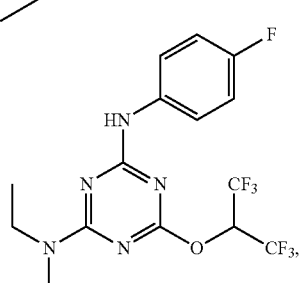
120
-continued
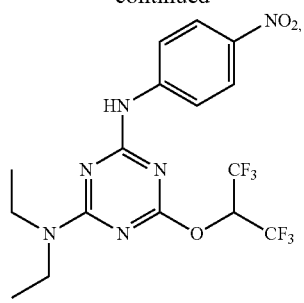
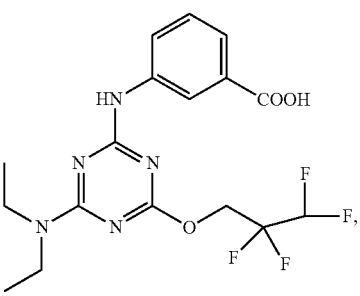
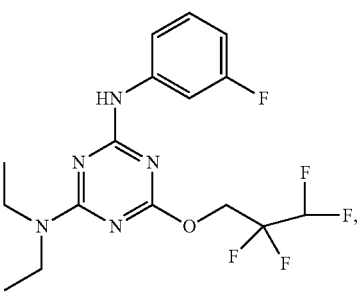
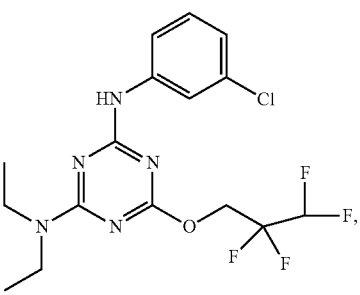
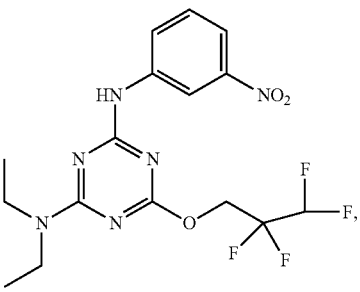

121

-continued

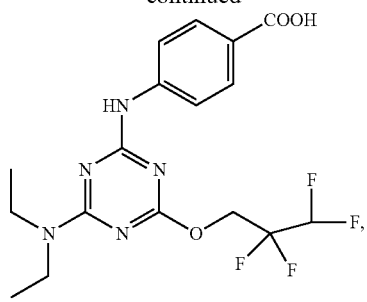

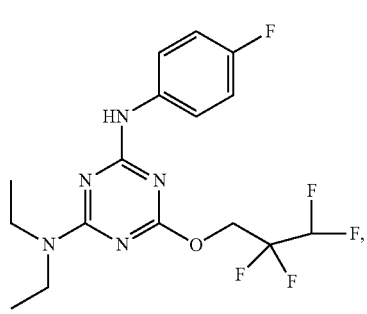

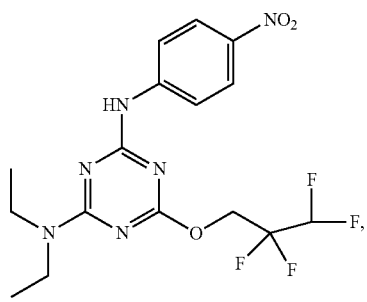

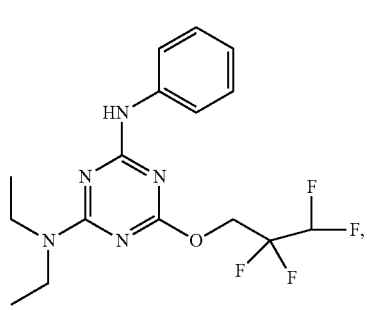

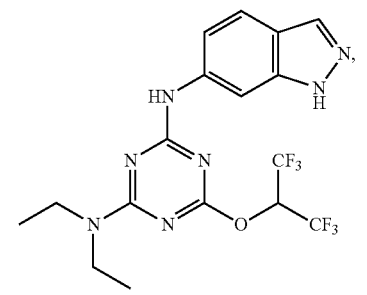

122

-continued

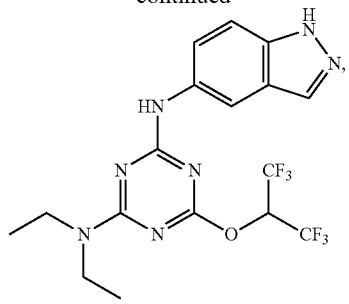

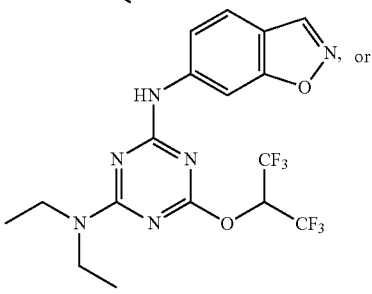

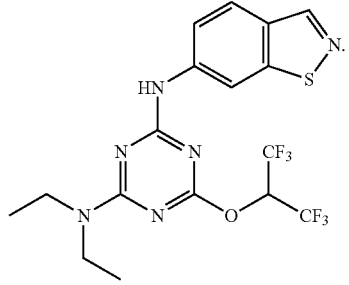

Embodiment 22

A compound of formula I:

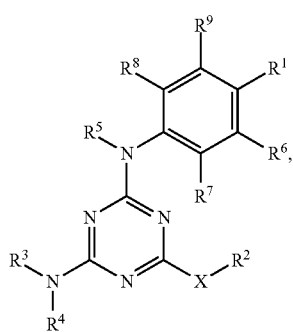

(I)

or a pharmaceutically acceptable salt thereof, wherein: X is —O—; $R^2$ is $C_2$-$C_4$ haloalkyl; $R^3$ is hydrogen; $R^4$ is —CH$_3$ or —CH$_2$CH$_3$; and $R^1$, $R^6$, $R^7$, $R^8$ and $R^9$ are hydrogen.

Embodiment 23

The compound of embodiment 22, wherein $R^2$ is substituted with at least four fluorines.

Embodiment 24

A pharmaceutical composition, comprising a pharmaceutically acceptable excipient, and a compound of Formula I:

(I)

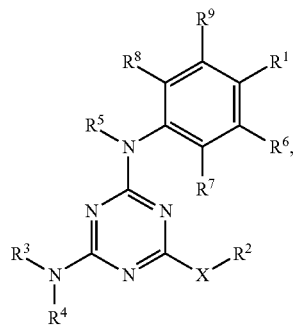

or a pharmaceutically acceptable salt thereof, wherein: X is —O— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)$NHNR^{1B}R^{1C}$, —NHC(O)$NR^{1B}R^{1C}$, —$N(O)_{m1}$, —$NR^{1B}R^{1C}$, —C(O)$R^{1D}$, —C(O)$OR^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, —$CX^{2.1}_3$, $CH_3$, —$(CH_2)_{n2}CX^{2.1}_3$, —$OR^{2A}$, substituted or unsubstituted $C_2$-$C_8$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, —C(O)$R^{3D}$, —C(O)$NHNR^{3B}R^{3C}$, —C(O)$OR^{3D}$, —$SO_2R^{3A}$, C(O)$NR^{3B}R^{3C}$, substituted or unsubstituted alkyl, substituted or unsubstituted heteroalkyl, substituted or unsubstituted heterocycloalkyl, substituted or unsubstituted aryl, substituted or unsubstituted heteroaryl; $R^4$ is hydrogen, —C(O)$R^{4D}$, —C(O)$NHNR^{4B}R^{4C}$, —C(O)$OR^{4D}$, —$SO_2R^{4A}$, C(O)$NR^{4B}R^{4C}$, substituted or unsubstituted alkyl, substituted or unsubstituted heteroalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, —C(O)$R^{5D}$, —C(O)$NHNR^{5B}R^{5C}$, —C(O)$OR^{5D}$, —$SO_2R^{5A}$, C(O)$NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —$N(O)_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NHNR^{7B}R^{7C}$, —$ONR^{7B}R^{7C}$, —NHC(O)$NHNR^{7B}R^{7C}$, —NHC(O)$NR^{7B}R^{7C}$, —$N(O)_{m7}$, —$NR^{7B}R^{7C}$, —C(O)$R^{7D}$, —C(O)$OR^{7D}$, —C(O)$NR^{7B}R^{7C}$, —$OR^{7A}$, —$NR^{7B}SO_2R^{7A}$, —$NR^{7A}C(O)R^{7C}$, —$NR^{7B}C(O)OR^{7D}$, —$NR^{7B}OR^{7D}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —$N(O)_{m8}$, —$NR^{8B}R^{8C}$, —C(O)$R^{8D}$, —C(O)$OR^{8D}$, —C(O)$NR^{8B}R^{8C}$, —$OR^{8A}$, —$NR^{8B}SO_2R^{8A}$, —$NR^{8B}C(O)R^{8D}$, —$NR^{8B}C(O)$ $OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —NHC(O)$NHNR^{9B}R^{9C}$, —NHC(O)$NR^{9B}R^{9C}$, —$N(O)_{m9}$, —$NR^{9B}R^{9C}$, —C(O)$R^{9D}$, —C(O)$OR^{9D}$, —C(O)$NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F; with the proviso that when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not —$NO_2$; and when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not —$NO_2$, and with the proviso that when X is —O— and $R^2$ is methyl substituted with cycloalkyl, then $R^3$ and $R^4$ are hydrogen.

Embodiment 25

The pharmaceutical composition of embodiment 24, wherein $R^2$ is —$CX^{2.1}_3$, —$(CH_2)_{n2}CX^{2.1}_3$ or $C_2$-$C_4$ haloalkyl.

Embodiment 26

The pharmaceutical composition of embodiment 24 or 25, wherein $R^3$, $R^4$ and $R^5$ are independently hydrogen, or substituted or unsubstituted $C_1$-$C_4$ alkyl.

Embodiment 27

The pharmaceutical composition of embodiment 24, 25 or 26, wherein: $R^1$ is hydrogen, halogen, —$CF_3$, —$CCl_3$, —$CBr_3$, —$CI_3$, —$CHF_2$, —$CH_{2F}$, —CN, —$NO_2$, —C(O)$R^{1D}$, —C(O)O$R^{1D}$, —$OCX^{1.1}_3$, —$OCHX^{1.1}_2$ or substituted or unsubstituted alkyl; $R^6$ is hydrogen, halogen, —$CX^{6.1}_3$, —$CHX^{6.1}_2$, —$CH_2X^{6.1}$, —CN, —$NO_2$, —C(O)$R^{6D}$, —C(O)O$R^{6D}$, —$OCX^{6.1}_3$, —$OCHX^{6.1}_2$ or substituted or unsubstituted alkyl; $R^7$ is hydrogen, —$CF_3$, —$CCl_3$, —$CBr_3$, —$CI_3$, —$CHF_2$, —$CH_{2F}$, —CN, —$NO_2$, —C(O)$R^{7D}$, —C(O)O$R^{7D}$, —$OCX^{7.1}_3$, —$OCHX^{7.1}_2$ or substituted or unsubstituted alkyl; $R^8$ is hydrogen, —$CF_3$, —$CCl_3$, —$CBr_3$, —$CI_3$, —$CHF_2$, —$CH_{2F}$, —CN, —$NO_2$, —C(O)$R^{8D}$, —C(O)O$R^{8D}$, —$OCX^{8.1}_3$, —$OCHX^{8.1}_2$ or substituted or unsubstituted alkyl; and $R^9$ is hydrogen, halogen, —$CF_3$, —$CCl_3$, —$CBr_3$, —$CI_3$, —$CHF_2$, —$CH_{2F}$, —CN, —$NO_2$, —C(O)$R^{9D}$, —C(O)O$R^{9D}$, —$OCX^{9.1}_3$, —$OCHX^{9.1}_2$ or substituted or unsubstituted alkyl, wherein $R^{1D}$, $R^{6D}$, $R^{7D}$, $R^{8D}$ and $R^{9D}$ are independent hydrogen or methyl.

Embodiment 28

The pharmaceutical composition of embodiment 27, wherein $R^7$ and $R^8$ are independently hydrogen.

Embodiment 29

The pharmaceutical composition of embodiment 24, wherein the compound is represented by Formula IA:

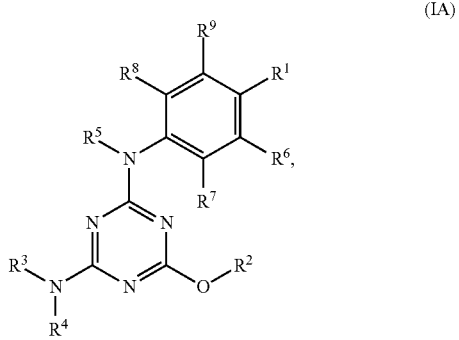

(IA)

or a pharmaceutically acceptable salt thereof.

Embodiment 30

The pharmaceutical composition of embodiment 29, wherein $R^2$ is —$CX^{2.1}_3$, —$(CH_2)_{n2}CX^{2.1}_3$ or $C_2$-$C_4$ haloalkyl.

Embodiment 31

The pharmaceutical composition of embodiment 29 or 30, wherein $R^3$, $R^4$ and $R^5$ are independently hydrogen, or substituted or unsubstituted $C_1$-$C_4$ alkyl.

Embodiment 32

The pharmaceutical composition of embodiment 29, 30 or 31, wherein: $R^1$ is hydrogen, halogen, —$CX^{1.1}_3$, —$CHX^{1.1}_2$, —$CH_2X^{1.1}$, —CN, —$NO_2$, —C(O)$R^{1D}$, —C(O)O$R^{1D}$, —$OCX^{1.1}_3$, —$OCHX^{1.1}_2$ or substituted or unsubstituted alkyl; $R^6$ is hydrogen, halogen, —$CX^{6.1}_3$, —$CHX^{6.1}_2$, —$CH_2X^{6.1}$, —CN, —$NO_2$, —C(O)$R^{6D}$, —C(O)O$R^{6D}$, —$OCX^{6.1}_3$, —$OCHX^{6.1}_2$ or substituted or unsubstituted alkyl; $R^7$ is hydrogen, —$CX^{7.1}_3$, —$CHX^{7.1}_2$, —$CH_2X^{7.1}$, —CN, —$NO_2$, —C(O)$R^{7D}$, —C(O)O$R^{7D}$, —$OCX^{7.1}_3$, —$OCHX^{7.1}_2$ or substituted or unsubstituted alkyl; $R^8$ is hydrogen, —$CX^{8.1}_3$, —$CHX^{8.1}_2$, —$CH_2X^{8.1}$, —CN, —$NO_2$, —C(O)$R^{8D}$, —C(O)O$R^{8D}$, —$OCX^{8.1}_3$, —$OCHX^{8.1}_2$ or substituted or unsubstituted alkyl; and $R^9$ is hydrogen, halogen, —$CX^{9.1}_3$, —$CHX^{9.1}_2$, —$CH_2X^{9.1}$, —CN, —$NO_2$, —C(O)$R^{9D}$, —C(O)O$R^{9D}$, —$OCX^{9.1}_3$, —$OCHX^{9.1}_2$ or substituted or unsubstituted alkyl.

Embodiment 33

The pharmaceutical composition of embodiment 32, wherein $R^7$ and $R^8$ are independently hydrogen.

Embodiment 34

The pharmaceutical composition of embodiment 29 or 30, wherein: $R^3$ and $R^4$ are independently methyl or ethyl; $R^5$ are independently hydrogen; $R^6$ is hydrogen, halogen, —$CX^{6.1}_3$, —$CHX^{6.1}_2$, —$CH_2X^{6.1}$, —CN, —C(O)$R^{6D}$, —C(O)O$R^{6D}$, —$OCX^{6.1}_3$, —$OCHX^{6.1}_2$ or substituted or unsubstituted alkyl; $R^7$ is hydrogen, —$CX^{7.1}_3$, —$CHX^{7.1}_2$, —$CH_2X^{7.1}$, —CN, —$NO_2$, —C(O)$R^{7D}$, —C(O)O$R^{7D}$, —$OCX^{7.1}_3$, —$OCHX^{7.1}_2$ or substituted or unsubstituted alkyl; $R^8$ is hydrogen, —$CX^{8.1}_3$, —$CHX^{8.1}_2$, —$CH_2X^{8.1}$, —CN, —$NO_2$, —C(O)$R^{8D}$, —C(O)O$R^{8D}$, —$OCX^{8.1}_3$, —$OCHX^{8.1}_2$ or substituted or unsubstituted alkyl; and $R^9$ is hydrogen, halogen, —$CX^{9.1}_3$, —$CHX^{9.1}_2$, —$CH_2X^{9.1}$, —CN, —C(O)$R^{9D}$, —C(O)O$R^{9D}$, —$OCX^{9.1}_3$, —$OCHX^{9.1}_2$ or substituted or unsubstituted alkyl; wherein $R^{1D}$, $R^{6D}$, $R^{7D}$, $R^{8D}$ and $R^{9D}$ are independently hydrogen or methyl, and $X^{1.1}$, $X^{2.1}$, $X^{6.1}$, $X^{7.1}$, $X^{8.1}$ and $X^{9.1}$ are independently are —F.

Embodiment 35

The pharmaceutical composition of embodiment 34, wherein: $R^1$ is hydrogen, halogen, —$NO_2$, or —COOH; $R^5$ is hydrogen; $R^6$ is hydrogen, halogen —$NO_2$, or —COOH; $R^7$ and $R^8$ are independently hydrogen; and $R^9$ is hydrogen, halogen $NO_2$, or —COOH.

Embodiment 36

The pharmaceutical composition of embodiment 29 or 30, wherein $R^3$ and $R^4$ are independently hydrogen, methyl or ethyl.

Embodiment 37

The pharmaceutical composition of embodiment 36, wherein $R^2$ is $C_2$-$C_4$ alkyl substituted with at least one fluorine.

Embodiment 38

The pharmaceutical composition of embodiment 37, wherein $R^1$, $R^6$, $R^7$, $R^8$ and $R^9$ are independently hydrogen.

Embodiment 39

The pharmaceutical composition of embodiment 29 or 30, wherein: $R^1$ and $R^6$ are joined to form, together with the atoms to which they are attached, a substituted or unsubstituted pyrazolyl, oxazolyl, or thiazolyl; and $R^3$ and $R^4$ are independently hydrogen, methyl or ethyl.

Embodiment 40

The pharmaceutical composition of embodiment 39, wherein the compound is represented with Formula IB, IC, ID, or IE:

(IB)

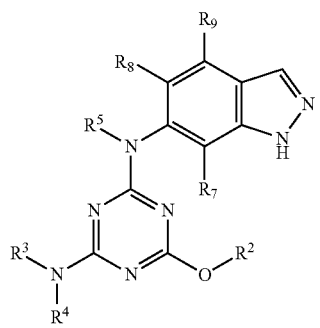

(IC)

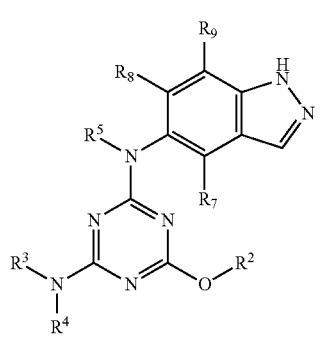

(ID)

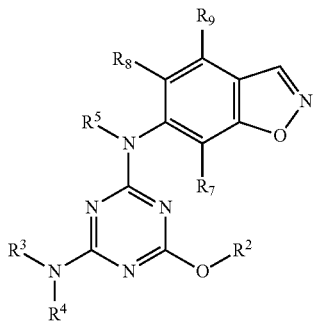

(IE)

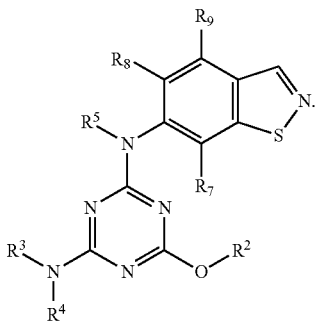

Embodiment 41

The pharmaceutical composition of embodiment 40, wherein $R^5$, $R^7$, $R^8$ and $R^9$ are independently hydrogen.

Embodiment 42

The pharmaceutical composition of embodiment 30, wherein $R^2$ is —$CH(CF_3)_2$ or —$CH_2(CF_2)_2H$.

Embodiment 43

The pharmaceutical composition of embodiment 24, wherein the compound is selected from:

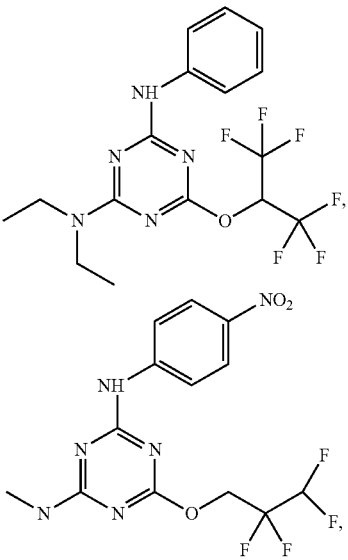

129
-continued
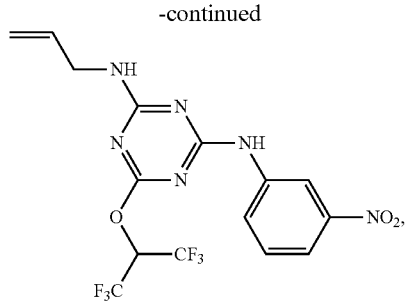
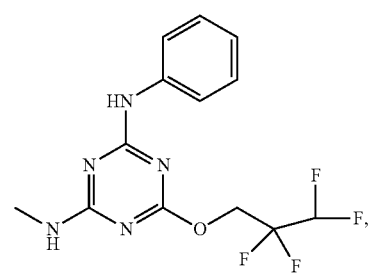
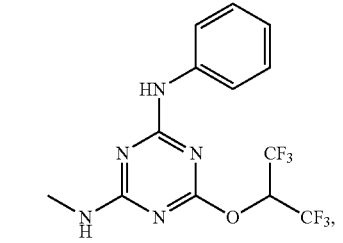
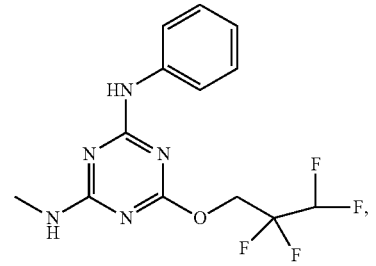
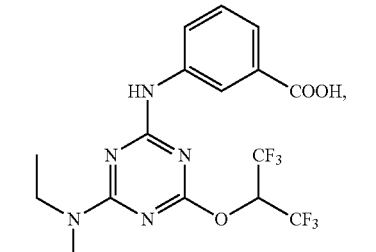
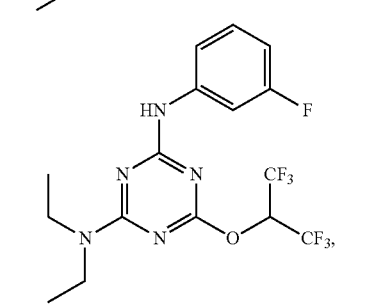
130
-continued
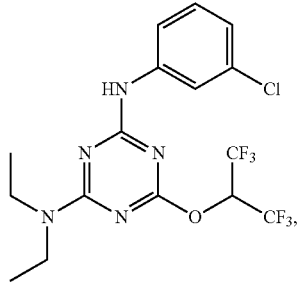
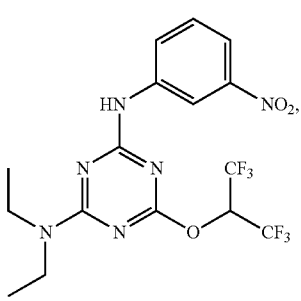
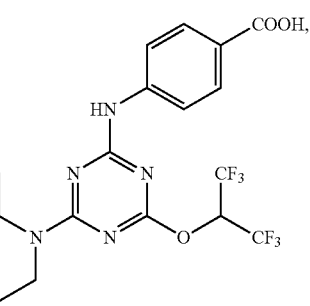
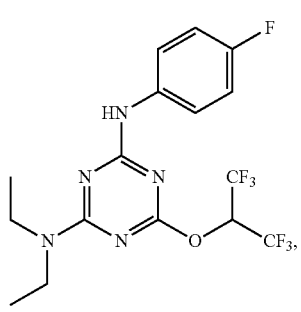
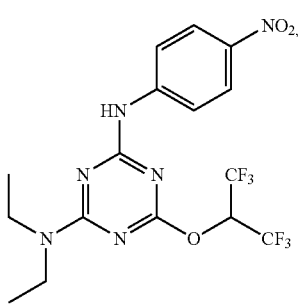

-continued

133

-continued

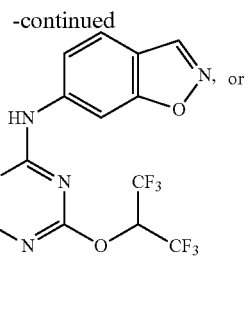

or

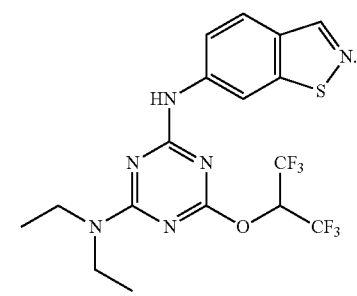

Embodiment 44

A pharmaceutical composition, comprising a pharmaceutically acceptable excipient, and compound of formula I:

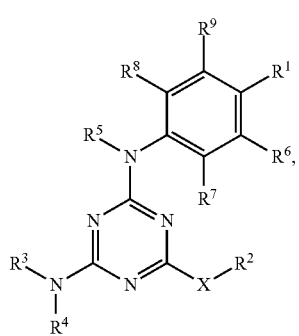

or a pharmaceutically acceptable salt thereof, wherein: X is —O—; $R^2$ is $C_2$-$C_4$ haloalkyl; $R^3$ is hydrogen; $R^4$ is —CH$_3$ or —CH$_2$CH$_3$; and $R^1$, $R^6$, $R^7$, $R^8$ and $R^9$ are hydrogen.

Embodiment 45

The pharmaceutical composition of embodiment 44, wherein $R^2$ is substituted with at least four fluorines.

Embodiment 46

A method of treating constipation in a subject in need thereof, comprising administering to the subject an effective amount of a compound of Formula I:

134

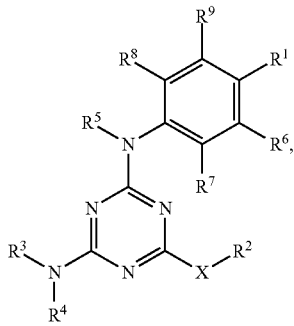

or a pharmaceutically acceptable salt thereof, wherein: X is —O—, —NH— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, —C(O)R$^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, —C(O)R$^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)

$NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, $-CN$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently $-Cl$, $-Br$, $-I$ or $-F$; with the proviso that when X is $-O-$; $R^2$ is $-(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not $-NO_2$; and when X is $-O-$; $R^2$ is $-(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not $-NO_2$.

Embodiment 47

The method of embodiment 46, further comprising administering to the subject an anti-constipation agent.

Embodiment 48

The method of embodiment 46 or 47, wherein the compound is administered orally.

Embodiment 49

The method of embodiment 46, 47 or 48, wherein the constipation is opioid-induced constipation, chronic idiopathic constipation or irritable bowel syndrome with constipation predominance.

Embodiment 50

A method of treating a dry eye disorder in a subject in need thereof, comprising administering to the subject an effective amount a compound of Formula I:

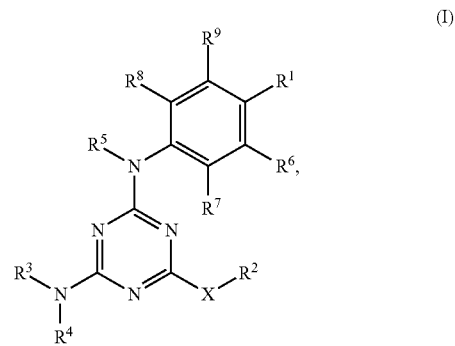

(I)

or a pharmaceutically acceptable salt thereof, wherein: X is $-O-$, $-NH-$ or $-S-$; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $-CHX^{2.1}_2$, $-(CH_2)_{n2}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, $-C(O)R^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, —$C(O)R^{4D}$, —$C(O)NHNR^{4B}R^{4C}$, —$C(O)OR^{4D}$, —$SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, —$C(O)R^{5D}$, —$C(O)NHNR^{5B}R^{5C}$, —$C(O)OR^{5D}$, —$SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NHNR^{7B}R^{7C}$, —$ONR^{7B}R^{7C}$, —$NHC(O)NHNR^{7B}R^{7C}$, —$NHC(O)NR^{7B}R^{7C}$, —$N(O)_{m7}$, —$NR^{7B}R^{7C}$, —$C(O)R^{7D}$, —$C(O)OR^{7D}$, —$C(O)NR^{7B}R^{7C}$, —$OR^{7A}$, —$NR^{7B}SO_2R^{7A}$, —$NR^{7A}C(O)R^{7C}$, —$NR^{7B}C(O)OR^{7D}$, —$NR^{7B}OR^{7D}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)$—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F; with the proviso that when X is —O—; $R^2$ is —$(CH_2)_{n2}CX^{2.1}_3$; n2 is 1; $X^{2.1}$ is fluorine; $R^3$ is hydrogen; and $R^4$ substituted or unsubstituted $C_1$-$C_3$ alkyl, then $R^6$ is not —$NO_2$; and when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not —$NO_2$.

Embodiment 51

The method of embodiment 50, wherein the dry eye disorder is a lacrimal gland disorder.

Embodiment 52

The method of embodiment 50 or 51, further comprising administering to the subject an anti-dry eye agent.

Embodiment 53

A method of increasing lacrimation in a subject in need thereof, comprising administering to the subject an effective amount of a compound of Formula I:

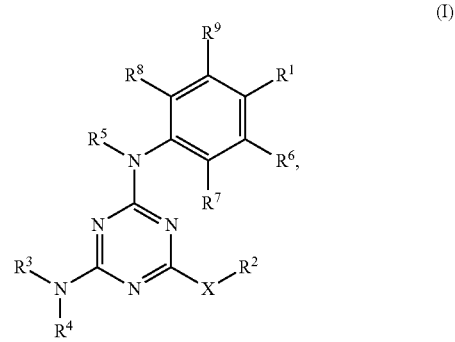

or a pharmaceutically acceptable salt thereof, wherein:
X is —O—, —NH— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; R$^3$ is hydrogen, —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^4$ is hydrogen, —C(O)R$^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form, together with the atoms to which they are attached, a substituted or unsubstituted heterocycloalkyl or substituted or unsubstituted heteroaryl, wherein R$^3$ and R$^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; R$^5$ is hydrogen, —C(O)R$^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form, together with the atoms to which they are attached, a substituted or unsubstituted heterocycloalkyl or substituted or unsubstituted heteroaryl; R$^6$ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ is hydrogen, halogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^8$ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^1$ and R$^6$, R$^6$ and R$^7$, R$^1$ and R$^9$, or R$^8$, and R$^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$ and R$^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$ and R$^{9C}$ substituents bonded to the same nitrogen atom may optionally be joined to form, together with the atoms to which they are attached, a substituted or unsubstituted heterocycloalkyl or substituted or unsubstituted heteroaryl; and X$^{1.1}$, X$^{2.1}$, X$^{6.1}$, X$^{7.1}$, X$^{8.1}$ and X$^{9.1}$ are independently —Cl, —Br, —I or —F; with the proviso that when X is —O—; R$^2$ is —(CH$_2$)$_{n2}$CX$^{2.1}_3$; n2 is 1; X$^{2.1}$ is fluorine; R$^3$ is hydrogen; and R$^4$ is substituted or unsubstituted C$_1$-C$_3$ alkyl, then R$^6$ is not —NO$_2$; and when X is —O—; R$^2$ is —(CH$_2$)$_{n2}$CX$^{2.1}_3$; n2 is 1; X$^{2.1}$ is fluorine; R$^3$ is hydrogen; and R$^4$ is substituted or unsubstituted C$_1$-C$_3$ alkyl, then R$^9$ is not —NO$_2$.

Embodiment 54

A method of activating a Cystic Fibrosis Transmembrane Conductance Regulator (CFTR), comprising contacting the CFTR with an effective amount of a compound of Formula I:

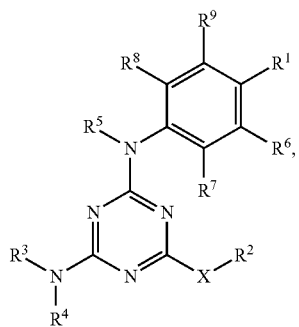

(I)

or a pharmaceutically acceptable salt thereof, wherein: X is —O—, —NH— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, $-CX^{1.1}_3$, $-CHX^{1.1}_2$, $-CH_2X^{1.1}$, —CN, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, $-CX^{2.1}_3$, $CHX^{2.1}_2$, $-(CH_2)_{n2}CX^{2.1}_3$, $-OR^{2A}$, substituted or unsubstituted alkyl, substituted or unsubstituted heteroalkyl, substituted or unsubstituted cycloalkyl, or unsubstituted heterocycloalkyl, substituted or unsubstituted aryl, substituted or unsubstituted heteroaryl or haloalkyl; $R^3$ is hydrogen, $-C(O)R^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, $-C(O)R^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, $-C(O)R^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, $-CX^{6.1}_3$, $-CHX^{6.1}_2$, $-CH_2X^{6.1}$, —CN, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, $-CX^{7.1}_3$, $-CHX^{7.1}_2$, $-CH_2X^{7.1}$, —CN, $-SO_{n7}R^{7A}$, $-SO_{v7}NR^{7B}R^{7C}$, $-NHNR^{7B}R^{7C}$, $ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, $-CX^{8.1}_3$, $-CHX^{8.1}_2$, $-CH_2X^{8.1}$, —CN, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, —CN, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)$—OH, —NHOH, $-OCF_3$, $-OCCl_3$, $-OCBr_3$, $-OCl_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —I or —F; with the proviso that when X is —O—; $R^2$ is $-(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not —NO$_2$; and when X is —O—; R$^2$ is —(CH$_2$)$_{n2}$CX$^{2.1}_3$; n2 is 1; X$^{2.1}$ is fluorine; R$^3$ is hydrogen; and R$^4$ is substituted or unsubstituted C$_1$-C$_3$ alkyl, then R$^9$ is not —NO$_2$.

Embodiment 55

A method of treating a cholestatic liver disease in a subject in need thereof, the method comprising administering to the subject an effective amount of a compound of Formula I:

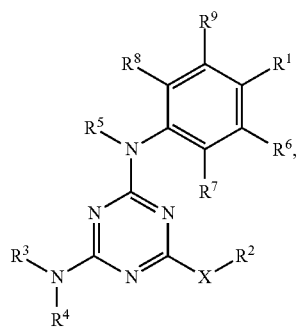

(I)

or a pharmaceutically acceptable salt thereof, wherein: X is —O—, —NH— or —S—; n1, n2, n6, n7, n8, and n9 are independently an integer from 0 to 4; m1, m6, m7, m8, m9, v1, v6, v7, v8, and v9 are each independently 1 or 2; R$^1$ is hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; R$^3$ is hydrogen, —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^4$ is hydrogen, —C(O)R$^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form, together with the atoms to which they are attached, a substituted or unsubstituted heterocycloalkyl or substituted or unsubstituted heteroaryl, wherein R$^3$ and R$^4$ are optionally be joined to form, together with the atoms to which they are attached, a substituted or unsubstituted heterocycloalkyl, substituted or unsubstituted aryl, or substituted or unsubstituted heteroaryl; R$^5$ is hydrogen, —C(O)R$^{5D}$, —C(O)NHNR$^{5B}$R$^{5C}$, —C(O) OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form, together with the atoms to which they are attached, a substituted or unsubstituted heterocycloalkyl or substituted or unsubstituted heteroaryl; R$^6$ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ is hydrogen, halogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^8$ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O) OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^1$ and R$^6$, R$^6$ and R$^7$, R$^1$ and R$^9$, or R$^8$, and R$^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$ and R$^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F; with the proviso that when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^6$ is not —$NO_2$; and when X is —O—; $R^2$ is —$(CH_2)_{n2}CX^{2.1}_3$; n2 is 1; $X^{2.1}$ is fluorine; $R^3$ is hydrogen; and $R^4$ is —$CH_3$, then $R^9$ is not —$NO_2$.

Embodiment 56

A method of treating a pulmonary disease or disorder in a subject in need thereof, the method comprising administrating to the subject an effective amount of a compound of Formula I:

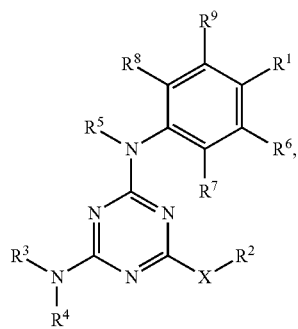

(I)

or a pharmaceutically acceptable salt thereof, wherein: X is —O—, —NH— or —S—; n1, n2, n6, n7, n8, and n9 are independently an integer from 0 to 4; m1, m6, m7, m8, m9, v1, v6, v7, v8, and v9 are each independently 1 or 2; $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{5C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, —$CX^{2.1}_3$, $CHX^{2.1}_2$, —$(CH_2)_{n2}CX^{2.1}_3$, —$OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl; $R^3$ is hydrogen, —$C(O)R^{3D}$, —$C(O)NHNR^{3B}R^{3C}$, —$C(O)OR^{3D}$, —$SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^4$ is hydrogen, —$C(O)R^{4D}$, —$C(O)NHNR^{4B}R^{4C}$, —$C(O)OR^{4D}$, —$SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl; $R^5$ is hydrogen, —$C(O)R^{5D}$, —$C(O)NHNR^{5B}R^{5C}$, —$C(O)OR^{5D}$, —$SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl; $R^6$ is hydrogen, halogen, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NHNR^{7B}R^{7C}$, —$ONR^{7B}R^{7C}$, —$NHC(O)NHNR^{7B}R^{7C}$, —$NHC(O)NR^{7B}R^{7C}$, —$N(O)_{m7}$, —$NR^{7B}R^{7C}$, —$C(O)R^{7D}$, —$C(O)OR^{7D}$, —$C(O)NR^{7B}R^{7C}$, —$OR^{7A}$, —$NR^{7B}SO_2R^{7A}$, —$NR^{7A}C(O)R^{7C}$, —$NR^{7B}C(O)OR^{7D}$, —$NR^{7B}OR^{7D}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{1D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F; with the proviso that when X is —O—; $R^2$ is —$(CH_2)_{n2}CX^{2.1}{}_3$; n2 is 1; $X^{2.1}$ is fluorine; $R^3$ is hydrogen; and $R^4$ is —$CH_3$, then $R^6$ is not —$NO_2$; and when X is —O—; $R^2$ is —$(CH_2)_{n2}CX^{2.1}{}_3$; n2 is 1; $X^{2.1}$ is fluorine; $R^3$ is hydrogen; and $R^4$ is —$CH_3$, then $R^9$ is not —$NO_2$.

Embodiment 57

The method of embodiment 56, wherein the pulmonary disease or disorder is chronic obstructive pulmonary disease, bronchitis, asthma, and cigarette smoke-induced lung dysfunction.

Embodiment 58

A method of treating constipation, comprising administering to a subject in need thereof a therapeutically effective amount a compound in any of embodiments 1 to 23.

Embodiment 59

The method of embodiment 58, further comprising administering to the subject an anti-constipation agent.

Embodiment 60

The method of embodiment 58 or 59, wherein the compound is administered orally.

Embodiment 61

The method of embodiment 58, 59 or 60, wherein the constipation is opioid-induced constipation, chronic idiopathic constipation or irritable bowel syndrome with constipation predominance.

Embodiment 62

A method of treating a dry eye disorder, comprising administering to a subject in need thereof a therapeutically effective amount of a compound in any of embodiments 1 to 23.

Embodiment 63

The method of embodiment 62, wherein the dry eye disorder is a lacrimal gland disorder.

Embodiment 64

The method of embodiment 62 or 63, further comprising administering to the subject an anti-dry eye agent.

Embodiment 65

A method of increasing lacrimation, comprising administering to a subject in need thereof a compound in any of embodiments 1 to 23.

Embodiment 66

A method of activating Cystic Fibrosis Transmembrane Conductance Regulator (CFTR), comprising contacting CFTR with a compound in any of embodiments 1 to 23.

Embodiment 67

A method of treating a cholestatic liver disease in a subject in need thereof, the method comprising administering to the subject an effective amount of a compound in any of embodiments 1 to 23.

Embodiment 68

A method of treating a pulmonary disease or disorder in a subject in need thereof, the method comprising administrating to the subject an effective amount of a compound in any of embodiments 1 to 23.

Embodiment 69

The method of embodiment 68, wherein the pulmonary disease or disorder is chronic obstructive pulmonary disease, bronchitis, asthma, and cigarette smoke-induced lung dysfunction.

V. EXAMPLES

Constipation

1. Example 1

A cell-based high-throughput screen was done for 120,000 drug-like, synthetic small molecules. Active compounds were characterized for mechanism of action and one lead compound was tested in a loperamide-induced constipation model in mice.

Several classes of novel CFTR activators were identified, one of which, the phenylquinoxalinone $CFTR_{act}$-J027, fully activated CFTR chloride conductance with $EC_{50}$ ~200 nM, without causing elevation of cytoplasmic cAMP. Orally administered $CFTR_{act}$-J027 normalized stool output and water content in a loperamide-induced mouse model of constipation with $ED_{50}$ ~0.5 mg/kg; $CFTR_{act}$-J027 was without effect in cystic fibrosis mice lacking functional CFTR. Short-circuit current, fluid secretion and motility measurements in mouse intestine indicated a pro-secretory action of $CFTR_{act}$-J027 without direct stimulation of intestinal motility. Oral administration of 10 mg/kg $CFTR_{act}$-J027 showed minimal bioavailability, rapid hepatic metabolism and blood levels <200 nM, and without apparent toxicity after chronic administration.

$CFTR_{act}$-J027 or alternative small-molecule CFTR-targeted activators may be efficacious for the treatment of constipation.

High-throughput screening was done using a diverse collection of 120,000 drug-like synthetic compounds obtained from ChemDiv Inc. (San Diego, Calif., USA) and Asinex (Winston-Salem, N.C., USA). For structure-activity analysis, 600 commercially available analogs (ChemDiv Inc.) of active compounds identified in the primary screen were tested. Other chemicals were purchased from Sigma-Aldrich (St. Louis, Mo., USA) unless indicated otherwise.

CFTR$_{act}$-J027 Synthesis

To a solution of o-phenylenediamine (1 g, 9.24 mmol) in DMF (30 mL) was added potassium carbonate (2.5 g, 18.4 mmol) and benzyl bromide (0.73 mL, 6.2 mmol) then stirred overnight at ambient temperature. The reaction mixture was diluted with CH$_2$Cl$_2$, washed with water, dried over MgSO$_4$ and concentrated under reduced pressure. The residue was purified by flash chromatography to give the intermediate N$^1$-benzylbenzene-1,2-diamine as a brown liquid. $^1$H NMR (300 MHz, CDCl$_3$): δ 7.45-7.31 (m, 5H), 6.86-6.69 (m, 4H), 4.35 (s, 2H), 3.50 (br, 3H); MS: m/z 199 (M+H). Then, a solution of the intermediate (400 mg, 2 mmol) and 5-nitroisatin (380 mg, 2 mmol) in acetic acid (5 mL) was refluxed for 2 h. The reaction mixture was cooled to room temperature and solvent removed under reduced pressure. The residue was dissolved with methanol and acetic acid was added to crystallize 3-(2-amino-5-nitrophenyl)-1-benzylquinoxalin-2(1H)-one (CFTR$_{act}$-J027) as a yellow powder with >99% purity. $^1$H NMR (300 MHz, DMSO-d6): δ 9.15 (d, 1H, J=2.8 Hz), 8.07 (dd, 1H, J=2.7, 9.2 Hz), 7.97 (dd, 1H, J=1.2, 7.9 Hz), 7.82 (brs, 2H), 7.60-7.27 (m, 7H), 6.92 (d, 1H, J=9.2 Hz), 5.59 (brs, 2H); $^{13}$C NMR (75 MHz, DMSO-d6): δ 155.0, 154.6, 153.3, 136.3, 135.3, 132.8, 132.2, 131.0, 130.0, 129.5, 129.1, 127.7, 127.3, 126.8, 124.1, 116.1, 115.9, 115.4, 45.9; MS: m/z 373 (M+H).

Cell Culture

Fischer Rat Thyroid (FRT) cells stably co-expressing human wild-type CFTR and the halide-sensitive yellow fluorescent protein (YFP)-H148Q were generated as previously described [12]. Cells were cultured on plastic in Coon's-modified Ham's F12 medium supplemented with 10% fetal bovine serum, 2 mM L-glutamine, 100 units/ml penicillin, and 100 µg/ml streptomycin. For high-throughput screening, cells were plated in black 96-well microplates (Corning-Costar Corp., Corning, N.Y., USA) at a density of 20,000 cells per well. Screening was done 24-48 hours after plating.

High-Throughput Screening

Screening was carried out using a Beckman Coulter integrated system equipped with a liquid handling system and two FLUOstar fluorescence plate readers (BMG Labtechnologies, Durham, N.C., USA), each equipped with dual syringe pumps and 500±10 nm excitation and 535±15 nm emission filters (details in ref. 12). CFTR- and YFP-expressing FRT cells were grown at 37° C./5% CO$_2$ for 24-48 hours after plating. At the time of assay, cells were washed three times with phosphate-buffered saline (PBS) and then incubated for 10 min with 60 µl of PBS containing test compounds (at 10 µM) and a low concentration of forskolin (125 nM). Each well was assayed individually for I$^-$ influx in a plate reader by recording fluorescence continuously (200 ms per point) for 2 s (baseline) and then for 12 s after rapid (<1 s) addition of 165 µL of PBS in which 137 mM Cl$^-$ was replaced by I$^-$. The initiate rate of I$^-$ influx was computed by determined using exponential regression. All compound plates contained negative controls (DMSO vehicle) and positive controls (20 µM forskolin).

Short-Circuit Current Measurement

Short-circuit current was measured in FRT cells stably expressing wild-type human CFTR cultured on porous filters as described [12]. The basolateral solution contained 130 mM NaCl, 2.7 mM KCl, 1.5 mM KH$_2$PO$_4$, 1 mM CaCl$_2$, 0.5 mM MgCl$_2$, 10 mM glucose, and 10 mM Na-HEPES (pH 7.3, 37° C.). In the apical solution 65 mM NaCl was replaced by Na gluconate, and CaCl$_2$ was increased to 2 mM, and the basolateral membrane was permeabilized with 250 µg/ml amphotericin B. Short-circuit current was measured in freshly harvested adult mouse colon at 37° C. using symmetrical Krebs-bicarbonate buffer.

cAMP Assay

Intracellular cAMP activity was measured using a GloSensor luminescence assay (Promega Corp., Madison, Wis., USA). FRT null cells were stably transfected with the pGloSensor cAMP plasmid and plated onto white 96-well microplates and grown to confluence. Cells were washed three times with PBS and incubated with 5 µM CFTR$_{act}$-J027 for 10 min in the absence and presence of 100 nM forskolin. cAMP was assayed according to the manufacturer's instructions.

Pharmacokinetics

All animal experiments were approved by UCSF Institutional Animal Care and Use Committee. Female CD1 mice were treated with 10 mg/kg CFTR$_{act}$-J027 (saline containing 5% DMSO and 10% Kolliphor HS 15) either intraperitoneally (ip) or orally. Blood was collected at 15, 30, 60, 150, 240 and 360 min after treatment by orbital puncture and centrifuged at 5000 rpm for 15 min to separate plasma. Plasma samples (60 µL) were mixed with 300 µL acetonitrile and centrifuged at 13000 rpm for 20 min, and 90 µL of the supernatant was used for LC/MS. The solvent system consisted of a linear gradient from 5 to 95% acetonitrile over 16 min (0.2 ml/min flow). Mass spectra was acquired on a mass spectrometer (Waters 2695 and Micromass ZQ) using electrospray (+) ionization, mass ranging from 100 to 1500 Da, cone voltage 40 V. Calibration standards were prepared in plasma from untreated mice to which known amounts of CFTR$_{act}$-J027 were added.

In Vitro Metabolic Stability

CFTR$_{act}$-J027 (5 µM) was incubated for specified times at 37° C. with mouse liver microsomes (1 mg protein/ml; Sigma-Aldrich) in potassium phosphate buffer (100 mM) containing 1 mM NADPH, as described [13]. The mixture was then chilled on ice, and 0.5 ml of ice-cold ethyl acetate was added. Samples were centrifuged for 15 min at 3000 rpm, the supernatant evaporated to dryness, and the residue was dissolved in 100 µL mobile phase (acetonitrile:water, 3:1) for LC/MS and assayed as described above.

Murine Model of Constipation

Female CD1 mice (age 8-10 weeks) were administered loperamide (0.3 mg/kg, ip, Sigma-Aldrich) to produce constipation. Various amounts of CFTR$_{act}$-J027 (0.1, 0.3, 1, 3 and 10 mg/kg) were given at the same time (for ip administration) or 1 h before (for oral administration) loperamide. Control mice were treated with vehicle only. Some mice were treated orally with lubiprostone (0.5 mg/kg, Sigma-Aldrich) or linaclotide (0.5 mg/kg, Toronto Research Chemicals Inc., Toronto, Ontario, Canada). After loperamide injection, mice were placed individually in metabolic cages with food and water provided ad libitum. Stool samples were collected for 3 h, and total stool weight and number of fecal pellets were quantified. To measure stool water content stool samples were dried at 80° C. for 24 h and water content was calculated as [wet weight-dry weight]/wet weight. Similar studies were done in cystic fibrosis (CF) mice (ΔF508 homozygous) lacking functional CFTR. Some studies were done using the chemically similar but inactive analog of $CFTR_{act}$-J027, 3-(2-amino-5-nitrophenyl)-1-(methyl)-2(1H)-quinoxalinone.

In Vivo Intestinal Transit and Ex Vivo Intestinal Contractility

Whole-gut transit time was determined using an orally administered marker (200 µL, 5% Evans Blue, 5% gum Arabic) and measuring the time of its appearance in stool. Mice were administered loperamide and $CFTR_{act}$-J027 (10 mg/kg) or vehicle intraperitoneally at zero time. For ex vivo contractility measurements, mice were euthanized by avertin overdose (200 mg/kg, 2,2,2-tribromethanol, Sigma-Aldrich) and ileum and colon segments of ~2 cm length were isolated and washed with Krebs-Henseleit buffer. The ends of the intestinal segments were tied, connected to a force transducer (Biopac Systems, Goleta, Calif., USA) and tissues were transferred to an organ chamber (Biopac Systems) containing Krebs-Henseleit buffer at 37° C. aerated with 95% $O_2$, 5% $CO_2$. Ileum and colon were stabilized for 60 min with resting tensions of 0.5 and 0.2 g respectively, and solutions were changed every 15 min. Effects of $CFTR_{act}$-J027 on baseline and loperamide-suppressed isometric intestinal contractions were recorded.

In Vivo Intestinal Secretion and Absorption

Mice (wildtype or CF) were given access to 5% dextrose water but not solid food for 24 h before experiments. Mice were anesthetized with isoflurane and body temperature was maintained during surgery at 36-38° C. using a heating pad. A small abdominal incision was made to expose the small intestine, and closed mid-jejunal loops (length 2-3 cm) were isolated by sutures. Loops were injected with 100 µL vehicle alone or 100 µg $CFTR_{act}$-J027 in vehicle. The abdominal incision was closed with sutures, and mice were allowed to recover from anesthesia. Intestinal loops were removed at 90 min and loop length and weight were measured to quantify fluid secretion. Intestinal absorption was measured in CF mice (to prevent secretion) as described above, except that the loops were removed at 0 or 30 min. Absorption was calculated as 1−(loop weight at 0 min−loop weight at 30 min)/loop weight at 0 min.

Chronic Administration and Toxicity Studies

Mice were administered 10 mg/kg $CFTR_{act}$-J027 or vehicle orally once a day for 7 d. One hour after the final dose mice were treated with loperamide (0.3 mg/kg, ip) and stool was collected for 3 h. In vivo toxicity was assessed in these mice by measuring lung wet/dry weight ratio, complete blood count (HEMAVET 950FS, Drew Scientific Inc., Florida, USA) and serum chemistry (Idexx Laboratories Inc., Sacramento, Calif., USA) 4 h after the last $CFTR_{act}$-J027 dose. In vitro cytotoxicity was measured in FRT cells incubated with 25 µM $CFTR_{act}$-J027 for 8 and 24 h. Cytotoxicity was measured by Alamar Blue assay according to the manufacturer's instructions (Invitrogen, Carlsbad, Calif., USA).

Statistical Analysis

Experiments with two groups were analyzed with Student's t-test, when there are 3 groups or more analysis was made with one-way analysis of variance and post-hoc Newman-Keuls multiple comparisons test. P<0.05 was taken as statistically significant.

2. Example 2

Identification and In Vitro Characterization of Small-Molecule CFTR Activators

The goal was to identify a potent, CFTR-targeted activator with pro-secretory activity in intestine in order test its efficacy in a mouse model of constipation. FIG. 1A summarizes the project strategy. The compounds evaluated here included small molecules identified in prior CFTR activator/potentiator screens [14] and from a new screen of synthetic small molecules not tested previously. The most active compounds emerging from the screen, along with commercially available chemical analogs, were prioritized based on an initial mechanism of action study (assay of cAMP elevation), in vitro toxicity, pro-secretory action in mouse intestine, and efficacy in a mouse model of constipation. FIG. 1B shows the cell-based plate reader screening method in which the initial rate of iodide influx was measured in FRT cells stably expressing human wildtype CFTR and a YFP fluorescent halide sensor following extracellular iodide addition. A CFTR activator increases the initial slope of the fluorescence quenching curve.

FIG. 1C shows chemical structures of six classes of CFTR candidate activators identified from the screens. Based on the criteria listed above, we focused further studies on $CFTR_{act}$-J027, a 3-phenyl-quinoxalinone with drug-like properties. $CFTR_{act}$-J027 was synthesized in pure crystalline form in two steps (FIG. 1D).

Figure 2A:
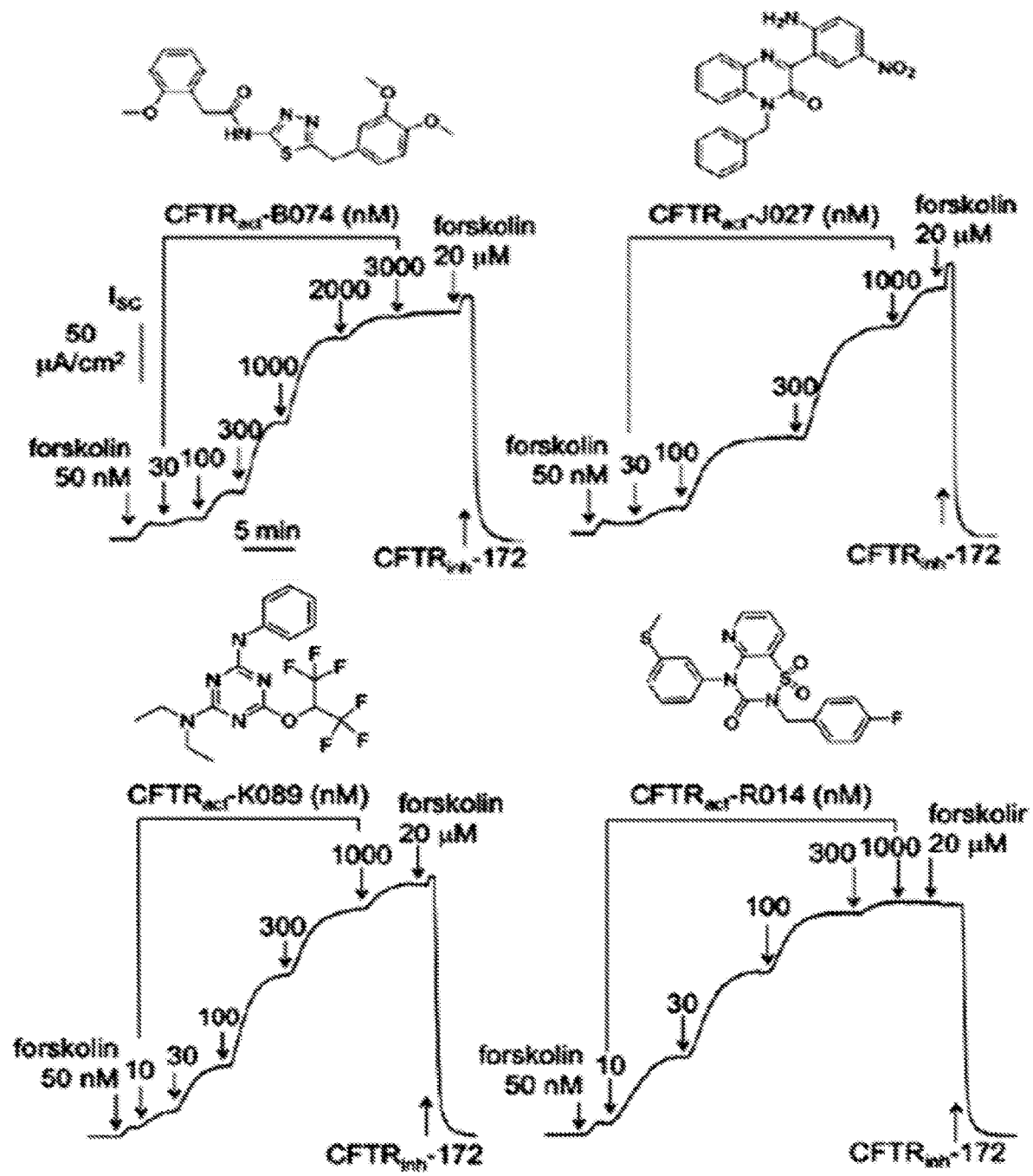
FIGS. 2A-2D. In vitro characterization of CFTR activators.
Figure 2B:
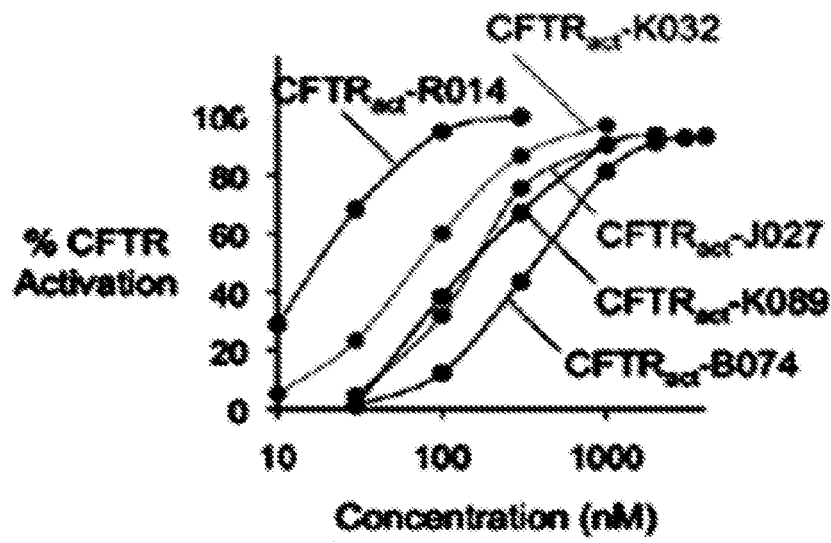
Figure 2C:
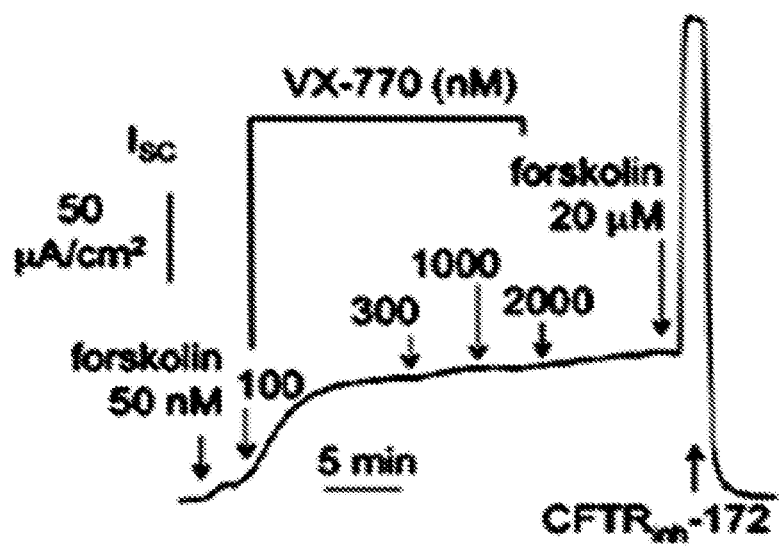
Figure 2D:
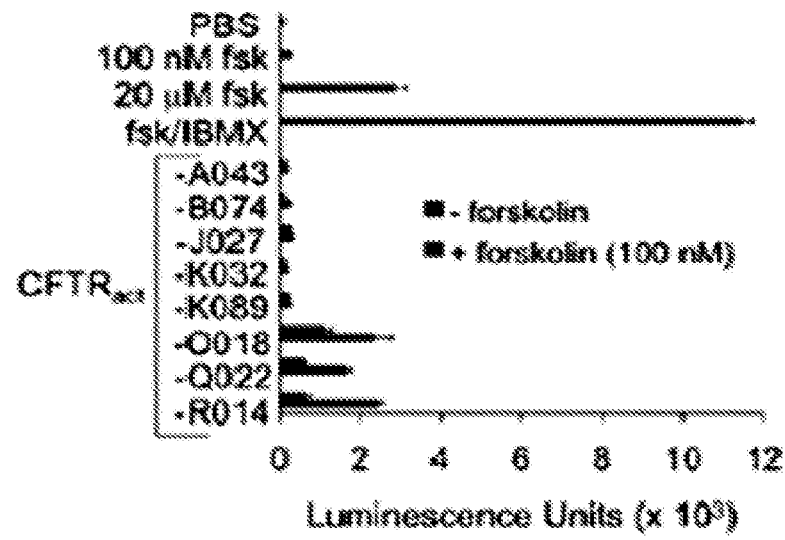

Short-circuit current measurements in CFTR-expressing FRT cells showed that $CFTR_{act}$-J027 fully activated CFTR (FIG. 2A), as the cAMP agonist forskolin produced no further increase in current, with an $EC_{50}$ ~200 nM (FIG. 2B). Interestingly, $CFTR_{act}$-J027 was only a weak potentiator of ΔF508-CFTR, as studied in FRT cells expressing ΔF508-CFTR after overnight incubation with a corrector (FIG. 2C). Cl⁻ secretion in freshly isolated mouse colon showed a concentration-dependent increase in short-circuit current with $EC_{50}$ ~300 nM (FIG. 2D). The increase in current at high $CFTR_{act}$-J027 was further increased by forskolin, which may be a consequence of activation of a basolateral membrane cAMP-sensitive $K^+$ channel that increases the driving force for apical membrane Cl⁻ secretion. The increase in current was fully inhibited by a CFTR-selective inhibitor. FIG. 2E shows that $CFTR_{act}$-J027 does not elevate cellular cAMP when added alone, and does not further increase cAMP when added together with forskolin, suggesting that CFTR activation involves a direct interaction mechanism rather than indirect action through cAMP elevation.

Figure 3A:
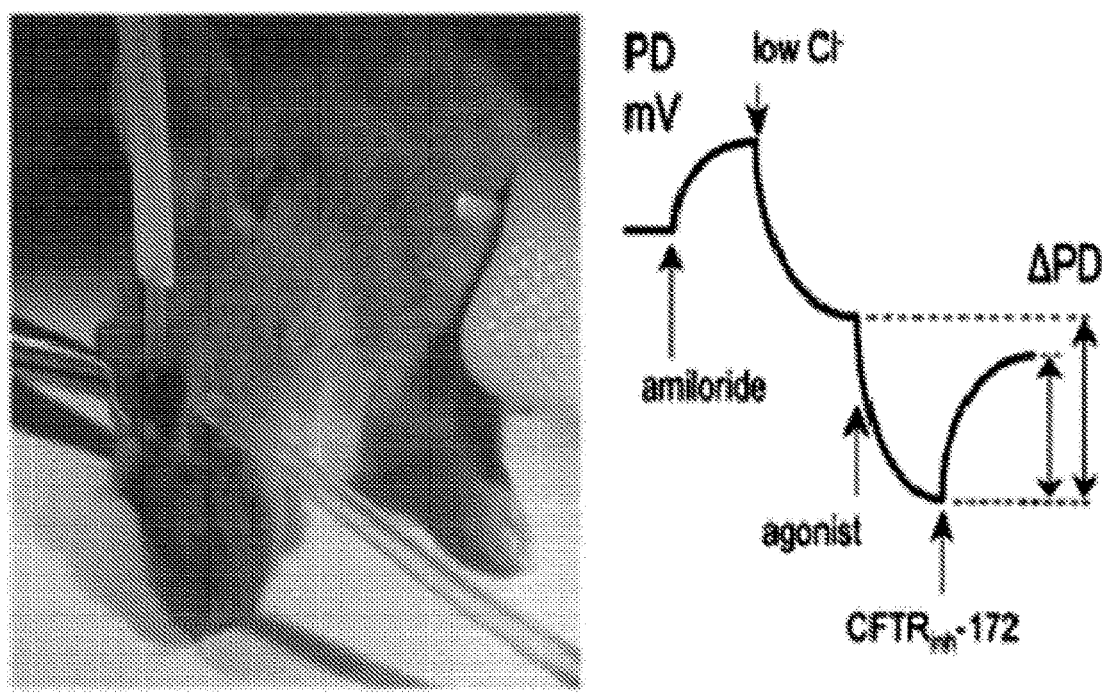
FIGS. 3A-3E. Potential difference (PD) measurements of CFTR activators at the ocular surface in live mice.

$CFTR_{act}$-J027 Normalizes Stool Output in a Mouse Model of Constipation $CFTR_{act}$-J027 was studied in the well-established loperamide-induced mouse model of constipation in which stool weight, pellet number and water content were measured over 3 h following intraperitoneal loperamide administration (FIG. 3A). Intraperitoneal administration of $CFTR_{act}$-J027 at 10 mg/kg normalized each of the stool parameters. $CFTR_{act}$-J027 did not affect stool output or water content in control (non-loperamide-treated) mice. Importantly, $CFTR_{act}$-J027 was without effect in cystic fibrosis mice lacking functional CFTR (FIG. 3B), nor was an inactive chemical analog of $CFTR_{act}$-J027 effective in wildtype mice (FIG. 3C). These results support a CFTR-selective action of $CFTR_{act}$-J027. Dose-response studies in mice showed an $ED_{50}$ of 2 mg/kg in the loperamide model by ip administration of $CFTR_{act}$-J027 (FIG. 3D).

Figure 4A:
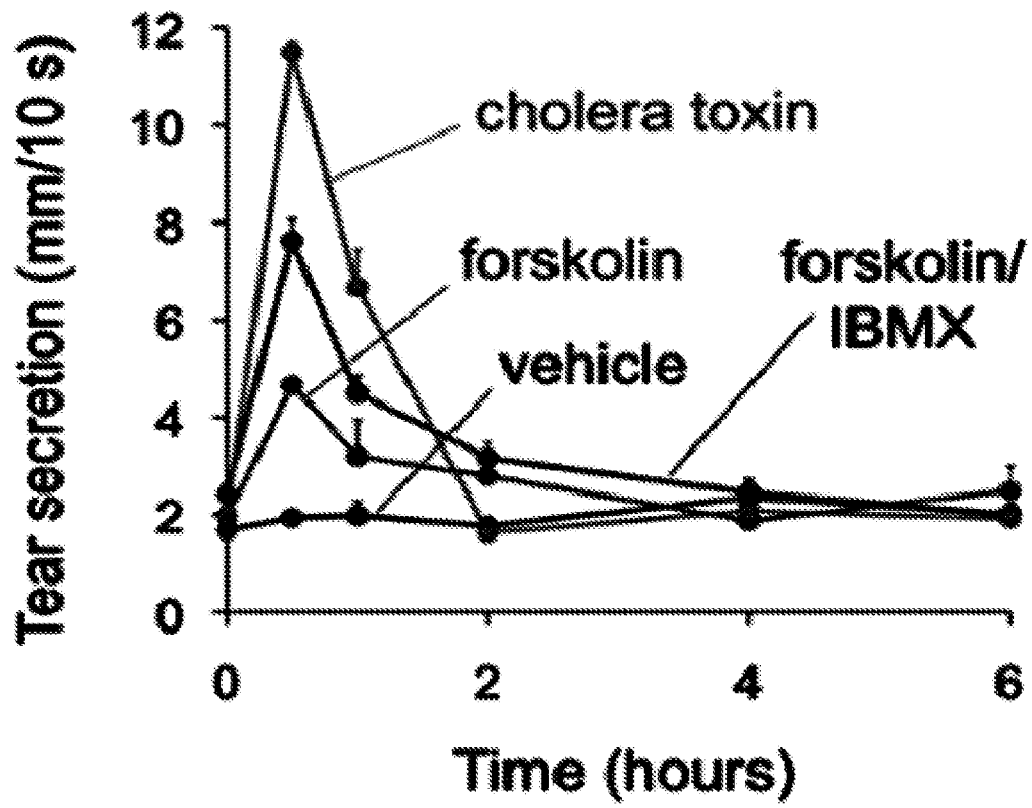
FIGS. 4A-4D. Tear fluid secretion measurement of CFTR activators in living mice.
Figure 4B:
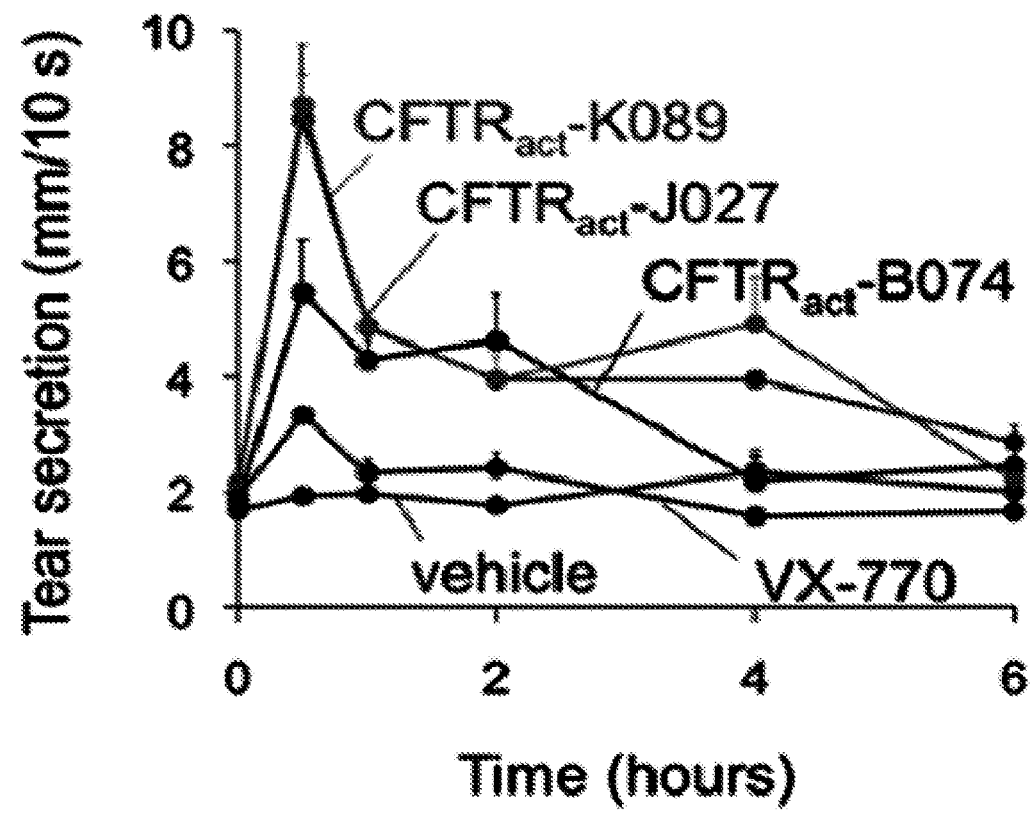
Figure 4C:
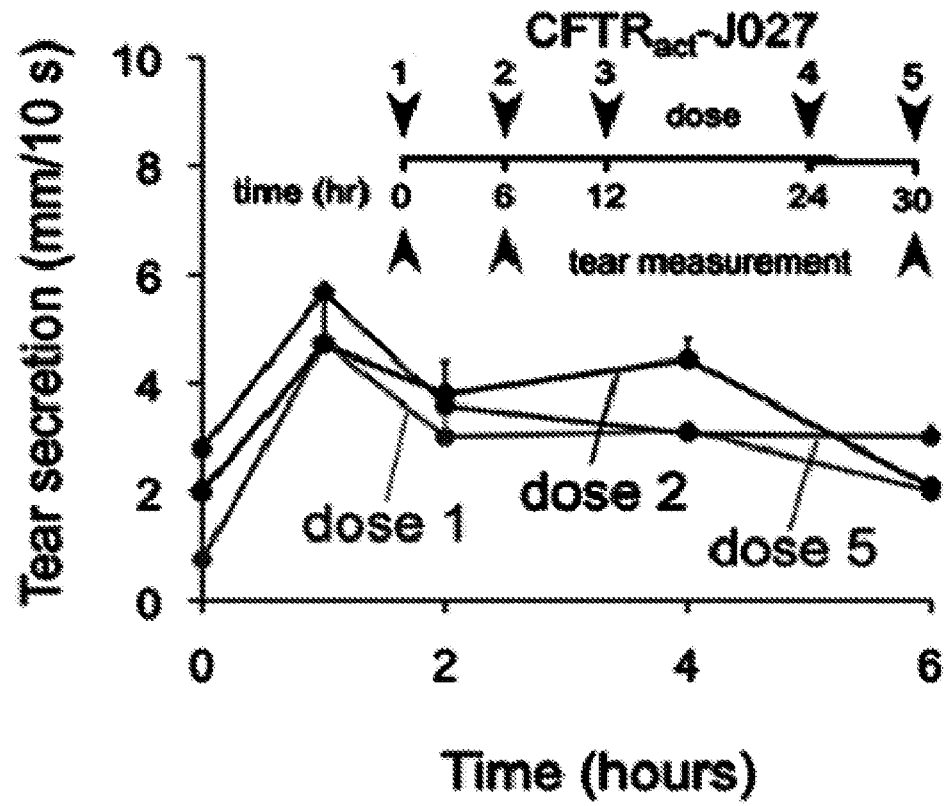

Oral administration of 10 mg/kg $CFTR_{act}$-J027 1 h prior to loperamide administration was also effective in normalizing stool output and water content in loperamide-treated mice, with no effect in control mice (FIG. 4A). The $ED_{50}$ for oral administration was 0.5 mg/kg, substantially lower than that for ip administration (FIG. 4B). In parallel studies, oral administration of the approved drugs lubiprostone or linaclotide at 250-500 fold greater mg/kg doses than given to humans for treatment of constipation, were less effective in normalizing stool output, producing 50% and 35% of the maximal CFTR$_{act}$-J027 response, respectively (FIG. 4C).

CFTR$_{act}$-J027 Actions on Intestinal Transit, Motility and Fluid Transport

Figure 5A:
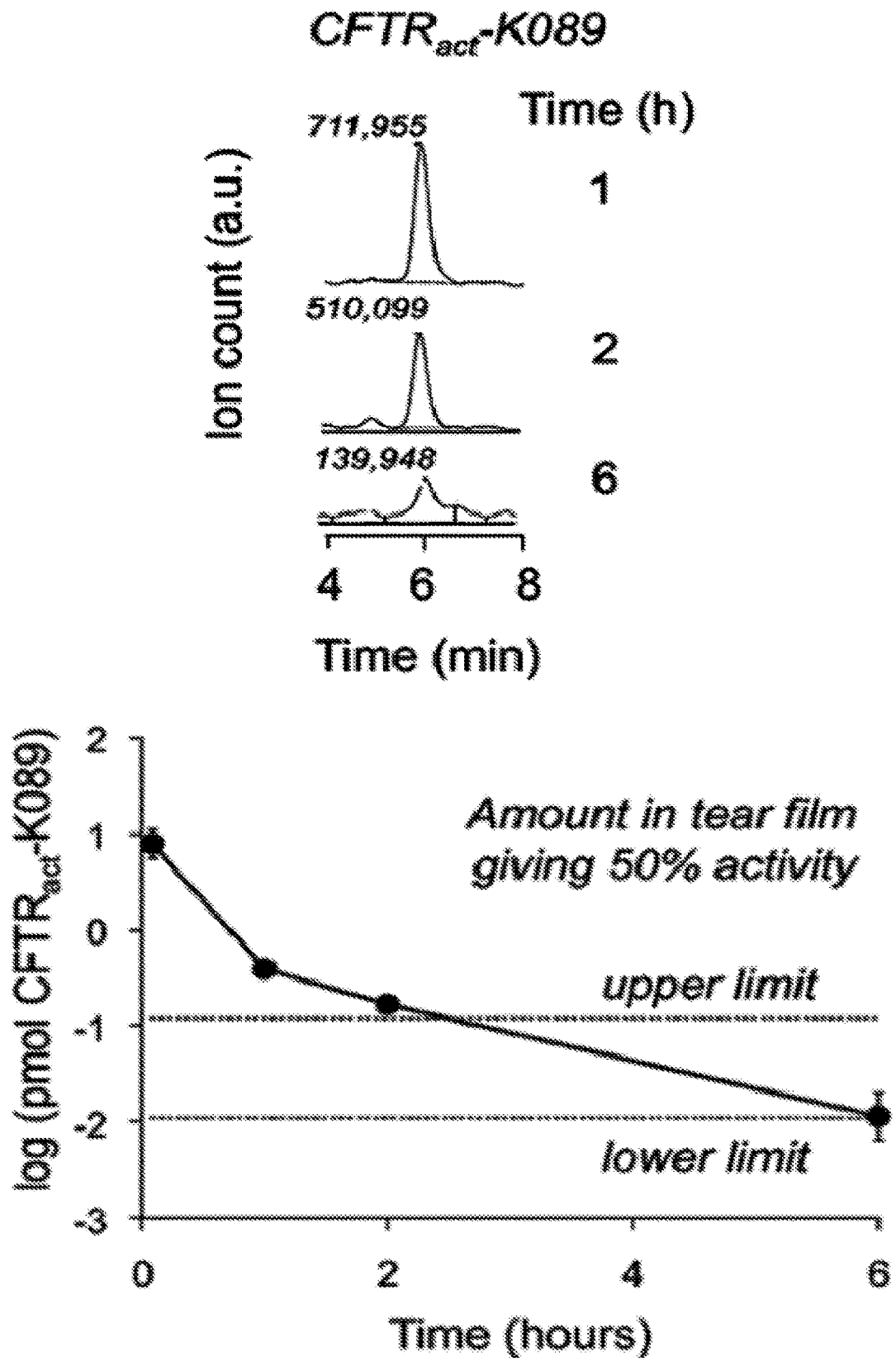
FIGS. 5A-5C. Compound pharmacology.
Figure 5B:
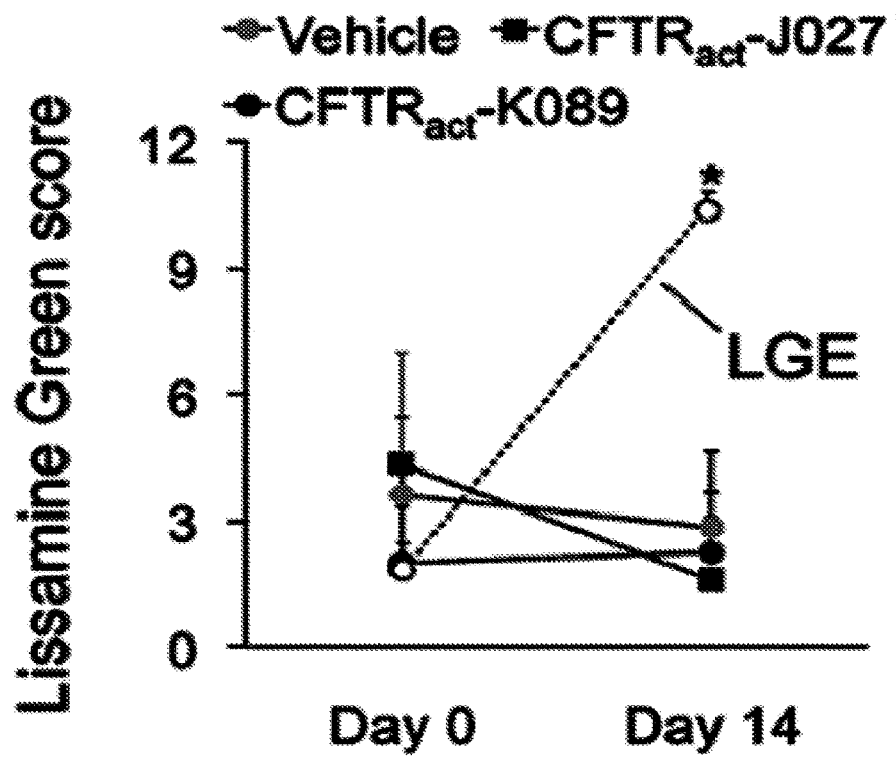

CFTR$_{act}$-J027 action on intestinal transit and motility was measured in vivo and in isolated intestinal strips, respectively. Whole-gut transit time, as measured by appearance of a marker in the stool after bolus oral gavage at the time of ip loperamide and CFTR$_{act}$-J027 administration, was normalized by CFTR$_{act}$-J027 (FIG. 5A, left panel). CFTR$_{act}$-J027 had no effect on whole-gut transit time in cystic fibrosis mice (right panel). In vitro measurements of intestinal contraction showed no effect of CFTR$_{act}$-J027 added alone or in the presence of 10 μM loperamide in isolated mouse ileum and colon strips (FIG. 5B). CFTR$_{act}$-J027 may thus increase intestinal transit in vivo by stimulating motility by secretion-induced stretch of the gut wall, without direct effect on intestinal smooth muscle.

To directly investigate the effects of CFTR$_{act}$-J027 on intestinal fluid secretion and absorption, an in vivo closed-intestinal loop model was used. CFTR$_{act}$-J027 was injected into closed, mid-jejunal loops and fluid accumulation was measured at 90 min. CFTR$_{act}$-J027 produced a 140% increase in loop weight/length ratio, indicating fluid secretion into the intestinal lumen in wild-type mice (FIG. 5C, upper panel), but was without effect in cystic fibrosis mice (lower panel), supporting a CFTR-selective mechanism of action. A closed-loop model was also used to study CFTR$_{act}$-J027 action on intestinal fluid absorption. Fluid without or with CFTR$_{act}$-J027 was injected into closed, mid-jejunal loops of cystic fibrosis mice (to avoid confounding fluid secretion) and fluid absorption was measured at 30 min. CFTR$_{act}$-J027 did not affect intestinal fluid absorption (FIG. 5D).

CFTR$_{act}$-J027 Pharmacology and Toxicity in Mice

Figure 6A:
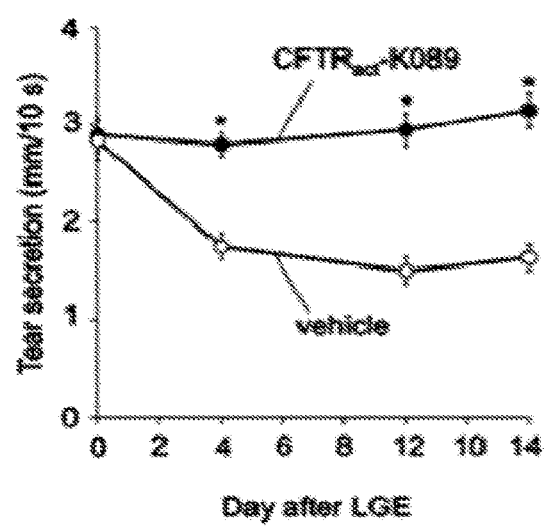
FIGS. 6A-6C. Topical CFTR$_{act}$-K089 restores tear secretion and prevents corneal epithelial disruption following LGE.

The in vitro metabolic stability of CFTR$_{act}$-J027 was measured by incubation with mouse liver microsomes in the presence of NADPH. CFTR$_{act}$-J027 was rapidly metabolized with ~21 min elimination half-life, with only 7% of the original compound remaining at 60 min (FIG. 6A).

Figure 6B:
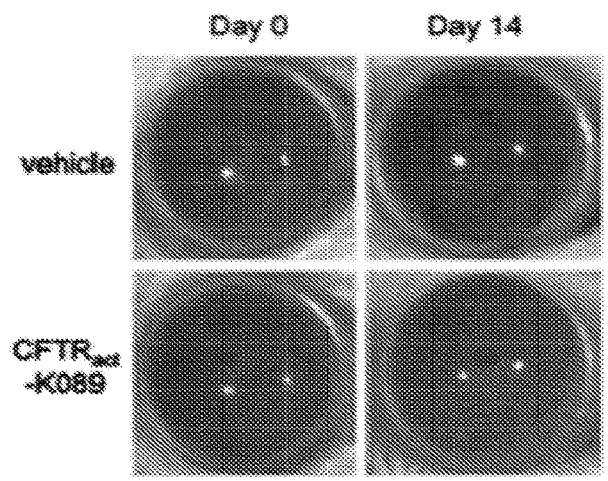

Pharmacokinetics was measured in mice following bolus intraperitoneal or oral administration of 10 mg/kg CFTR$_{act}$-J027. Following ip administration serum CFTR$_{act}$-J027 concentration decreased with an elimination half-life of ~16 min, and was undetectable at 150 min (FIG. 6B). Following oral administration serum CFTR$_{act}$-J027 concentration reached 180 nM at 30 min and was undetectable at other time points (FIG. 6B).

Figure 6C:
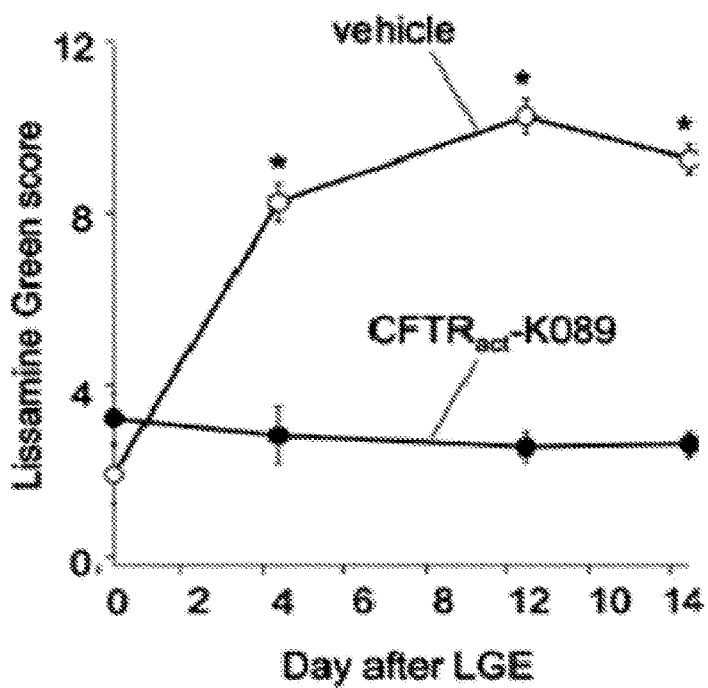

Preliminary toxicological studies of CFTR$_{act}$-J027 were done in cell cultures and mice. CFTR$_{act}$-J027, at a concentration of 20 μM near its solubility limit, did not show cytotoxicity as measured by the Alamar Blue assay (FIG. 6C). In the 7-day treated mice, CFTR$_{act}$-J027 did not affect the major serum chemistry and blood parameters (Table 1), nor did it change body weight or produce airway/lung fluid accumulation (FIG. 6D).

Last, to determine whether chronically administered CFTR$_{act}$-J027 retained efficacy, mice were treated orally for 7 days with 10 mg/kg CFTR$_{act}$-J027 or vehicle, and loperamide was given 1 h after the final dose. FIG. 6E shows that chronically administered CFTR$_{act}$-J027 remained effective in normalizing stool output and water content following loperamide.

TABLE 1

Complete blood count and serum chemistries of mice treated for 7 days with 10 mg/kg CFTR$_{act}$-J027 or vehicle orally once per day (mean ± SE., 5 mice per group). Student's t-test.

|  | Vehicle | CFTR$_{act}$-J027 | P value |
| --- | --- | --- | --- |
| Hemoglobin (g/dL) | 13.3 ± 0.2 | 12.8 ± 0.3 | >0.05 |
| Leukocytes (10³/μL) | 1.9 ± 0.3 | 1.9 ± 0.5 | >0.05 |
| Thrombocytes (10³/μL) | 790 ± 109 | 900 ± 48 | >0.05 |
| Total protein (g/dL) | 4.7 ± 0.2 | 5.2 ± 0.1 | >0.05 |
| Albumin (g/dL) | 2.6 ± 0.1 | 2.9 ± 0.03 | >0.05 |
| Globulin (g/dL) | 2.1 ± 0.1 | 2.2 ± 0.1 | >0.05 |
| ALT (U/L) | 52 ± 16 | 44 ± 6 | >0.05 |
| AST (U/L) | 131 ± 17 | 105 ± 11 | >0.05 |
| ALP (U/L) | 47 ± 8.5 | 53 ± 2.5 | >0.05 |
| Total bilirubin (mg/dl) | 0.1 ± 0 | 0.1 ± 0 | >0.05 |
| Glucose (mg/dl) | 156 ± 22 | 164 ± 6 | >0.05 |
| Cholesterol (mg/dl) | 121 ± 14 | 121 ± 6 | >0.05 |
| CK (U/L) | 344 ± 85 | 312 ± 62 | >0.05 |
| Sodium (mmol/L) | 149 ± 2.3 | 151 ± 0.7 | >0.05 |
| Potassium (mmol/L) | 5.0 ± 0.1 | 4.4 ± 0.1 | >0.05 |
| Chloride (mmol/L) | 113 ± 1 | 115 ± 1 | >0.05 |
| Calcium (mg/dl) | 8.5 ± 0.2 | 8.5 ± 0.04 | >0.05 |
| Phosphorus (mg/dl) | 6.6 ± 0.9 | 6.8 ± 0.3 | >0.05 |
| BUN (mg/dl) | 15.3 ± 3 | 18.4 ± 1.2 | >0.05 |
| Creatinine (mg/dl) | 0.2 ± 0 | 0.2 ± 0 | >0.05 |
| Bicarbonate (mmol/L) | 15.3 ± 1.6 | 16 ± 1.7 | >0.05 |

Dry Eye

3. Example 3

Mice

Wild-type (WT) and CF (homozygous ΔF508-CFTR mutant) mice in a CD1 genetic background were bred at the University of California San Francisco (UCSF) Animal Facility. Mice aged 8 to 12 weeks (25 to 35 g) were used. Female BALB/c mice (7-8 weeks old) were purchased from the Harlan Laboratory (Livermore, Calif., USA). Animal protocols were approved by the UCSF Institutional Animal Care and Use Committee and were in compliance with the ARVO Statement for the Use of Animals in Ophthalmic and Vision Research.

Short-Circuit Current

Fischer rat thyroid (FRT) cells stably expressing wild-type human CFTR were cultured on Snapwell inserts (Corning Costar, Corning N.Y., USA) for short-circuit current ($I_{sc}$) measurements. After 6-9 days in culture, when the transepithelial resistance was >1000 Ω/cm², the inserts were mounted in an Ussing chamber system (World Precision Instruments, Sarasota, Fla., USA). The basolateral solution contained 130 mM NaCl, 2.7 mM KCl, 1.5 mM KH$_2$PO$_4$, 1 mM CaCl$_2$, 0.5 mM MgCl$_2$, 10 mM glucose, and 10 mM Na-HEPES (pH 7.3). In the apical bathing solution, 65 mM NaCl was replaced by Na gluconate, and CaCl$_2$ was increased to 2 mM. Both solutions were bubbled with air and maintained at 37° C. The basolateral membrane was permeabilized with 250 μg/ml amphotericin B (26, 27). Hemichambers were connected to a DVC-1000 voltage clamp via Ag/AgCl electrodes and 3 M KCl agar bridges for $I_{sc}$ recording.

cAMP and Cytotoxicity Assays

Intracellular cAMP activity was measured using a GloSensor luminescence assay (Promega Corp., Madison, Wis., USA). FRT cells stably transfected with the pGloSensor cAMP plasmid (Promega Corp.) were cultured in white 96-well microplates (Corning Costar) overnight. Cells were then washed three times with PBS and incubated with 5 μM test compound for 10 min in the absence and presence of 100 nM forskolin. To assay cytotoxicity, FRT cells were cultured overnight in black 96-well Costar microplate wells and incubated with test compounds at up to 100 µM (the maximum solubility in PBS) for 1 or 24 h. Cytotoxicity was measured by Alamar Blue assay according to the manufacturer's instructions (Invitrogen, Carlsbad, Calif., USA).

Ocular Surface Potential Difference Measurements

Open-circuit transepithelial PD were measured continuously in anesthetized mice in response to serial perfusions of different solutions over the ocular surface, as described (21). Mice were anesthetized with Avertin (2,2,2-tribromoethanol, 125 mg/kg intraperitoneal, Sigma-Aldrich, St. Louis, Mo., USA), and core temperature was maintained at 37° C. using a heating pad. Eyes were oriented with the cornea and conjunctiva facing upward and exposed by retracting the eyelid with cross-action forceps. Solutions were isosmolar (320±10 mOsM; compositions provided in ref. 21) and contained 10µ☐☐ Qindomethacin to prevent CFTR activation by prostaglandins. The ocular surface was perfused at 6 mL/min through plastic tubing using a multireservoir gravity pinch-valve system (ALA Scientific, Westbury, N.Y., USA) and variable-flow peristaltic pump (medium flow model; Fisher Scientific, Fair Lawn, N.J., USA). A probe catheter was fixed 1 mm above the cornea using a micropositioner and a suction cannula was positioned 3 mm from the orbit. The measuring electrode was in contact to the perfusion catheter and connected to a high-impedance voltmeter (IsoMilivolt Meter; WPI). The reference electrode was grounded via a winged 21-gauge needle filled with isosmolar saline, and inserted subcutaneously in the abdomen. Measuring and reference electrodes consisted of Ag/AgCl with 3 M KCl agar bridges.

Tear Secretion

To measure unstimulated tear production, phenol red threads (Zone-Quick, Oasis Medical, Glendora, Calif., USA) were placed for 10 s in the lateral canthi of isofluorane-anesthetized mice using jewelers' forceps. Tear volume was measured as the length of thread wetting, as visualized under a dissecting microscope. Serial measurements were used to evaluate compound pharmacodynamics after application of 2-µL drops of compound formulations (50-100 µM compound in PBS containing 0.5% polysorbate and 0.5% DMSO) comparing to vehicle.

Lissamine Green Staining

To assess corneal epithelial disruption, 5 µL of lissamine green (LG) dye (1%) was applied to the ocular surface of isofluorane-anesthetized mice. Photographs of the eye were taken using a Nikon Digital camera adapted to an Olympus Zoom Stereo Microscope (Olympus, Center Valley, Pa., USA). Each corneal quadrant was scored on a 3-point scale by one blinded, trained observer, with the extent of staining in each quadrant classified as: 0, no staining; 1, sporadic (involving <25% of the total surface) staining; grade 2, diffuse punctate staining (25-75%); and grade 3, coalesced punctate staining (≥75%). The total grade is reported as the sum of scores from all four quadrants, ranging from 0 to 12.

Pharmacokinetics and Tissue Distribution

To determine the residence time of CFTR activators in the pre-ocular mouse tear film, compounds were recovered for liquid chromatography/mass spectroscopy (LC/MS) following single-dose ophthalmic delivery. Three eye washes (3 µL PBS each) were recovered from the lateral and medial canthi with 5-µL microcapillary tubes (Drummond Scientific Co., Broomhall, Pa., USA) after manual eyelid blinking (9). Pooled washes were diluted with acetonitrile/water (1:1) containing 0.1% formic acid and analyzed by LC/MS using an Xterra MS C18 column (2.1 mm×100 mm, 3.5-µm particle size) connected to a Waters 2695 HPLC solvent delivery system and a Waters Micromass ZQ mass spectrometer with positive electrospray ionization.

To study compound accumulation in systemic tissues, mouse blood, brain, kidney and liver were analyzed after 14 days of three-times daily topical dosing (0.1 nmol, 2 µL, 50 µM). Blood samples were collected from the left ventricle into K3 EDTA mini-tubes (Greiner, Kremsmunster, Austria) and centrifuged (28). The supernatant was extracted with an equal volume of ethyl acetate and the extract was dried with an air stream. Organs from treated and control mice were removed following ventricular perfusion with heparinized PBS (10 units/mL), weighed, mixed with acetic acid and water (100 µL/g tissue), and homogenized (29). Ethyl acetate (10 mL/g tissue) was added, samples were vortexed and centrifuged (3000 rpm for 15 min), and the ethyl acetate-containing supernatant was evaporated. Residues obtained from organic extracts of serum and organ homogenates were then reconstituted and analyzed by LC/MS as described above.

Mouse Model of Dry Eye Produced by Lacrimal Gland Excision

A lacrimal gland excision (LGE) model of aqueous-deficient dry eye was adapted from a reported method (30). The extraorbital lacrimal gland was exposed on each side of wild-type female BALB/c mice (7-8 weeks of age) by 3-mm linear skin incisions. Lacrimal ducts were cauterized and the entire gland was removed bilaterally, avoiding facial vessels and nerves. Incisions were each closed with a single interrupted 6-0 silk suture. Orbital lacrimal tissue remained functional. Eyes with reduced corneal sensation (<5% of mice studied), as identified from neurotrophic corneal ulcers within 1 day of LGE, were excluded. Mice were randomized to receive either treatment (in both eyes) with $CFTR_{act}$-K089 (0.1 nmol) or vehicle. Mice were treated three times daily (8 AM, 2 PM and 8 PM) for 2 weeks starting on Day 1 after LGE. Tear secretion and LG staining were performed immediately prior to, and one hour after the initial dose on day 4, 10 and 14 after LGE.

Statistics

Data are expressed as the mean±standard error of the mean (SEM). For direct comparisons between two means, the two-sided Students' t-test was used. For longitudinal measurements of tear secretion and LG scores in the dry eye prevention study, a linear mixed effects regression was used, adjusting for non-independence of measurements taken on the same eye and on both eyes of the same animal. Analysis was conducted in R v.3.2 for Mac (R Foundation for Statistical Computing, Vienna, Austria), using packages lme4 and robustlmm.

Characterization of Small-Molecule CFTR Activators

Figure 7:
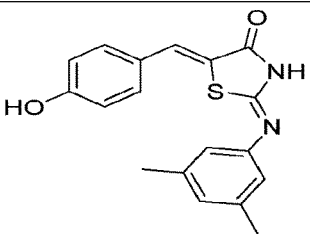
FIG. 7. A summary of EC$_{50}$ and V$_{max}$ values for compounds screened against CFTR A cell-based functional high-throughput screen of 120,000 compounds at 10 μM identified 20 chemical classes of small-molecule activators of wild-type CFTR that produced >95% of maximal CFTR activation. The screen was done in FRT epithelial cells co-expressing human wild-type CFTR and a cytoplasmic YFP halide sensor in 96-well format (26, 31, 32). Details of the primary screen will be reported separately. Secondary screening involved $I_{sc}$ measurement in CFTR-expressing FRT cells pretreated with submaximal forskolin (50 nM). Twenty-one compounds from eight chemical classes produced large increases in $I_{sc}$ at 1 µM (>75% of maximal current produced by 20 µM forskolin).
Figure 7:
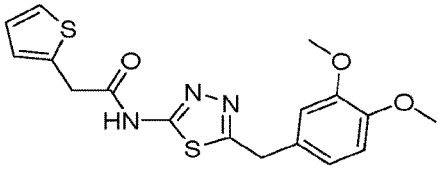
Figure 7:
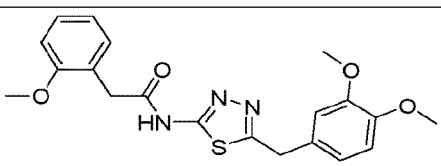
Figure 7:
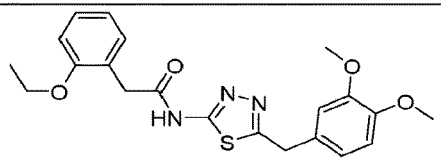
Figure 7:
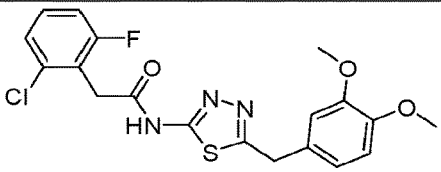
Figure 7:
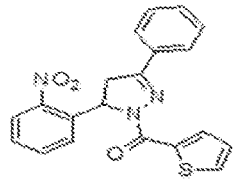
Figure 7:
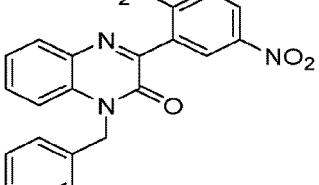

A cell-based functional high-throughput screen of 120,000 compounds at 10 µM identified 20 chemical classes of small-molecule activators of wild-type CFTR that produced >95% of maximal CFTR activation. The screen was done in FRT epithelial cells co-expressing human wild-type CFTR and a cytoplasmic YFP halide sensor in 96-well format (26, 31, 32). Secondary screening involved $I_{sc}$ measurement in CFTR-expressing FRT cells pretreated with submaximal forskolin (50 nM). Twenty-one compounds from eight chemical classes produced large increases in $I_{sc}$ at 1µ☐ (>75% of maximal current produced by 20 µM forskolin). A summary of $EC_{50}$ and $V_{max}$ values for each compound is provided in FIG. 7.

Structures of activators from the four most active chemical classes are shown in FIG. 2A, along with corresponding concentration-dependence data from $I_{sc}$ measurements. Each compound fully activated CFTR, as a high concentration of forskolin produced little further increase in $I_{sc}$, and the increase in $I_{sc}$ was fully inhibited by a CFTR inhibitor, $CFTR_{inh}$-172. $EC_{50}$ values ranged from 20-350 nM (FIG. 2B). VX-770 showed relatively weak activity against wild-type CFTR (FIG. 2C). $CFTR_{act}$-K032 and $CFTR_{act}$-K089 showed incomplete CFTR activation (~50% $V_{max}$).

Compounds that directly target CFTR without causing elevation of cellular cAMP were sought to minimize potential off-target effects (FIG. 2D). Compounds producing elevations in intracellular cAMP (from Classes O, Q, and R), probably by phosphodiesterase inhibition, were excluded from further consideration. Nanomolar-potency compounds from Classes B, J and K, which did not increase cAMP, were selected for further characterization in living mice.

CFTR Activators Increase Ocular Surface Chloride and Fluid Secretion In Vivo

An open-circuit potential difference (PD) method developed in our lab was used to evaluate compound activity at the ocular surface in vivo, as depicted in FIG. 3A (21). Cl⁻ channel function was quantified by measuring PD during continuous perfusion of the ocular surface with a series of solutions that imposed a transepithelial Cl⁻ gradient and contained various channel agonists and/or inhibitors. The ocular surface was first perfused with isosmolar saline to record the baseline PD. Amiloride was then added to the perfusate, followed by exchange to a low Cl⁻ solution in which Cl⁻ with an impermeant anion, gluconate. These maneuvers allow for direct visualization of CFTR activation in response to addition of candidate CFTR activators.

Figure 3B:
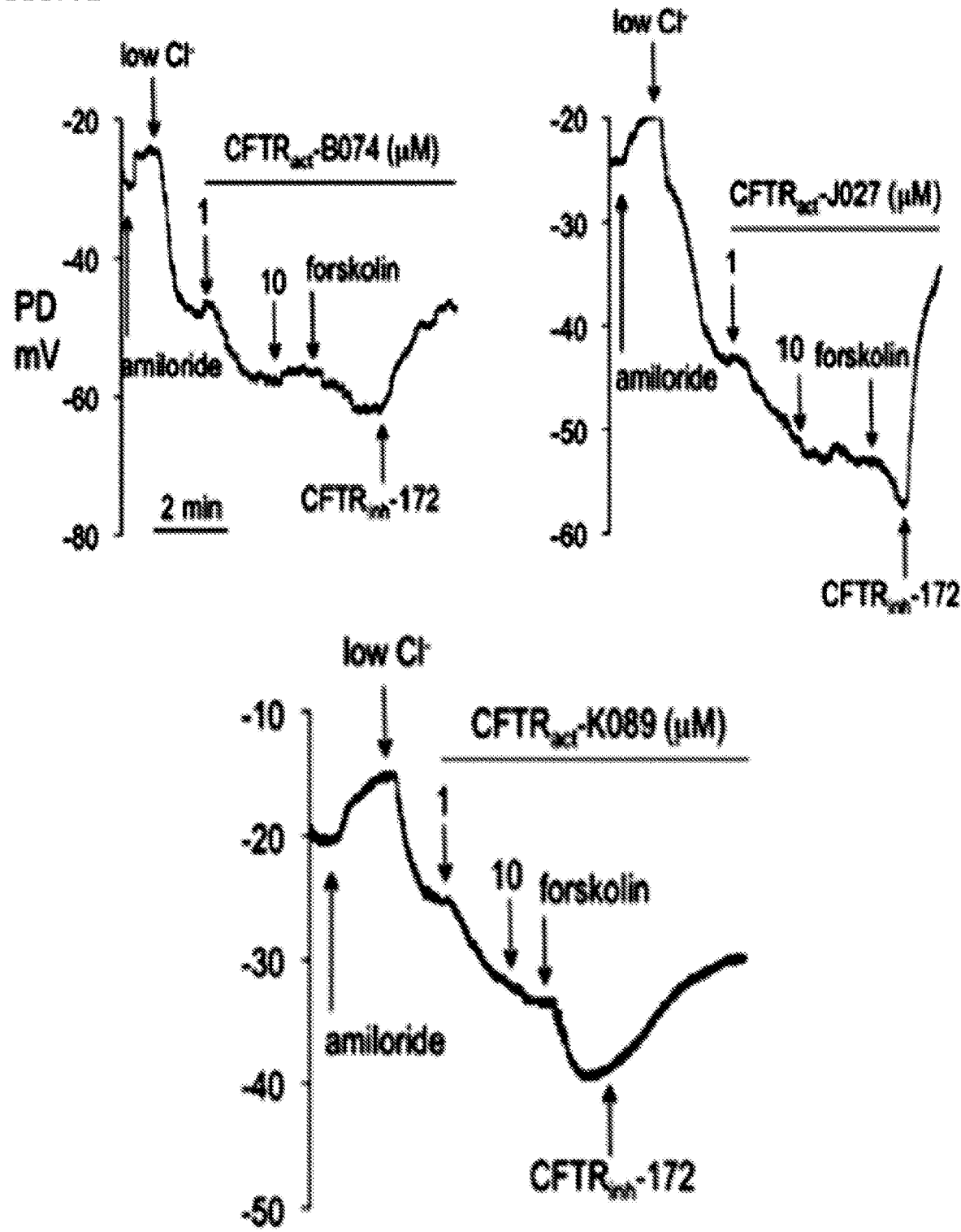
Figure 3C:
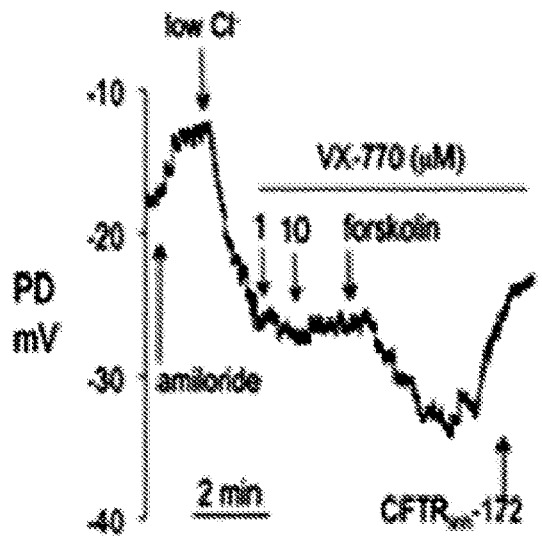
Figure 3D:
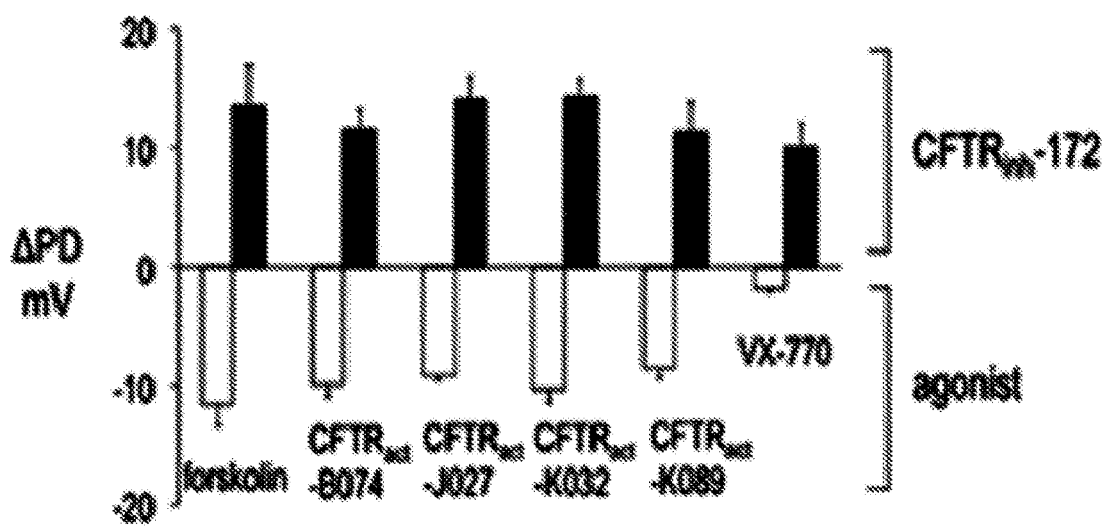
Figure 3E:
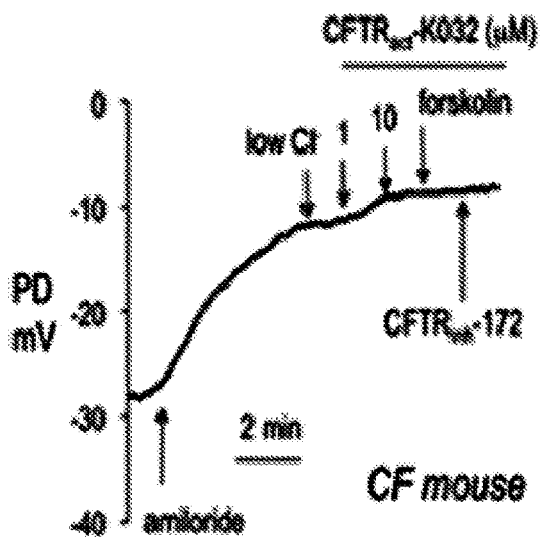

FIG. 3B shows large hyperpolarizations following exposure to $CFTR_{act}$-B074, $CFTR_{act}$-J027 and $CFTR_{act}$-K089, which were increased relatively little by forskolin and were reversed by $CFTR_{inh}$-172. In comparison, VX-770 produced minimal changes in ocular surface PD (FIG. 3C). FIG. 3D summarizes PD data for indicated activators, with data for additional compounds reported in FIG. 7. Control studies done in CF mice lacking functional CFTR showed no changes in PD following addition of each of the compounds tested, with a representative curve shown for $CFTR_{act}$-K032 (FIG. 3E).

Figure 4D:
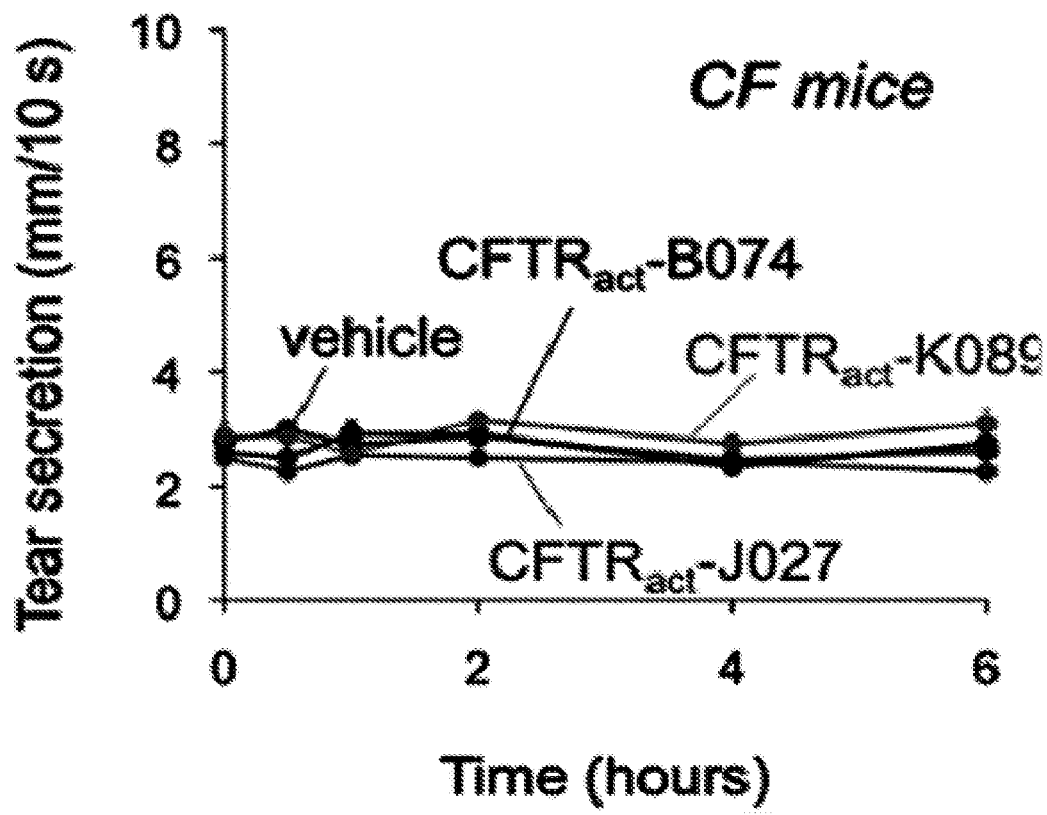

CFTR activators were next tested for their efficacy in augmenting tear production in mice. Preliminary experiments identified a standard ophthalmic formulation (0.5% polysorbate) that increased compound solubility and duration-of-action. Following a single topical dose, the indirect CFTR activators cholera toxin, forskolin, and 3-isobutyl-1-methylxanthine (IBMX) substantially increased basal tear secretion at 30 min, but these effects were transient and undetectable after 2 hours (FIG. 4A). However, the direct CFTR activators identified here, $CFTR_{act}$-B074, $CFTR_{act}$-J027 and $CFTR_{act}$-K089, increased tear fluid secretion by approximately two-fold for at least four hours. VX-770 produced little tear secretion (FIG. 4B). Repeated topical administrations (three times daily for up to 2 weeks) produced sustained tear hypersecretion without tachyphylaxis (FIG. 4C). CFTR activators did not increase tear fluid secretion in CF mice, demonstrating selective CFTR targeting (FIG. 4D).

Toxicity and Pharmacokinetics

Tear collection methods were validated by demonstrating reproducible recovery of tetramethylrhodamine dextran (3 kDa) from the ocular surface up to six hours after instillation. The pharmacokinetics of $CFTR_{act}$-K089 at the ocular surface was determined by LC/MS of recovered tear washes. Following instillation of 0.1 nmol of $CFTR_{act}$-K089 (2 µL, 50 µM) to the ocular surface, 7.9±2.4 pmol and 0.011±0.004 pmol were recovered at five min and six hours, respectively (FIG. 5A). The amount of $CFTR_{act}$-K089 required for 50% CFTR activation ($EC_{50}$ ~250 nM) lies between the dashed lines, reflecting concentrations calculated from the highest and lowest reported normal tear volumes in mice (33, 34). The quantity of $CFTR_{act}$-K089 recovered from tear fluid predicts therapeutic levels for at least six hours. Tear fluid pharmacokinetics of $CFTR_{act}$-J027 could not be measured because the LC/MS sensitivity was low for this compound.

Figure 5C:
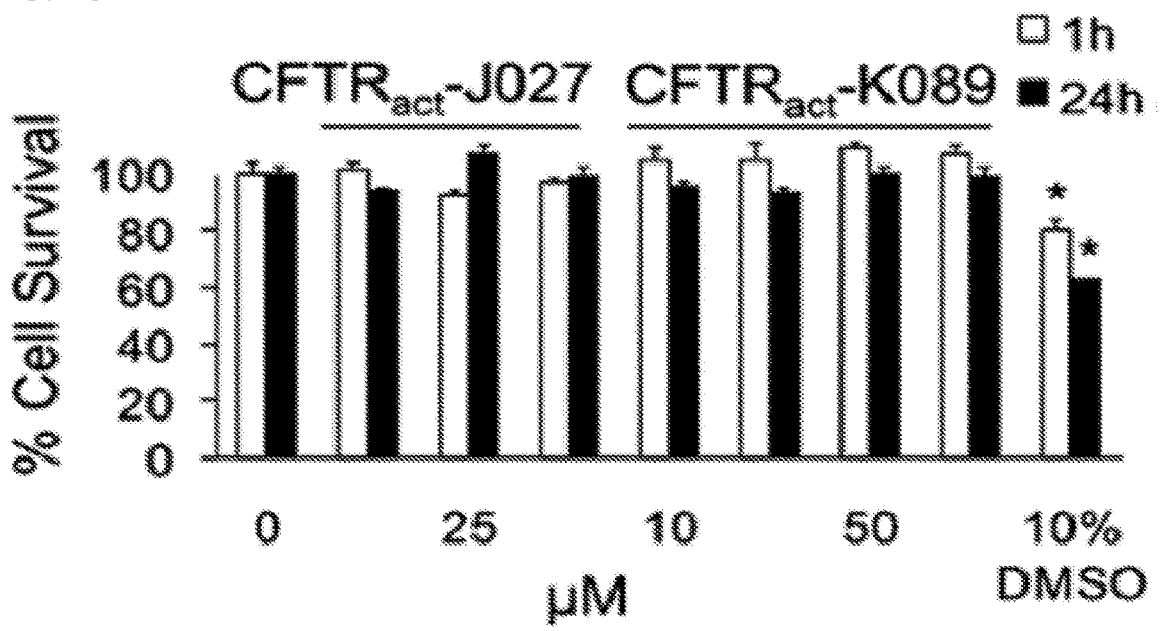

Following two weeks of three times per day dosing, the amounts of $CFTR_{act}$-K089 and $CFTR_{act}$-J027 were below the limits of detection (~10 and ~700 fmol, respectively) in mouse blood, brain, liver and kidney, indicating minimal systemic accumulation. The chronically treated mice showed no signs of ocular toxicity, as assessed by slit-lamp evaluation for conjunctival hyperemia, anterior chamber inflammation, and lens clarity. LG staining showed no corneal or conjunctival epithelial disruption (FIG. 5B). The compounds also produced no appreciable in vitro cytotoxicity in cell cultures at concentrations up to 100 µM (FIG. 5C).

CFTR Activator Prevents Dry Eye in a Lacrimal Gland Excision Model in Mice

On the basis of its favorable tear film pharmacokinetics, $CFTR_{act}$-K089 was selected for testing in a mouse model of aqueous-deficient dry eye produced by LGE. Following extraorbital LGE in BALB/c mice, $CFTR_{act}$-K089-treated mice (0.1 nmol, administered three times daily) maintained basal tear volume, whereas tear volume from vehicle-treated mice was significantly reduced at all subsequent time-points (FIG. 6A), and for at least 30 days. Similar to what was reported in C57/bl6 mice (30), decreased lacrimation in vehicle-treated BALB/c mice was associated with progressive epithelial disruption from Day 0 to Day 14, shown pictorially (FIG. 6B top) and quantitatively (FIG. 6C). $CFTR_{act}$-K089 not only restored tear secretion in LGE mice but remarkably prevented ocular surface epithelial disruption at all time points (FIG. 6B bottom, C). Vehicle-treated eyes developed diffuse, progressive corneal epitheliopathy (LG score increase of 7.3±0.6 by Day 14), whereas eyes treated with $CFTR_{act}$-K089 had minimal LG staining at all time points (LG score change, −0.6±0.6).

Example 4—Constipation II

Abstract. Background & Aims: Constipation is a common clinical problem that negatively impacts quality of life and is associated with significant health care costs. Activation of the cystic fibrosis transmembrane regulator (CFTR) chloride channel is the primary pathway that drives fluid secretion in the intestine, which maintains lubrication of luminal contents. We hypothesized that direct activation of CFTR would cause fluid secretion and reverse the excessive dehydration of stool found in constipation. Methods: A cell-based high-throughput screen was done for 120,000 drug-like, synthetic small molecules. Active compounds were characterized for mechanism of action and one lead compound was tested in a loperamide-induced constipation model in mice. Results: Several classes of novel CFTR activators were identified, one of which, the phenylquinoxalinone $CFTR_{act}$-J027, fully activated CFTR chloride conductance with $EC_{50}$ ~200 nM, without causing elevation of cytoplasmic cAMP. Orally administered $CFTR_{act}$-J027 normalized stool output and water content in a loperamide-induced mouse model of constipation with $ED_{50}$ ~0.5 mg/kg; $CFTR_{act}$-J027 was without effect in cystic fibrosis mice lacking functional CFTR. Short-circuit current, fluid secretion and motility measurements in mouse intestine indicated a pro-secretory action of CFTR$_{act}$-J027 without direct stimulation of intestinal motility. Oral administration of 10 mg/kg CFTR$_{act}$-J027 showed minimal bioavailability, rapid hepatic metabolism and blood levels <200 nM, and without apparent toxicity after chronic administration. Conclusions: CFTR$_{act}$-J027 or alternative small-molecule CFTR-targeted activators may be efficacious for the treatment of constipation.

Introduction

Constipation is a common clinical complaint in adults and children that negatively impacts quality of life. The prevalence of chronic constipation has been estimated to be 15% in the US population, with annual health-care costs estimated at ~7 billion dollars with >800 million dollars spent on laxatives [1, 2]. The mainstay of constipation therapy includes laxatives that increase stool bulk, such as soluble fiber; create an osmotic load, such as polyethylene glycol; or stimulate intestinal contraction, such as the diphenylmethanes. There are also surface laxatives that soften stool such as docusate sodium and probiotics such as *Lactobacillus paracasei* [3]. The FDA-approved drug linaclotide, a peptide agonist of the guanylate cyclase C receptor, acts by inhibiting visceral pain, stimulating intestinal motility, and increasing intestinal secretion [4, 5]. A second approved drug, lubiprostone, a prostaglandin E analog, is thought to activate a putative enterocyte ClC-2 channel [6], though the mechanistic data are less clear. Despite the wide range of therapeutic options, there is a continued need for safe and effective drugs to treat constipation.

Intestinal fluid secretion involves active Cl$^-$ secretion across the enterocyte epithelium through the basolateral membrane Na$^+$/K$^+$/2Cl$^-$ cotransporter (NKCC1) and the luminal membrane cystic fibrosis transmembrane regulator (CFTR) Cl$^-$ channel and Ca$^{2+}$-activated Cl$^-$ channel (CaCC). The electrochemical and osmotic forces created by Cl$^-$ secretion drive Na$^+$ and water secretion [7]. In cholera and Traveler's diarrhea CFTR is strongly activated by bacterial enterotoxins through elevation of intracellular cyclic nucleotides [8, 9]. CFTR is an attractive target to increase intestinal fluid secretion in constipation as it is robustly expressed throughout the intestine and its activation strongly increases intestinal fluid secretion. An activator targeting CFTR directly is unlikely to produce the massive, uncontrolled intestinal fluid secretion seen in cholera because the enterotoxins in cholera act irreversibly to produce sustained elevation of cytoplasmic cAMP, which not only activates CFTR but also basolateral K$^+$ channels, which increase the electrochemical driving force for Cl$^-$ secretion; cholera enterotoxins also inhibit the luminal NHE3 Na$^+$/H$^+$ exchanger involved in intestinal fluid absorption [10, 11].

Motivated by these considerations and the continuing need for safe and effective drug therapy of constipation, here we report the identification and characterization of a nanomolar-potency, CFTR-targeted small-molecule activator, and provide proof of concept for its pro-secretory action in intestine and efficacy in constipation.

Methods.

Materials. High-throughput screening was done using a diverse collection of 120,000 drug-like synthetic compounds obtained from ChemDiv Inc. (San Diego, Calif., USA) and Asinex (Winston-Salem, N.C., USA). For structure-activity analysis, 600 commercially available analogs (ChemDiv Inc.) of active compounds identified in the primary screen were tested. Other chemicals were purchased from Sigma-Aldrich (St. Louis, Mo., USA) unless indicated otherwise.

CFTR$_{act}$-J027 synthesis. To a solution of o-phenylenediamine (1 g, 9.24 mmol) in DMF (30 mL) was added potassium carbonate (2.5 g, 18.4 mmol) and benzyl bromide (0.73 mL, 6.2 mmol) then stirred overnight at ambient temperature. The reaction mixture was diluted with CH$_2$Cl$_2$, washed with water, dried over MgSO$_4$ and concentrated under reduced pressure. The residue was purified by flash chromatography to give the intermediate N$^1$-benzylbenzene-1,2-diamine as a brown liquid. $^1$H NMR (300 MHz, CDCl$_3$): δ 7.45-7.31 (m, 5H), 6.86-6.69 (m, 4H), 4.35 (s, 2H), 3.50 (br, 3H); MS: m/z 199 (M+H). Then, a solution of the intermediate (400 mg, 2 mmol) and 5-nitroisatin (380 mg, 2 mmol) in acetic acid (5 mL) was refluxed for 2 h. The reaction mixture was cooled to room temperature and solvent removed under reduced pressure. The residue was dissolved with methanol and acetic acid was added to crystallize 3-(2-amino-5-nitrophenyl)-1-benzylquinoxalin-2 (1H)-one (CFTR$_{act}$-J027) as a yellow powder with >99% purity. $^1$H NMR (300 MHz, DMSO-d6): δ 9.15 (d, 1H, J=2.8 Hz), 8.07 (dd, 1H, J=2.7, 9.2 Hz), 7.97 (dd, 1H, J=1.2, 7.9 Hz), 7.82 (brs, 2H), 7.60-7.27 (m, 7H), 6.92 (d, 1H, J=9.2 Hz), 5.59 (brs, 2H); $^{13}$C NMR (75 MHz, DMSO-d6): δ 155.0, 154.6, 153.3, 136.3, 135.3, 132.8, 132.2, 131.0, 130.0, 129.5, 129.1, 127.7, 127.3, 126.8, 124.1, 116.1, 115.9, 115.4, 45.9; MS: m/z 373 (M+H).

Cell culture. Fischer Rat Thyroid (FRT) cells stably co-expressing human wild-type CFTR and the halide-sensitive yellow fluorescent protein (YFP)-H148Q were generated as previously described [12]. Cells were cultured on plastic in Coon's-modified Ham's F12 medium supplemented with 10% fetal bovine serum, 2 mM L-glutamine, 100 units/ml penicillin, and 100 □g/ml streptomycin. For high-throughput screening, cells were plated in black 96-well microplates (Corning-Costar Corp., Corning, N.Y., USA) at a density of 20,000 cells per well. Screening was done 24-48 hours after plating.

High-throughput screening. Screening was carried out using a Beckman Coulter integrated system equipped with a liquid handling system and two FLUOstar fluorescence plate readers (BMG Labtechnologies, Durham, N.C., USA), each equipped with dual syringe pumps and 500±10 nm excitation and 535±15 nm emission filters (details in ref 12). CFTR- and YFP-expressing FRT cells were grown at 37° C./5% CO$_2$ for 24-48 hours after plating. At the time of assay, cells were washed three times with phosphate-buffered saline (PBS) and then incubated for 10 min with 60 μl of PBS containing test compounds (at 10 μM) and a low concentration of forskolin (125 nM). Each well was assayed individually for I$^-$ influx in a plate reader by recording fluorescence continuously (200 ms per point) for 2 s (baseline) and then for 12 s after rapid (<1 s) addition of 165 μL of PBS in which 137 mM Cl$^-$ was replaced by I$^-$. The initiate rate of I$^-$ influx was computed by determined using exponential regression. All compound plates contained negative controls (DMSO vehicle) and positive controls (20 OM forskolin).

Short-circuit current measurement. Short-circuit current was measured in FRT cells stably expressing wild-type human CFTR cultured on porous filters as described [12]. The basolateral solution contained 130 mM NaCl, 2.7 mM KCl, 1.5 mM KH$_2$PO$_4$, 1 mM CaCl$_2$, 0.5 mM MgCl$_2$, 10 mM glucose, and 10 mM Na-HEPES (pH 7.3, 37° C.). In the apical solution 65 mM NaCl was replaced by Na gluconate, and CaCl$_2$ was increased to 2 mM, and the basolateral membrane was permeabilized with 250 μg/ml amphotericin B. Short-circuit current was measured in freshly harvested adult mouse colon at 37° C. using symmetrical Krebs-bicarbonate buffer.

cAMP assay. Intracellular cAMP activity was measured using a GloSensor luminescence assay (Promega Corp., Madison, Wis., USA). FRT null cells were stably transfected with the pGloSensor cAMP plasmid and plated onto white 96-well microplates and grown to confluence. Cells were washed three times with PBS and incubated with 5 μM $CFTR_{act}$-J027 for 10 min in the absence and presence of 100 nM forskolin. cAMP was assayed according to the manufacturer's instructions.

Pharmacokinetics. All animal experiments were approved by UCSF Institutional Animal Care and Use Committee. Female CD1 mice were treated with 10 mg/kg $CFTR_{act}$-J027 (saline containing 5% DMSO and 10% Kolliphor HS 15) either intraperitoneally (ip) or orally. Blood was collected at 15, 30, 60, 150, 240 and 360 min after treatment by orbital puncture and centrifuged at 5000 rpm for 15 min to separate plasma. Plasma samples (60 μL) were mixed with 300 μL acetonitrile and centrifuged at 13000 rpm for 20 min, and 90 μL of the supernatant was used for LC/MS. The solvent system consisted of a linear gradient from 5 to 95% acetonitrile over 16 min (0.2 ml/min flow). Mass spectra was acquired on a mass spectrometer (Waters 2695 and Micromass ZQ) using electrospray (+) ionization, mass ranging from 100 to 1500 Da, cone voltage 40 V. Calibration standards were prepared in plasma from untreated mice to which known amounts of $CFTR_{act}$-J027 were added.

In vitro metabolic stability. $CFTR_{act}$-J027 (5 μM) was incubated for specified times at 37° C. with mouse liver microsomes (1 mg protein/ml; Sigma-Aldrich) in potassium phosphate buffer (100 mM) containing 1 mM NADPH, as described [13]. The mixture was then chilled on ice, and 0.5 ml of ice-cold ethyl acetate was added. Samples were centrifuged for 15 min at 3000 rpm, the supernatant evaporated to dryness, and the residue was dissolved in 100 μL mobile phase (acetonitrile:water, 3:1) for LC/MS and assayed as described above.

Murine model of constipation. Female CD1 mice (age 8-10 weeks) were administered loperamide (0.3 mg/kg, ip, Sigma-Aldrich) to produce constipation. Various amounts of $CFTR_{act}$-J027 (0.1, 0.3, 1, 3 and 10 mg/kg) were given at the same time (for ip administration) or 1 h before (for oral administration) loperamide. Control mice were treated with vehicle only. Some mice were treated orally with lubiprostone (0.5 mg/kg, Sigma-Aldrich) or linaclotide (0.5 mg/kg, Toronto Research Chemicals Inc., Toronto, Ontario, Canada). After loperamide injection, mice were placed individually in metabolic cages with food and water provided ad libitum. Stool samples were collected for 3 h, and total stool weight and number of fecal pellets were quantified. To measure stool water content stool samples were dried at 80° C. for 24 h and water content was calculated as [wet weight-dry weight]/wet weight. Similar studies were done in cystic fibrosis (CF) mice (ΔF508 homozygous) lacking functional CFTR. Some studies were done using the chemically similar but inactive analog of $CFTR_{act}$-J027, 3-(2-amino-5-nitrophenyl)-1-(methyl)-2(1H)-quinoxalinone.

In vivo intestinal transit and ex vivo intestinal contractility. Whole-gut transit time was determined using an orally administered marker (200 μL, 5% Evans Blue, 5% gum Arabic) and measuring the time of its appearance in stool. Mice were administered loperamide and $CFTR_{act}$-J027 (10 mg/kg) or vehicle intraperitoneally at zero time. For ex vivo contractility measurements, mice were euthanized by avertin overdose (200 mg/kg, 2,2,2-tribromethanol, Sigma-Aldrich) and ileum and colon segments of ~2 cm length were isolated and washed with Krebs-Henseleit buffer. The ends of the intestinal segments were tied, connected to a force transducer (Biopac Systems, Goleta, Calif., USA) and tissues were transferred to an organ chamber (Biopac Systems) containing Krebs-Henseleit buffer at 37° C. aerated with 95% $O_2$, 5% $CO_2$. Ileum and colon were stabilized for 60 min with resting tensions of 0.5 and 0.2 g respectively, and solutions were changed every 15 min. Effects of $CFTR_{act}$-J027 on baseline and loperamide-suppressed isometric intestinal contractions were recorded.

In vivo intestinal secretion and absorption. Mice (wild-type or CF) were given access to 5% dextrose water but not solid food for 24 h before experiments. Mice were anesthetized with isoflurane and body temperature was maintained during surgery at 36-38° C. using a heating pad. A small abdominal incision was made to expose the small intestine, and closed mid-jejunal loops (length 2-3 cm) were isolated by sutures. Loops were injected with 100 μL vehicle alone or 100 μg $CFTR_{act}$-J027 in vehicle. The abdominal incision was closed with sutures, and mice were allowed to recover from anesthesia. Intestinal loops were removed at 90 min and loop length and weight were measured to quantify fluid secretion. Intestinal absorption was measured in CF mice (to prevent secretion) as described above, except that the loops were removed at 0 or 30 min. Absorption was calculated as 1−(loop weight at 0 min−loop weight at 30 min)/loop weight at 0 min.

Chronic administration and toxicity studies. Mice were administered 10 mg/kg $CFTR_{act}$-J027 or vehicle orally once a day for 7 d. One hour after the final dose mice were treated with loperamide (0.3 mg/kg, ip) and stool was collected for 3 h. In vivo toxicity was assessed in these mice by measuring lung wet/dry weight ratio, complete blood count (HEMAVET 950FS, Drew Scientific Inc., Florida, USA) and serum chemistry (Idexx Laboratories Inc., Sacramento, Calif., USA) 4 h after the last $CFTR_{act}$-J027 dose. In vitro cytotoxicity was measured in FRT cells incubated with 25 μM $CFTR_{act}$-J027 for 8 and 24 h. Cytotoxicity was measured by Alamar Blue assay according to the manufacturer's instructions (Invitrogen, Carlsbad, Calif., USA).

Statistical analysis. Experiments with two groups were analyzed with Student's t-test, when there are 3 groups or more analysis was made with one-way analysis of variance and post-hoc Newman-Keuls multiple comparisons test. $P<0.05$ was taken as statistically significant.

Results.

Figure 8A:
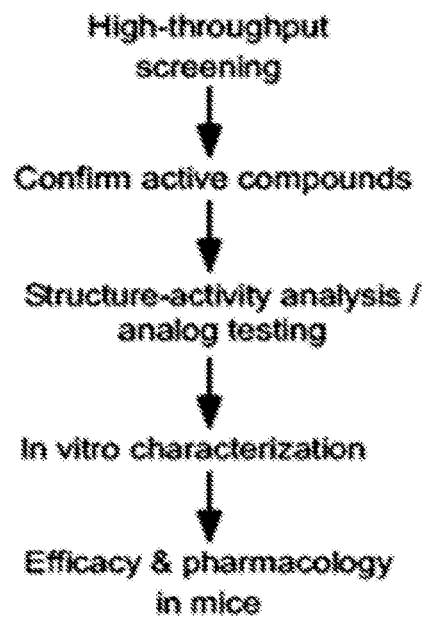
FIGS. 8A-8D. Identification of small-molecule CFTR activators.
Figure 8B:
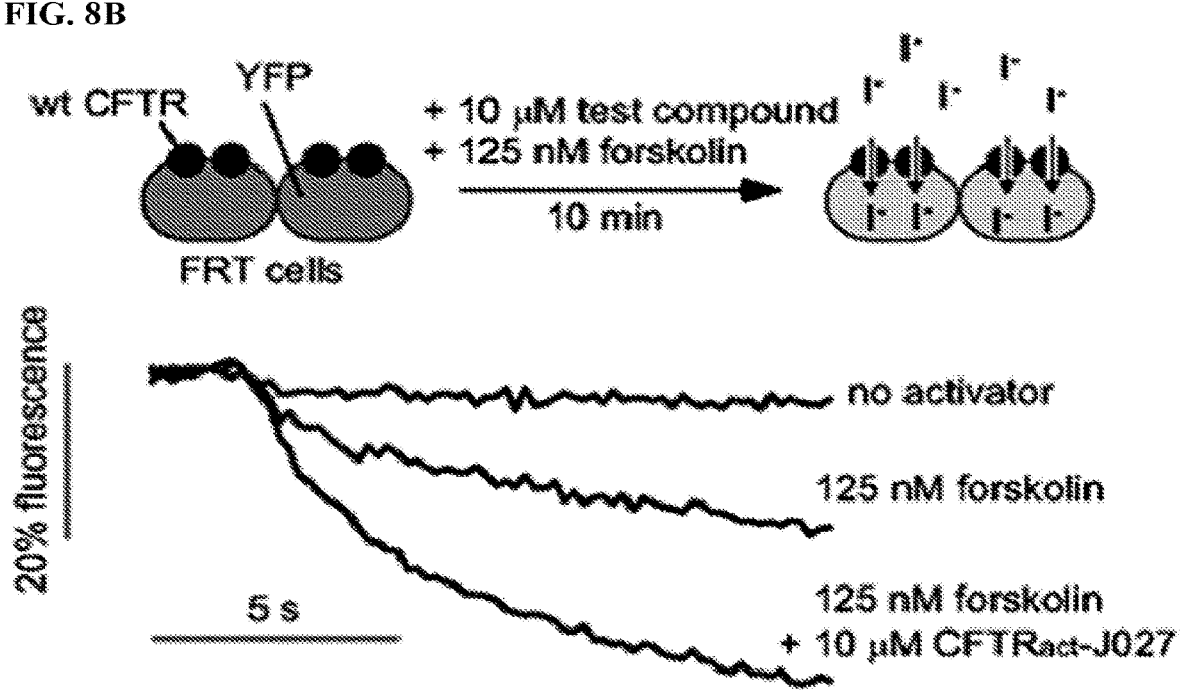

Identification and in vitro characterization of small-molecule CFTR activators. The goal was to identify a potent, CFTR-targeted activator with pro-secretory activity in intestine in order test its efficacy in a mouse model of constipation. FIG. 8A summarizes the project strategy. The compounds evaluated here included small molecules identified in prior CFTR activator/potentiator screens [14] and from a new screen of synthetic small molecules not tested previously. The most active compounds emerging from the screen, along with commercially available chemical analogs, were prioritized based on an initial mechanism of action study (assay of cAMP elevation), in vitro toxicity, pro-secretory action in mouse intestine, and efficacy in a mouse model of constipation. FIG. 8B shows the cell-based plate reader screening method in which the initial rate of iodide influx was measured in FRT cells stably expressing human wildtype CFTR and a YFP fluorescent halide sensor following extracellular iodide addition. A CFTR activator increases the initial slope of the fluorescence quenching curve.

Figure 8C:
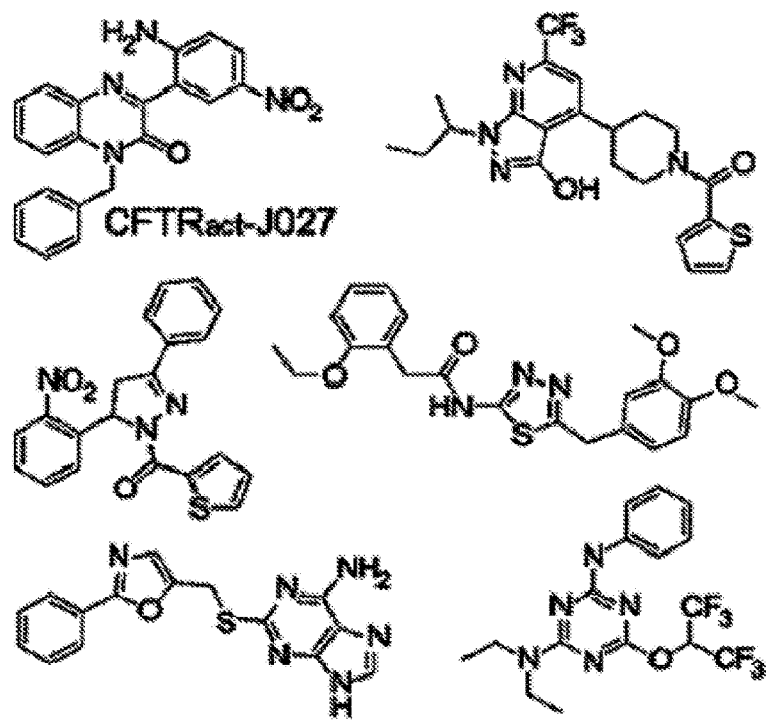
Figure 8D:
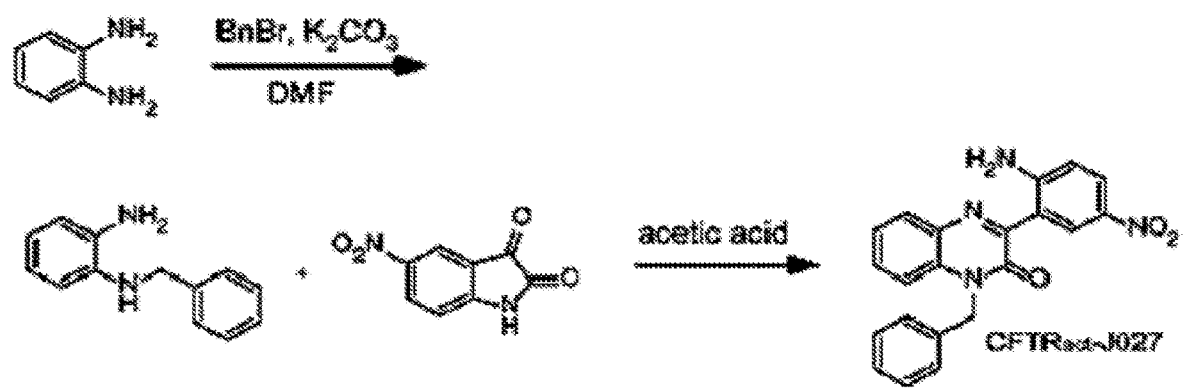

FIG. 8C shows chemical structures of six classes of CFTR candidate activators identified from the screens. Based on the criteria listed above, we focused further studies on $CFTR_{act}$-J027, a 3-phenyl-quinoxalinone with drug-like properties. CFTR$_{act}$-J027 was synthesized in pure crystalline form in two steps (FIG. 8D).

Figure 9A:
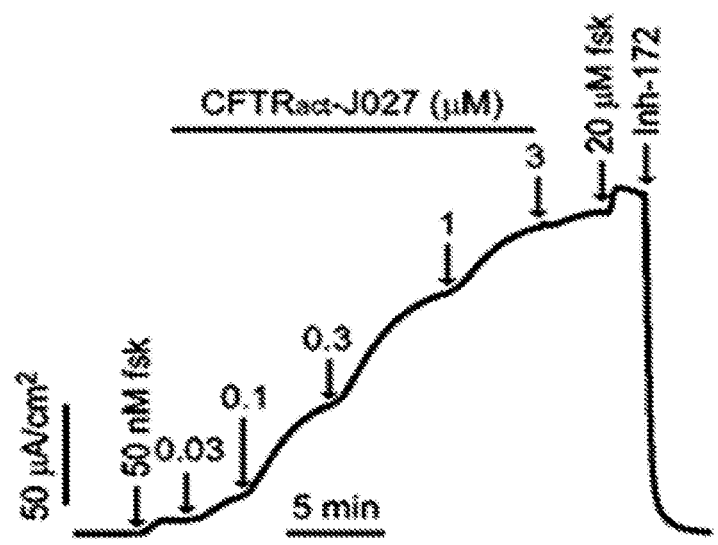
FIGS. 9A-9E. Characterization of CFTR activation by $CFTR_{act}$-J027. Short-circuit current measured in FRT cells expressing human wild-type CFTR (FIG. 9A) and ΔF508-CFTR (FIG. 9C) showing responses to indicated concentrations of forskolin (fsk), $CFTR_{act}$-J027, and VX-770. The ΔF508-CFTR-expressing FRT cells were corrected with 3 µM VX-809 at 37° C. for 24 h before measurement. $CFTR_{inh}$-172 (Inh-172, 10 µM) was added where indicated.
Figure 9B:
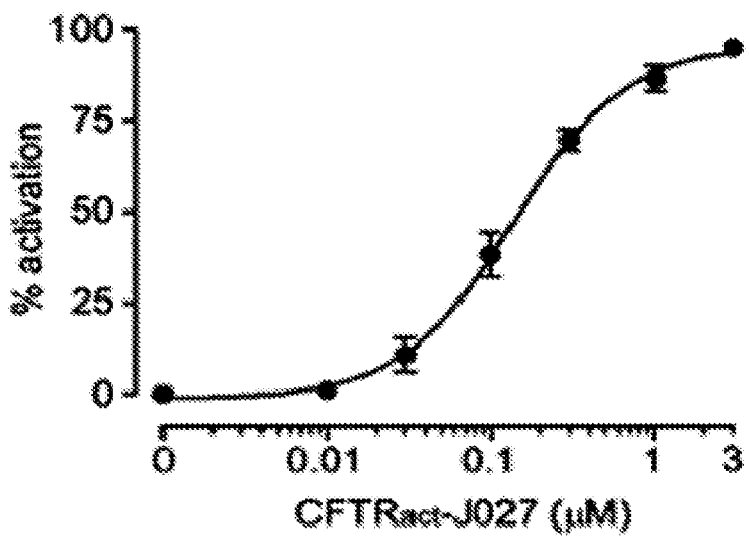
Figure 9C:
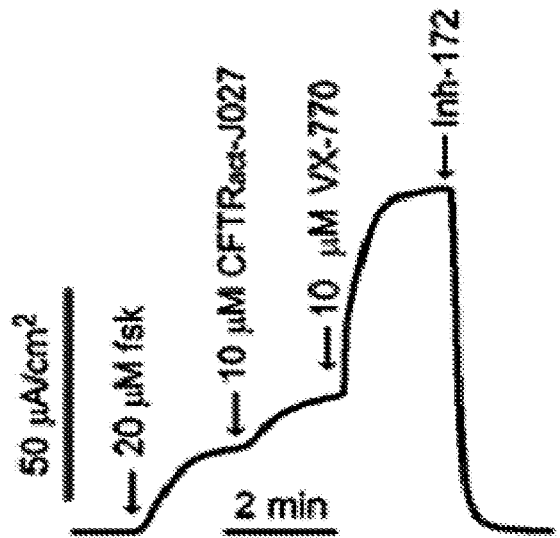
Figure 9D:
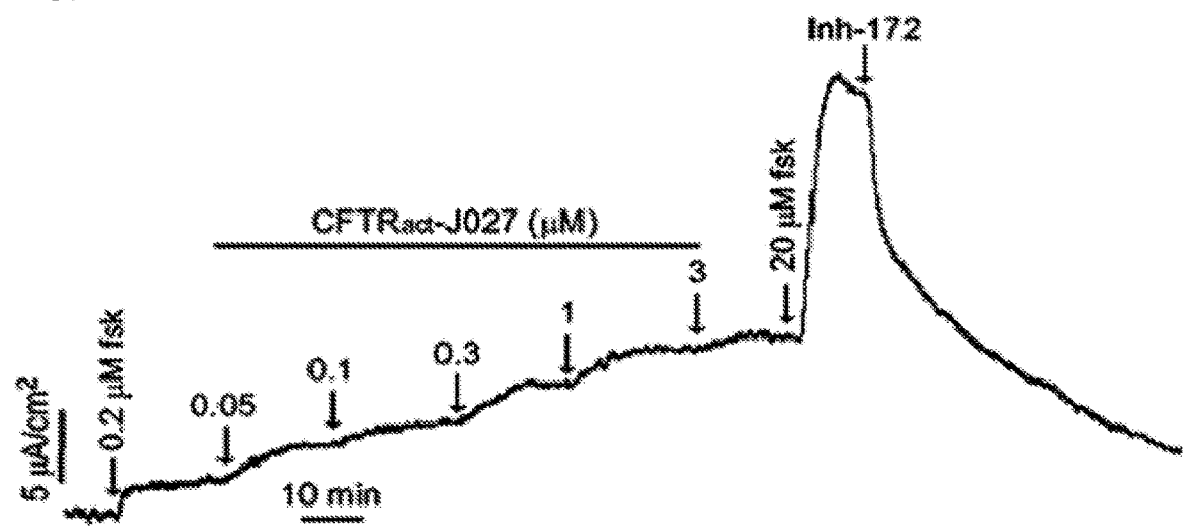
Figure 9E:
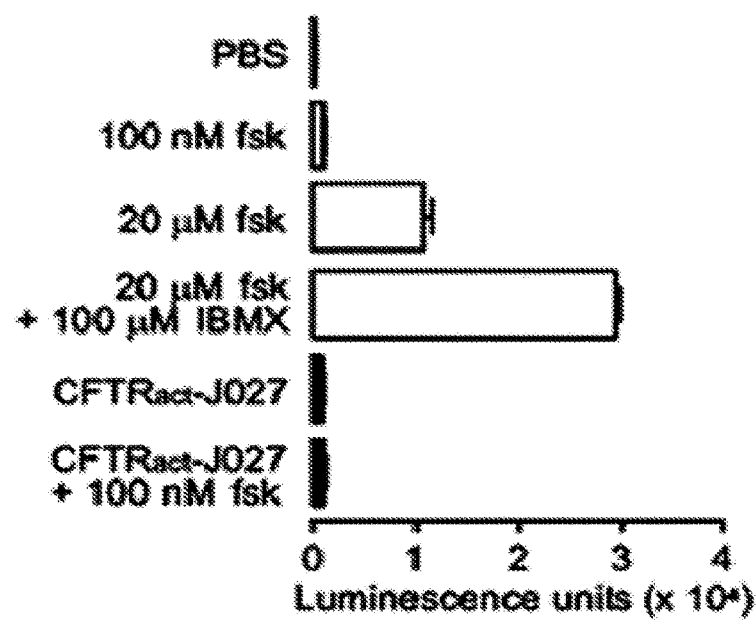

Short-circuit current measurements in CFTR-expressing FRT cells showed that CFTR$_{act}$-J027 fully activated CFTR (FIG. 9A), as the cAMP agonist forskolin produced no further increase in current, with an EC$_{50}$ ~200 nM (FIG. 9B). Interestingly, CFTR$_{act}$-J027 was only a weak potentiator of ΔF508-CFTR, as studied in FRT cells expressing ΔF508-CFTR after overnight incubation with a corrector (FIG. 9C). Cl$^-$ secretion in freshly isolated mouse colon showed a concentration-dependent increase in short-circuit current with EC$_{50}$ ~300 nM (FIG. 9D). The increase in current at high CFTR$_{act}$-J027 was further increased by forskolin, which may be a consequence of activation of a basolateral membrane cAMP-sensitive K$^+$ channel that increases the driving force for apical membrane Cl$^-$ secretion. The increase in current was fully inhibited by a CFTR-selective inhibitor. FIG. 9E shows that CFTR$_{act}$-J027 does not elevate cellular cAMP when added alone, and does not further increase cAMP when added together with forskolin, suggesting that CFTR activation involves a direct interaction mechanism rather than indirect action through cAMP elevation.

Figure 10A:
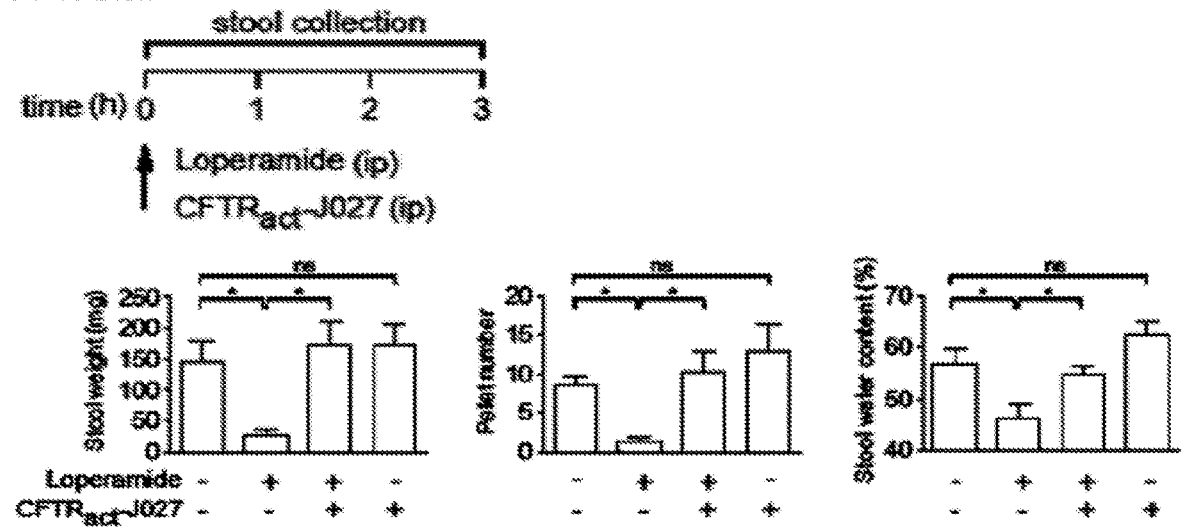
FIGS. 10A-10D. $CFTR_{act}$-J027 normalizes stool output and water content in loperamide-treated mice.
Figure 10B:
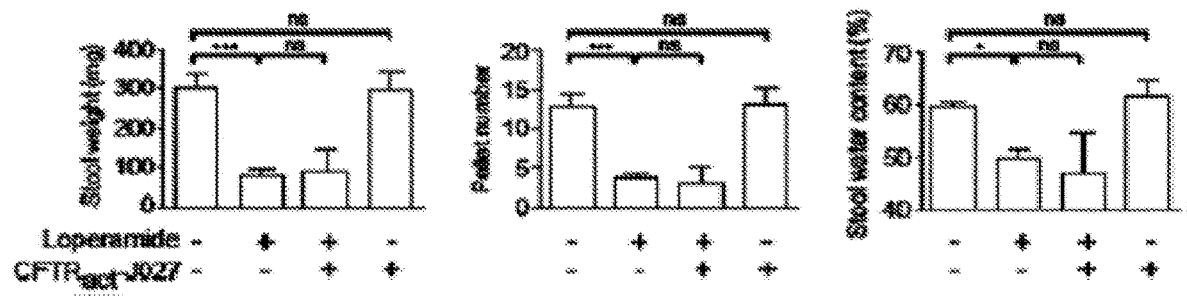
Figure 10C:
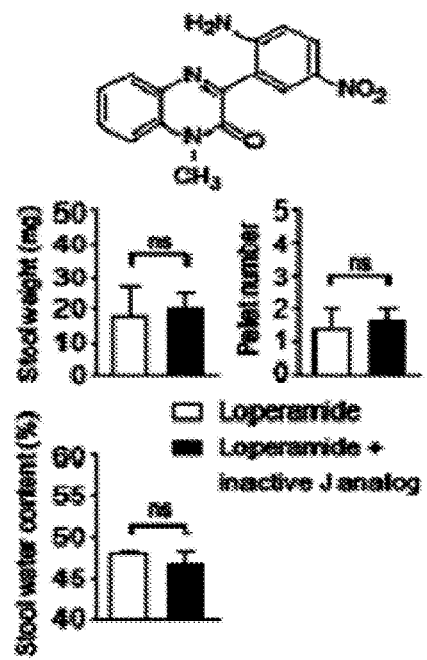
Figure 10D:
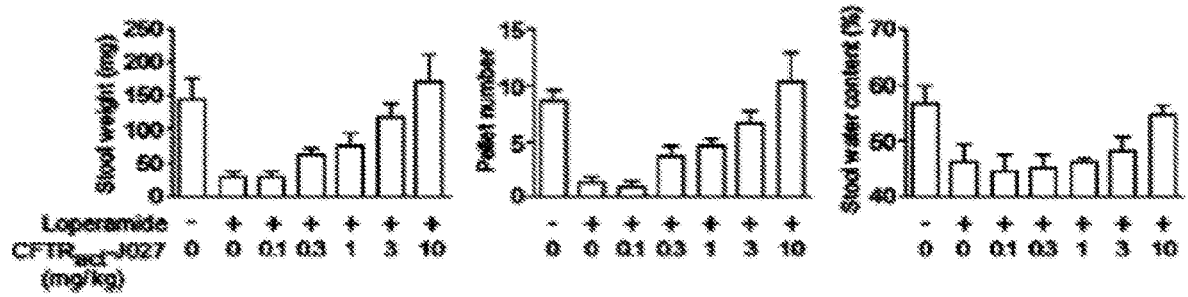

CFTR$_{act}$-J027 normalizes stool output in a mouse model of constipation. CFTR$_{act}$-J027 was studied in the well-established loperamide-induced mouse model of constipation in which stool weight, pellet number and water content were measured over 3 h following intraperitoneal loperamide administration (FIG. 10A). Intraperitoneal administration of CFTR$_{act}$-J027 at 10 mg/kg normalized each of the stool parameters. CFTR$_{act}$-J027 did not affect stool output or water content in control (non-loperamide-treated) mice. Importantly, CFTR$_{act}$-J027 was without effect in cystic fibrosis mice lacking functional CFTR (FIG. 10B), nor was an inactive chemical analog of CFTR$_{act}$-J027 effective in wildtype mice (FIG. 10C). These results support a CFTR-selective action of CFTR$_{act}$-J027. Dose-response studies in mice showed an ED$_{50}$ of 2 mg/kg in the loperamide model by ip administration of CFTR$_{act}$-J027 (FIG. 10D).

Figure 11A:
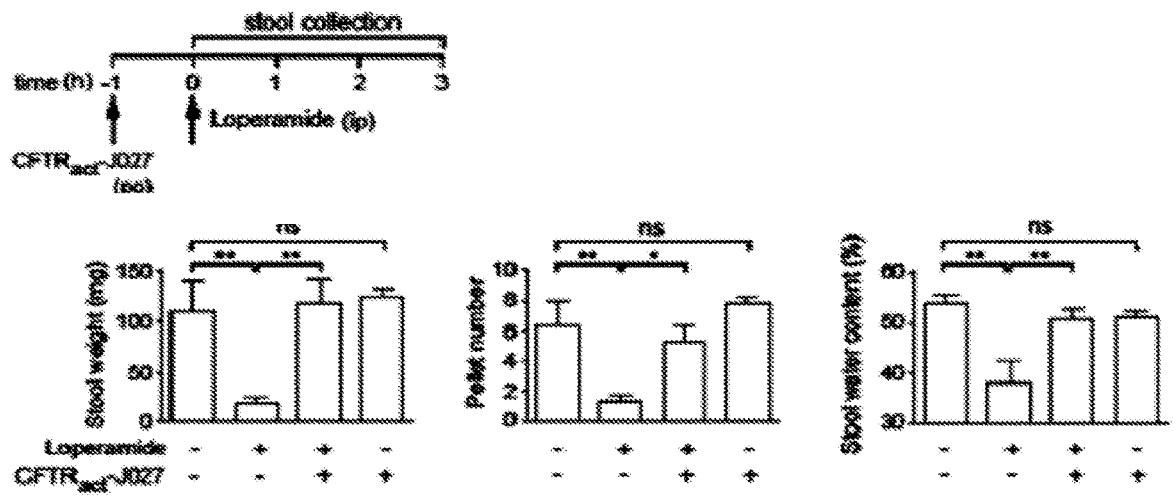
FIGS. 11A-11C. Orally administered $CFTR_{act}$-J027 normalizes stool output and water content in loperamide-treated mice.
Figure 11B:
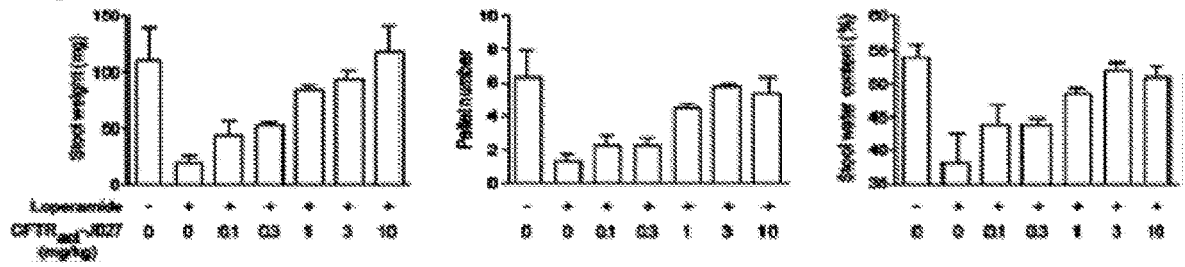
Figure 11C:
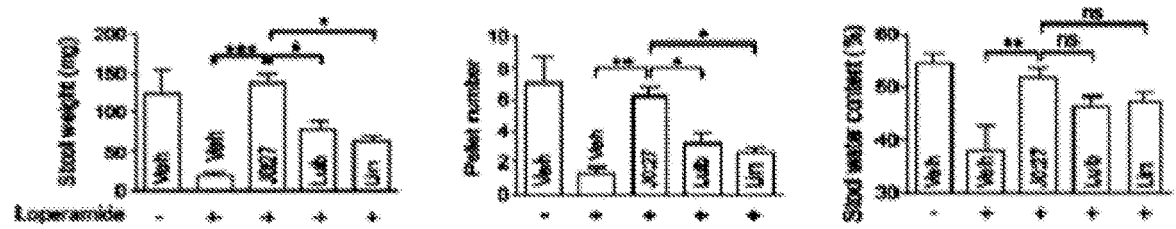

Oral administration of 10 mg/kg CFTR$_{act}$-J027 1 h prior to loperamide administration was also effective in normalizing stool output and water content in loperamide-treated mice, with no effect in control mice (FIG. 11A). The ED$_{50}$ for oral administration was 0.5 mg/kg, substantially lower than that for ip administration (FIG. 11B). In parallel studies, oral administration of the approved drugs lubiprostone or linaclotide at 250-500 fold greater mg/kg doses than given to humans for treatment of constipation, were less effective in normalizing stool output, producing 50% and 35% of the maximal CFTR$_{act}$-J027 response, respectively (FIG. 11C).

Figure 12A:
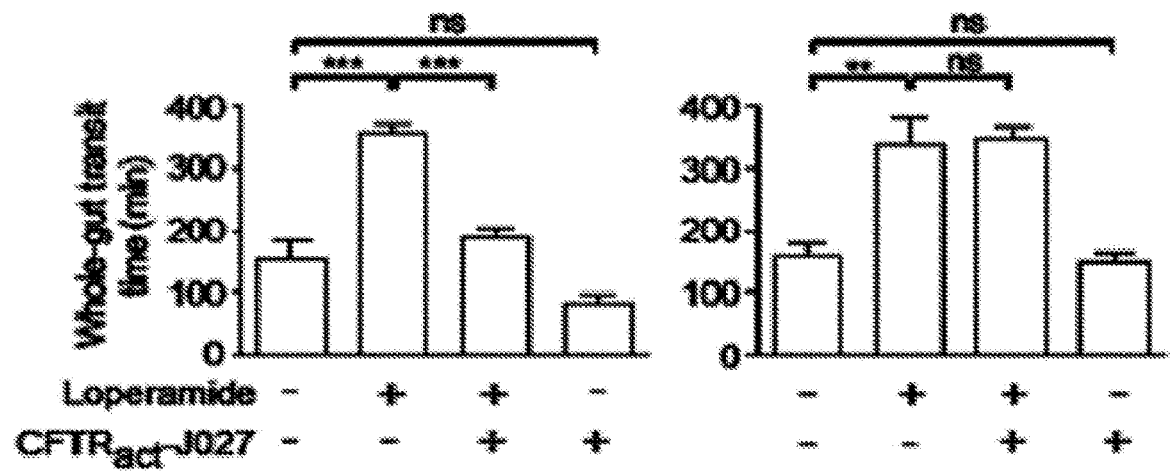
FIGS. 12A-12D. $CFTR_{act}$-J027 actions on intestinal fluid secretion, absorption and motility.
Figure 12B:
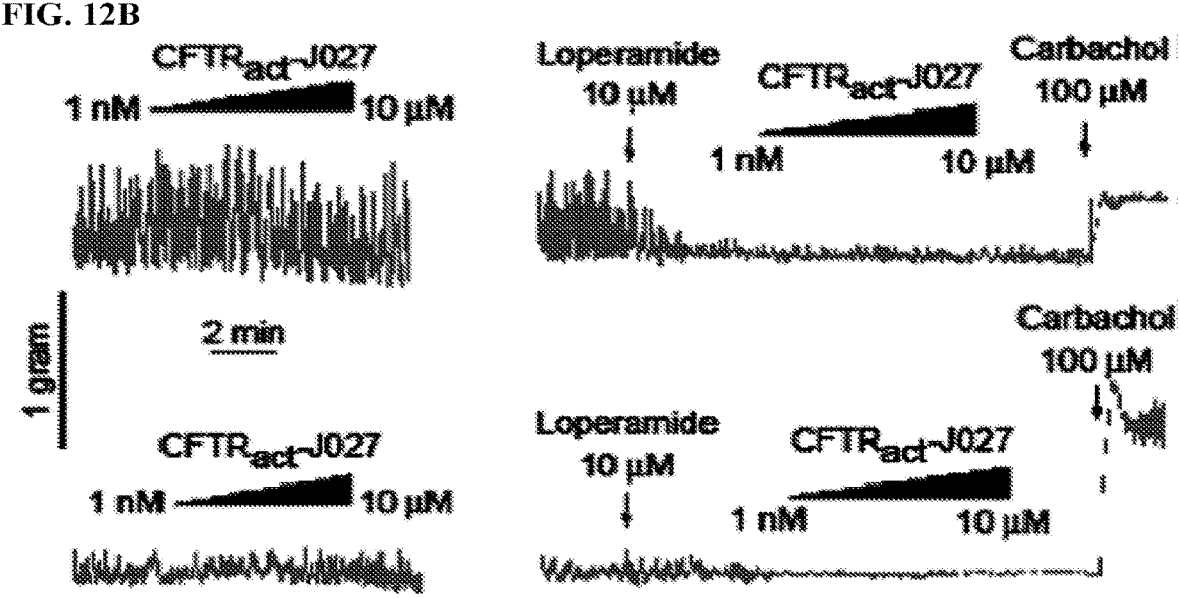

CFTR$_{act}$-J027 actions on intestinal transit, motility and fluid transport. CFTR$_{act}$-J027 action on intestinal transit and motility was measured in vivo and in isolated intestinal strips, respectively. Whole-gut transit time, as measured by appearance of a marker in the stool after bolus oral gavage at the time of ip loperamide and CFTR$_{act}$-J027 administration, was normalized by CFTR$_{act}$-J027 (FIG. 12A, left panel). CFTR$_{act}$-J027 had no effect on whole-gut transit time in cystic fibrosis mice (right panel). In vitro measurements of intestinal contraction showed no effect of CFTR$_{act}$-J027 added alone or in the presence of 10 μM loperamide in isolated mouse ileum and colon strips (FIG. 12B). CFTR$_{act}$-J027 may thus increase intestinal transit in vivo by stimulating motility by secretion-induced stretch of the gut wall, without direct effect on intestinal smooth muscle.

Figure 12C:
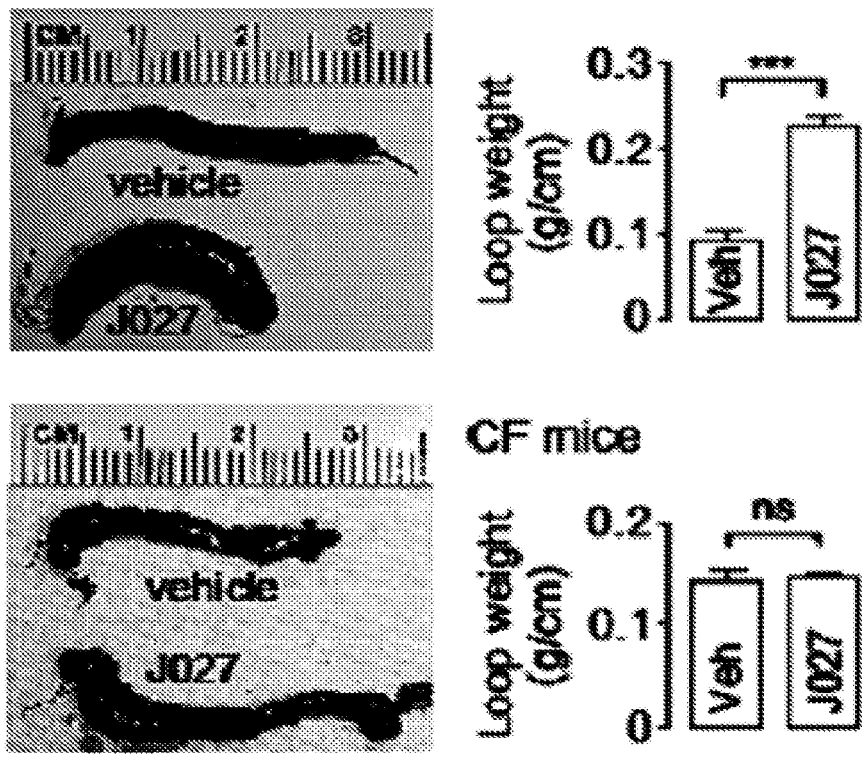
Figure 12D:
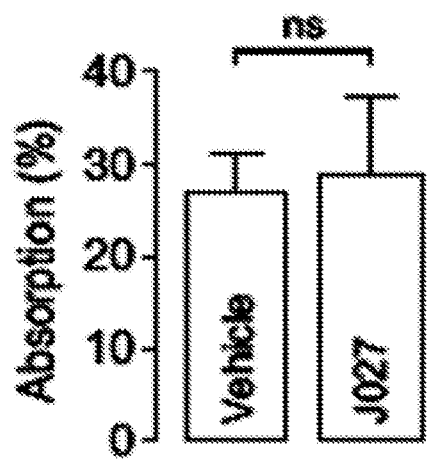

To directly investigate the effects of CFTR$_{act}$-J027 on intestinal fluid secretion and absorption, an in vivo closed-intestinal loop model was used. CFTR$_{act}$-J027 was injected into closed, mid-jejunal loops and fluid accumulation was measured at 90 min. CFTR$_{act}$-J027 produced a 140% increase in loop weight/length ratio, indicating fluid secretion into the intestinal lumen in wild-type mice (FIG. 12C, upper panel), but was without effect in cystic fibrosis mice (lower panel), supporting a CFTR-selective mechanism of action. A closed-loop model was also used to study CFTR$_{act}$-J027 action on intestinal fluid absorption. Fluid without or with CFTR$_{act}$-J027 was injected into closed, mid-jejunal loops of cystic fibrosis mice (to avoid confounding fluid secretion) and fluid absorption was measured at 30 min. CFTR$_{act}$-J027 did not affect intestinal fluid absorption (FIG. 12D).

Figure 13A:
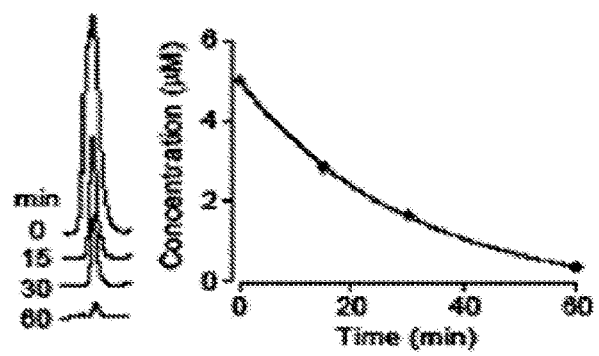
FIGS. 13A-13E.

CFTR$_{act}$-J027 pharmacology and toxicity in mice. The in vitro metabolic stability of CFTR$_{act}$-J027 was measured by incubation with mouse liver microsomes in the presence of NADPH. CFTR$_{act}$-J027 was rapidly metabolized with ~21 min elimination half-life, with only 7% of the original compound remaining at 60 min (FIG. 13A).

Figure 13B:
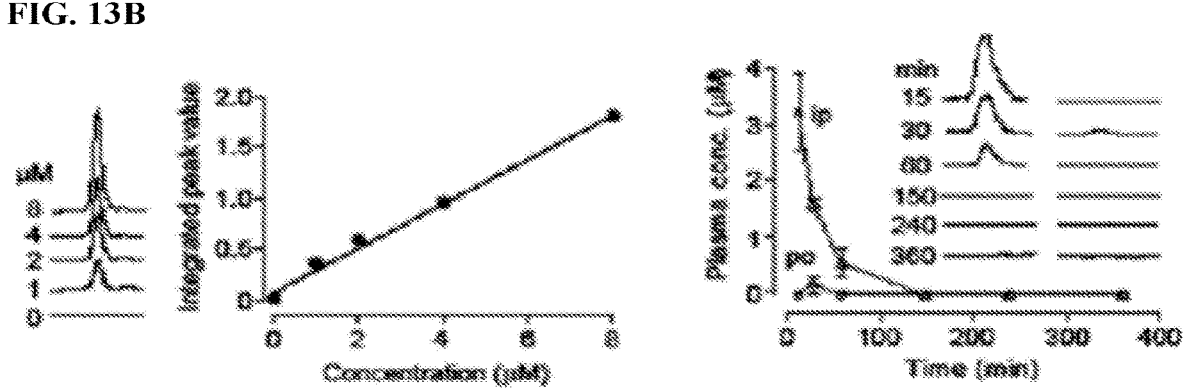

Pharmacokinetics was measured in mice following bolus intraperitoneal or oral administration of 10 mg/kg CFTR$_{act}$-J027. Following ip administration serum CFTR$_{act}$-J027 concentration decreased with an elimination half-life of ~16 min, and was undetectable at 150 min (FIG. 13B). Following oral administration serum CFTR$_{act}$-J027 concentration reached 180 nM at 30 min and was undetectable at other time points (FIG. 13B).

Figure 13C:
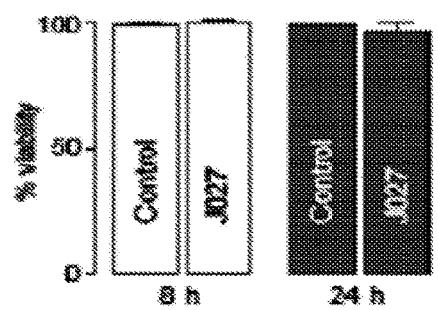
Figure 13D:
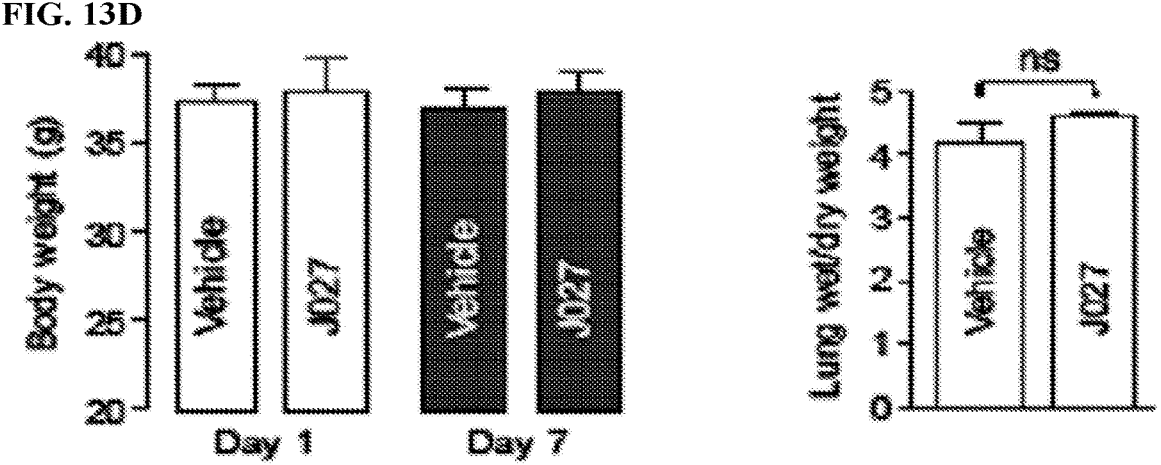

Preliminary toxicological studies of CFTR$_{act}$-J027 were done in cell cultures and mice. CFTR$_{act}$-J027, at a concentration of 20 μM near its solubility limit, did not show cytotoxicity as measured by the Alamar Blue assay (FIG. 13C). In the 7-day treated mice, CFTR$_{act}$-J027 did not affect the major serum chemistry and blood parameters (Table 1, Example 1), nor did it change body weight or produce airway/lung fluid accumulation (FIG. 13D).

Figure 13E:
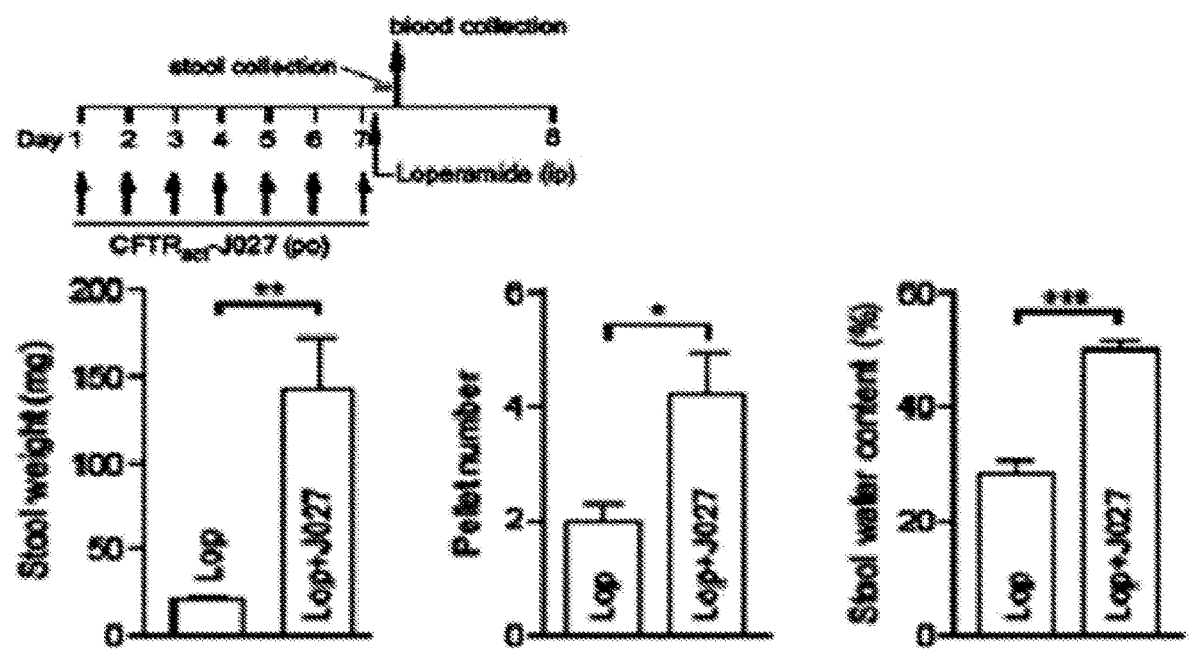

Last, to determine whether chronically administered CFTR$_{act}$-J027 retained efficacy, mice were treated orally for 7 days with 10 mg/kg CFTR$_{act}$-J027 or vehicle, and loperamide was given 1 h after the final dose. FIG. 13E shows that chronically administered CFTR$_{act}$-J027 remained effective in normalizing stool output and water content following loperamide.

Discussion

We identified by high-throughput screening a nanomolar-affinity, small-molecule CFTR activator, CFTR$_{act}$-J027, and demonstrated its pro-secretory action in mouse intestine and its efficacy in normalizing stool output in a loperamide-induced mouse model of constipation. Constipation remains a significant clinical problem in outpatient and hospitalized settings. Opioid-induced constipation is a common adverse effect in patients after surgery, undergoing chemotherapy and with chronic pain.

CFTR-targeted activation adds to the various mechanisms of action of anti-constipation therapeutics. It is notable that pure CFTR activation is able to produce a robust Cl$^-$ current and fluid secretion response in the intestine, without causing global elevation of cyclic nucleotide concentration, direct stimulation of intestinal contractility, or alteration of intestinal fluid absorption. Linaclotide, a peptide agonist of the guanylate cyclase C receptor that increases intestinal cell cGMP concentration. Linaclotide inhibits activation of colonic sensory neurons and activates motor neurons, which reduces pain and increases intestinal smooth muscle contraction; in addition, elevation in cGMP concentration in enterocytes may activate CFTR and have a pro-secretory action [4, 5]. A second approved drug, the prostaglandin E analog lubiprostone, is thought to activate a putative enterocyte ClC-2 channel [6], though the mechanistic data are less clear. Compared with these drugs, a pure CFTR activator has a single, well-validated mechanism of action and does not produce a global cyclic nucleotide response in multiple cell types. Of note, linaclotide and lubiprostone showed limited efficacy in clinical trials. Linaclotide was effective in ~20% of chronic constipation patients of whom ~5% also responded to placebo [15], and lubiprostone was effective in ~13% of IBS-C patients of whom ~7% responded to placebo [16]. Based on our mouse data showing substantially greater efficacy of CFTR$_{act}$-J027 compared to supramaximal doses of linaclotide or lubiprostone, we speculate that CFTR activators may have greater efficacy in clinical trials.

CFTR$_{act}$-J027 is substantially more potent for activation of wildtype CFTR than VX-770 (ivacaftor), the FDA-approved drug for treatment of cystic fibrosis (CF) caused by certain CFTR gating mutations. In FRT cells expressing wild-type CFTR, short-circuit current measurement showed nearly full activation of CFTR by CFTR$_{act}$-J027 at 3 □M whereas VX-770 maximally activated CFTR by only 15%. However, CFTR$_{act}$-J027 was substantially less potent than ivacaftor as a 'potentiator' of defective chloride channel gating of the most common CF-causing mutation, ΔF508, which is not unexpected, as potentiator efficacy in CF is mutation-specific. In addition to its potential therapeutic utility for constipation, a small-molecule activator of wild-type CFTR may be useful for treatment of chronic obstructive pulmonary disease and bronchitis, asthma, cigarette smoke-induced lung dysfunction, dry eye and cholestatic liver disease [17-19].

Substituted quinoxalinones were reported as selective antagonists of the membrane efflux transporter multiple-drug-resistance protein 1 [20]. Quinoxalinones have also been reported to show anti-diabetic activity by stimulating insulin secretion in pancreatic INS-1 cells [21], and inhibitory activity against serine proteases for potential therapy of thrombotic disorders [22]. Recently, quinoxalinones have been reported to inhibit aldose reductase [23]. These reports suggest that the quinoxalinone scaffold has drug-like properties. Synthetically, quinoxalinone can be prepared in one to four steps from commercially available starting materials [24], which allows facile synthesis of targeted analogs.

In addition to compound-specific off-target actions, the potential side-effects profile of a CFTR activator could include pro-secretory activity in the airway/lungs and various glandular and other epithelia. Off-target effects for constipation therapy could be limited by oral administration of a CFTR activator with limited intestinal absorption and/or rapid systemic clearance to minimize systemic exposure. CFTR$_{act}$-J027 when administered orally at a high dose (10 mg/kg) showed very low bioavailability with blood levels well below the EC$_{50}$ for CFTR activation, which may be due to first-pass effect as evidenced its rapid in vitro metabolism in liver microsomes. CFTR$_{act}$-J027 did not show significant in vitro cytotoxicity at a concentration of 25 μM, >100-fold greater than its EC$_{50}$ for CFTR activation, or in vivo toxicity in mice in a 7-day study at a maximal efficacious dose that normalized stool output in the loperamide model of constipation. The potentially most significant off-target action, stimulation of lung/airway fluid secretion, was not seen as evidenced by normal lung water content in the 7-day treated mice. These limited toxicity studies offer proof of concept for application of a CFTR activator in constipation.

In summary, without wishing to be bound by theory, it is believed that the data herein provide evidence for the pro-secretory action of a CFTR activator in mouse intestine and proof of concept for its use in treatment of various types of constipation, which could include opioid-induced constipation, chronic idiopathic constipation, and irritable bowel syndrome with constipation predominance.

References (Example 4)

[1]. Pinto Sanchez M I, Bercik P. Epidemiology and burden of chronic constipation. *Canadian Journal of Gastroenterology* 2011, 25(Suppl B): 11B-15B; [2]. Mugie S M, Di Lorenzo C, Benninga M A. Constipation in childhood. *Nature Reviews Gastroenterology and Hepatology* 2011, 8(9):502-511; [3]. Menees S, Saad R, Chey W D. Agents that act luminally to treat diarrhoea and constipation. *Nature Reviews Gastroenterology and Hepatology* 2012, 9(11):661-674; [4]. Castro J, Harrington A M, Hughes P A et al. Linaclotide inhibits colonic nociceptors and relieves abdominal pain via guanylate cyclase-C and extracellular cyclic guanosine 3',5'-monophosphate. *Gastroenterology* 2013, 145(6):1334-1346; [5]. Busby R W, Bryant A P, Bartolini W P et al. Linaclotide, through activation of guanylate cyclase C, acts locally in the gastrointestinal tract to elicit enhanced intestinal secretion and transit. *European Journal of Pharmacology* 2010, 649(1-3):328-335; [6]. Fei G, Raehal K, Liu S et al. Lubiprostone reverses the inhibitory action of morphine on intestinal secretion in Guinea pig and mouse. *Journal of Pharmacology and Experimental Therapeutics* 2010, 334(1):333-340; [7]. Thiagarajah J R, Donowitz M, Verkman A S. Secretory diarrhoea: mechanisms and emerging therapies. *Nature Reviews Gastroenterology and Hepatology* 2015, 12(8):446-457; [8]. Field M, Fromm D, Al-Awqati Q et al. Effect of cholera enterotoxin on ion transport across isolated ileal mucosa. *The Journal of Clinical Investigation* 1972, 51(4):796-804; [9]. Rao M C, Guandalini S, Smith P L et al. Mode of action of heat-stable *Escherichia coli* enterotoxin Tissue and subcellular specificities and role of cyclic GMP. *Biochimica et Biophysica Acta (BBA)—General Subjects* 1980, 632(1):35-46; [10]. Subramanya S B, Rajendran V M, Srinivasan P et al. Differential regulation of cholera toxin-inhibited Na—H exchange isoforms by butyrate in rat ileum. *American Journal of Physiology—Gastrointestinal and Liver Physiology* 2007, 293(4):G857-G863; [11]. Hecht G, Hodges K, Gill R K et al. Differential regulation of Na$^+$/H$^+$ exchange isoform activities by enteropathogenic *E. coli* in human intestinal epithelial cells. *American Journal of Physiology—Gastrointestinal and Liver Physiology* 2004, 287(2):G370-G378; [12]. Galietta L J V, Springsteel M F, Eda M et al. Novel CFTR chloride channel activators identified by screening of combinatorial libraries based on flavone and benzoquinolizinium lead compounds. *Journal of Biological Chemistry* 2001, 276(23):19723-19728; [13]. Esteva-Font C, Cil O, Phuan P W et al. Diuresis and reduced urinary osmolality in rats produced by small-molecule UT-A-selective urea transport inhibitors. *The FASEB Journal* 2014, 28(9):3878-3890; [14]. Ma T, Vetrivel L, Yang H et al. High-affinity activators of cystic fibrosis transmembrane conductance regulator (CFTR) chloride conductance identified by high-throughput screening. *Journal of Biological Chemistry* 2002, 277(40): 37235-37241; [15]. Lembo A J, Schneier H A, Shiff S J et al. Two randomized trials of linaclotide for chronic constipation. *New England Journal of Medicine* 2011, 365(6):527-536; [16]. Website: www.amitizahcp.com; [17]. Gras D, Chanez P, Vachier I et al. Bronchial epithelium as a target for innovative treatments in asthma. *Pharmacology & Therapeutics* 2013, 140(3):290-305; [18]. Srivastava A. Progressive familial intrahepatic cholestasis. *Journal of Clinical* and *Experimental Hepatology* 2014, 4(1):25-36; [19]. Levin M H, Verkman A S. CFTR-regulated chloride transport at the ocular surface in living mice measured by potential differences. *Investigative Ophthalmology & Visual Science* 2005, 46(4):1428-1434; [20]. Lawrence D S, Copper J E, Smith C D. Structure-activity studies of substituted quinoxalinones as multiple-drug-resistance antagonists. *Journal of Medicinal Chemistry* 2001, 44(4):594-601; [21]. Botton G, Valeur E, Kergoat M et al. Preparation of quinoxalinone derivatives as insulin secretion stimulators useful for the treatment of diabetes. PCT Int Appl 2009, WO 2009109258 A1 20090911 (patent); [22]. Dudley D A, Edmunds J J. Preparation of quinoxalinones as serine protease inhibitors for treatment of thrombotic disorders. PCT Int Appl 1999:WO 9950254 A9950251 19991007 (patent); [23]. Qin X, Hao X, Han H et al. Design and Synthesis of potent and multifunctional aldose reductase inhibitors based on auinoxalinones. *Journal of Medicinal Chemistry* 2015, 58(3):1254-1267; [24]. Shaw A D, Denning C R, Hulme C. One-pot two-step synthesis of quinoxalinones and diazepinones via a tandem oxidative amidation-deprotection-cyclization sequence. *Synthesis* 2013, 45(4):459-462.

Example 5—Dry Eye—II

Abbreviations: CFTR, cystic fibrosis transmembrane conductance regulator; cAMP, cyclic adenosine monophosphate; ENaC, epithelial sodium channel; YFP, yellow fluorescent protein; CF, cystic fibrosis; FRT cells, Fischer rat thyroid cells; $I_{SC}$, short-circuit current; PD, potential difference; IBMX, 3-isobutyl-1-methylxanthine; fsk, forskolin; LC/MS, liquid chromatography/mass spectroscopy; LG, lissamine green; LGE, lacrimal gland excision.

Abstract. Dry eye disorders, including Sjögren's syndrome, constitute a common problem in the aging population with limited effective therapeutic options available. The cAMP-activated Cl– channel CFTR (cystic fibrosis transmembrane conductance regulator) is a major pro-secretory chloride channel at the ocular surface. Here, we investigated whether compounds that target CFTR can correct the abnormal tear film in dry eye. Small-molecule activators of human wild-type CFTR identified by high-throughput screening were evaluated in cell culture and in vivo assays to select compounds that stimulate Cl–-driven fluid secretion across the ocular surface in mice. An aminophenyl-1,3,5-triazine, $CFTR_{act}$-K089, fully activated CFTR in cell cultures with EC50 ~250 nM and produced a ~8.5 mV hyperpolarization in ocular surface potential difference. When delivered topically, $CFTR_{act}$-K089 doubled basal tear secretion for four hours and had no effect in CF mice. $CFTR_{act}$-K089 showed sustained tear film bioavailability without detectable systemic absorption. In a mouse model of aqueous-deficient dry eye produced by lacrimal gland excision, topical administration of 0.1 nmol $CFTR_{act}$-K089 three times daily restored tear secretion to basal levels and fully prevented the corneal epithelial disruption seen in vehicle-treated controls. Our results support potential utility of CFTR-targeted activators as a novel pro-secretory treatment for dry eye.

Introduction.

Dry eye is a heterogeneous group of disorders with common features of reduced tear volume and tear fluid hyperosmolarity, which lead to inflammation at the ocular surface. The clinical consequences, which include eye discomfort and visual disturbance, represent a major public health concern in an aging population. Dry eye affects up to one-third of the global population (1), including five million Americans age 50 and over (2, 3). The economic burden of dry eye is substantial, with direct annual health care costs estimated at $3.84 billion dollars in the United States (4).

Ninety-four percent of surveyed ophthalmologists believe that additional treatments are needed for moderate-to-severe dry eye (7).

The ocular surface is a collection of anatomically continuous epithelial and glandular tissues that are functionally linked to maintain the tear film (8). While lacrimation contributes the bulk of reflex tearing, the cornea and conjunctiva regulate basal tear volume and composition. The principal determinants of water movement across the ocular surface into the tear film include apical chloride (Cl–) secretion through cAMP- and calcium ($Ca^{2+}$)-dependent Cl– transporters, and sodium ($Na^+$) absorption largely though the epithelial $Na^+$ channel (ENaC).

The cystic fibrosis transmembrane conductance regulator (CFTR) is a cAMP-activated Cl– channel expressed in some secretory epithelial cells, including those in cornea and conjunctiva (14-16). We found substantial capacity for active CFTR-facilitated Cl– at the ocular surface in mice (21, 22), as subsequently shown in rat conjunctiva (23), providing a rational basis for investigation of CFTR activators as a pro-secretory strategy for dry eye. The only clinically approved CFTR activator, VX-770 (ivacaftor), is indicated for potentiating the channel gating of certain CFTR mutants causing CF, but only weakly activates wild-type CFTR (24, 25).

Here, we evaluated and prioritized novel small-molecule activators of wild-type CFTR identified by high-throughput screening as potential topical therapy for dry eye, with the research strategy summarized in FIG. 1. The goal was to improve upon our previously identified CFTR activators (26), which lack suitable potency and chemical properties to be advanced to clinical development, and to demonstrate efficacy of newly identified CFTR activator(s) in a mouse model of dry eye.

Materials and Methods.

Mice. Wild-type (WT) and CF (homozygous ΔF508-CFTR mutant) mice in a CD1 genetic background were bred at the University of California San Francisco (UCSF) Animal Facility. Mice aged 8 to 12 weeks (25 to 35 g) were used. Female BALB/c mice (7-8 weeks old) were purchased from the Harlan Laboratory (Livermore, Calif., USA). Animal protocols were approved by the UCSF Institutional Animal Care and Use Committee and were in compliance with the ARVO Statement for the Use of Animals in Ophthalmic and Vision Research.

Short-circuit current. Fischer rat thyroid (FRT) cells stably expressing wild-type human CFTR were cultured on Snapwell inserts (Corning Costar, Corning N.Y., USA) for short-circuit current ($I_{sc}$) measurements. After 6-9 days in culture, when the transepithelial resistance was >1000 $\Omega/cm^2$, the inserts were mounted in an Ussing chamber system (World Precision Instruments, Sarasota, Fla., USA). The basolateral solution contained 130 mM NaCl, 2.7 mM KCl, 1.5 mM $KH_2PO_4$, 1 mM $CaCl_2$, 0.5 mM $MgCl_2$, 10 mM glucose, and 10 mM Na-HEPES (pH 7.3). In the apical bathing solution, 65 mM NaCl was replaced by Na gluconate, and $CaCl_2$ was increased to 2 mM. Both solutions were bubbled with air and maintained at 37° C. The basolateral membrane was permeabilized with 250 µg/ml amphotericin B (26, 27). Hemichambers were connected to a DVC-1000 voltage clamp via Ag/AgCl electrodes and 3 M KCl agar bridges for $I_{sc}$ recording.

cAMP and cytotoxicity assays. Intracellular cAMP activity was measured using a GloSensor luminescence assay (Promega Corp., Madison, Wis., USA). FRT cells stably transfected with the pGloSensor cAMP plasmid (Promega Corp.) were cultured in white 96-well microplates (Corning Costar) overnight. Cells were then washed three times with PBS and incubated with 5 µM test compound for 10 min in the absence and presence of 100 nM forskolin. To assay cytotoxicity, FRT cells were cultured overnight in black 96-well Costar microplate wells and incubated with test compounds at up to 100 µM (the maximum solubility in PBS) for 1 or 24 h. Cytotoxicity was measured by Alamar Blue assay according to the manufacturer's instructions (Invitrogen, Carlsbad, Calif., USA).

Ocular surface potential difference measurements. Open-circuit transepithelial PD were measured continuously in anesthetized mice in response to serial perfusions of different solutions over the ocular surface, as described (21). Mice were anesthetized with Avertin (2,2,2-tribromoethanol, 125 mg/kg intraperitoneal, Sigma-Aldrich, St. Louis, Mo., USA), and core temperature was maintained at 37° C. using a heating pad. Eyes were oriented with the cornea and conjunctiva facing upward and exposed by retracting the eyelid with cross-action forceps. Solutions were isosmolar (320±10 mOsM; compositions provided in ref. 21) and contained 10µM indomethacin to prevent CFTR activation by prostaglandins. The ocular surface was perfused at 6 mL/min through plastic tubing using a multireservoir gravity pinch-valve system (ALA Scientific, Westbury, N.Y., USA) and variable-flow peristaltic pump (medium flow model; Fisher Scientific, Fair Lawn, N.J., USA). A probe catheter was fixed 1 mm above the cornea using a micropositioner and a suction cannula was positioned 3 mm from the orbit. The measuring electrode was in contact to the perfusion catheter and connected to a high-impedance voltmeter (IsoMilivolt Meter; WPI). The reference electrode was grounded via a winged 21-gauge needle filled with isosmolar saline, and inserted subcutaneously in the abdomen. Measuring and reference electrodes consisted of Ag/AgCl with 3 M KCl agar bridges.

Tear secretion. To measure unstimulated tear production, phenol red threads (Zone-Quick, Oasis Medical, Glendora, Calif., USA) were placed for 10 s in the lateral canthi of isofluorane-anesthetized mice using jewelers' forceps. Tear volume was measured as the length of thread wetting, as visualized under a dissecting microscope. Serial measurements were used to evaluate compound pharmacodynamics after application of 2-µL drops of compound formulations (50-100 µM compound in PBS containing 0.5% polysorbate and 0.5% DMSO) comparing to vehicle.

Lissamine green staining. To assess corneal epithelial disruption, 5 µL of lissamine green (LG) dye (1%) was applied to the ocular surface of isofluorane-anesthetized mice. Photographs of the eye were taken using a Nikon Digital camera adapted to an Olympus Zoom Stereo Microscope (Olympus, Center Valley, Pa., USA). Each corneal quadrant was scored on a 3-point scale by one blinded, trained observer, with the extent of staining in each quadrant classified as: 0, no staining; 1, sporadic (involving <25% of the total surface) staining; grade 2, diffuse punctate staining (25-75%); and grade 3, coalesced punctate staining (≥75%). The total grade is reported as the sum of scores from all four quadrants, ranging from 0 to 12.

Pharmacokinetics and tissue distribution. To determine the residence time of CFTR activators in the pre-ocular mouse tear film, compounds were recovered for liquid chromatography/mass spectroscopy (LC/MS) following single-dose ophthalmic delivery. Three eye washes (3 µL PBS each) were recovered from the lateral and medial canthi with 5-µL microcapillary tubes (Drummond Scientific Co., Broomhall, Pa., USA) after manual eyelid blinking (9). Pooled washes were diluted with acetonitrile/water (1:1) containing 0.1% formic acid and analyzed by LC/MS using an Xterra MS C18 column (2.1 mm×100 mm, 3.5-µm particle size) connected to a Waters 2695 HPLC solvent delivery system and a Waters Micromass ZQ mass spectrometer with positive electrospray ionization.

To study compound accumulation in systemic tissues, mouse blood, brain, kidney and liver were analyzed after 14 days of three-times daily topical dosing (0.1 nmol, 2 µL, 50 µM). Blood samples were collected from the left ventricle into K3 EDTA mini-tubes (Greiner, Kremsmunster, Austria) and centrifuged (28). The supernatant was extracted with an equal volume of ethyl acetate and the extract was dried with an air stream. Organs from treated and control mice were removed following ventricular perfusion with heparinized PBS (10 units/mL), weighed, mixed with acetic acid and water (100 µL/g tissue), and homogenized (29). Ethyl acetate (10 mL/g tissue) was added, samples were vortexed and centrifuged (3000 rpm for 15 min), and the ethyl acetate-containing supernatant was evaporated. Residues obtained from organic extracts of serum and organ homogenates were then reconstituted and analyzed by LC/MS as described above.

Mouse model of dry eye produced by lacrimal gland excision. A lacrimal gland excision (LGE) model of aqueous-deficient dry eye was adapted from a reported method (30). The extraorbital lacrimal gland was exposed on each side of wild-type female BALB/c mice (7-8 weeks of age) by 3-mm linear skin incisions. Lacrimal ducts were cauterized and the entire gland was removed bilaterally, avoiding facial vessels and nerves. Incisions were each closed with a single interrupted 6-0 silk suture. Orbital lacrimal tissue remained functional. Eyes with reduced corneal sensation (<5% of mice studied), as identified from neurotrophic corneal ulcers within 1 day of LGE, were excluded. Mice were randomized to receive either treatment (in both eyes) with $CFTR_{act}$-K089 (0.1 nmol) or vehicle. Mice were treated three times daily (8 AM, 2 PM and 8 PM) for 2 weeks starting on Day 1 after LGE. Tear secretion and LG staining were performed immediately prior to, and one hour after the initial dose on day 4, 10 and 14 after LGE.

Statistics. Data are expressed as the mean±standard error of the mean (SEM). For direct comparisons between two means, the two-sided Students' t-test was used. For longitudinal measurements of tear secretion and LG scores in the dry eye prevention study, a linear mixed effects regression was used, adjusting for non-independence of measurements taken on the same eye and on both eyes of the same animal. Analysis was conducted in R v.3.2 for Mac (R Foundation for Statistical Computing, Vienna, Austria), using packages lme4 and robustlmm.

Results.

Characterization of small-molecule CFTR activators. A cell-based functional high-throughput screen of 120,000 compounds at 10 µM identified 20 chemical classes of small-molecule activators of wild-type CFTR that produced >95% of maximal CFTR activation. The screen was done in FRT epithelial cells co-expressing human wild-type CFTR and a cytoplasmic YFP halide sensor in 96-well format (26, 31, 32). Secondary screening involved $I_{sc}$ measurement in CFTR-expressing FRT cells pretreated with submaximal forskolin (50 nM). Twenty-one compounds from eight chemical classes produced large increases in $I_{sc}$ at 1µM (>75% of maximal current produced by 20 µM forskolin). A summary of $EC_{50}$ and $V_{max}$ values for each compound is provided in FIG. 7.

Structures of activators from the four most active chemical classes are shown in FIG. 2A, along with corresponding concentration-dependence data from $I_{sc}$ measurements. Each compound fully activated CFTR, as a high concentration of forskolin produced little further increase in $I_{sc}$, and the increase in $I_{sc}$ was fully inhibited by a CFTR inhibitor, $CFTR_{inh}$-172. $EC_{50}$ values ranged from 20-350 nM (FIG. 2B). VX-770 showed relatively weak activity against wild-type CFTR (FIG. 2C). $CFTR_{act}$-K032 and $CFTR_{act}$-K089 had lower potency and showed less CFTR activation (~50% $V_{max}$).

Compounds that directly target CFTR without causing elevation of cellular cAMP were sought to minimize potential off-target effects (FIG. 2D). Compounds producing elevations in intracellular cAMP (from Classes O, Q, and R), probably by phosphodiesterase inhibition, were excluded from further consideration. Nanomolar-potency compounds from Classes B, J and K, which did not increase cAMP, were selected for further characterization in living mice.

CFTR activators increase ocular surface chloride and fluid secretion in vivo. An open-circuit potential difference (PD) method developed in our lab was used to evaluate compound activity at the ocular surface in vivo, as depicted in FIG. 3A (21). Cl⁻ channel function was quantified by measuring PD during continuous perfusion of the ocular surface with a series of solutions that imposed a transepithelial Cl⁻ gradient and contained various channel agonists and/or inhibitors. The ocular surface was first perfused with isosmolar saline to record the baseline PD. Amiloride was then added to the perfusate, followed by exchange to a low Cl⁻ solution in which Cl⁻ with an impermeant anion, gluconate. These maneuvers allow for direct visualization of CFTR activation in response to addition of candidate CFTR activators.

FIG. 3B shows large hyperpolarizations following exposure to $CFTR_{act}$-B074, $CFTR_{act}$-J027 and $CFTR_{act}$-K089, which were increased relatively little by forskolin and were reversed by $CFTR_{inh}$-172. In comparison, VX-770 produced minimal changes in ocular surface PD (FIG. 3C). FIG. 3D summarizes PD data for indicated activators, with data for additional compounds reported in FIG. 7. Control studies done in CF mice lacking functional CFTR showed no changes in PD following addition of each of the compounds tested, with a representative curve shown for $CFTR_{act}$-K032 (FIG. 3E).

CFTR activators were next tested for their efficacy in augmenting tear production in mice. Preliminary experiments identified a standard ophthalmic formulation (0.5% polysorbate) that increased compound solubility and duration-of-action. Following a single topical dose, the indirect CFTR activators cholera toxin, forskolin, and 3-isobutyl-1-methylxanthine (IBMX) substantially increased basal tear secretion at 30 min, but these effects were transient and undetectable after 2 hours (FIG. 4A). However, the direct CFTR activators identified here, $CFTR_{act}$-B074, $CFTR_{act}$-J027 and $CFTR_{act}$-K089, increased tear fluid secretion by approximately two-fold for at least four hours. VX-770 produced little tear secretion (FIG. 4B). Repeated topical administrations (three times daily for up to 2 weeks) produced sustained tear hypersecretion without tachyphylaxis (FIG. 4C). CFTR activators did not increase tear fluid secretion in CF mice, demonstrating selective CFTR targeting (FIG. 4D).

Toxicity and pharmacokinetics. Tear collection methods were validated by demonstrating reproducible recovery of tetramethylrhodamine dextran (3 kDa) from the ocular surface up to six hours after instillation. The pharmacokinetics of $CFTR_{act}$-K089 at the ocular surface was determined by LC/MS of recovered tear washes. Following instillation of 0.1 nmol of $CFTR_{act}$-K089 (2 µL, 50 µM) to the ocular surface, 7.9±2.4 pmol and 0.011±0.004 pmol were recovered at five min and six hours, respectively (FIG. 5A). The amount of $CFTR_{act}$-K089 required for 50% CFTR activation ($EC_{50}$ ~250 nM) lies between the dashed lines, reflecting concentrations calculated from the highest and lowest reported normal tear volumes in mice (33, 34). The quantity of $CFTR_{act}$-K089 recovered from tear fluid predicts therapeutic levels for at least six hours. Tear fluid pharmacokinetics of $CFTR_{act}$-J027 could not be measured because the LC/MS sensitivity was low for this compound.

Following two weeks of three times per day dosing, the amounts of $CFTR_{act}$-K089 and $CFTR_{act}$-J027 were below the limits of detection (~10 and ~700 fmol, respectively) in mouse blood, brain, liver and kidney, indicating minimal systemic accumulation. The chronically treated mice showed no signs of ocular toxicity, as assessed by slit-lamp evaluation for conjunctival hyperemia, anterior chamber inflammation, and lens clarity. LG staining showed no corneal or conjunctival epithelial disruption (FIG. 5B). The compounds also produced no appreciable in vitro cytotoxicity in cell cultures at concentrations up to 100 µM (FIG. 5C).

CFTR activator prevents dry eye in a lacrimal gland excision model in mice. On the basis of its favorable tear film pharmacokinetics, $CFTR_{act}$-K089 was selected for testing in a mouse model of aqueous-deficient dry eye produced by LGE. Following extraorbital LGE in BALB/c mice, $CFTR_{act}$-K089-treated mice (0.1 nmol, administered three times daily) maintained basal tear volume, whereas tear volume from vehicle-treated mice was significantly reduced at all subsequent time-points (FIG. 6A), and for at least 30 days. Similar to what was reported in C57/bl6 mice (30), decreased lacrimation in vehicle-treated BALB/c mice was associated with progressive epithelial disruption from Day 0 to Day 14, shown pictorially (FIG. 6B top) and quantitatively (FIG. 6C). $CFTR_{act}$-K089 not only restored tear secretion in LGE mice but remarkably prevented ocular surface epithelial disruption at all time points (FIG. 6B). Vehicle-treated eyes developed diffuse, progressive corneal epitheliopathy (LG score increase of 7.3±0.6 by Day 14), whereas eyes treated with $CFTR_{act}$-K089 had minimal LG staining at all time points (LG score change, −0.6±0.6).

Discussion.

A goal of this study was to investigate the potential utility of small-molecule activators of CFTR for dry eye therapy. After several prior development failures, dry eye remains an unmet need in ocular disease. In dry eye disorders, tear film hyperosmolarity stimulates pro-inflammatory signaling, secretion of cytokines and metalloproteinases, and disruption of corneal epithelial cell integrity (35-38). By minimizing tear film hyperosmolarity, CFTR activation is predicted to prevent these downstream ocular surface changes.

We identified small-molecule CFTR activators by high-throughput screening that produced sustained Cl⁻-driven aqueous fluid secretion across the ocular surface by a mechanism involving direct CFTR activation rather than upstream cAMP signaling. The rationale to choose compounds that activate CFTR directly was to minimize potential off-target effects of generalized cAMP stimulation and to reduce the likelihood of tachyphylaxis for compounds targeting signaling receptors. These compounds had low-nano-molar $EC_{50}$ for activation of human CFTR in vitro and produced full activation at higher concentrations. Large CFTR-dependent PD hyperpolarizations and tear hypersecretion were demonstrated in mice. Substantial compound activities in mice and humans will facilitate translation of data here to humans.

We found that $CFTR_{act}$-K089 restored tear secretion and prevented epithelial disruption in an experimental mouse model of lacrimal insufficiency. CFTR activators may be particularly suited for disorders of the lacrimal gland, such as primary Sjögren's syndrome, by stimulating fluid transport across the intact corneal and conjunctival epithelia. CFTR activators probably exert their major pro-secretory effect at the ocular surface, although there is indirect for CFTR expression and function in lacrimal gland (39-42). Direct stimulation of lacrimal secretion is unlikely in the studies here because of minimal compound penetration to lacrimal tissues following topical delivery, and the demonstrated compound efficacy in a model of lacrimal insufficiency. At the ocular surface, the conjunctiva probably contributes the bulk of fluid secretion given its much larger surface area compared to cornea (43).

Alternative pro-secretory therapies targeting different ocular surface ion channels have been considered. The only FDA-approved CFTR activator, VX-770, was developed as a "potentiator" to treat CF by correcting the channel gating of certain CFTR mutations (44). However, VX-770 showed relatively little activity against wild-type CFTR in cell cultures and in mice in vivo. Chronic application of VX-770 may also diminish CFTR functional expression (24) and cause cataracts (seen in juvenile rats; ref. 42), which is likely an off-target effect because CFTR is not expressed in lens.

$CFTR_{act}$-K089 and $CFTR_{act}$-J027 showed favorable pharmacodynamics and could be conveniently administered topically several times daily in a standard ophthalmic formulation.

In conclusion, without wishing to be bound by theory, it is believed that the efficacy of $CFTR_{act}$-K089 in a clinically relevant mouse model of aqueous-deficient dry eye disease provides proof-of-principle for topical, pro-secretory CFTR activator therapy to restore basal tear secretion and prevent ocular surface pathology. Compared with immunosuppressive approaches, CFTR activation has the advantage of addressing an early event in dry eye pathogenesis. Our data thus support the development potential of CFTR activators as first-in-class dry eye therapy.

Referenced (Example 5)

[1]. The definition and definition of dry eye disease: report of the Definition and Classification Subcommittee of the International Dry Eye WorkShop 2007 (DEWS) (2007). Ocul. Surf. 5, 65-204; [2]. Schaumberg, D. A., Dana, R., Buring, J. E., and Sullivan, D. A. (2009). Prevalence of dry eye disease among US men: estimates from the Physicians' Health Studies. Arch. Ophthalmol. 127, 763-768; [3]. Schaumberg, D. A., Sullivan, D. A., Buring, J. E., and Dana, M. R. (2003). Prevalence of dry eye syndrome among US women. Am. J. Ophthalmol. 136, 318-326; [4]. Yu, J., Asche, C. V., and Fairchild, C. J. (2011). The economic burden of dry eye disease in the United States: a decision tree analysis. Cornea 30, 379-387; [5]. Alves, M., Foseca, E. C., Alves, M. F., Malki, L. T., Arruda, G. V., Reinach, P. S., and Rocha, E. M. (2013). Dry eye disease treatment: a systematic review of published trials and critical appraisal of therapeutic strategies. Ocul. Surf. 11, 181-192; [6]. Sheppard, J. D., Torkildsen, G. L., Lonsdale, J. D., D'Ambrosio Jr., F. A., McLaurin, E. B., Eiferman, R. A., Kennedy, K. S. and Semba, C. P.; OPUS-1 Study Group (2014). Lifitegrast ophthalmic solution 5.0% for treatment of dry eye disease: results of the OPUS-1 phase 3 study. Ophthalmology 121, 475-483; [7]. Asbell P. A., and Spiegel S. (2010). Ophthalmologist perceptions regarding treatment of moderate-to-severe dry eye: results of a physician survey. Eye Contact Lens 36, 33-38; [8]. The epidemiology of dry eye disease: report of the Epidemiology Subcommittee of the International Dry Eye WorkShop 2007 (DEWS) (2007). Ocul. Surf. 5, 65-204; [9]. Thelin, W. R., Johnson, M. R., Hirsh, A. J., Kublin, C. L. and Zoukhri, D. J. (2012). Effect of topically applied epithelial sodium channel inhibitors on tear production in normal mice and in mice with induced aqueous tear deficiency. Ocul. Pharmacol. Ther. 28, 433-438; [10]. Nichols, K. K., Yerxa, B. and Kellerman, D. J. (2004). Diquafosol tetrasodium: a novel dry eye therapy. Expert. Opin. Investig. Drugs 13, 47-54; [11]. Koh, S., Ikeda, C., Takai, Y., Watanabe, H., Maeda, N., and Nishida, K. (2013). Long-term results of treatment with diquafosol ophthalmic solution for aqueous-deficient dry eye. Jpn. J. Ophthalmol. 57, 440-446; [12]. Takamura, E., Tsubota, K., Watanabe, H., and Ohashi, Y.; Diquafosol Ophthalmic Solution Phase 3 Study Group (2012). A randomised, double-masked comparison study of diquafosol versus sodium hyaluronate ophthalmic solutions in dry eye patients. Br. J. Ophthalmol. 96, 1310-1315; [13]. Tauber, J., Davitt, W. F., Bokosky, J. E., Nichols, K. K., Yerxa, B. R., Schaberg, A. E., LaVange, L. M., Mills-Wilson, M. C., and Kellerman, D. J. (2004). Double-masked placebo-controlled safety and efficacy trial of diquafosol tetrasodium (INS365) ophthalmic solution for the treatment of dry eye. Cornea 23, 784-792; [14]. Al-Nakkash, L., and Reinach, P. S. (2001). Activation of a CFTR-mediated chloride current in a rabbit corneal epithelial cell line. Invest. Ophthalmol. Vis. Sci. 42, 2353-2370; [15]. Shiue, M. H., Gukasyan, H. J, Kim, K. J., Loo, D. D., and Lee, V. H (2002). Characterization of cyclic AMP-regulated chloride conductance in the pigmented rabbit conjunctival epithelial cells. Can. J. Physiol. Pharmacol. 80, 533-540; [16]. Turner, H. C., Bernstein, A., and Candia, O. A. (2002). Presence of CFTR in the conjunctival epithelium. Curr. Eye Res. 24, 182-187; [17]. Ansari, E. A., Sahni, K., Etherington, C., Morton, A., Conway, S. P., Moya, E., and Littlewood, J. M. (1999). Ocular signs and symptoms and vitamin A status in patients with cystic fibrosis treated with daily vitamin A supplements. Br. J. Ophthalmol. 83, 688-691; [18]. Botelho, S. Y., Goldstein, A. M., and Rosenlund, M. L. (1973). Tear sodium, potassium, chloride, and calcium at various flow rates: children with cystic fibrosis and unaffected siblings with and without corneal staining. J. Pediatr. 83, 601-606; [19]. Morkeberg, J. C., Edmund, C., Prause, J. U., Lanng, S., Koch, C., and Michaelsen, K. F. (1995). Ocular findings in cystic fibrosis patients receiving vitamin A supplementation. Graefes Arch. Clin. Exp. Ophthalmol. 233, 709-713; [20]. Mrugacz, M., Kaczmarski, M., Bakunowicz-Lazarczyk, A., Zelazowska, B., Wysocka, J., and Minarowska, A. (2006). IL-8 and IFN-gamma in tear fluid of patients with cystic fibrosis. J. Interferon Cytokine Res. 26, 71-75; [21]. Levin, M. H. and Verkman, A. S. (2005). CFTR-regulated chloride transport at the ocular surface in living mice measured by potential differences. Invest. Ophthalmol. Vis. Sci. 46, 1428-1434; [22]. Levin, M. H., Kim, J. K., Hu, J., and Verkman A. S. (2006). Potential difference measurements of ocular surface Na+ absorption analyzed using an electrokinetic model. Invest. Ophthalmol. Vis. Sci. 47, 306-316; [23]. Yu, D., Thelin, W. R., Rogers, T. D., Stutts, M. J., Randell, S. H., Grubb, B. R., and Boucher, R. C. (2012). Regional differences in rat conjunctival ion transport activities. Am. J. Physiol. Cell Physiol. 303, C767-780; [24]. Cholon, D. M., Quinney, N. L., Fulcher, M. L., Esther Jr., C. R., Das, J., Dokholyan, N. V., Randell, S. H., Boucher, R. C., and Gentzsch, M. (2014). Potentiator ivacaftor abrogates pharmacological correction of ΔF508 CFTR in cystic fibrosis. Sci. Transl. Med. 6, 246-296; [25]. Ramsey, B. W., Davies, J., McElvaney, N. G., Tullis, E., Bell, S. C., Dřevínek, P., Griese, M., McKone, E. F., Wainwright, C. E., Konstan, M. W., Moss, R., Ratjen, F., Sermet-Gaudelus, I., Rowe, S. M., Dong, Q., Rodriguez, S., Yen, K., Ordoñez, C., and Elborn, J. S.; VX08-770-102 Study Group (2011). A CFTR potentiator in patients with cystic fibrosis and the G551D mutation. N. Engl. J. Med. 365, 1663-1672; [26]. Ma, T., Vetrivel, L., Yang, H., Pedemonte, N., Zegarra-Moran, O., Galietta, L. J., and Verkman, A. S. (2002). High-affinity activators of CFTR chloride conductance identified by high-throughput screening. J. Biol. Chem. 277, 37235-37241; [27]. Galietta, L. J., Springsteel, M. F., Eda, M., Niedzinski, E. J., By, K., Haddadin, M. J., Kurth, M. J., Nantz, M. H., and Verkman, A. S. (2001). Novel CFTR chloride channel activators identified by screening of combinatorial libraries based on flavone and benzoquinolizinium lead compounds. J. Biol. Chem. 276, 19723-19728; [28]. Esteva-Font, C., Cil, O., Phuan, P. W., Tao, S., Lee, S., Anderson, M. O., and Verkman, A. S. (2014) Diuresis and reduced urinary osmolality in rats produced by small-molecule UT-A-selective urea transport inhibitors. FASEB J. 28, 3878-3890; [29]. Yao C, Anderson, M. O., Zhang J., Yang B., Phuan P. W., and Verkman, A. S. (2012) Triazolothienopyrimidine inhibitors of urea transporter UT-B reduce urine concentration. J. Am. Soc. Nephrol. 23, 1210-1220; [30]. Stevenson, W., Chen, Y., Lee, S. M., Lee, H. S., Hua, J., Dohlman, T., Shiang, T., and Dana, R. (2014). Extraorbital lacrimal gland excision: a reproducible model of severe aqueous tear-deficient dry eye disease. Cornea 33, 1336-1341; [31]\. Galietta, L. J., Haggie, P. M., and Verkman, A. S. (2001). Green fluorescent protein-based halide indicators with improved chloride and iodide affinities. FEBS Lett. 499, 220-224; [32]. Galietta, L. V., Jayaraman, S., and Verkman, A. S. (2001). Cell-based assay for high-throughput quantitative screening of CFTR chloride transport agonists. Am. J. Physiol. Cell Physiol. 281, C1734-1742; [33]. Sullivan, D. A., Krenzer, K. L., Sullivan, B. D., Tolls, D. B., Toda, I., and Dana, M. R. (1999). Does androgen insufficiency cause lacrimal gland inflammation and aqueous tear deficiency? Invest. Ophthalmol. Vis. Sci. 40, 1261-1265; [34]. Villareal, A. L., Farley, W., and Pflugfelder, S. C. (2006). Effect of topical ophthalmic epinastine and olopatadine on tear volume in mice. Eye Contact Lens 32, 272-276; [35]. Lemp, M. A., Bron, A., Baudouin, C., Benítez Del Castillo, J., Geffen, D., Tauber, J., Foulks, G., Pepose, J. and Sullivan, B. D. (2011). Tear osmolarity in the diagnosis and management of dry eye disease. Am. J. Ophthalmol. 151, 792-798; [36]. Luo, L., Li, D. Q., Corrales, R. M., and Pflugfelder, S. C. (2005). Hyperosmolar saline is a proinflammatory stress on the mouse ocular surface. Eye Contact Lens 31, 186-193; [37]. Liu, H., Begley, C., Chen, M., Bradley, A., Bonanno, J., McNamara, N., Nelson, J., and Simpson, T. (2009). A link between tear instability and hyperosmolarity in dry eye. Invest. Ophthalmol. Vis. Sci. 50, 3671-3679; [38]. Gilbard, J. P., Carter, J., Sang, D., Refojo, M., Hanninen, L. and Kenyon, K. R. (1984). Morphologic effect of hyperosmolarity on rabbit corneal epithelium. Ophthalmology 91, 1205-1212; [39]. Rosemary, R., Evans, M., Cuthbert, A., MacVinish, J. L., Foster, D., Anderson, J., and Colledge, W. H. (1993). Nature Genetics 4, 35-41; [40]. Lu, M. and Ding, C. (2012). CFTR-mediated Cl(−) transport in the acinar and duct cells of rabbit lacrimal gland. Curr. Eye Res. 37, 671-677; [41]. Nandoskar, P., Wang, Y., Wei, R., Liu, Y., Zhao, P., Lu, M., Huang, J., Thomas, P., Trousdale, M., and Ding, C. (2012). Changes of chloride channels in the lacrimal glands of a rabbit model of Sjögren syndrome. Cornea 31, 273-279; [42]. Kalydeco [Product Monograph] Laval, Quebec: Vertex Pharmaceuticals (Canada) Inc.; 2012; [43]. Watsky, M. A., Jablonski, M., and Edelhauser, H. F. (1988). Comparison of conjunctival and corneal surface area in rabbit and human. Curr. Eye Res. 7, 483-486; [44]. Van Goor, F., Hadida, S., and Grootenhuis, P. D. J. (2008). Pharmacological rescue of mutant CFTR function for the treatment of cystic fibrosis. Top. Med. Chem. 3, 91-120; [45]. Wolosin, J. M., and Candia, O. A. (1987). Cl− secretagogues increase basolateral K+ conductance of frog corneal epithelium. Am. J. Physiol. 253, C555-560; [46]. Kompella, U. B., Kim, K. J., and Lee, V. H. (1993). Active chloride transport in the pigmented rabbit conjunctiva. Curr. Eye Res. 12, 1041-1048; [47]. Turner, H. C., Alvarez, L. J., and Candia, O. A. (2000). Cyclic AMP-dependent stimulation of basolateral K(+)conductance in the rabbit conjunctival epithelium. Exp. Eye Res. 70, 295-305.

Example 6. Nanomolar-Potency Aminophenyl-1,3,5-Triazine CFTR Chloride Channel Activators for Pro-Secretory Therapy of Dry Eye Diseases Compound numbering and substituents numbering within Example 6 is with respect to Example 6 only.

Abstract. Dry eye disorders are a significant health problem for which limited therapeutic options are available. CFTR (cystic fibrosis transmembrane conductance regulator) is a major pro-secretory chloride channel at the ocular surface. We previously identified, by high-throughput screening, aminophenyl-1,3,5-triazine $CFTR_{act}$-K089 (1) that activated CFTR with $EC_{50}$ ~250 nM, which when delivered topically increased tear fluid secretion in mice and showed efficacy in an experimental dry eye model. Here, functional analysis of synthesized aminophenyl-1,3,5-triazine analogs elucidated structure-activity relationships for CFTR activation and identified substantially more potent analogs than 1. The most potent compound, 12, fully activated CFTR chloride conductance with $EC_{50}$ ~30 nM, without causing cAMP or calcium elevation. 12 was non-toxic, stable at 100 µM in an ophthalmic vehicle, and rapidly metabolized by hepatic microsomes, which supports its topical use in dry eye disease. Analogs with greater metabolic stability were also identified for possible treatment of liver and lung disorders. Single topical administration of 25 pmol 12 increased tear volume in wildtype mice with sustained action for 8 hours, and was without effect in CFTR-deficient mice. Topically delivered 12 may be efficacious in human dry eye diseases.

Introduction.

CFTR (cystic fibrosis transmembrane conductance regulator) is a cAMP-gated chloride channel with pro-secretory activity in the airways, gastrointestinal organs, testis and exocrine glands [1-4]. Loss-of-function mutations in CFTR cause cystic fibrosis, and inappropriate activation of CFTR causes certain secretory diarrheas such as cholera [5-7]. CFTR is an important drug target for which major advances have been made in the development of potentiators and correctors of mutant CFTRs in cystic fibrosis, with two drugs having received FDA approval [8]. Activators of wildtype CFTR have potential clinical indications for pro-secretory therapy of constipation and dry eye disorders, and possibly for disorders of the liver, pancreas and airways

[9-12], and CFTR inhibitors are under development for certain secretory diarrheas and polycystic kidney disease [13,14].

Figure 14A:
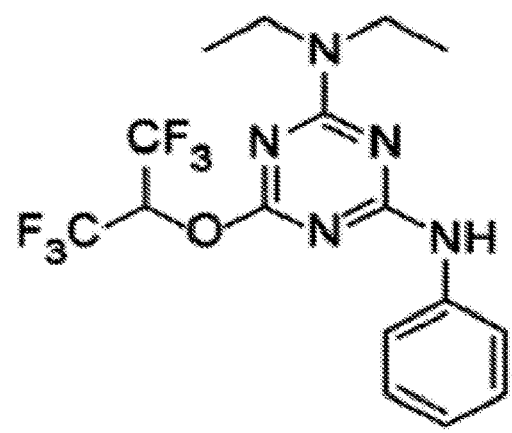
FIGS. 14A-14B. Structure-activity analysis of aminophenyl-1,3,5-triazine CFTR activators.

We previously identified, by high-throughput screening, small-molecule activators of wildtype CFTR that function by a direct activation mechanism [12-15]. One class of phenylquinoxalinone CFTR activators showed efficacy following oral administration in experimental mouse models of constipation [9,10]. A second class of CFTR activators, which includes the aminophenyl-1,3,5-triazine $CFTR_{act}$-K089 (compound 1, FIG. 14A), activated ocular surface CFTR activity in mice and increased tear fluid secretion after topical delivery [12]. In a mouse model of aqueous-deficient dry eye produced by lacrimal gland excision, topical delivery of 1 three times daily corrected defective tear fluid secretion and prevented ocular surface clinical signs. An ideal dry eye therapeutic would produce sustained tear fluid secretion with once or twice daily dosing.

Here, we report structure-activity relationship studies of aminophenyl-1,3,5-triazine CFTR activators with a focus on dry eye applications. Dry eye is a heterogeneous group of disorders associated with reduced tear volume and tear fluid hyperosmolarity, resulting in ocular surface inflammation, eye discomfort and visual disturbance. Dry eye is a major health problem in an aging population, with five million patients in the U.S. age 50 and over [16,17]. The only approved dry eye drugs, topical cyclosporine and lifitegrast, act by an anti-inflammatory mechanism [18,19]. CFTR activators would be first-in-class dry eye therapeutics that function by a pro-secretory mechanism. Synthesis and characterization of aminophenyl-1,3,5-triazines here produced potential lead candidates with substantially improved potency and in vivo pro-secretory efficacy compared to 1, as well as compounds with greater metabolic stability for potential treatment of non-ocular conditions.

Chemistry.

General synthesis of aminophenyl-1,3,5-triazine analogs. The synthesis of aminophenyl-1,3,5-triazine analogs was accomplished by serial substitution of cyanuric chloride using fluorinated alkoxides, diethyl amine, and anilines (Scheme 1). Substitution of cyanuric chloride with 1,1,1,3,3,3-hexafluoroisopropanol or 2,2,3,3-tetrafluoro-1-propanol afforded 2 and 3, respectively. Amination of 2 and 3 using diethyl amine afforded intermediates 4 and 5. Refluxing of 4 and 5 with aniline afforded 1 and 7a, respectively. Refluxing m-orp-F, Cl, $NO_2$, $CO_2$H-substituted anilines with 4 and 5 afforded aminophenyl-1,3,5-triazines 6a-g and 7b-g, respectively. 5 was refluxed with 6-aminobenzothiazole, 6-aminobenzoxazole, 5- or 6-aminoindazole under basic condition to afford 6h-6k.

Scheme 1

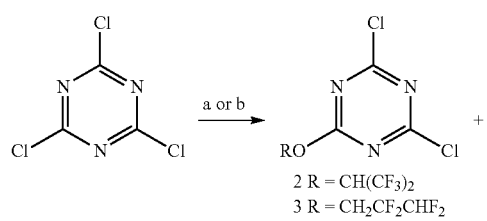

2 R = $CH(CF_3)_2$
3 R = $CH_2CF_2CHF_2$

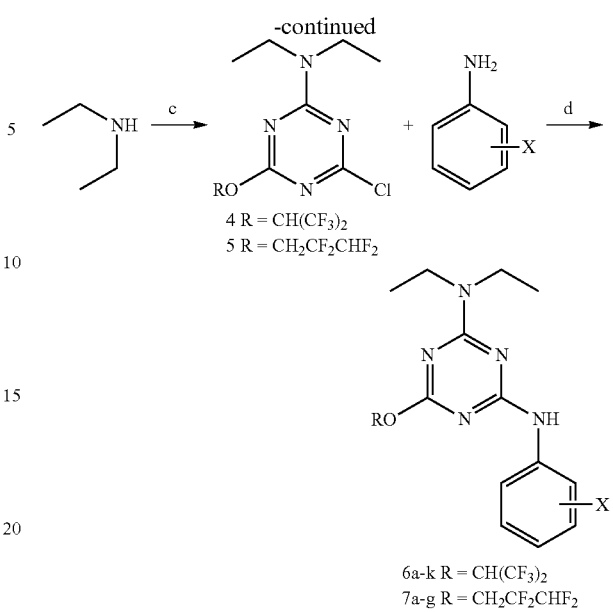

4 R = $CH(CF_3)_2$
5 R = $CH_2CF_2CHF_2$ 6a-k R = $CH(CF_3)_2$
7a-g R = $CH_2CF_2CHF_2$

Synthesis of N,N-diethyl-1,3,5-triazine analogs. (a) $(CF_3)_2CHOH$, $K_2CO_3$, THF, -80° C., 62% for 2. (b) $CHF_2CF_2CH_2OH$, $K_2CO_3$, THF, -80° C., 68% for 3. (c) Et-2-NH, DIPEA, THF, 0° C., 55%. (d) DIPEA, THF, reflux, 25-81%.

N-Methylamine-1,3,5-triazine analogs 11 and 12 were synthesized as shown in Scheme 2. Methylamine was substituted with cyanuric chloride to afford N-methyl-4,6-dichloro-1,3,5-triazine-2-amine 8 in 72% yield. With 8 in hand, substitution with 1,1,1,3,3,3-hexafluoro-2-propanol or 2,2,3,3-tetrafluoro-1-propanol afforded 9 and 10, respectively. Aniline substitution on 9 and 10 afforded N-methyl-amino-N'-phenylamino-1,3,5-triazine analogs 11 and 12, respectively.

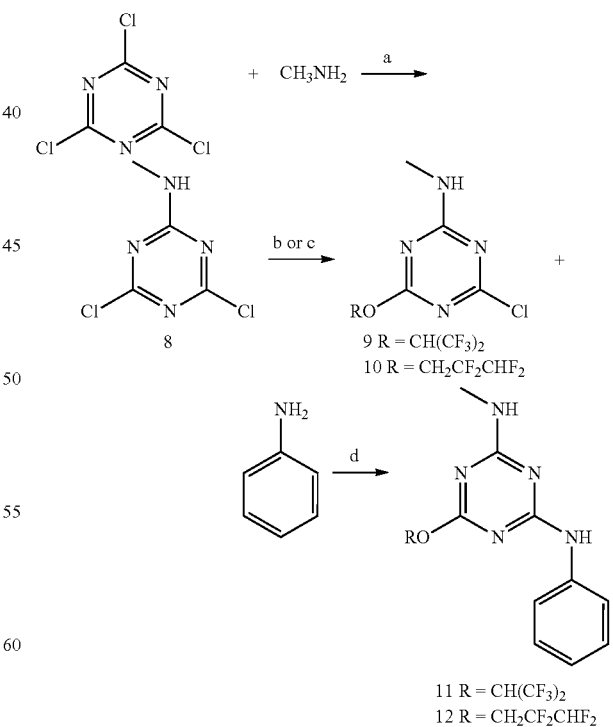

11 R = $CH(CF_3)_2$
12 R = $CH_2CF_2CHF_2$

Synthesis of N-methylamino-N'-phenylamino-1,3,5-triazine analogs. (a) DIPEA, THF, 0° C., 75%. (b) $(CF_3)_2CHOH$, $K_2CO_3$, THF, 0° C., 43% for 9. (c) $CHF_2CF_2CH_2OH$, $K_2CO_3$, THF, 0° C., 66% for 10. (d) DIPEA, THF, reflux, 74% for 12; 68% for 11.

General Synthesis Procedures. All solvents and chemicals were used as purchased without further purification. The progress of all reactions was monitored on Merck pre-coated silica gel plates (with fluorescence at 254 nm) using ethyl acetate/n-hexane as solvent system. Column chromatography was done with Fluka silica gel 60 (230-400 mesh ASTM) with specified solvent mixtures. Proton ($^1$H) and carbon ($^{13}$C) NMR spectra were recorded on a Bruker Avance 300 or 500 (500.13 MHz for $^1$H; 125.76 MHz for $^{13}$C) using CDCl$_3$ (δ 7.26), CD$_3$OD (δ=4.87 and 3.31), acetone-d$_6$ (δ 2.05), or DMSO-d$_6$ (δ 2.5) as solvents. Chemical shifts are given in parts per million (ppm) (δ relative to residual solvent peak for $^1$H and $^{13}$C). HRMS was performed using a hybrid quadrupole orbitrap mass analyzer, QExactive (Thermo, Bremen, Germany), with an electrospray ionization source. The mass resolution was set as 70,000 at m/z 200 and the mass accuracy was less than 3 ppm. Purity of all final compounds was 95% or higher.

N,N-Diethyl-N'-phenyl-6-(2,2,3,3-tetrafluoropropoxy)-1,3,5-triazine-2,4-diamine (6a). Purified by flash chromatography (1:10 EtOAc/Hex) to afford 6a as a white powder (100 mg, 38%). $^1$H NMR (300 MHz, CDCl$_3$): δ=7.60 (d, 2H, J=8.4 Hz), 7.34 (t, 2H, J=7.4 Hz), 7.08 (t, 1H, J=7.3 Hz), 6.06 (tt, 1H, J=4.9, 53.0 Hz), 3.68-3.59 (m, 2H), 4.78-4.70 (m, 4H), 1.28-1.20 (m, 6H); $^{13}$C NMR (75 MHz, CDCl$_3$), δ=169.2, 165.2, 164.8, 138.6, 128.7, 123.1, 120.0, 114.4 (t, J=26 Hz), 112.3 (t, J=34 Hz), 109.0 (t, J=34 Hz), 105.7 (t, J=34 Hz), 62.1 (t, J=30 Hz), 42.1, 41.7, 13.1, 12.9; HRMS (ESI): m/z calculated for C16H20F4N5O [M+H+]: 374.1599. Found: 374.1597.

3-{[4-(Diethylamino)-6-(2,2,3,3-tetrafluoropropoxy)-1,3,5-triazin-2-yl]amino}benzoic acid (6b). Purified by flash chromatography (1:5 EtOAc/Hex) to afford 6b as a white powder (60%). $^1$H NMR (300 MHz, acetone-d6): δ=8.68 (brs, 1H), 7.92 (m, 1H), 7.74-7.71 (m, 1H), 7.46 (t, 1H, J=7.84 Hz), 6.45 (tt, 1H, J=Hz), 4.91-4.82 (m, 2H), 3.74-3.65 (m, 4H), 1.28-1.18 (m, 6H); $^{13}$C NMR (75 MHz, acetone-d6): δ=169.12, 164.68, 159.89, 157.96, 142.33, 134.51, 131.28, 125.52, 121.99, 118.77, 115.45, 115.27, 114.35, 112.35, 111.29, 111.01, 110.73, 110.07, 109.29, 109.02, 108.75, 107.31, 107.03, 106.76, 62.71, 62.37, 62.13, 61.89, 42.13, 41.84, 29.67, 13.06, 12.86, 12.77; HRMS (ESI): m/z calculated for C17H20F4N5O3 [M+H+]: 418.1497. Found: 418.1501.

N,N-Diethyl-N'-(3-fluorophenyl)-6-(2,2,3,3-tetrafluoropropoxy)-1,3,5-triazine-2,4-diamine (6c). Purified by flash chromatography (1:10 EtOAc/Hex) to afford 6c as a white powder (40%). $^1$H NMR (300 MHz, CDCl$_3$): δ=7.73 (dt, 1H, J=2.1, 7.73 Hz), 7.37 (brs, 1H), 7.26 (td, 1H, J=6.31, 8.19 Hz), 7.12 (ddd, 1H, J=0.9, 2.0, 8.16 Hz), 6.76 (ddt, 1H, J=0.9, 2.5, 8.2 Hz), 6.02 (tt, 1H, J=4.92, 53.01 Hz), 4.74 (tt, 2H, J=1.6, 12.4 Hz), 3.64 (sex, 4H, J=7.02 Hz), 1.23 (m, 6H); $^{13}$C NMR (75 MHz, CDCl$_3$): δ=169.2, 165.2, 164.8, 164.6, 161.4, 140.4, 140.3, 129.8, 129.7, 114.9, 114.9, 114.7, 114.3, 114.0, 112.7, 112.3, 111.0, 109.7, 109.47, 109.42, 109.0, 108.5, 107.3, 107.0, 105.7, 62.5, 62.1, 61.7, 42.3, 41.9, 13.0, 12.8; HRMS (ESI): m/z calculated for C16H19F5N5O [M+H+]: 392.1505. Found: 392.1505.

N'-(3-Chlorophenyl)-N,N-diethyl-6-(2,2,3,3-tetrafluoropropoxy)-1,3,5-triazine-2,4-diamine (6d). Purified by flash chromatography (1:10 EtOAc/Hex) to afford 6d as a white powder (81%). $^1$H NMR (300 MHz, CDCl$_3$): δ=7.99 (brs, 1H), 7.25 (m, 3H), 7.04 (dt, 1H, J=7.01, 2.01 Hz), 6.02 (t, 1H, J=4.89 Hz), 4.73 (t, 2H, J=12.3 Hz), 3.64 (m, 4H), 1.84 (brs, 1H), 1.25 (m, 6H); $^{13}$C NMR (75 MHz, CDCl$_3$): δ=169.2, 165.2, 164.7, 139.9, 134.5, 129.6, 122.9, 120.0, 117.6, 114.5, 114.3, 114.1, 112.3, 111.3, 111.0, 110.7, 109.3, 109.0, 108.8, 107.3, 107.0, 106.8, 62.4, 62.1, 61.9, 42.4, 42.0, 13.0, 12.9; HRMS (ESI): m/z calculated for C16H19ClF4N4O [M+H+]: 408.1209. Found: 408.1210.

N,N-Diethyl-N'-(3-nitrophenyl)-6-(2,2,3,3-tetrafluoropropoxy)-1,3,5-triazine-2,4-diamine (6e). Purified by flash chromatography (1:10 EtOAc/Hex) to afford 6e as a yellowish powder (61%). $^1$H NMR (300 MHz, CDCl$_3$): δ=9.12 (brs, 1H), 8.15 (brs, 1H), 7.90 (dd, 1H, J=8.20, 1.58 Hz), 7.57 (d, 1H, J=7.57 Hz), 7.44 (t, 1H, J=8.04 Hz), 5.96 (m, 1H), 4.75 (t, 2H, J=12.61 Hz), 3.72 (q, 2H, J=6.94 Hz), 3.65 (q, 2H, J=6.94), 2.12 (brs, 1H), 1.31 (t, 3H, J=7.09 Hz), 1.24 (t, 3H, J=7.09 Hz); $^{13}$C NMR (75 MHz, CDCl$_3$): δ=169.1, 164.9, 164.7, 148.6, 140.1, 129.2, 124.8, 117.4, 116.2, 114.6, 114.5, 114.2, 114.0, 112.3, 111.3, 111.0, 110.7, 109.3, 109.0, 108.7, 107.3, 107.0, 106.7, 62.3, 62.1, 61.8, 42.6, 42.1, 12.9, 12.8; HRMS (ESI): m/z calculated for C16H19F4N6O3 [M+H+]: 419.1450. Found: 419.1449.

4-({4-(Diethylamino)-6-[(1,1,1,3,3,3-hexafluoropropan-2-yl)oxy]-1,3,5-triazin-2-yl}amino)benzoic acid (6f). Purified by flash chromatography (1:10 EtOAc/Hex) to afford 6f as a white powder (37%). $^1$H NMR (300 MHz, acetone-d6): δ=8.97 (brs, 1H), 8.04-7.96 (m, 4H), 6.45 (tt, 1H, J=5.07, 52.41 Hz), 4.88 (t, 2H, J=13.5 Hz), 3.74-3.64 (m, 4H), 1.29-1.19 (m, 6H); $^{13}$C NMR (75 MHz, acetone-d6): δ=169.7, 166.4, 165.5, 165.4, 144.2, 130.5, 124.0, 118.8, 109.6, 109.1, 62.1, 61.7, 61.4 (t, J=Hz), 41.8, 41.5, 12.4, 12.3; HRMS (ESI): m/z calculated for C17H20F4N5O3 [M+H+]: 418.1497. Found: 418.1499.

N,N-Diethyl-N'-(4-fluorophenyl)-6-(2,2,3,3-tetrafluoropropoxy)-1,3,5-triazine-2,4-diamine (6g). Purified by flash chromatography (1:10 EtOAc/Hex) to afford 6g as a white powder (45%). $^1$H NMR (300 MHz, CDCl$_3$): δ=7.53 (m, 2H), 7.36 (brs, 1H), 7.02 (m, 2H), 6.03 (m, 1H), 4.73 (m, 2H), 3.61 (m, 4H), 1.24 (m, 6H); $^{13}$C NMR (75 MHz, CDCl$_3$): δ=169.1, 164.6, 159.8, 157.9, 142.3, 134.5, 131.2, 125.5, 121.9, 118.7, 115.4, 115.2, 114.3, 112.3, 111.2, 111.0, 110.7, 110.07, 109.2, 109.0, 108.7, 107.3, 107.0, 106.7, 62.7, 62.3, 62.1, 61.8, 42.1, 41.8, 29.6, 13.0, 12.8, 12.7; HRMS (ESI): m/z calculated for C16H19F5N5O [M+H+]: 392.1505. Found: 392.1503.

3-({4-(diethylamino)-6-[(1,1,1,3,3,3-hexafluoropropan-2-yl)oxy]-1,3,5-triazin-2-yl}amino)benzoic acid (7a). Purified by flash chromatography (1:6 EtOAc/Hex) to afford 7a as a white powder (55%). $^1$H NMR (300 MHz, acetone-d6): δ=9.02 (brs, 1H), 8.79 (brs, 1H), 7.90 (d, 1H, J=8.07 Hz), 7.76 (dt, 1H, J=1.29, 7.86 Hz), 7.48 (t, 1H, J=7.92 Hz), 6.79 (quint, 1H, J=6.4 Hz), 3.78-3.66 (m, 4H), 1.29-1.20 (m, 6H); $^{13}$C NMR (75 MHz, acetone-d6): δ=168.6, 166.8, 165.3, 139.6, 131.1, 128.7, 123.9, 123.1, 121.2, 119.3, 68.9, 68.5, 68.0, 67.6, 67.1 (quint, J=34 Hz), 42.1, 41.6, 12.35, 12.32; HRMS (ESI): m/z calculated for C17H18F6N5O3 [M+H+]: 454.1309. Found: 454.1311.

N,N-Diethyl-N'-(3-fluorophenyl)-6-[(1,1,1,3,3,3-hexafluoropropan-2-yl)oxy]-1,3,5-triazine-2,4-diamine (7b). Purified by flash chromatography (1:8 EtOAc/Hex) to afford 7b as a white powder (45%). $^1$H NMR (300 MHz, CDCl$_3$): δ=7.69 (m, 1H), 7.48 (brs, 1H), 7.26 (m, 1H), 7.11 (d, 1H, J=7.88 Hz), 6.79 (td, 1H, J=8.2, 2.5 Hz), 6.31 (dt, 1H, J=12.37, 6.27 Hz), 3.64 (m, 4H), 1.25 (m, 6H); $^{13}$C NMR (75 MHz, CDCl$_3$): δ=34168.5, 165.1, 164.8, 164.6, 161.3, 140.1, 139.9, 129.8, 129.7, 122.7, 118.9, 115.1, 110.0, 109.7, 107.6, 107.2, 68.8, 68.4, 67.9 (t, J=34 Hz), 42.6, 42.2, 12.8, 12.7; HRMS (ESI): m/z calculated for C16H17F7N5O [M+H+]: 428.1316. Found: 428.1316.

N,N-Diethyl-6-[(1,1,1,3,3,3-hexafluoropropan-2-yl)oxy]-N-(3-nitrophenyl)-1,3,5-triazine-2,4-diamine (7d). Yellowish powder, 62% yield. $^1$H NMR (300 MHz, CDCl$_3$): δ=9.15

(brs, 1H), 8.23-7.74 (m, 2H), 7.70-7.34 (1m, 2H), 6.31 (quint, 1H, J=6.15 Hz), 3.74 (q, 2H, J=6.94 Hz), 3.63 (q, 2H, J=7.04 Hz), 1.89 (brs, 1H, 1.33 (t, 3H, J=7.09 Hz), 1.24 (t, 4H, J=7.09 Hz); $^{13}$C NMR (75 MHz, CDCl$_3$): δ=168.4, 165.1, 164.8, 148.6, 139.8, 129.3, 128.4, 126.3, 125.2, 122.6, 118.8, 115.1 (q, J=280 Hz), 125.0, 117.8, 114.8, 68.9, 68.4, 68.0 (t, J=34 Hz), 42.9, 42.4, 12.8, 12.7; HRMS (ESI): m/z calculated for C16H17F6N6O3 [M+H+]: 455.1261. Found: 455.1263.

4-({4-(Diethylamino)-6-[(1,1,1,3,3,3-hexafluoropropan-2-yl)oxy]-1,3,5-triazin-2-yl}amino)benzoic acid (7e). Purified by flash chromatography (1:10 EtOAc/Hex) to afford 7e as a white powder (56%). $^1$H NMR (300 MHz, acetone-d6): δ=9.12 (brs, 1H), 8.05-7.89 (m, 4H), 6.80 (quint, 1H, J=6.39 Hz), 3.72, (quint, 4H, J=7.2 Hz), 1.31-1.18 (m, 7H); $^{13}$C NMR (75 MHz, acetone-d6): δ=168.66, 165.91, 165.44, 165.34, 137.51, 133.65, 132.32, 131.53, 126.93, 123.46, 123.20, 123.16, 121.85, 119.46, 119.42, 115.73, 113.32, 112.69, 111.18, 109.84, 68.94, 68.44, 68.01, 67.56, 42.06, 41.55, 12.45, 12.31; HRMS (ESI): m/z calculated for C17H18F6N5O3 [M+H+]: 454.1309. Found: 454.1308.

N,N-Diethyl-N'-(4-fluorophenyl)-6-[(1,1,1,3,3,3-hexafluoropropan-2-yl)oxy]-1,3,5-triazine-2,4-diamine (7f). Purified by flash chromatography (1:10 EtOAc/Hex) to afford 7f as a white powder (35%). $^1$H NMR (300 MHz, CDCl$_3$): δ=7.55-7.50 (m, 2H), 7.25 (brs, 1H), 7.08-7.01 (m, 2H), 6.32 (quint, 1H, J=6.30 Hz), 3.61 (dq, 4H, J=3.06, 7.08 Hz), 1.23 (q, 6H, J=7.17 Hz); $^{13}$C NMR (75 MHz, CDCl$_3$): δ=168.5, 165.1, 160.7, 157.4, 134.2, 122.7, 122.2, 118.9, 115.5, 115.2, 69.2, 68.8, 68.3, 67.9 (quint, J=34 Hz), 42.3, 42.0, 12.9, 12.8; HRMS (ESI): m/z calculated for C16H17F7N5O [M+H+]: 428.1316. Found: 428.1319.

N,N-Diethyl-6-[(1,1,1,3,3,3-hexafluoropropan-2-yl)oxy]-N-(4-nitrophenyl)-1,3,5-triazine-2,4-diamine (7g). Purified by flash chromatography (1:10 EtOAc/Hex) to afford 7g as a yellowish powder (75%). $^1$H NMR (300 MHz, CDCl$_3$): δ=8.37 (brs, 1H), 8.24-8.19 (m, 2H), 7.84-7.79 (m, 2H), 6.33 (quint, 1H, J=6.24 Hz), 3.71-3.60 (m, 4H), 1.27 (dt, 6H, J=7.05, 17.33 Hz); $^{13}$C NMR (75 MHz, (CDCl$_3$): δ=168.4, 164.9, 164.8, 144.7, 142.7, 126.3, 122.6, 118.8, 115.1 (q, J=281 Hz), 124.8, 119.2, 69.4, 68.9, 68.5, 68.0, 67.6 (quint, J=34 Hz), 42.7, 42.4, 12.78, 12.75; HRMS (ESI): m/z calculated for C16H17F6N6O3 [M+H+]: 455.1261. Found: 455.1264.

N,N-Diethyl-6-[(1,1,1,3,3,3-hexafluoropropan-2-yl)oxy]-N'-(1H-indazol-5-yl)-1,3,5-triazine-2,4-diamine (7h). Purified by flash chromatography (1:6 EtOAc/Hex) to afford 7h as a off-white powder (28%). $^1$H NMR (300 MHz, acetone-d6): δ=12.22 (brs, 1H), 8.85 (brs, 1H), 8.29 (brs, 1H), 8.03 (d, 1H, J=0.96 Hz), 7.67 (d, 1H, J=8.94 Hz), 7.57 (d, 1H, J=8.94 Hz), 6.79 (quint, 1H, J=6.45 Hz), 3.68 (q, 4H, J=6.99 Hz), 1.28-1.17 (m, 6H); $^{13}$C NMR (75 MHz, acetone-d6): δ=168.6, 165.9, 165.4, 165.3, 137.5, 133.6, 132.3, 131.5, 126.9, 123.4, 123.2, 123.1, 121.8, 119.46, 119.42, 115.7, 113.3, 112.6, 111.1, 109.8, 68.4, 68.0, 67.5 (quint, J=34 Hz), 42.0, 41.5, 12.4, 12.3; HRMS (ESI): m/z calculated for C17H18F6N7O [M+H+]: 450.1472. Found: 450.1472.

N,N-Diethyl-6-[(1,1,1,3,3,3-hexafluoropropan-2-yl)oxy]-N-(1H-indazol-6-yl)-1,3,5-triazine-2,4-diamine (7i). Purified by flash chromatography (1:6 EtOAc/Hex) to afford 7i as a off-white powder (28%). $^1$H NMR (300 MHz, acetone-d6): δ=8.96 (brs, 1H), 8.38 (brs, 1H), 7.97 (d, 1H, J=1.05 Hz), 7.71 (dd, 1H, J=0.72, 8.67 Hz), 7.34 (dd, 1H, J=1.77, 8.70 Hz), 6.79 (quint, 1H, J=6.48 Hz), 3.79 (m, 4H), 1.32-1.21 (m, 6H); $^{13}$C NMR (75 MHz, acetone-d6): δ=168.6, 165.3, 162.8, 140.9, 137.7, 133.5, 126.9, 123.1, 120.4, 119.5, 115.3, 68.0, 42.1, 41.6, 12.4, 12.2; 169.12, 164.68, 159.89, 157.96, 142.33, 134.51, 131.28, 125.52, 121.99, 118.77, 115.45, 115.27, 114.35, 112.35, 111.29, 111.01, 110.73, 110.07, 109.29, 109.02, 108.75, 107.31, 107.03, 106.76, 62.71, 62.37, 62.13, 61.89, 42.13, 41.84, 29.67, 13.06, 12.86, 12.77; HRMS (ESI): m/z calculated for C17H18F6N7O [M+H+]: 450.1472. Found: 450.1475.

N'-(1,3-Benzoxazol-6-yl)-N,N-diethyl-6-[(1,1,1,3,3,3-hexafluoropropan-2-yl)oxy]-1,3,5-triazine-2,4-diamine (7j). Purified by flash chromatography (1:8 EtOAc/Hex) to afford 7j as a purple powder (25%). $^1$H NMR (300 MHz, acetone-d6): δ=9.08 (brs, 1H), 8.46 (brs, 1H), 8.39 (s, 1H), 7.70 (d, 1H, J=8.61 Hz), 7.63 (dd, 1H, J=1.92, 8.61 Hz), 6.80 (quint. 1H, J=6.75 Hz), 3.76-3.67 (m, 4H), 1.31-1.18 (m, 6H); $^{13}$C NMR (75 MHz, CDCl$_3$): δ=168.50, 164.53, 152.91, 149.69, 136.08, 134.72, 123.52, 121.96, 119.88, 119.68, 112.77, 97.34, 68.99, 68.70, 68.45, 42.71, 42.36, 12.92, 12.85; HRMS (ESI): m/z calculated for C17H17F6N6O2 [M+H+]: 451.1312. Found: 451.1313.

N'-(1,3-Benzothiazol-6-yl)-N,N-diethyl-6-[(1,1,1,3,3,3-hexafluoropropan-2-yl)oxy]-1,3,5-triazine-2,4-diamine (7k). Purified by flash chromatography (1:7 EtOAc/Hex) to afford 7k as a off-white powder (40%). $^1$H NMR (300 MHz, CDCl$_3$): δ=8.93 (brs, 1H), 8.47 (brs, 1H), 8.02 (d, 1H, J=8.51 Hz), 7.52 (dd, 2H, J=8.83, 2.21 Hz), 6.30 (m, 1H), 3.66 (m, 4H), 1.27 (m, 6H); $^{13}$C NMR (75 MHz, CDCl$_3$): δ=168.5, 164.5, 152.9, 149.6, 136.0, 134.7, 123.5, 121.9, 119.8, 119.6, 112.7, 97.3, 68.9, 68.7, 68.4, 42.7, 42.3, 12.9, 12.8; HRMS (ESI): m/z calculated for C17H17F6N6OS [M+H+]: 467.1083. Found: 467.1089.

Results

Figure 14B:
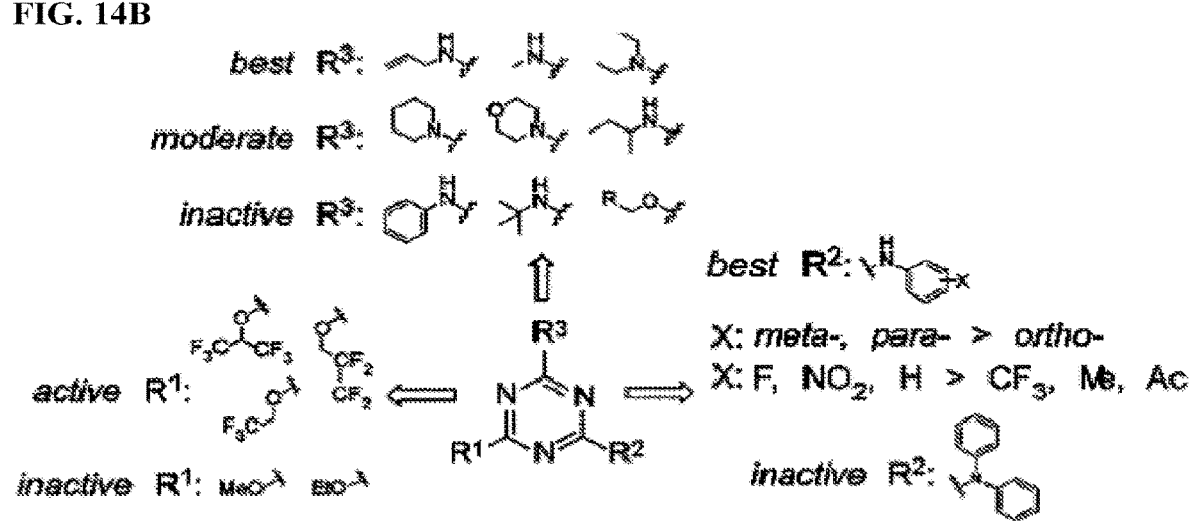

Preliminary structure-activity analysis of commercially available analogs. Initial evaluation of compound activity was done using a cell-based plate reader assay of CFTR function. FIG. 14B summarizes preliminary SAR analysis from functional assays on 91 commercially available analogs of 1 (data for all commercial compounds provided in Table 2). The commercial 1,3,5-triazine analogs tested here were tri-substituted at the 2-, 4-, 6-positions with various substituents, including alkoxide, aniline (amino-phenyl), and primary or secondary amines. SAR analysis revealed that trisubstituted-1,3,5-triazines whose three substituents contain a fluorinated alkoxide ($R^1$), an aniline ($R^2$) and an alkylamine ($R^3$) gave the best potency (compounds K032, K059 and K089, Table 2). Analogs with two-alkoxide substituents or non-fluorinated alkoxide greatly reduced activity (K010-018, K023). Further, ortho-substituted aniline ($R^2$) reduced activity as compared to meta- and para-substitution (K007, K032, K059). Electron-donating groups including methoxy, acetyl, trifluoromethoxy (K001, K024-028, K079) reduced activity as compared to electron-withdrawing group such as nitro as in K032. Finally, sterically bulky alkylamines ($R^3$) including cyclic, tert-butyl- and isobutylamine reduced activity (K029, K056, K060-065). Short alkylamines such as methylamine and diethylamine gave greatest activity.

TABLE 2

Chemical structures and data for CFTR activation.

| Code | structure | % Activation (EC$_{50}$, nM) |
|---|---|---|
| K001 | 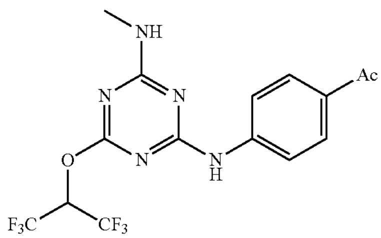 [SMILES: CNc1nc(Nc2ccc(C(C)=O)cc2)nc(OC(C(F)(F)F)C(F)(F)F)n1] | 32 |
| K002 | 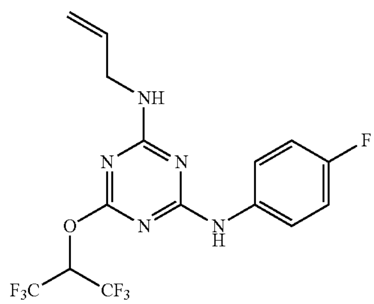 [SMILES: C=CCNc1nc(Nc2ccc(F)cc2)nc(OC(C(F)(F)F)C(F)(F)F)n1] | 63 |
| K003 | 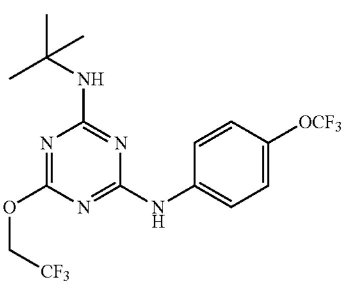 [SMILES: CC(C)(C)Nc1nc(Nc2ccc(OC(F)(F)F)cc2)nc(OCC(F)(F)F)n1] | 16 |
| K004 | 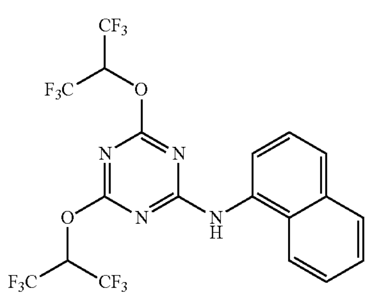 [SMILES: FC(F)(F)C(Oc1nc(Nc2cccc3ccccc23)nc(OC(C(F)(F)F)C(F)(F)F)n1)C(F)(F)F] | 16 |
| K005 | 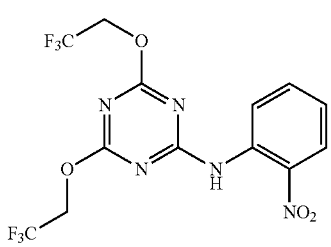 [SMILES: O=[N+]([O-])c1ccccc1Nc1nc(OCC(F)(F)F)nc(OCC(F)(F)F)n1] | 29 |
| K006 | 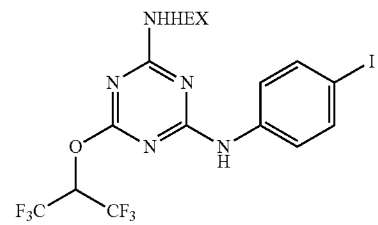 | 16 |
| K007 | 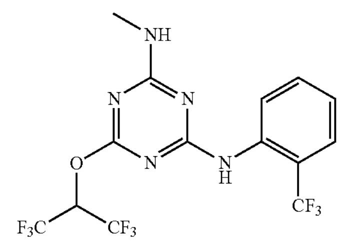 [SMILES: CNc1nc(Nc2ccccc2C(F)(F)F)nc(OC(C(F)(F)F)C(F)(F)F)n1] | 21 |
| K008 | 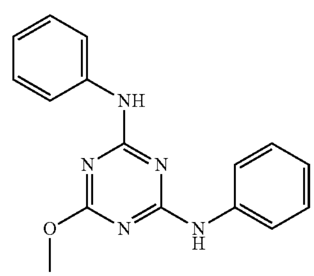 [SMILES: COc1nc(Nc2ccccc2)nc(Nc2ccccc2)n1] | 32 |
| K009 | 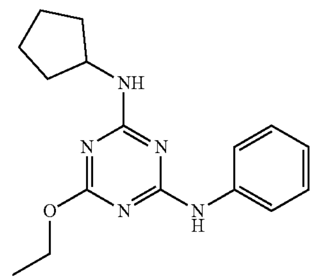 [SMILES: CCOc1nc(Nc2ccccc2)nc(NC2CCCC2)n1] | 57 |
| K010 | 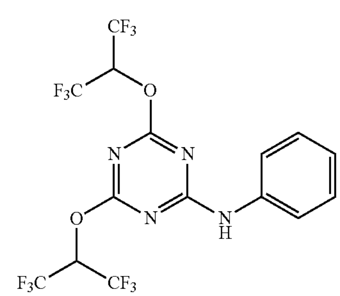 [SMILES: FC(F)(F)C(Oc1nc(Nc2ccccc2)nc(OC(C(F)(F)F)C(F)(F)F)n1)C(F)(F)F] | 21 |

TABLE 2-continued

Chemical structures and data for CFTR activation.

| Code | structure | % Activation (EC$_{50}$, nM) |
|---|---|---|
| K011 | 4,6-bis(1,1,1,3,3,3-hexafluoropropan-2-yloxy)-N-(p-tolyl)-1,3,5-triazin-2-amine | 20 |
| K012 | 4,6-bis(1,1,1,3,3,3-hexafluoropropan-2-yloxy)-N-(o-tolyl)-1,3,5-triazin-2-amine | 19 |
| K013 | 4,6-bis(1,1,1,3,3,3-hexafluoropropan-2-yloxy)-N-(2-nitrophenyl)-1,3,5-triazin-2-amine | 15 |
| K014 | 4,6-bis(1,1,1,3,3,3-hexafluoropropan-2-yloxy)-N-(3-nitrophenyl)-1,3,5-triazin-2-amine | 18 |
| K015 | 4,6-bis(1,1,1,3,3,3-hexafluoropropan-2-yloxy)-N-(4-nitrophenyl)-1,3,5-triazin-2-amine | 6 |
| K016 | 1-(4-((4,6-bis(1,1,1,3,3,3-hexafluoropropan-2-yloxy)-1,3,5-triazin-2-yl)amino)phenyl)ethan-1-one | 19 |
| K017 | 4,6-bis(1,1,1,3,3,3-hexafluoropropan-2-yloxy)-N-(pyridin-3-yl)-1,3,5-triazin-2-amine | 16 |
| K018 | N-phenyl-4,6-bis(2,2,2-trifluoroethoxy)-1,3,5-triazin-2-amine | 60 |
| K019 | N-(o-tolyl)-4,6-bis(2,2,2-trifluoroethoxy)-1,3,5-triazin-2-amine | 28 |
| K020 | N-methyl-N',N'-diphenyl-6-(2,2,2-trifluoroethoxy)-1,3,5-triazine-2,4-diamine | 37 |

TABLE 2-continued
Chemical structures and data for CFTR activation.
| Code | structure | % Activation (EC$_{50}$, nM) |
|---|---|---|
| K021 | 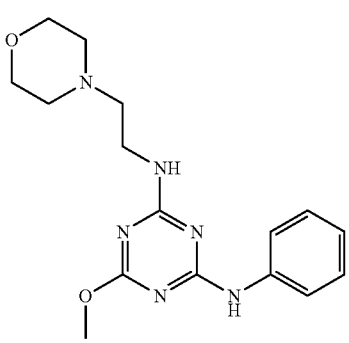 [SMILES: COc1nc(NCCN2CCOCC2)nc(Nc2ccccc2)n1] | 16 |
| K022 | 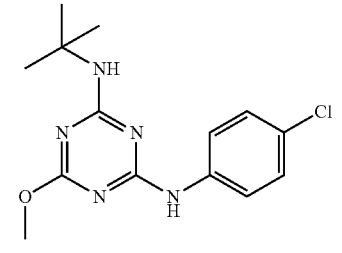 [SMILES: COc1nc(Nc2ccc(Cl)cc2)nc(NC(C)(C)C)n1] | 53 |
| K023 | 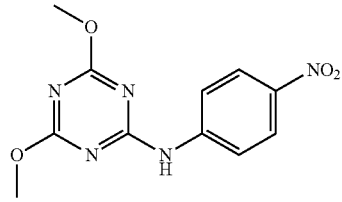 [SMILES: COc1nc(Nc2ccc([N+](=O)[O-])cc2)nc(OC)n1] | 41 |
| K024 | 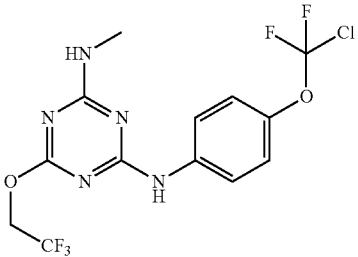 [SMILES: CNc1nc(Nc2ccc(OC(F)(F)Cl)cc2)nc(OCC(F)(F)F)n1] | 64 |
| K025 | 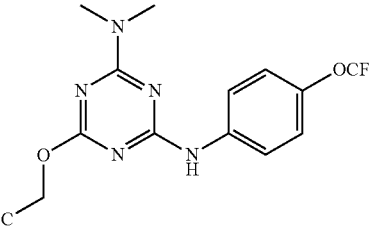 | 19 |
| K026 | 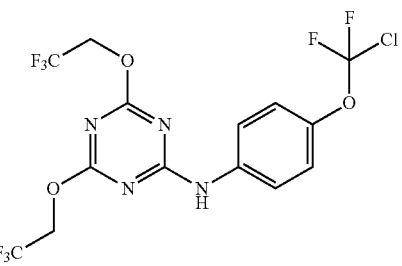 | 16 |
| K027 | 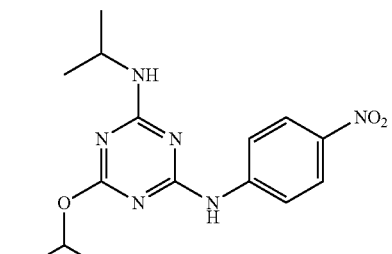 | 20 |
| K028 | 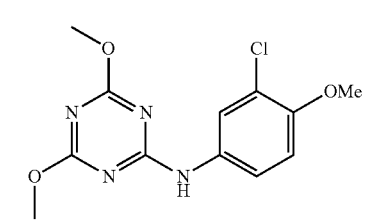 [SMILES: COc1nc(Nc2ccc(OC)c(Cl)c2)nc(OC)n1] | 23 |
| K029 | 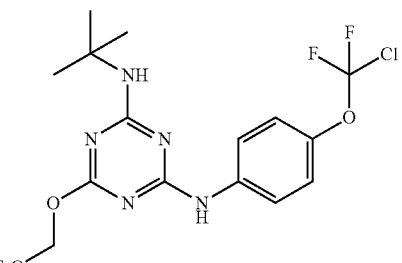 | 9 |
| K030 | 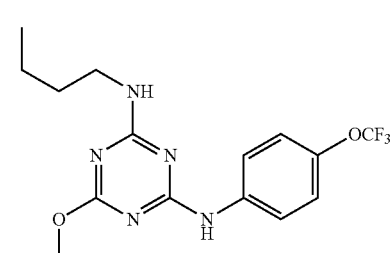 | 16 |

TABLE 2-continued

Chemical structures and data for CFTR activation.

| Code | structure | % Activation (EC$_{50}$, nM) |
|---|---|---|
| K031 | (4-methoxy-6-((1,1,1,3,3,3-hexafluoropropan-2-yl)oxy)-1,3,5-triazin-2-yl)(4-hydroxyphenyl)amine | 61 |
| K032 | N-methyl-6-(2,2,3,3-tetrafluoropropoxy)-N'-(4-nitrophenyl)-1,3,5-triazine-2,4-diamine | 105 (70) |
| K033 | 2-((4-((4-chlorophenyl)amino)-6-methoxy-1,3,5-triazin-2-yl)amino)ethan-1-ol | 22 |
| K034 | N-allyl-N'-(4-chlorophenyl)-6-methoxy-1,3,5-triazine-2,4-diamine | 73 |
| K035 | N-(4-chlorophenyl)-N'-cyclohexyl-6-methoxy-1,3,5-triazine-2,4-diamine | 55 |
| K036 | N-(4-chlorophenyl)-6-ethoxy-N'-hexyl-1,3,5-triazine-2,4-diamine | 46 |
| K037 | 2-((4-((4-chlorophenyl)amino)-6-ethoxy-1,3,5-triazin-2-yl)amino)ethan-1-ol | 36 |
| K038 | N-(4-chlorophenyl)-N'-cyclohexyl-6-ethoxy-1,3,5-triazine-2,4-diamine | 53 |
| K039 | N-hexyl-N'-(4-iodophenyl)-6-methoxy-1,3,5-triazine-2,4-diamine | 27 |
| K040 | 2-((4-((4-iodophenyl)amino)-6-methoxy-1,3,5-triazin-2-yl)amino)ethan-1-ol | 17 |

TABLE 2-continued

Chemical structures and data for CFTR activation.

| Code | structure | % Activation (EC$_{50}$, nM) |
|---|---|---|
| K041 | (allyl-NH, methoxy, 4-iodoanilino triazine) | 35 |
| K042 | (cyclohexyloxy, methoxy, 4-iodoanilino triazine) | 15 |
| K043 | (HO-ethyl-NH, ethoxy, 4-iodoanilino triazine) | 19 |
| K044 | (allyl-NH, ethoxy, 4-iodoanilino triazine) | 55 |
| K045 | (morpholinoethyl-NH, ethoxy, 4-iodoanilino triazine) | 15 |
| K046 | (cyclohexyl-NH, ethoxy, 4-iodoanilino triazine) | 16 |
| K047 | (HO-ethyl-NH, methoxy, 4-nitroanilino triazine) | 17 |
| K048 | (allyl-NH, methoxy, 4-nitroanilino triazine) | 46 |
| K049 | (HO-ethyl-NH, ethoxy, 4-nitroanilino triazine) | 28 |
| K050 | (allyl-NH, ethoxy, 4-nitroanilino triazine) | 66 |

TABLE 2-continued
Chemical structures and data for CFTR activation.
| Code | structure | % Activation (EC50, nM) |
|---|---|---|
| K051 | 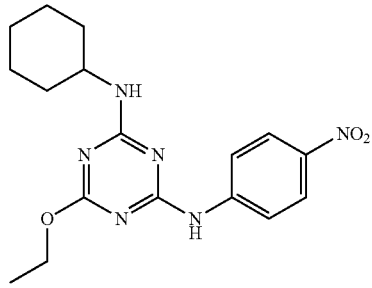 [SMILES: CCOc1nc(Nc2ccc([N+](=O)[O-])cc2)nc(NC2CCCCC2)n1] | 45 |
| K052 | 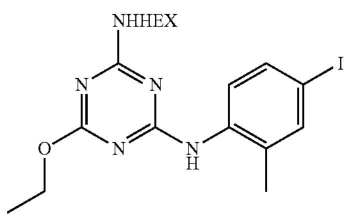 | 15 |
| K053 | 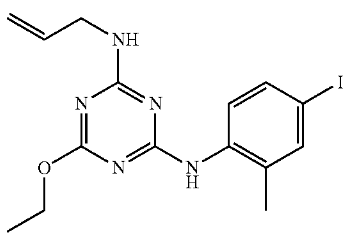 [SMILES: C=CCNc1nc(Nc2ccc(I)cc2C)nc(OCC)n1] | 24 |
| K054 | 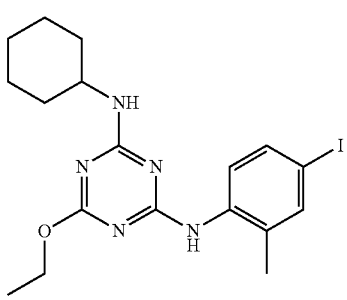 [SMILES: CCOc1nc(Nc2ccc(I)cc2C)nc(NC2CCCCC2)n1] | 14 |
| K055 | 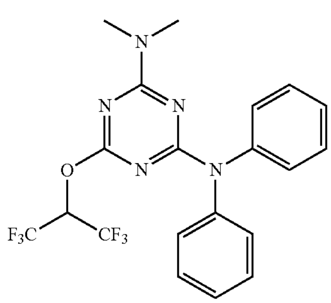 [SMILES: CN(C)c1nc(OC(C(F)(F)F)C(F)(F)F)nc(N(c2ccccc2)c2ccccc2)n1] | 42 |
| K056 | 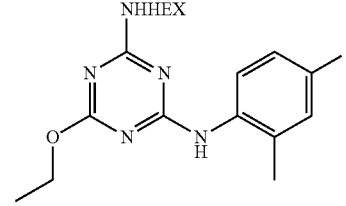 | 38 |
| K057 | 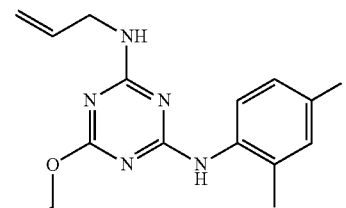 | 28 |
| K058 | 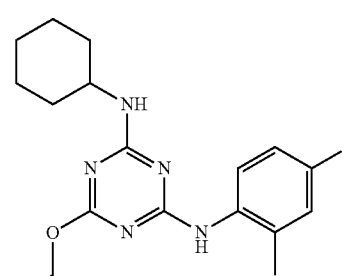 | 37 |
| K059 | 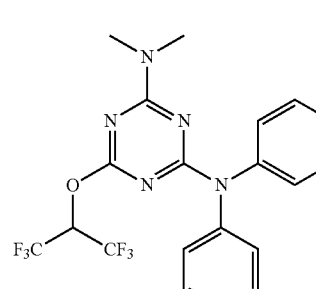 | 90 (750) |

TABLE 2-continued
Chemical structures and data for CFTR activation.
| Code | structure | % Activation (EC$_{50}$, nM) |
|---|---|---|
| K060 | 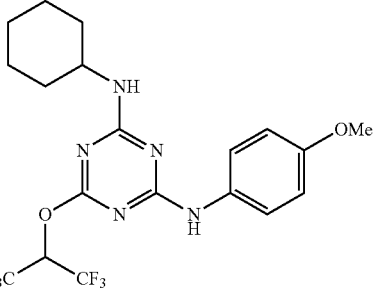 | 38 |
| K061 | 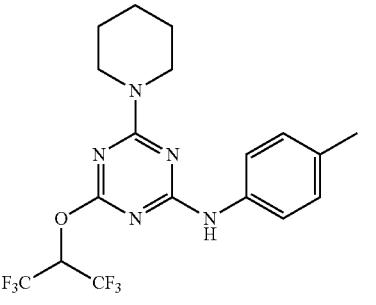 [SMILES: Cc1ccc(Nc2nc(OC(C(F)(F)F)C(F)(F)F)nc(N3CCCCC3)n2)cc1] | 31 |
| K062 | 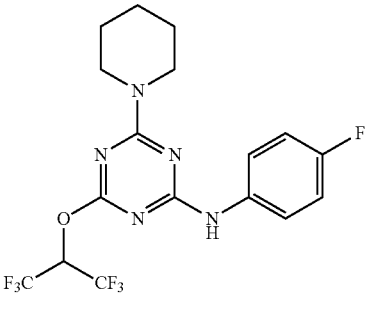 [SMILES: Fc1ccc(Nc2nc(OC(C(F)(F)F)C(F)(F)F)nc(N3CCCCC3)n2)cc1] | 49 |
| K063 | 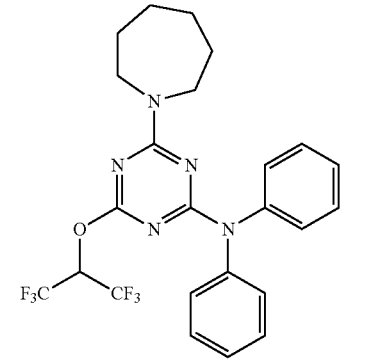 [SMILES: FC(F)(F)C(Oc1nc(N2CCCCCC2)nc(N(c2ccccc2)c2ccccc2)n1)C(F)(F)F] | 41 |
| K064 | 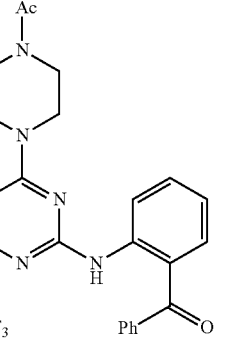 | 40 |
| K065 | 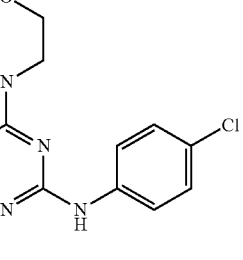 | 38 |
| K066 | 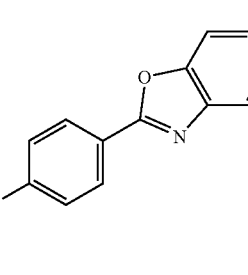 | 87 (2900) |
| K067 | 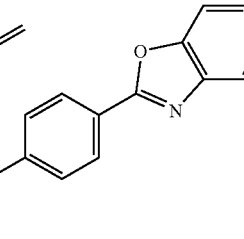 | 49 |

TABLE 2-continued

Chemical structures and data for CFTR activation.

| Code | structure | % Activation (EC$_{50}$, nM) |
| --- | --- | --- |
| K068 | *2-hydroxyethylamino / ethoxy triazine / benzoxazole-phenyl-NH* | 84 (4100) |
| K069 | *morpholino / 2,2,2-trifluoroethoxy triazine / 4-(chlorodifluoromethoxy)phenyl-NH* | 37 |
| K070 | *piperidino / 2,2,2-trifluoroethoxy triazine / 4-(chlorodifluoromethoxy)phenyl-NH* | 28 |
| K071 | *4-methylpiperazino / 2,2,2-trifluoroethoxy triazine / 4-(chlorodifluoromethoxy)phenyl-NH* | 25 |
| K072 | *morpholino / 2,2,2-trifluoroethoxy triazine / 4-(trifluoromethoxy)phenyl-NH* | 31 |
| K073 | *piperidino / 2,2,2-trifluoroethoxy triazine / 4-(trifluoromethoxy)phenyl-NH* | 19 |
| K074 | *4-methylpiperazino / 2,2,2-trifluoroethoxy triazine / 4-(trifluoromethoxy)phenyl-NH* | 25 |
| K075 | *dimethylamino / 2,2,2-trifluoroethoxy triazine / 4-(chlorodifluoromethoxy)phenyl-NH* | 32 |

TABLE 2-continued

Chemical structures and data for CFTR activation.

| Code | structure | % Activation (EC$_{50}$, nM) |
|---|---|---|
| K076 | 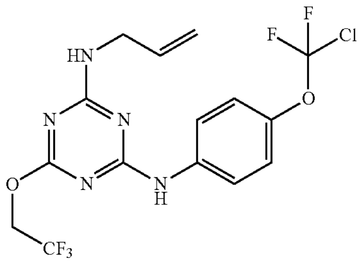 [SMILES: C=CCNc1nc(Nc2ccc(OC(F)(F)Cl)cc2)nc(OCC(F)(F)F)n1] | 46 |
| K077 | 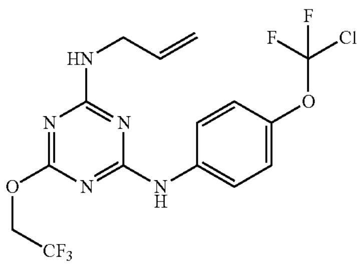 [SMILES: C=CCNc1nc(Nc2ccc(OC(F)(F)Cl)cc2)nc(OCC(F)(F)F)n1] | 29 |
| K078 | 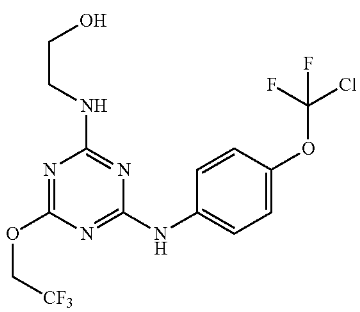 [SMILES: OCCNc1nc(Nc2ccc(OC(F)(F)Cl)cc2)nc(OCC(F)(F)F)n1] | 28 |
| K079 | 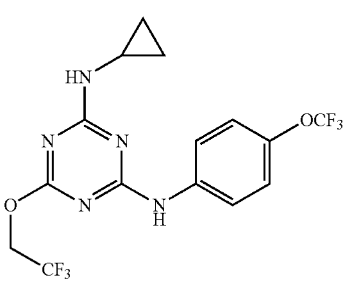 [SMILES: FC(F)(F)COc1nc(Nc2ccc(OC(F)(F)F)cc2)nc(NC2CC2)n1] | 40 |
| K080 | 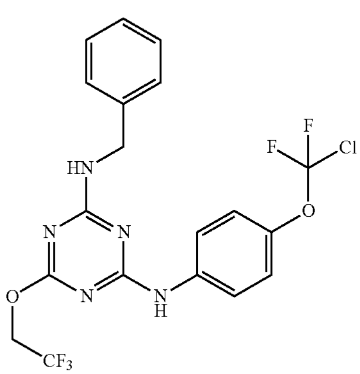 [SMILES: FC(F)(F)COc1nc(NCc2ccccc2)nc(Nc2ccc(OC(F)(F)Cl)cc2)n1] | 26 |
| K081 | 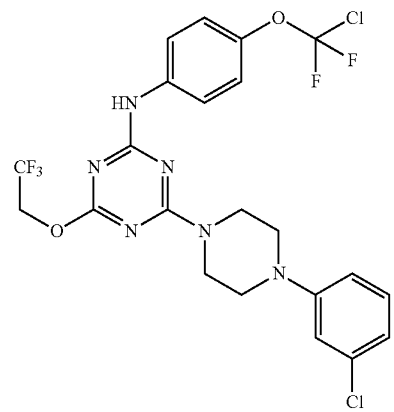 [SMILES: FC(F)(F)COc1nc(Nc2ccc(OC(F)(F)Cl)cc2)nc(N2CCN(c3cccc(Cl)c3)CC2)n1] | 24 |
| K082 | 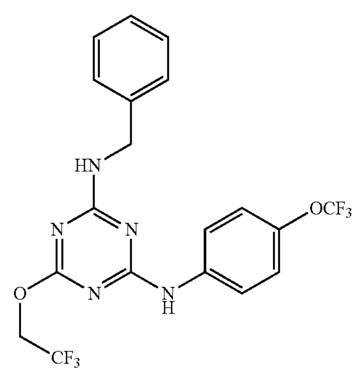 [SMILES: FC(F)(F)COc1nc(NCc2ccccc2)nc(Nc2ccc(OC(F)(F)F)cc2)n1] | 28 |
| K083 | 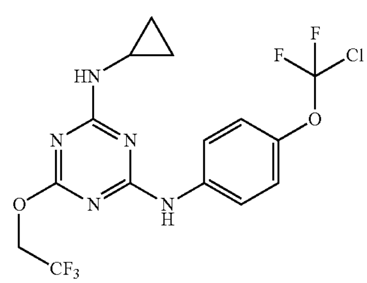 [SMILES: FC(F)(F)COc1nc(Nc2ccc(OC(F)(F)Cl)cc2)nc(NC2CC2)n1] | 54 |
| K084 | 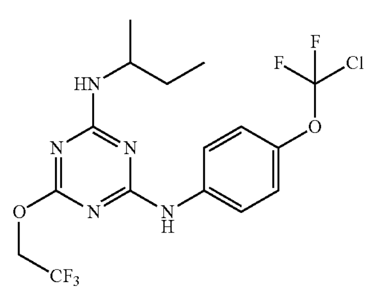 [SMILES: CCC(C)Nc1nc(Nc2ccc(OC(F)(F)Cl)cc2)nc(OCC(F)(F)F)n1] | 22 |

TABLE 2-continued

Chemical structures and data for CFTR activation.

| Code | structure | % Activation (EC$_{50}$, nM) |
|---|---|---|
| K085 | 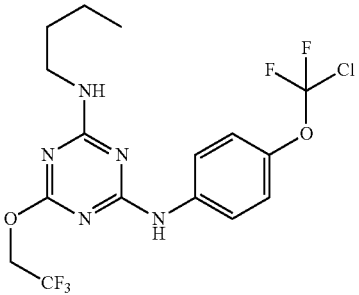 [SMILES: CCCCNc1nc(Nc2ccc(OC(F)(F)Cl)cc2)nc(OCC(F)(F)F)n1] | 25 |
| K086 | 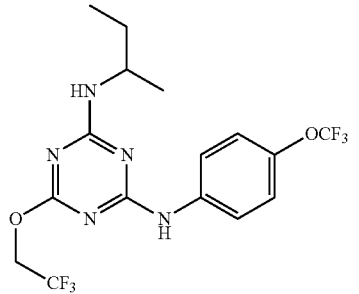 [SMILES: CCC(C)Nc1nc(Nc2ccc(OC(F)(F)F)cc2)nc(OCC(F)(F)F)n1] | 20 |
| K087 | 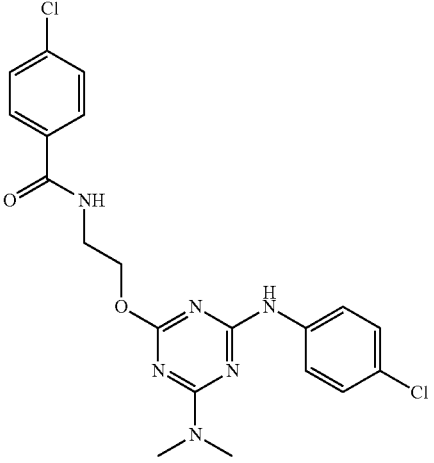 [SMILES: CN(C)c1nc(Nc2ccc(Cl)cc2)nc(OCCNC(=O)c2ccc(Cl)cc2)n1] | 47 |
| K088 | 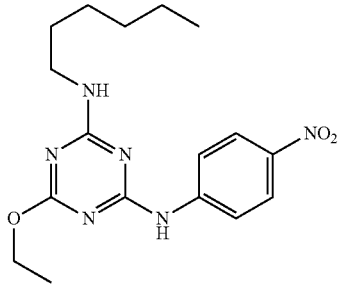 [SMILES: CCCCCCNc1nc(Nc2ccc([N+](=O)[O-])cc2)nc(OCC)n1] | 33 |
| K089 | 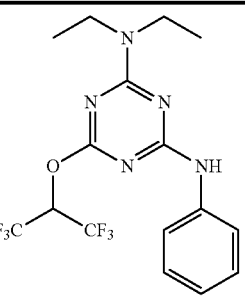 | 111 (250) |
| K090 | 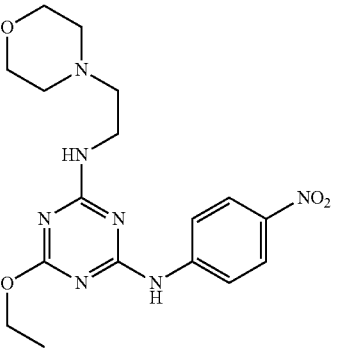 [SMILES: CCOc1nc(NCCN2CCOCC2)nc(Nc2ccc([N+](=O)[O-])cc2)n1] | 52 |
| K091 | 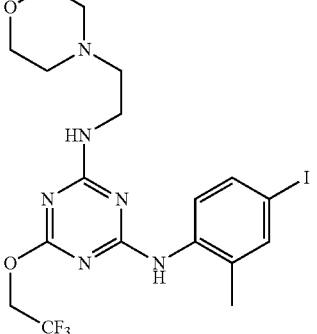 | 43 |

% Activation of commercial analogs.
For compounds >80% activation were measured EC$_{50}$s from full-dose response assay.

Because the initial SAR data from commercial analogs was limited and confounded by simultaneous variations in $R^1$, $R^2$ and $R^3$, we synthesized targeted trisubstituted-1,3,5-triazine analogs. EC$_{50}$ values for CFTR activation for the synthesized compounds are summarized in Tables 3-5. Active compounds produced full activation of CFTR, as seen by the similar activity produced by maximal forskolin (20 μM), but with different EC$_{50}$ values.

Modifications of substituted anilines and fluorinated alkoxides. Since both fluorinated alkoxide ($R^1$) and short alkylamine ($R^3$) appeared to be crucial for activity, we first prepared N-aryl-1,3,5-triazine amines with $R^3$ as diethylamine and explored the activity of two fluorinated alkoxides, 1,1,1,3,3,3-hexafluoro-2-propanol and 2,2,3,3-tetrafluoro-1-propanol. As shown in Table 3, hexafluoroisopropanol (1)

was more potent than tetrafluoropropanol (7a). With various aryl ($R^2$) substituent, hexafluoroisopropanol analogs (6a-6f) were ~3 to 8-fold more potent than corresponding tetrafluoropropanol analogs (7b-7g). To investigate aniline substituents ($R^2$), meta- and para-substituted aniline analogs with electron-neutral and electron-withdrawing groups were prepared. In general, meta-substituted anilines (6a and 6b) were more active than para-substituted aniline analogs (6e and 6f). Among meta-substituted anilines, F— (6b), $NO_2$— (6d), and $CO_2H$-aniline (6a) had comparable or slightly better potency than non-substituted aniline (1), but chloroaniline (6c) had significantly reduced activity. With this result we hypothesized that hydrogen bonding formation is important to the activity, so we kept focus on the aniline moiety ($R^2$) and synthesized more analogs on $R^2$.

TABLE 3

Structures of N,N-diethyl-N'-aryl-1,3,5-triazine diamine analogs and their $EC_{50}$ (μM).

| | meta-$CO_2H$ | meta-F | meta-Cl | meta-$NO_2$ |
|---|---|---|---|---|
| $R^1$ = $OCH(CF_3)_2$ | 6a | 6b | 6c | 6d |
| | 0.16 | 0.14 | 2.8 | 0.2 |
| $R^1$ = $OCH_2(CF_2)_2H$ | 7b | 7c | 7d | 7e |
| | 0.5 | 1.6 | 5.4 | 1.2 |

| | para-$CO_2H$ | para-F | para-$NO_2$ | H |
|---|---|---|---|---|
| $R^1$ = $OCH(CF_3)_2$ | 6e | 6f | 6g | 1 |
| | 0.9 | 0.7 | 18 | 0.24 |
| $R^1$ = $OCH_2(CF_2)_2H$ | 7f | 7g | | 7a |
| | 2.5 | 4.8 | | 2.0 |

Modifications of bicyclic anilines. To further investigate aniline substituents, compounds were synthesized with bicyclic anilines at the $R^2$ position with diethylamine ($R^3$) and hexafluoroisopropanol ($R^1$), including 5- or 6-aminoindazole (6h and 6i), 6-aminobenzoxazole (6j) and 6-aminobenzothiazole (6k). As shown in Table 4, the indazole analog 6h was ~3-fold more potent than its regioisomer 6i, which also supports the conclusion that hydrogen bonding formation on meta-position increases activity. Replacement of indazole (6h) by benzoxazole (6j) were more potent than 1. Notably, replacing benzoxazole (6j) by benzothiazole (6k) increased potency by ~3-fold to $EC_{50}$ ~50 nM, supporting the importance of hydrogen bonding acceptor function.

TABLE 4

Substitution with bicyclic anilines and their activity.

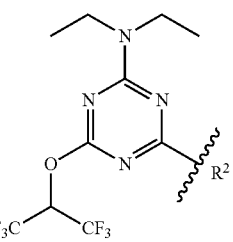

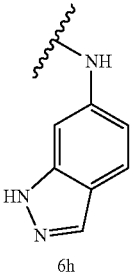 [SMILES: *Nc1ccc2cn[nH]c2c1]

Modifications with N-methylamine. Finally, N,N-diethylamine at $R^3$ was replaced by methylamine with two fluorinated alkoxides (Table 5). Notably, N-methylamine-2,2,3,3-tetrafluoro-1-propanoxy-1,3,5-triazine 12 had $EC_{50}$ ~50-fold better than diethylamine analog 6a. Interestingly, for diethylamine ($R^3$) analogs, hexafluoropropanol (1) is more potent than tetrafluoropropanol (7a), whereas for methylamine ($R^3$) analogs, tetrafluoropropanol analog 12 was ~3 fold more potent than hexafluoropropanol analog 11. The most potent compounds emerging from the SAR analysis were chosen for biological characterizations and efficacy studies.

TABLE 5

N-methyl-N'-phenyl-1,3,5-triazine diamine analogs and their activity.

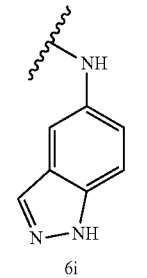 [SMILES: *Nc1ccc2[nH]ncc2c1]

Biology

Figure 15A:
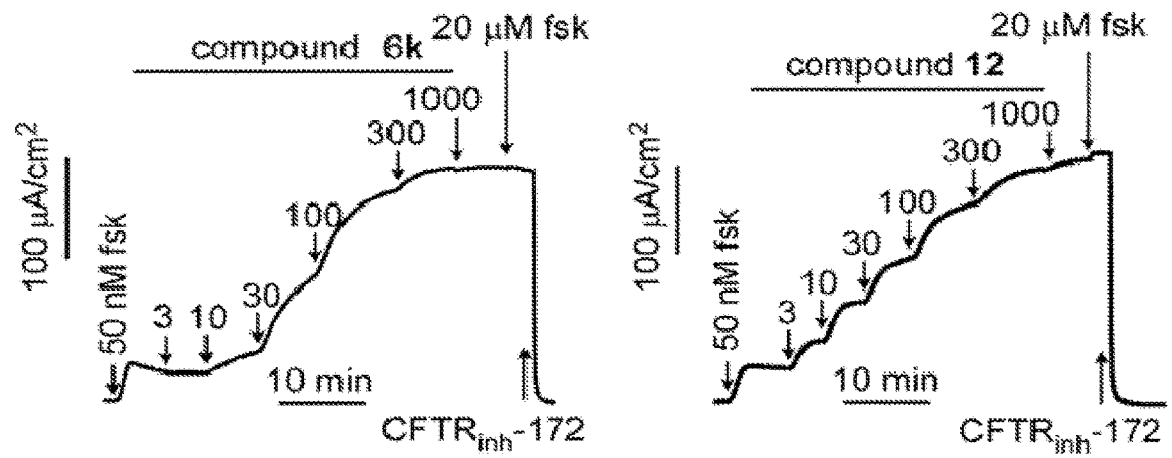
FIGS. 15A-15B. Short-circuit current measurement of CFTR activation by 6k and 12.
Figure 15B:
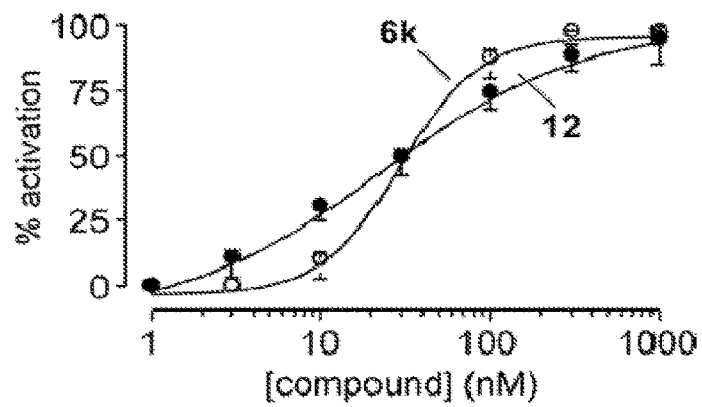

In vitro characterization of amino-phenyl-1,3-5-triazines. Short-circuit current measurements were done on CFTR-expressing FRT cells using a transepithelial chloride gradient and following permeabilization of the cell basolateral membrane, such that short-circuit current magnitude provides a quantitative, linear measure of CFTR chloride conductance. Representative data in FIG. 15A for 6k and 12 shows a small increase in current with addition of a low concentration of forskolin, followed by concentration-dependent increases in current following compound additions. The compounds produced full CFTR activation, as little further increase in current was seen following a maximal concentration of forskolin. $EC_{50}$ values were 30 nM for 6k and 31 nM for 12 (FIG. 15B).

Figure 16A:
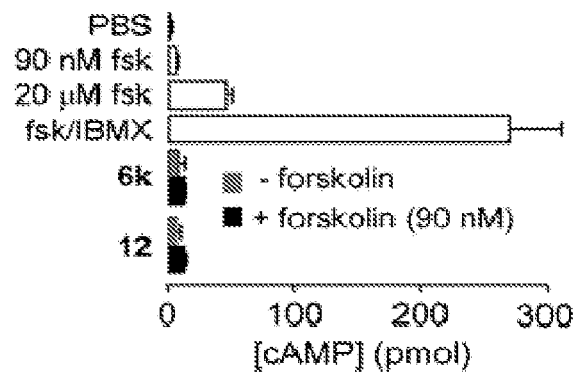
FIGS. 16A-16E. Characterization of 6k and 12.
Figure 16B:
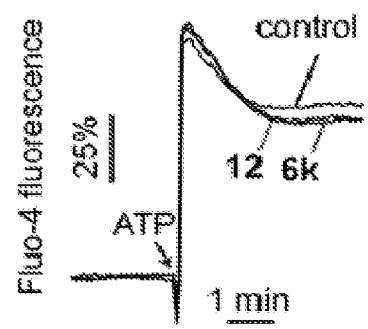
Figure 16C:
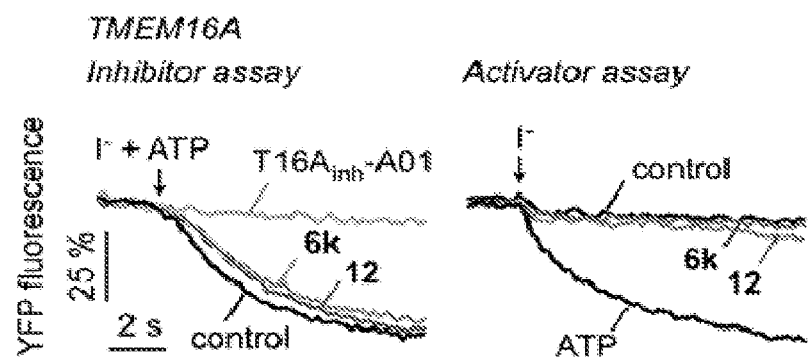
Figure 16D:
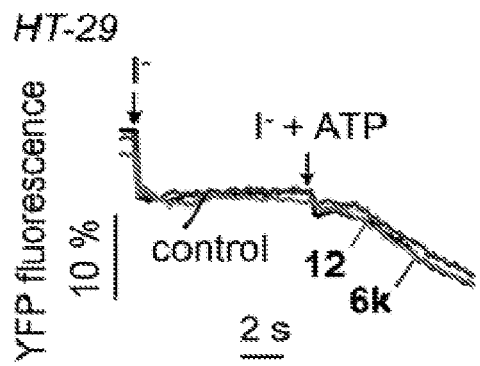
Figure 16E:
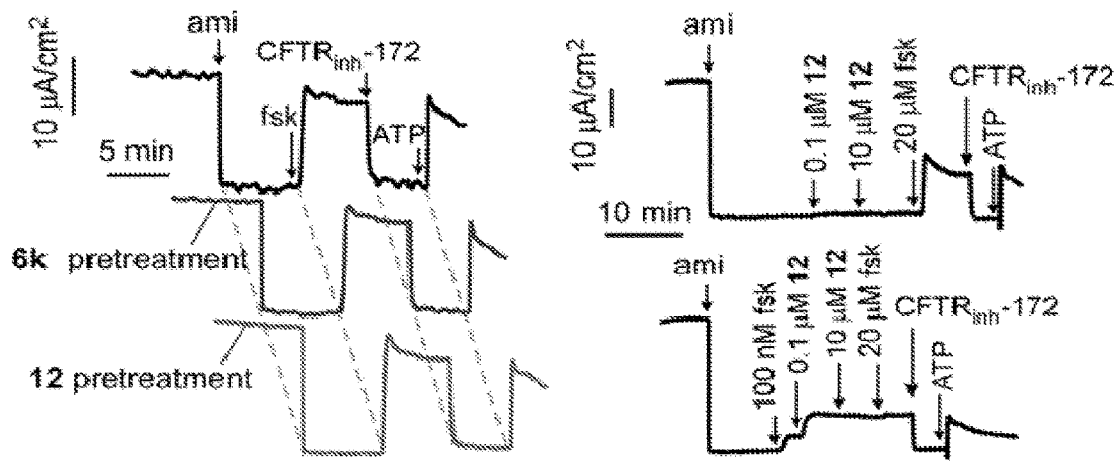

Possible off-target effects on cell signaling and relevant non-CFTR ion channels were investigated. 6k and 12 at 10 µM did not elevate cellular cAMP (FIG. 16A), increase cytoplasmic calcium, or inhibit the ATP-stimulated elevation in cytoplasmic calcium (FIG. 16B). Also, 6k and 12 at 10 µM neither inhibited nor activated calcium-activated chloride channels in TMEM16A-expressing FRT cells (FIG. 16C) or HT-29 cells (FIG. 16D). To further investigate specificity, the major ion transport pathways in human bronchial epithelial (HBE) cells were studied by short-circuit current. HBE cells were sequentially treated with amiloride to inhibit the epithelial sodium channel (ENaC), forskolin to activate CFTR, $CFTR_{inh}$-172 to inhibit CFTR, and ATP to activate CaCC, which produced the anticipated changes in short-circuit current in control cells (FIG. 16E left). Pretreatment of cells for 10 min with 10 µM 6k or 12 did not alter short-circuit current responses to ENaC, maximal forskolin or ATP, indicating that the compound do not effect ENaC or CaCC, or the supporting epithelial cell transporters necessary to generate current (NKCC1, epithelial $K^+$ channels, $Na^+/K^+$ pump). 12 did not activate CFTR in HBE cells in the absence of basal CFTR phosphorylation produced by forskolin (FIG. 16E, right top), whereas 0.1 µM 12 fully activated CFTR following 100 nM forskolin (FIG. 16E, right bottom).

Pharmacological Properties and In Vivo Efficacy.

Figure 17A:
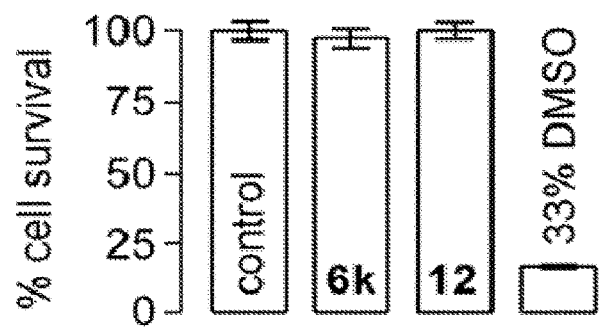
FIGS. 17A-17B. Compound pharmacology.
Figure 17B:
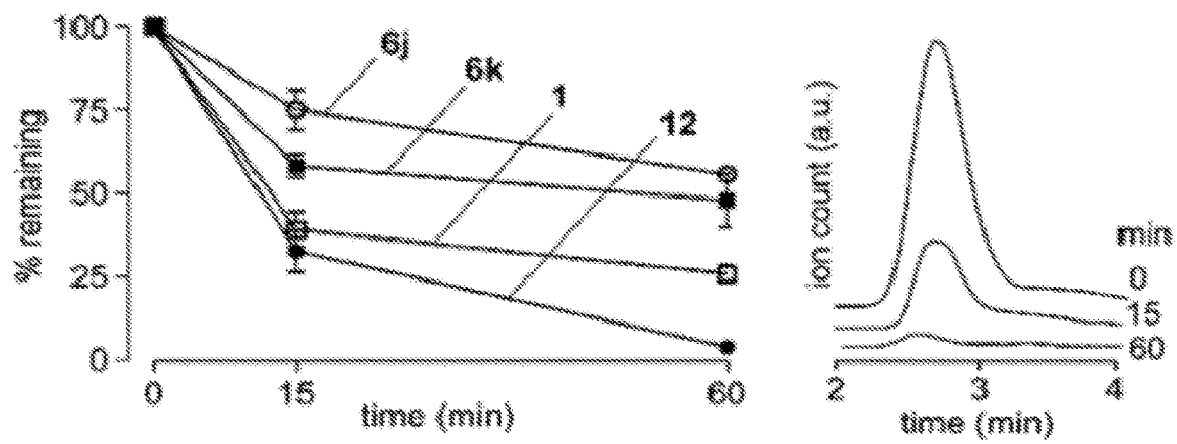

Compounds were further studied for their solution and metabolic stability, and cellular toxicity. FIG. 17A shows that 6k and 12 did not produce significant toxicity using an Alamar blue assay, with 33% DMSO as positive control. When dissolved at 100 µM in an ophthalmic vehicle containing 0.3% CMC in Ringer's solution, 12 remained chemically stable for 24 h at 40° C. as assayed by LC/MS (data not shown). To assess metabolic stability, compounds at 5 µM were incubated with rat hepatic microsomes in the presence of NADPH. FIG. 17B shows the kinetics of compound metabolism, and LC/MS profiles of 12. 1 and 12, which contain non-substituted anilines, were metabolized rapidly with <40% of the original compounds remaining at 15 min, whereas 6j and 6k, which contain bicyclic anilines, were metabolized slowly with ~60% of the original compounds remaining at 60 min. The benzoxazole-containing analog 6j showed greater metabolic stability than benzothiazole analog 6k, which may be due to relative lability of the sulfide in benzothiazole versus the oxygen in benzoxazole. Low metabolic stability is desirable for a dry eye therapeutic to minimize systemic exposure following potential absorption, whereas high metabolic stability is desirable for liver and lung application of CFTR activators where systemic exposure and organ accumulation are needed.

Figure 18A:
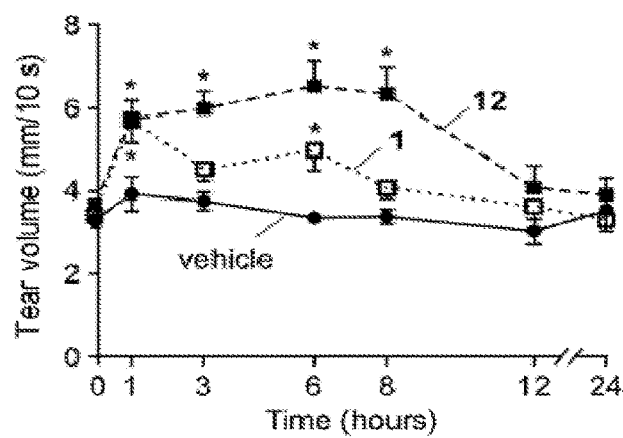
FIGS. 18A-18C. Tear fluid volume in mice following ocular delivery of 1 or 12.
Figure 18B:
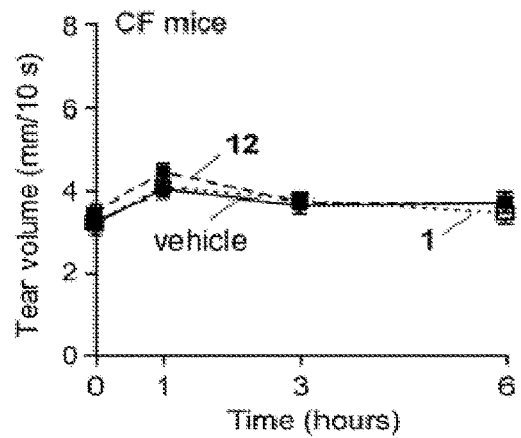
Figure 18C:
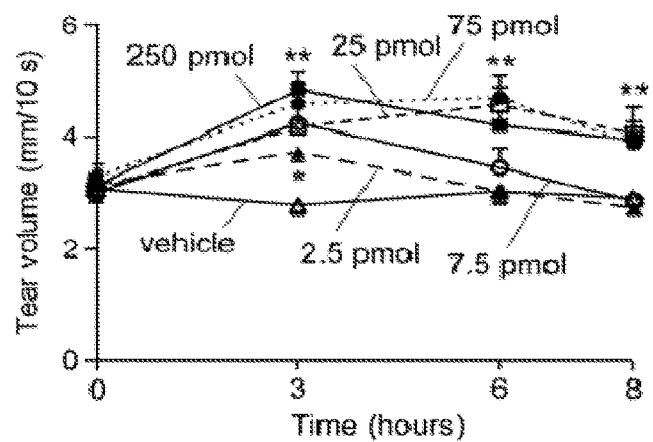

Measurements of tear fluid volume were done following a single ophthalmic dosing of test compound in 2.5 µL of an ophthalmic vehicle, or vehicle alone as control. Compound 12 was selected following preliminary testing of compound efficacy at 6 hours. At 100 μM (250 pmol) 12 produced a sustained increase in tear volume for 8 hours that returned to baseline over 12-24 h, with improved kinetics compared to 1 (FIG. 18A). As evidence for compound specificity, 12 did not increase tear volume in CF mice, which lack functional CFTR (FIG. 18B). A dose-response study was done to determine the minimal amount of 12 that produced sustained tear fluid secretion. FIG. 18C shows similar activity of 12 at doses down to 25 pmol with maximal tear volume at 1-3 hours and sustained effect to 8 hours.

Discussion

The structure-activity study here identified analogs of 1 with substantially greater CFTR activation potency, with the most potent compound 12 having $EC_{50}$ ~30 nM, CFTR selectivity, and sustained in vivo efficacy for at least 8 hours in mice. CFTR selectivity was demonstrated in cellular studies and by the lack of increase in tear fluid volume in CFTR-deficient mice. 12 was chemically stable, including when formulated in a standard ophthalmic vehicle. Minimal systemic exposure of 12 is predicted based on the small amount needed to stimulate tear secretion and its rapid predicted hepatic metabolism. Further studies supporting its clinical development will be needed, such as ocular tissue pharmacokinetics, long-term toxicity and patient tolerability, which are beyond the scope of this medicinal chemistry study. Of note, synthesized analogs 6j and 6k had substantially greater in vitro metabolic stability than 1 or 12, and therefore have potential utility in therapy of liver and lung diseases where systemic exposure is necessary.

Various biological activities have been reported for the 1,3,5-triazines scaffold. Atrazine, a chlorotriazine with two alkylamines substituent, is a widely used herbicide[20]. Some N,N-di-aminobenzyl-N-isopropyl-1,3,5-triazines were found to have anti-tubulin activities in vitro and in vivo[21]. In addition, triazines containing bulky piperazinyl- and cyclohexylamino-substitutions were reported to have cathepsin inhibition activity [22]. The substituents in these biologically active triazines are very different from those that conferred CFTR activation in this study. Structure-activity analysis of commercial and synthesized aminophenyl-1,3,5-triazines determined that three specific substituent—alkoxide, alkylamine, and phenylamine—on the triazine are needed for CFTR activity. For each of the substituent, (i) fluorinated alkoxides showed superior activity than non-fluorinated alkoxides; (ii) short and linear alkylamines are crucial for activity while bulky amines greatly reduced activity; and (iii) phenylamines containing electron-withdrawing groups, including nitro, carboxylic acid or fluoride, in the meta-position increased activity. Of note, compound 12 has drug-like properties, including favorable molecular weight (331 Da), topological polar surface area (70.3 Å$^2$) and c Log P (4.51), that latter much improved compared to c Log P of 5.99 for 1.

CFTR is a compelling target for dry eye therapy as it is expressed in corneal and conjunctival epithelia at the ocular surface [23-26] where it functions as a prosecretory chloride channel [27,28]. While CFTR is largely inactive under basal conditions, when activated it has the capacity to drive secretion of tear fluid onto the ocular surface. By analogy, CFTR is largely inactive in the intestine under basal conditions, but when activated by bacterial enterotoxins as in cholera it can promote massive secretion of fluid into the intestinal lumen. As topically delivered CFTR activators act primary on ocular surface epithelia, they are predicted to be efficacious in dry eye produced by multiple etiologies, including disorders targeting lacrimal glands such as Sjogren's syndrome. It is noted, however, that a pure prosecretory therapeutic replaces primarily the aqueous compartment of the tear film, which also contains lipid and mucin components. This potential limitation also applies to anti-absorptive therapeutics in development targeting the ENaC sodium channel [29]. Notwithstanding this potential limitation, the demonstration of efficacy in rodent models [30] and the known pathogenesis of dry eye in which tear film hyperosmolality produces downstream pathology [31,32] support the utility of CFTR activator therapy in human dry eye.

In conclusion, CFTR activator therapy is predicted to have broad clinical indications for prosecretory therapy of dry eye caused by a variety of etiologies, including 'idiopathic' dry eye. Because of their unique mechanism of action CFTR activators are combinable with approved immunosuppressants and possible future therapeutics such as ENaC inhibitors. Compared with immunosuppressant drugs, CFTR activator therapy rescues an early, initiating event in dry eye pathogenesis in an etiology-agnostic manner. The aminophenyl-1,3,5-triazines synthesized and tested herein are candidate lead compounds for further preclinical development.

Experimental Details and Data

Synthesis Procedures

General Procedures. All solvents and chemicals were used as purchased without further purification. Reaction progress was monitored on Merck pre-coated silica gel plates (with fluorescence at 254 nm) using ethyl acetate/n-hexane as solvent system. Column chromatography was done with Fluka silica gel 60 (230-400 mesh). Proton ($^1$H) and carbon ($^{13}$C) NMR spectra were recorded on a Bruker Avance 300 or 500 (500.13 MHz for $^1$H; 125.76 MHz for $^{13}$C) using CDCl$_3$ (δ 7.26), CD$_3$OD (δ=4.87 and 3.31), acetone-d$_6$ (δ 2.05), or DMSO-d$_6$ (δ 2.5) as solvents. Chemical shifts are given in parts per million (ppm) (δ relative to residual solvent peak for $^1$H and $^{13}$C). HRMS was performed using a hybrid quadrupole Orbitrap mass analyzer, QExactive (Thermo, Bremen, Germany), with an electrospray ionization source. The mass resolution was set as 70,000 at m/z 200 and the mass accuracy was less than 3 ppm. Purity of all final compounds was 95% or higher. Below we report synthesis and analytic data for intermediates and representative final compounds 1 and 12. Analytic data for 6a-6k, 7a-7g, and 11 are reported in Supporting Information.

2,4-Dichloro-6-[(1,1,1,3,3,3-hexafluoropropan-2-yl) oxy]-1,3,5-triazine (2). To a solution of cyanuric chloride (2 g, 10.84 mmol) in THF (50 ml) at −80° C. was added potassium carbonate (3.0 g, 21.74 mmol). A solution of 1,1,1,3,3,3-hexafluoro-2-propanol (1.36 ml, 10.30 mmol) in THF (20 ml) was then added dropwise over 30 min. The mixture was stirred for additional 30 min at −80° C. and quenched with water. The reaction mixture was diluted with EtOAc and washed with 1N HCl solution. The organic layer was washed with brine and dried over MgSO$_4$. The solvent was removed under reduced pressure to afford a white solid (1.5 g, 62%). The residue was used for further reaction without purification.

2,4-Dichloro-6-[(2,2,3,3-tetrafluoropropan)oxy]-1,3,5-triazine (3). To a solution of cyanuric chloride (2 g, 10.84 mmol) in THF (50 ml) at −80° C. was added potassium carbonate (3 μg, 21.74 mmol). A solution of 2,2,3,3-tetrafluoropropanol (1.2 ml, 10.3 mmol) in THF (20 ml) was then added dropwise over 30 min. The mixture was stirred for additional 30 min at −80° C. and quenched with water. The reaction mixture was diluted with EtOAc and the organic layer was washed with brine and dried over MgSO$_4$. The solvent was removed under reduced pressure to afford a white solid (1.3 g, 68%). The residue was used for further reaction without purification. $^1$H NMR (300 MHz, CDCl$_3$): δ=6.01 (tt, 1H, J=3.96, 52.9 Hz), 4.90-4.79 (m, 2H); $^{13}$C NMR (75 MHz, CDCl$_3$): δ=168.5, 165.1, 165.0, 138.4, 128.7, 123.4, 122.7, 120.3, 119.0, 68.3 (t, 34 Hz), 42.4, 42.0, 12.9, 12.8; LRMS-ESI: m/z 279.

4-Chloro-N,N-diethyl-6-[(1,1,1,3,3,3-hexafluoropropan-2-yl)oxy]-1,3,5-triazin-2-amine (4). To a solution of 2 (1.6 g, 5.06 mmol) in THF (40 ml) was added diisopropylethylamine (1.06 ml, 6.08 mmol) and diethylamine (0.5 ml, 5.0 mmol) at 0° C. The mixture was stirred for 1 h at 0° C., then quenched with water. The reaction mixture was extracted with EtOAc, washed with water and brine, and dried over MgSO$_4$. The solvent was removed under reduced pressure to afford a white solid (950 mg, 55%).

4-Chloro-N,N-diethyl-6-[(2,2,3,3-tetrafluoropropan)oxy]-1,3,5-triazin-2-amine (5). To a solution of 3 (1.3 g, 5 mmol) in THF (30 ml) was added diisopropylethylamine (1 ml, 6 mmol) and diethylamine (0.5 ml, 5.0 mmol) at 0° C. The mixture was stirred for 1 h at 0° C., then quenched with water. The reaction mixture was extracted with EtOAc, washed with water and brine, and dried over MgSO4. The solvent was removed under reduced pressure to afford yellow oil (900 mg, 57%).

Analogs 6a-6k and 7a-7g were prepared as described for 1, with various substituted anilines and 4 or 5.

N,N-Diethyl-6-[(1,1,1,3,3,3-hexafluoropropan-2-yl)oxy]-N'-phenyl-1,3,5-triazine-2,4-diamine (1). To a solution of 4 (500 mg, 1.42 mmol) in THF (30 ml) was added diisopropylethylamine (0.49 ml, 2.83 mmol) and aniline (0.15 ml, 1.7 mmol). The mixture was refluxed for 16 h. After cooling to room temperature the reaction mixture was extracted with EtOAc, washed with brine and dried over MgSO$_4$. The solvent was removed under reduced pressure and purified by flash chromatography (1:10 EtOAc/Hex) to afford 1 as a white powder (280 mg, 48%). $^1$H NMR (300 MHz, CDCl$_3$): δ=7.61 (d, 2H, J=7.8 Hz), 7.55 (brs, 1H), 7.35 (t, 1H, J=7.5 Hz), 7.11 (t, 1H, J=7.4 Hz), 6.37 (sep, 1H, J=6.2 Hz), 3.69-3.58 (m, 4H), 1.29-1.20 (m, 6H); $^{13}$C NMR (75 MHz, CDCl$_3$): δ=168.5, 165.1, 165.0, 138.4, 128.7, 123.4, 122.7, 120.3, 119.0, 68.3 (t, 34 Hz), 42.4, 42.0, 12.9, 12.8; HRMS (ESI): m/z calculated for C$_{16}$H$_{18}$F$_6$N$_5$O [M+H$^+$]: 410.1410. Found: 410.1411.

4,6-Dichloro-N-methyl-1,3,5-triazine-2-amine (8). To a solution of cyanuric chloride (5 g, 27.3 mmol) in acetone (30 ml) at 0° C. was added methylamine (13.7 ml, 2 M in THF) dropwise over 30 min. The mixture was stirred for 1 h at 0° C. and then crushed ice was added. The resulting precipitate was filtered and washed with water to afford 8 as a white solid (3.7 g, 75.7%), which was used for further reaction without purification. $^1$H NMR (300 MHz, CDCl$_3$) δ=6.21-5.81 (m, 1H), 4.81-4.67 (m, 2H), 3.06-3.03 (m, 3H); $^{13}$C NMR (75 MHz, CDCl$_3$) δ=170.8, 169.2, 168.4, 108.9, 63.3, 25.5.

4-Chloro-6-((1,1,1,3,3,3-hexafluoropropan-2-yl)oxy)-N-methyl-1,3,5-triazin-2-amine (9). To a solution of 8 (2 g, 11.17 mmol) in THF (40 ml) at 0° C. was added potassium carbonate (11.56 g, 83.8 mmol) and 1,1,1,3,3,3-hexafluoro-2-propanol (1.4 ml, 13.4 mmol). The mixture was stirred overnight at ambient temperature. The reaction mixture was diluted with EtOAc, and then organic layer was washed with brine and dried over MgSO$_4$. The solvent was removed under reduced pressure. A white solid was obtained (1.4 g, 43%).

4-Chloro-6-[(2,2,3,3-tetrafluoropropan)oxy]N-methyl-1,3,5-triazine-2-amine (10). To a solution of 8 (630 mg, 3.52 mmol) in THF (30 ml) at 0° C. was added potassium carbonate (970 mg, 7.04 mmol). A solution of 2,2,3,3-tetrafluoropropanol (0.31 ml, 3.52 mmol) in THF (20 ml) was added dropwise over 30 min. The mixture was stirred for additional 30 min at 0° C., then quenched with water. The reaction mixture was diluted with EtOAc, and the organic layer was washed with brine and dried over MgSO$_4$. Solvent was removed under reduced pressure to afford a white solid (640 mg, 66%). The residue was used for further reaction without purification. $^1$H NMR (300 MHz, CDCl$_3$): δ=6.98-5.79 (m, 1H), 4.87-4.69 (m, 2H), 3.05 (d, 3H).

N-methyl-N'-phenyl-6-(2,2,3,3-tetrafluoropropoxy)-1,3,5-triazine-2,4-diamine (12). To a solution of 10 (70 mg, 0.26 mmol) in THF (3 ml) was added diisopropylethylamine (0.09 ml, 0.51 mmol) and aniline (0.03 ml, 0.31 mmol). The mixture was refluxed for 16 h. After cooling to room temperature the reaction mixture was extracted with EtOAc, washed with brine and dried over MgSO$_4$. Solvent was removed under reduced pressure and purified by flash chromatography (1:2 EtOAc/Hex) to afford 12 as a white powder (63 mg, 74%). $^1$H NMR (300 MHz, CDCl$_3$): δ=7.61 (d, 2H, J=7.8 Hz), 7.55 (brs, 1H), 7.35 (t, 1H, J=7.5 Hz), 7.11 (t, 1H, J=7.4 Hz), 6.37 (sep, 1H, J=6.2 Hz), 3.69-3.58 (m, 4H), 1.29-1.20 (m, 6H); $^{13}$C NMR (75 MHz, CDCl$_3$): δ=168.5, 165.1, 165.0, 138.4, 128.7, 123.4, 122.7, 120.3, 119.0, 68.3 (t, 34 Hz), 42.4, 42.0, 12.9, 12.8; HRMS (ESI): m/z calculated for C$_{13}$H$_{14}$F$_4$N$_5$O [M+H+]: 332.1129. Found: 332.1127.

Mice. Wildtype and CF (homozygous ΔF508-CFTR mutant) mice in a CD1 genetic background were bred at the University of California San Francisco (UCSF) Animal Facility. Mice aged 8 to 12 weeks (25 to 35 g) were used. Animal protocols were approved by the UCSF Institutional Animal Care and Use Committee and were in compliance with the ARVO Statement for the Use of Animals in Ophthalmic and Visual Research.

Cell Culture. Fischer Rat Thyroid (FRT) cells stably co-expressing human wildtype CFTR or TMEM16A and the halide-sensitive yellow fluorescent protein (YFP)-H148Q were cultured as described [15,33]. HT-29 expressing YFP were cultured as described [34]. Primary cultures of human bronchial epithelial (HBE) cells were maintained at an air-liquid interface as described previously [35].

Platereader assays of chloride channel function. CFTR activity was assayed as described [15]. FRT cells co-expressing YFP and wildtype CFTR were washed with phosphate-buffered saline (PBS) and then incubated for 10 min with test compounds in PBS containing 125 nM forskolin. I$^-$ influx was measured in a plate reader with initial baseline read for 2 s and then for 12 s after rapid addition of an I$^-$-containing solution. TMEM16A activity was assayed similarly as described [33] using FRT cells co-expressing YFP and TMEM16A. Activity of non-TMEM16A CaCC was assayed as described [34] in HT-29 cells expressing YFP. In each assay initial rates of I$^-$ influx were computed as a linear measure of channel function.

Short-circuit current measurement. Short-circuit current measurements were done as described [9]. Briefly, Snapwell (Corning Costar, Corning, N.Y.) inserts containing CFTR-expressing FRT cells or human bronchial epithelial cells were mounted in Ussing chambers (Physiological Instruments, San Diego, Calif.). For FRT cells the hemichambers were filled with 5 ml of HCO$_3^-$-buffered solution (basolateral) and half-Cl$^-$ solution (apical), and the basolateral membrane was permeabilized with 250 µg/ml amphotericin B. Symmetrical $HCO_3^-$-buffered solutions were used for human bronchial epithelial cells. Solutions were bubbled with 95% $O_2$/5% $CO_2$ and maintained at 37° C., and short-circuit current was measured on a DVC-1000 voltage clamp (World Precision Instruments Inc., Sarasota, Fla.) using Ag/AgCl electrodes and 3 M KCl agar bridges.

cAMP and $Ca^{2+}$ assays. FRT cells expressing wildtype CFTR were cultured in 12-well plates. After washing with PBS, cells were incubated for 10 min with compounds in the absence or presence of 90 nM forskolin and then lysed. Lysates were assayed for cAMP content using a cAMP immunoassay kit (Parameter cAMP Immunoassay Kit, R&D Systems, Minneapolis, Minn.). For cytoplasmic calcium measurements, FRT cells in 96-well black-walled microplates were loaded with Fluo-4 NW (Invitrogen, Carlsbad, Calif.) and Fluo-4 fluorescence was measured with a plate reader equipped with syringe pumps and monochromators.

Cytotoxicity. FRT cells were cultured overnight in black 96-well Costar microplates and incubated with test compounds at up to 10 µM (the maximum solubility in PBS) for 8 h. Cytotoxicity was measured by Alamar Blue assay (Invitrogen, Carlsbad, Calif.).

Tear volume. Tear volume was measured using phenol red threads (Zone-Quick, Oasis Medical, Glendora, Calif.) as described [36]. Threads were placed for 10 s in the lateral canthi of isofluorane-anesthetized mice using jewelers' forceps. Tear volume was determined from the length of thread wetting as visualized under a dissecting microscope. Serial measurements were done to evaluate compound pharmacodynamics after topical application of a single, 2.5-µL drop of ophthalmic formulation containing 0-100 µM of 1 or 12 in Ringer's solution with 0.3% carboxymethylcellulose (high viscosity, VWR, Radnor, Pa.), 0.015% benzalkonium chloride preservative, and 1% DMSO. Both eyes in each mouse received the same treatment to control for potential contralateral effects of a given treatment.

In vitro metabolic stability. Compounds (each 5 µM) were incubated for specified times at 37° C. with rat liver microsomes (1 mg/ml; Sigma-Aldrich) in potassium phosphate buffer containing 1 mM NADPH, as described[14]. Ice-cold EtOAc was then added and the mixture was centrifuged for 15 min at 3000 rpm. The supernatant was analyzed by low-resolution mass spectrometry using a LC/MS system (Waters 2695 HPLC with Micromass ZQ). LC was done on a Xterra MS C18 column (2.1 mm×100 mm, 3.5 µm) with 0.2 mL/min water/acetonitrile (containing 0.1% formic acid), 12 min linear gradient, 5 to 95% acetonitrile. UV absorbance was detected at 254 nm.

Statistics. Statistical analysis was performed using Prism 5 GraphPad Software package (San Diego, Calif.). Serial tear volume measurements were analyzed by two-way ANOVA with Dunnett post-hoc analysis. Data are presented as mean±standard error of the mean (S.E.M.), and statistical significance was set at $p<0.01$ (*).

Abbreviations. CFTR, cystic fibrosis transmembrane conductance regulator; cAMP, cyclic adenosine monophosphate; YFP, yellow fluorescent protein; CF, cystic fibrosis; FRT cells, Fischer rat thyroid cells; LC/MS, liquid chromatography/mass spectrometry; fsk, forskolin; SAR, structure-activity relationships.

References (Example 6)

[1] Verkman, A. S.; Galietta, L. J. Chloride channels as drug targets. *Nat. Rev. Drug Disc.* 2009, 8, 153-171; [2] Schmidt, B. Z.; Haaf, J. B.; Leal, T.; Noel, S. Cystic fibrosis transmembrane conductance regulator modulators in cystic fibrosis: current perspectives. *Clin. Pharmacol.* 2016, 21, 127-140; [3] Thiajarajah, J. R.; Donowitz, M.; Verkman, A. S. Secretory diarrhea: mechanisms and emerging therapies. *Nature Rev. Gastroenterol. Hepatol.* 2015, 12, 446-457; [4] Ong, T.; Ramsey, B. W. New rherapeutic approaches to modulate and correct cystic fibrosis transmembrane conductance regulator. *Pediatr. Clin. North. Am.* 2016, 63, 751-764; [5] Chao, A. C.; de Sauvage, F. J.; Dong, Y. J.; Wagner, J. A; Goeddel, D. V.; Gardner, P. Activation of intestinal CFTR Cl– channel by heat-stable enterotoxin and guanylin via cAMP-dependent protein kinase. *EMBO J.* 1994, 13, 1065-1072; [6] Moon, C.; Zhang, W.; Sundaram, N.; Yarlagadda, S.; Reddy, V. S.; Arora, K.; Helmrath, M. A.; Naren, A. P. Drug-induced secretory diarrhea: A role for CFTR. *Pharmacol. Res.* 2015, 102, 107-112; [7] Field, M.; Mechanisms of action of cholera and *Escherichia coli* enterotoxins. *Am. J. Clin. Nutr.* 1979, 32, 189-196; [8] Solomon G. M.; Marshall, S. G.; Ramsey, B. W.; Rowe, S. M. Breakthrough therapies: Cystic fibrosis (CF) potentiators and correctors. *Pediatr. Pulmonol.* 2015, 50, S3-S13; [9] Cil, O.; Phuan, P. W.; Lee, S.; Tan, J.; Haggie, P. M.; Levin, M. H.; Sun, L.; Thiagarajah, J. R.; Ma, T.; Verkman, A. S. CFTR activator increases intestinal fluid secretion and normalizes stool output in a mouse model of constipation. *Cell. Mol. Gastroentrol. Hepatol.* 2016, 2, 317-327; [10] Cil, O.; Phuan, P. W.; Son, J. H.; Zhu, J. S.; Ku, C. K.; Tabib, N. A.; Teuthorn, A. P.; Ferrera, L.; Zachos, N. C.; Lin, R.; Galietta, L. J.; Donowitz, M.; Kurth, M. J.; Verkman, A. S. Phenylquinoxalinone CFTR activator as potential prosecretory therapy for constipation. *Transl. Res.* 2016, (in press); [11] Solomon, G. M.; Raju, S. V.; Dransfield, M. T.; Rowe, S. M. Therapeutic approaches to acquired cystic fibrosis transmembrane conductance regulator dysfunction in chronic bronchitis. *Ann. Am. Thorac. Soc.* 2016, 13, Suppl 2:S169-S176; [12] Flores, A. M.; Casey, S. D.; Felix, C. M.; Phuan, P. W.; Verkman, A. S.; Levin, M. H. Small-molecule CFTR activators increase tear secretion and prevent experimental dry eye disease. *FASEB J.* 2016, 30, 1789-1797; [13] Cil, O.; Phuan, P. W.; Gillespie, A. M.; Lee, S.; Tradtrantip, L.; Yin, J.; Tse, M.; Zachos, N. C.; Lin, R.; Donowitz, M.; Verkman, A. S. Benzopyrimido-pyrrolo-oxazine-dione CFTR inhibitor (R)-BPO-27 for antisecretory therapy of diarrheas caused by bacterial enterotoxins. *FASEB J.* 2016 (in press); [14] Snyder, D. S.; Tradtrantip, L.; Yao, C.; Kurth, M. J.; Verkman, A. S. Potent, metabolically stable benzopyrimido-pyrrolo-oxazine-dione (BPO) CFTR inhibitors for polycystic kidney disease. *J. Med. Chem.* 2011, 54, 5468-5477; [15] Ma, T.; Vetrivel, L.; Yang, H.; Pedemonte, N.; Zegarra-Moran, O.; Galietta, L. J.; Verkman, A. S. High-affinity activators of CFTR chloride conductance identified by high-throughput screening. *J. Biol. Chem.* 2002, 277, 37235-37241; [16] Schaumberg, D. A.; Dana, R., Buring, J. E.; Sullivan, D. A. Prevalence of dry eye disease among US men: estimates from the Physicians' Health Studies. *Arch. Ophthalmol.* 2009, 127, 763-768; [17] Schaumberg, D. A.; Sullivan, D. A.; Buring, J. E.; Dana, M. R. Prevalence of dry eye syndrome among US women. *Am. J. Ophthalmol.* 2003, 136, 318-326; [18] Alves, M.; Foseca, E. C.; Alves, M. F.; Malki, L. T.; Arruda, G. V.; Reinach, P. S.; Rocha, E. M. Dry eye disease treatment: a systematic review of published trials and critical appraisal of therapeutic strategies. *Ocul. Surf.* 2013, 11, 181-192; [19] Sheppard, J. D.; Torkildsen, G. L.; Lonsdale, J. D.; D'Ambrosio Jr. F. A.; McLaurin, E. B.; Eiferman, R. A.; Kennedy, K. S.; Semba, C. P.; OPUS-1 Study Group. Lifitegrast ophthalmic solution 5.0% for treatment of dry eye disease: results of the OPUS-1 phase 3 study. *Ophthalmology* 2014, 121, 475-483; [20] Jowa, L.;

Howd, R. Should atrazine and related chlorotriazines be considered carcinogenic for human health risk assessment? *J. Environ. Sci. Health C Environ. Carcinog. Ecotoxicol Rev.* 2011, 29, 91-144; [21] Moon, H.-S.; Jacobson, E. M.; Khersonsky, S. M.; Luzung, M. R.; Walsh, D. P.; Xiong, W.; Lee J. W.; Parikh, P. B.; Lam, J. C.; Kang, T.-W.; Rosania, G. R.; Schier, A. F.; Chang, Y.-T. A novel microtubule destabilizing entity from orthogonal synthesis of triazine library and zebrafish embryo screening. *J. Am. Chem. Soc.* 2002, 124, 11608-11609; [22] Plebanek, E.; Chevrier, F.; Roy, V.; Garnne, T.; Lecaille, F.; Warszycki, D.; Bojarski, A. J.; Lalmanach, G.; Agrofoglio, L. A. Straightforward synthesis of 2,4,6-trisubstituted 1,3,5-triazine compounds targeting cysteine cathepsins K and S. *Eur. J. Med. Chem.* 2016, 121, 12-20; [23] Kompella, U. B.; Kim, K. J.; Lee, V. H. Active chloride transport in the pigmented rabbit conjunctiva. *Curr. Eye Res.* 1993, 12, 1041-1048; [24] Turner, H. C.; Bernstein, A.; Candia, O. A. Presence of CFTR in the conjunctival epithelium. *Curr. Eye Res.* 2002, 24, 182-187; [25] Al-Nakkash, L.; Reinach, P. S. Activation of a CFTR-mediated chloride current in a rabbit corneal epithelial cell line. *Invest. Ophthalmol. Vis. Sci.* 2001, 42, 2353-2370; [26] Shiue, M. H.; Gukasyan, H. J; Kim, K. J.; Loo, D. D.; Lee, V. H. Characterization of cyclic AMP-regulated chloride conductance in the pigmented rabbit conjunctival epithelial cells. *Can. J. Physiol. Pharmacol.* 2002, 80, 533-540; [27] Levin, M. H.; Verkman, A. S. CFTR-regulated chloride transport at the ocular surface in living mice measured by potential differences. *Invest. Ophthalmol. Vis. Sci.* 2005, 46, 1428-1434; [28] Levin, M. H.; Kim, J. K.; Hu, J.; Verkman A. S. Potential difference measurements of ocular surface $Na^+$ absorption analyzed using an electrokinetic model. *Invest. Ophthalmol. Vis. Sci.* 2006, 47, 306-316; [29] Yu, D.; Thelin, W. R.; Rogers, T. D.; Stutts, M. J.; Randell, S. H.; Grubb, B. R.; Boucher, R. C. Regional differences in rat conjunctival ion transport activities. *Am. J. Physiol. Cell-Physiol.* 2012, 303, C767-780; [30] Thelin, W. R.; Johnson, M. R.; Hirsh, A. J.; Kublin, C. L.; Zoukhri, D. J. Effect of topically applied epithelial sodium channel inhibitors on tear production in normal mice and in mice with induced aqueous tear deficiency. *Ocul. Pharmacol. Ther.* 2012, 28, 433-438; [31] Gilbard, J. P.; Carter, J.; Sang, D.; Refojo, M.; Hanninen, L.; Kenyon, K. R. Morphologic effect of hyperosmolarity on rabbit corneal epithelium. *Ophthalmology* 1984, 91, 1205-1212; [32] Liu, H.; Begley, C.; Chen, M.; Bradley, A.; Bonanno, J.; McNamara, N.; Nelson, J.; Simpson, T. A link between tear instability and hyperosmolarity in dry eye. *Invest. Ophthalmol. Vis. Sci.* 2009, 50, 3671-3679; [33] Namkung, W.; Phuan, P. W.; Verkman, A. S. TMEM16A inhibitors reveal TMEM16A as a minor component of calcium-activated chloride channel conductance in airway and intestinal epithelial cells. *J. Biol. Chem.* 2011, 286, 2365-2374; [34] De La Fuente, R.; Namkung, W.; Mills, A.; Verkman, A. S. Small-molecule screen identifies inhibitors of a human intestinal calcium-activated chloride channel. *Mol. Pharmacol.* 2008, 73, 758-768; [35] Haggie, P. M.; Phuan, P. W.; Tan, J. A.; Zlock, L.; Finkbeiner, W. E.; Verkman, A. S. Inhibitors of pendrin anion exchange identified in a small molecule screen increase airway surface liquid volume in cystic fibrosis. *FASEB J.* 2016, 30, 2187-2197; [36] Stewart, P.; Chen, Z; Farley, W.; Olmos, L.; Pflugfelder, S. C. Effect of experimental dry eye on tear sodium concentration in the mouse. *Eye Contact Lens* 2005, 31, 175-178;

What is claimed is:
1. A method of treating constipation in a subject in need thereof, comprising administering to the subject an effective amount of a compound of Formula I:

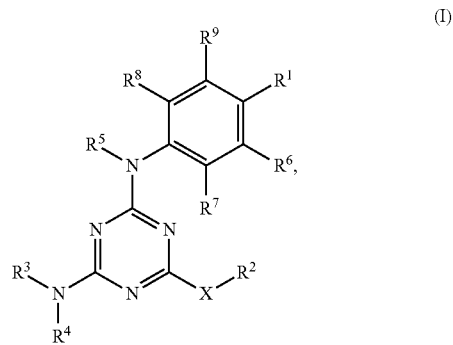

or a pharmaceutically acceptable salt thereof,
wherein:
X is —O—, —NH— or —S—;
n1, n2, n6, n7, n8, and n9 are independently an integer from 0 to 4;
m1, m6, m7, m8, m9, v1, v6, v7, v8, and v9 are each independently 1 or 2;
$R^1$ is hydrogen, halogen, $—CX^{1.1}_3$, $—CHX^{1.1}_2$, $—CH_2X^{1.1}$, —CN, $—SO_{n1}R^{1A}$, $—SO_{v1}NR^{1B}R^{1C}$, $—NHNR^{1B}R^{1C}$, $—ONR^{1B}R^{1C}$, —NHC(O)NHNR^{1B}R^{1C}$, $—NHC(O)NR^{1B}R^{1C}$, $—N(O)_{m1}$, $—NR^{1B}R^{1C}$, $—C(O)R^{1D}$, $—C(O)OR^{1D}$, $—C(O)NR^{1B}R^{1C}$, $—OR^{1A}$, $—NR^{1B}SO_2R^{1A}$, $—NR^{1B}C(O)R^{1D}$, $—NR^{1B}C(O)OR^{1D}$, $—NR^{1B}OR^{1D}$, $—OCX^{1.1}_3$, $—OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, $—CX^{2.1}_3$, $CHX^{2.1}_2$, $—(CH_2)_{n2}CX^{2.1}_3$, $—OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl;
$R^3$ is hydrogen, $—C(O)R^{3D}$, $—C(O)NHNR^{3B}R^{3C}$, $—C(O)OR^{3D}$, $—SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R^4$ is hydrogen, $—C(O)R^{4D}$, $—C(O)NHNR^{4B}R^{4C}$, $—C(O)OR^{4D}$, $—SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;

215

R⁵ is hydrogen, —C(O)R$^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R³ and R⁴ may optionally be joined to form, together with the atoms to which they are attached, a substituted or unsubstituted heterocycloalkyl or substituted or unsubstituted heteroaryl;

R⁶ is hydrogen, halogen, —CX$^{6.1}_3$, —CHX$^{6.1}_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁷ is hydrogen, halogen, —CX$^{7.1}_3$, —CHX$^{7.1}_2$, —CH$_2$X$^{7.1}$, —CN, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁸ is hydrogen, halogen, —CX$^{8.1}_3$, —CHX$^{8.1}_2$, —CH$_2$X$^{8.1}$, —CN, —SO$_{n8}$R$^{8A}$, —SO$_{v8}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m8}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹ and R⁶, R⁶ and R⁷, R¹ and R⁹, or R⁸, and R⁹ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$,

216

R$^{9B}$, R$^{9C}$ and R$^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$ and R$^{9C}$ substituents bonded to the same nitrogen atom may optionally be joined to form, together with the atoms to which they are attached, a substituted or unsubstituted heterocycloalkyl or substituted or unsubstituted heteroaryl; and X$^{1.1}$, X$^{2.1}$, X$^{6.1}$, X$^{7.1}$, X$^{8.1}$ and X$^{9.1}$ are independently —Cl, —Br, —I or —F;

with the proviso that when X is —O—; R² is —(CH$_2$)$_{n2}$CX$^{2.1}_3$; n2 is 1; X$^{2.1}$ is fluorine; R³ is hydrogen; and R⁴ is substituted or unsubstituted C$_1$-C$_3$ alkyl, then R⁶ is not —NO$_2$; and when X is —O—; R² is —(CH$_2$)$_{n2}$CX$^{2.1}_3$; n2 is 1; X$^{2.1}$ is fluorine; R³ is hydrogen; and R⁴ is substituted or unsubstituted C$_1$-C$_3$ alkyl, then R⁹ is not —NO$_2$.

2. The method of claim 1, further comprising administering to the subject an anti-constipation agent.

3. The method of claim 1, wherein the compound is administered orally.

4. The method of claim 1, wherein the constipation is opioid-induced constipation, chronic idiopathic constipation or irritable bowel syndrome with constipation predominance.

5. A method of treating a dry eye disorder in a subject in need thereof, comprising administering to the subject an effective amount a compound of Formula I:

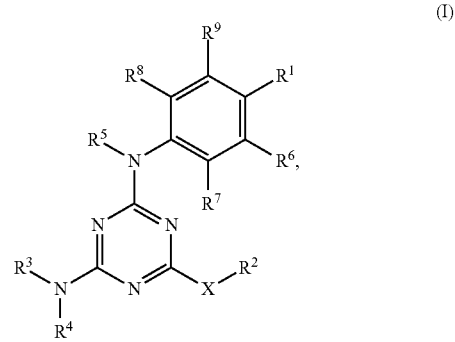

(I)

or a pharmaceutically acceptable salt thereof,
wherein:

X is —O—, —NH— or —S—;

n1, n2, n6, n7, n8, and n9 are independently an integer from 0 to 4;

m1, m6, m7, m8, m9, v1, v6, v7, v8, and v9 are each independently 1 or 2;

R¹ is hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)

$NR^{1B}R^{1C}$, $-OR^{1A}$, $-NR^{1B}SO_2R^{1A}$, $-NR^{1B}C(O)$ $R^{1D}$, $-NR^{1B}C(O)OR^{1D}$, $-NR^{1B}OR^{1D}$, $-OCX^{1.1}{}_3$, $-OCHX^{1.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, $-CX^{2.1}{}_3$, $CHX^{2.1}{}_2$, $-(CH_2)_{n2}CX^{2.1}{}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl;

$R^3$ is hydrogen, $-C(O)R^{3D}$, $-C(O)NHNR^{3B}R^{3C}$, $-C(O)OR^{3D}$, $-SO_2R^{3A}$, $C(O)NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^4$ is hydrogen, $-C(O)R^{4D}$, $-C(O)NHNR^{4B}R^{4C}$, $-C(O)OR^{4D}$, $-SO_2R^{4A}$, $C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;

$R^5$ is hydrogen, $-C(O)R^{5D}$, $-C(O)NHNR^{5B}R^{5C}$, $-C(O)OR^{5D}$, $-SO_2R^{5A}$, $C(O)NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl;

$R^6$ is hydrogen, halogen, $-CX^{6.1}{}_3$, $-CHX^{6.1}{}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}{}_3$, $-OCHX^{6.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CX^{7.1}{}_3$, $-CHX^{7.1}{}_2$, $-CH_2X^{7.1}$, $-CN$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}{}_3$, $-OCHX^{7.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-CX^{8.1}{}_3$, $-CHX^{8.1}{}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}{}_3$, $-CHX^{9.1}{}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently $-Cl$, $-Br$, $-I$ or $-F$;

with the proviso that when X is $-O-$; $R^2$ is $-(CH_2)_{n2}CX^{2.1}{}_3$; n2 is 1; $X^{2.1}$ is fluorine; $R^3$ is hydrogen; and $R^4$ is substituted or unsubstituted $C_1$-$C_3$ alkyl, then $R^6$ is not $-NO_2$; and when X is $-O-$; $R^2$ is $-(CH_2)_{n2}CX^{2.1}{}_3$; n2 is 1; $X^{2.1}$ is fluorine; $R^3$ is hydrogen; and $R^4$ is substituted or unsubstituted $C_1$-$C_3$ alkyl, then $R^9$ is not $-NO_2$.

6. The method of claim 5, wherein the dry eye disorder is a lacrimal gland disorder.

7. The method of claim 5, further comprising administering to the subject an anti-dry eye agent.

8. A method of increasing lacrimation in a subject in need thereof, comprising administering to the subject an effective amount of a compound of Formula I:

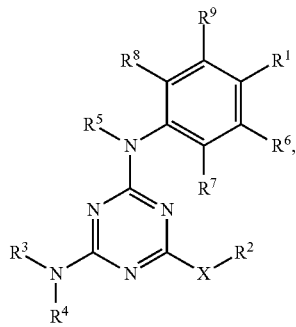

(I)

or a pharmaceutically acceptable salt thereof,
wherein:
X is —O—, —NH— or —S—;
n1, n2, n6, n7, n8, and n9 are independently an integer from 0 to 4;
m1, m6, m7, m8, m9, v1, v6, v7, v8, and v9 are each independently 1 or 2;
$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}R^{1C}$, —NHC(O)NR$^{1B}R^{1C}$, —N(O)$_{m1}$, —NR$^{1B}R^{1C}$, —C(O)R$^{1D}$, —C(O)OR$^{1D}$, —C(O)NR$^{1B}R^{1C}$, —OR$^{1A}$, —NR$^{1B}SO_2R^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, —$CX^{2.1}_3$, $CHX^{2.1}_2$, —$(CH_2)_{n2}CX^{2.1}_3$, —OR$^{2A}$, substituted or unsubstituted alkyl, substituted or unsubstituted heteroalkyl, or unsubstituted cycloalkyl, substituted or unsubstituted heterocycloalkyl, substituted or unsubstituted aryl, substituted or unsubstituted heteroaryl or haloalkyl;
$R^3$ is hydrogen, —C(O)R$^{3D}$, —C(O)NHNR$^{3B}R^{3C}$, —C(O)OR$^{3D}$, —SO$_2R^{3A}$, C(O)NR$^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R^4$ is hydrogen, —C(O)R$^{4D}$, —C(O)NHNR$^{4B}R^{4C}$, —C(O)OR$^{4D}$, —SO$_2R^{4A}$, C(O)NR$^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;
$R^5$ is hydrogen, —C(O)R$^{5D}$, —C(O)NHNR$^{5B}R^{5C}$, —C(O)OR$^{5D}$, —SO$_2R^{5A}$, C(O)NR$^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl;
$R^6$ is hydrogen, halogen, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)NHNR$^{6B}R^{6C}$, —NHC(O)NR$^{6B}R^{6C}$, —N(O)$_{m6}$, —NR$^{6B}R^{6C}$, —C(O)R$^{6D}$, —C(O)OR$^{6D}$, —C(O)NR$^{6B}R^{6C}$, —OR$^{6A}$, —NR$^{6B}SO_2R^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NHNR^{7B}R^{7C}$, —$ONR^{7B}R^{7C}$, —NHC(O)NHNR$^{7B}R^{7C}$, —NHC(O)NR$^{7B}R^{7C}$, —N(O)$_{m7}$, —NR$^{7B}R^{7C}$, —C(O)R$^{7D}$, —C(O)OR$^{7D}$, —C(O)NR$^{7B}R^{7C}$, —OR$^{7A}$, —NR$^{7B}SO_2R^{7A}$, —NR$^{7A}$C(O)R$^{7C}$, —NR$^{7B}$C(O)OR$^{7D}$, —NR$^{7B}$OR$^{7D}$, —OCX$^{7.1}_3$, —OCHX$^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —NHC(O)NHNR$^{8B}R^{8C}$, —NHC(O)NR$^{8B}R^{8C}$, —N(O)$_{m8}$, —NR$^{8B}R^{8C}$, —C(O)R$^{8D}$, —C(O)OR$^{8D}$, —C(O)NR$^{8B}R^{8C}$, —OR$^{8A}$, —NR$^{8B}SO_2R^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —NHC(O)NHNR$^{9B}R^{9C}$, —NHC(O)NR$^{9B}R^{9C}$, —N(O)$_{m9}$, —NR$^{9B}R^{9C}$, —C(O)R$^{9D}$, —C(O)OR$^{9D}$, —C(O)NR$^{9B}R^{9C}$, —OR$^{9A}$, —NR$^{9B}SO_2R^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;
$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F;

with the proviso that when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^6$ is not —$NO_2$; and when X is —O—; $R^2$ is —$(CH_2)_{n2}CX^{2.1}_3$; n2 is 1; $X^{2.1}$ is fluorine; $R^3$ is hydrogen; and $R^4$ is substituted or unsubstituted $C_1$-$C_3$ alkyl, then $R^9$ is not —$NO_2$.

9. A method of activating a Cystic Fibrosis Transmembrane Conductance Regulator (CFTR), comprising contacting the CFTR with an effective amount of a compound of Formula I:

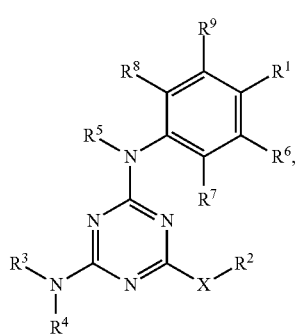

(I)

or a pharmaceutically acceptable salt thereof,
wherein:
X is —O—, —NH— or —S—;
n1, n2, n6, n7, n8, and n9 are independently an integer from 0 to 4;
m1, m6, m7, m8, m9, v1, v6, v7, v8, and v9 are each independently 1 or 2;
$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)$NHNR^{1B}R^{1C}$, —NHC(O)$NR^{1B}R^{1C}$, —$N(O)_{m1}$, —$NR^{1B}R^{1C}$, —C(O)$R^{1D}$, —C(O)$OR^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, —$CX^{2.1}_3$, $CHX^{2.1}_2$, —$(CH_2)_{n2}CX^{2.1}_3$, —$OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl;

$R^3$ is hydrogen, —C(O)$R^{3D}$, —C(O)$NHNR^{3B}R^{3C}$, —C(O)$OR^{3D}$, —$SO_2R^{3A}$, C(O)$NR^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^4$ is hydrogen, —C(O)$R^{4D}$, —C(O)$NHNR^{4B}R^{4C}$, —C(O)$OR^{4D}$, —$SO_2R^{4A}$, C(O)$NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;

$R^5$ is hydrogen, —C(O)$R^{5D}$, —C(O)$NHNR^{5B}R^{5C}$, —C(O)$OR^{5D}$, —$SO_2R^{5A}$, C(O)$NR^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl;

$R^6$ is hydrogen, halogen, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —$N(O)_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^{7.1}_3$, —$CHX^{7.1}_2$, —$CH_2X^{7.1}$, —CN, —$SO_{n7}R^{7A}$, —$SO_{v7}NR^{7B}R^{7C}$, —$NHNR^{7B}R^{7C}$, —$ONR^{7B}R^{7C}$, —NHC(O)$NHNR^{7B}R^{7C}$, —NHC(O)$NR^{7B}R^{7C}$, —$N(O)_{m7}$, —$NR^{7B}R^{7C}$, —C(O)$R^{7D}$, —C(O)$OR^{7D}$, —C(O)$NR^{7B}R^{7C}$, —$OR^{7A}$, —$NR^{7B}SO_2R^{7A}$, —$NR^{7A}C(O)R^{7C}$, —$NR^{7B}C(O)OR^{7D}$, —$NR^{7B}OR^{7D}$, —$OCX^{7.1}_3$, —$OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —$N(O)_{m8}$, —$NR^{8B}R^{8C}$, —C(O)$R^{8D}$, —C(O)$OR^{8D}$, —C(O)

NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}_3$, —CHX$^{9.1}_2$, —CH$_2$X$^{9.1}$, —CN, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^6$, R$^6$ and R$^7$, R$^1$ and R$^9$, or R$^8$, and R$^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$ and R$^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$ and R$^{9C}$ substituents bonded to the same nitrogen atom may optionally be joined to form, together with the atoms to which they are attached, a substituted or unsubstituted heterocycloalkyl or substituted or unsubstituted heteroaryl; and X$^{1.1}$, X$^{2.1}$, X$^{6.1}$, X$^{7.1}$, X$^{8.1}$ and X$^{9.1}$ are independently —Cl, —Br, —I or —F;

with the proviso that when X is —O—; R$^2$ is —(CH$_2$)$_{n2}$CX$^{2.1}_3$; n2 is 1; X$^{2.1}$ is fluorine; R$^3$ is hydrogen; and R$^4$ is substituted or unsubstituted C$_1$-C$_3$ alkyl, then R$^6$ is not —NO$_2$; and when X is —O—; R$^2$ is —(CH$_2$)$_{n2}$CX$^{2.1}_3$; n2 is 1; X$^{2.1}$ is fluorine; R$^3$ is hydrogen; and R$^4$ is substituted or unsubstituted C$_1$-C$_3$ alkyl, then R$^9$ is not —NO$_2$.

10. A method of treating a cholestatic liver disease in a subject in need thereof, the method comprising administering to the subject an effective amount of a compound of Formula I:

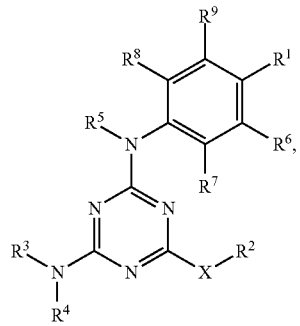

(I)

or a pharmaceutically acceptable salt thereof,
wherein:
X is —O—, —NH— or —S—;
n1, n2, n6, n7, n8, and n9 are independently an integer from 0 to 4;
m1, m6, m7, m8, m9, v1, v6, v7, v8, and v9 are each independently 1 or 2;
R$^1$ is hydrogen, halogen, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is hydrogen, —CX$^{2.1}_3$, CHX$^{2.1}_2$, —(CH$_2$)$_{n2}$CX$^{2.1}_3$, —OR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl;
R$^3$ is hydrogen, —C(O)R$^{3D}$, —C(O)NHNR$^{3B}$R$^{3C}$, —C(O)OR$^{3D}$, —SO$_2$R$^{3A}$, C(O)NR$^{3B}$R$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
R$^4$ is hydrogen, —C(O)R$^{4D}$, —C(O)NHNR$^{4B}$R$^{4C}$, —C(O)OR$^{4D}$, —SO$_2$R$^{4A}$, C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein R$^3$ and R$^4$ may optionally be joined to form, together with the atoms to which they are attached, a substituted or unsubstituted heterocycloalkyl or substituted or unsubstituted heteroaryl, wherein R$^3$ and R$^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;
R$^5$ is hydrogen, —C(O)R$^{5D}$, —C(O)NHNR$^{5B}$R$^{5C}$, —C(O)OR$^{5D}$, —SO$_2$R$^{5A}$, C(O)NR$^{5B}$R$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl;

$R^6$ is hydrogen, halogen, $-CX^{6.1}_3$, $-CHX^{6.1}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CX^{7.1}_3$, $-CHX^{7.1}_2$, $-CH_2X^{7.1}$, $-CN$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7A}C(O)R^{7C}$, $-NR^{7B}C(O)OR^{7D}$, $-NR^{7B}OR^{7D}$, $-OCX^{7.1}_3$, $-OCHX^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}_3$, $-CHX^{9.1}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently $-Cl$, $-Br$, $-I$ or $-F$;

with the proviso that when X is $-O-$; $R^2$ is $-(CH_2)_{n2}CX^{2.1}_3$; n2 is 1; $X^{2.1}$ is fluorine; $R^3$ is hydrogen; and $R^4$ is $-CH_3$, then $R^6$ is not $-NO_2$; and when X is $-O-$; $R^2$ is $-(CH_2)_{n2}CX^{2.1}_3$; n2 is 1; $X^{2.1}$ is fluorine; $R^3$ is hydrogen; and $R^4$ is $-CH_3$, then $R^9$ is not $-NO_2$.

11. A method of treating a pulmonary disease or disorder in a subject in need thereof, the method comprising administrating to the subject an effective amount of a compound of Formula I:

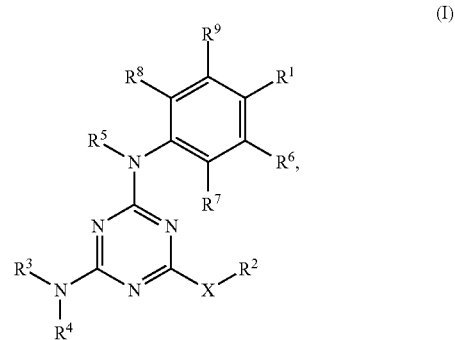

(I)

or a pharmaceutically acceptable salt thereof,
wherein:

X is $-O-$, $-NH-$ or $-S-$;

n1, n2, n6, n7, n8, and n9 are independently an integer from 0 to 4;

m1, m6, m7, m8, m9, v1, v6, v7, v8, and v9 are each independently 1 or 2;

$R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, $-CX^{2.1}_3$, $CHX^{2.1}_2$, $-(CH_2)_{n2}CX^{2.1}_3$, $-OR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl or haloalkyl;

$R^3$ is hydrogen, —C(O)$R^{3D}$, —C(O)NHN$R^{3B}R^{3C}$, —C(O)O$R^{3D}$, —SO$_2R^{3A}$, C(O)N$R^{3B}R^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^4$ is hydrogen, —C(O)$R^{4D}$, —C(O)NHN$R^{4B}R^{4C}$, —C(O)O$R^{4D}$, —SO$_2R^{4A}$, C(O)N$R^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl, wherein $R^3$ and $R^4$ are optionally be joined to form, together with the atoms to which they are attached, a substituted or unsubstituted cycloalkyl, substituted or unsubstituted heterocycloalkyl, substituted or unsubstituted aryl, or substituted or unsubstituted heteroaryl;

$R^5$ is hydrogen, —C(O)$R^{5D}$, —C(O)NHN$R^{5B}R^{5C}$, —C(O)O$R^{5D}$, —SO$_2R^{5A}$, C(O)N$R^{5B}R^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^3$ and $R^4$ may optionally be joined to form, together with the atoms to which they are attached, a substituted or unsubstituted heterocycloalkyl or substituted or unsubstituted heteroaryl;

$R^6$ is hydrogen, halogen, —C$X^{6.1}_3$, —CH$X^{6.1}_2$, —CH$_2X^{6.1}$, —CN, —SO$_{n6}R^{6A}$, —SO$_{v6}$N$R^{6B}R^{6C}$, —NHN$R^{6B}R^{6C}$, —ON$R^{6B}R^{6C}$, —NHC(O)NHN$R^{6B}R^{6C}$, —NHC(O)N$R^{6B}R^{6C}$, —N(O)$_{m6}$, —N$R^{6B}R^{6C}$, —C(O)$R^{6D}$, —C(O)O$R^{6D}$, —C(O)N$R^{6B}R^{6C}$, —O$R^{6A}$, —N$R^{6B}$SO$_2R^{6A}$, —N$R^{6B}$C(O)$R^{6D}$, —N$R^{6B}$C(O)O$R^{6D}$, —N$R^{6B}$O$R^{6D}$, —OC$X^{6.1}_3$, —OCH$X^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —C$X^{7.1}_3$, —CH$X^{7.1}_2$, —CH$_2X^{7.1}$, —CN, —SO$_{n7}R^{7A}$, —SO$_{v7}$N$R^{7B}R^{7C}$, —NHN$R^{7B}R^{7C}$, —ON$R^{7B}R^{7C}$, —NHC(O)NHN$R^{7B}R^{7C}$, —NHC(O)N$R^{7B}R^{7C}$, —N(O)$_{m7}$, —N$R^{7B}R^{7C}$, —C(O)$R^{7D}$, —C(O)O$R^{7D}$, —C(O)N$R^{7B}R^{7C}$, —O$R^{7A}$, —N$R^{7B}$SO$_2R^{7A}$, —N$R^{7A}$C(O)$R^{7C}$, —N$R^{7B}$C(O)O$R^{7D}$, —N$R^{7B}$O$R^{7D}$, —OC$X^{7.1}_3$, —OCH$X^{7.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —C$X^{8.1}_3$, —CH$X^{8.1}_2$, —CH$_2X^{8.1}$, —CN, —SO$_{n8}R^{8A}$, —SO$_{v8}$N$R^{8B}R^{8C}$, —NHN$R^{8B}R^{8C}$, —ON$R^{8B}R^{8C}$, —NHC(O)NHN$R^{8B}R^{8C}$, —NHC(O)N$R^{8B}R^{8C}$, —N(O)$_{m8}$, —N$R^{8B}R^{8C}$, —C(O)$R^{8D}$, —C(O)O$R^{8D}$, —C(O)N$R^{8B}R^{8C}$, —O$R^{8A}$, —N$R^{8B}$SO$_2R^{8A}$, —N$R^{8B}$C(O)$R^{8D}$, —N$R^{8B}$C(O)O$R^{8D}$, —N$R^{8B}$O$R^{8D}$, —OC$X^{8.1}_3$, —OCH$X^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —C$X^{9.1}_3$, —CH$X^{9.1}_2$, —CH$_2X^{9.1}$, —CN, —SO$_{n9}R^{9A}$, —SO$_{v9}$N$R^{9B}R^{9C}$, —NHN$R^{9B}R^{9C}$, —ON$R^{9B}R^{9C}$, —NHC(O)NHN$R^{9B}R^{9C}$, —NHC(O)N$R^{9B}R^{9C}$, —N(O)$_{m9}$, —N$R^{9B}R^{9C}$, —C(O)$R^{9D}$, —C(O)O$R^{9D}$, —C(O)N$R^{9B}R^{9C}$, —O$R^{9A}$, —N$R^{9B}$SO$_2R^{9A}$, —N$R^{9B}$C(O)$R^{9D}$, —N$R^{9B}$C(O)O$R^{9D}$, —N$R^{9B}$O$R^{9D}$, —OC$X^{9.1}_3$, —OCH$X^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^6$, $R^6$ and $R^7$, $R^1$ and $R^9$, or $R^8$, and $R^9$ are optionally joined to form, together with the atoms to which they are attached, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$ and $R^{9D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$ and $R^{9C}$ substituents bonded to the same nitrogen atom may optionally be joined to form, together with the atoms to which they are attached, a substituted or unsubstituted heterocycloalkyl or substituted or unsubstituted heteroaryl; and $X^{1.1}$, $X^{2.1}$, $X^{6.1}$, $X^{7.1}$, $X^{8.1}$ and $X^{9.1}$ are independently —Cl, —Br, —I or —F;

with the proviso that when X is —O—; $R^2$ is —(CH$_2$)$_{n2}$C$X^{2.1}_3$; n2 is 1; $X^{2.1}$ is fluorine; $R^3$ is hydrogen; and $R^4$ is —CH$_3$, then $R^6$ is not —NO$_2$; and when X is —O—; $R^2$ is —(CH$_2$)$_{n2}$C$X^{2.1}_3$; n2 is 1; $X^{2.1}$ is fluorine; $R^3$ is hydrogen; and $R^4$ is —CH$_3$, then $R^9$ is not —NO$_2$.

12. The method of claim 11, wherein the pulmonary disease or disorder is chronic obstructive pulmonary disease, bronchitis, asthma, and cigarette smoke-induced lung dysfunction.

* * * * *

UNITED STATES PATENT AND TRADEMARK OFFICE
CERTIFICATE OF CORRECTION

PATENT NO. : 11,230,535 B2
APPLICATION NO. : 16/785417
DATED : January 25, 2022
INVENTOR(S) : Alan S. Verkman et al.

It is certified that error appears in the above-identified patent and that said Letters Patent is hereby corrected as shown below:

In the Claims

Column 221, Claim 9, Line 62:
"-NR$^B$OR$^{1D}$," should read: -- -NR$^{1B}$OR$^{1D}$,--.

Signed and Sealed this
Thirteenth Day of February, 2024

Katherine Kelly Vidal
Director of the United States Patent and Trademark Office